United States Patent [19]

Bergeron et al.

[11] Patent Number: 5,994,066
[45] Date of Patent: Nov. 30, 1999

[54] SPECIES-SPECIFIC AND UNIVERSAL DNA PROBES AND AMPLIFICATION PRIMERS TO RAPIDLY DETECT AND IDENTIFY COMMON BACTERIAL PATHOGENS AND ASSOCIATED ANTIBIOTIC RESISTANCE GENES FROM CLINICAL SPECIMENS FOR ROUTINE DIAGNOSIS IN MICROBIOLOGY LABORATORIES

[75] Inventors: Michel G. Bergeron, Sillery; François J. Picard, Ste-Foy; Marc Ouellette, Quebec; Paul H. Roy, Loretteville, all of Canada

[73] Assignee: Infectio Diagnostic, Inc., Quebec, Canada

[21] Appl. No.: 08/743,637

[22] Filed: Nov. 4, 1996

Related U.S. Application Data

[63] Continuation-in-part of application No. 08/526,840, Sep. 11, 1995.

[51] Int. Cl.⁶ .............................. C12Q 1/68; C12P 19/34; C07H 21/02
[52] U.S. Cl. ............................ 435/6; 435/91.2; 536/22.1
[58] Field of Search ................................. 435/5, 6, 91.2; 536/22.1

[56] References Cited

U.S. PATENT DOCUMENTS

| | | | |
|---|---|---|---|
| 4,816,389 | 3/1989 | Sansonnetti et al. | 435/6 |
| 5,030,556 | 7/1991 | Beaulieu et al. | 435/6 |
| 5,041,372 | 8/1991 | Lampel et al. | 435/6 |
| 5,084,565 | 1/1992 | Parodos et al. | 536/27 |
| 5,232,831 | 8/1993 | Milliman et al. | 436/6 |
| 5,292,874 | 3/1994 | Milliman | 536/24 |
| 5,298,392 | 3/1994 | Atlas et al. | 435/600 |
| 5,334,501 | 8/1994 | Adams et al. | 435/6 |
| 5,401,631 | 3/1995 | Lane et al. | 435/6 |
| 5,437,978 | 8/1995 | Ubukata et al. | 435/6 |
| 5,472,843 | 12/1995 | Milliman | 435/6 |

FOREIGN PATENT DOCUMENTS

| | | |
|---|---|---|
| 2052822 | 4/1992 | Canada . |
| 0272009 | 6/1988 | European Pat. Off. . |
| 0277237 | 8/1988 | European Pat. Off. . |
| 0297291 | 1/1989 | European Pat. Off. . |
| 0 438 115 | 7/1991 | European Pat. Off. . |
| 0527628 | 2/1993 | European Pat. Off. . |
| 0577523 | 1/1994 | European Pat. Off. . |
| 0652291 | 5/1995 | European Pat. Off. . |
| 0695803 | 2/1996 | European Pat. Off. . |
| 2 584 419 | 1/1987 | France . |
| 2584419 | 1/1987 | France . |
| 2 599 743 | 12/1987 | France . |
| 2599743 | 12/1987 | France . |
| 2636075 | 3/1990 | France . |
| 2 685 334 | 12/1991 | France . |
| 2685334 | 6/1993 | France . |
| 2 699 539 | 6/1994 | France . |
| 2699539 | 6/1994 | France . |
| 6-54700 | 3/1994 | Japan . |
| 6-90798 | 4/1994 | Japan . |
| 6-165681 | 6/1994 | Japan . |
| 7-67657 | 3/1995 | Japan . |
| 7-209294 | 8/1995 | Japan . |
| 90/14444 | 11/1990 | WIPO . |
| 91/08 305 | 6/1991 | WIPO . |
| 91/08305 | 6/1991 | WIPO . |
| 91/11531 | 8/1991 | WIPO . |
| 91/16454 | 10/1991 | WIPO . |
| 91/18926 | 12/1991 | WIPO . |
| 92/14488 | 9/1992 | WIPO . |
| 93/03 186 | 2/1993 | WIPO . |
| 93/03186 | 2/1993 | WIPO . |
| 94/02 645 | 2/1994 | WIPO . |
| 95/00650 | 1/1995 | WIPO . |
| 95/09025 | 4/1995 | WIPO . |
| 95/20055 | 7/1995 | WIPO . |
| 96/00298 | 1/1996 | WIPO . |
| 96/02648 | 2/1996 | WIPO . |

OTHER PUBLICATIONS

Persing, D.H. (1993). "In Vitro Nucleic Acid Amplification Techniques". In Persing, D.H. et Diagnostic Molecular Microbiology: Principles and Applications. Am. Soc. for Microbiology. pp. 51–87.

Persing, D.H. (1993). "Target Selection and Optimization of Amplification Reaction". In Diagnostic Molecular Microbiology: Principles and Applications. Am. Soc. for Microbiology pp. 88–104.

Pezzlo, M. (1988). "Detection of Urinary Tract Infections by Rapid Methods".Clin. Microbiol. Rev. 1(2): 268–280.

Pezzlo, M. et al. (1992). "Detection of Bacteriuria and Pyuria by Uriscreen, a Rapid Enzymatic Screening Test". J. of Clin. Microbiol. 30: 680–684.

Sanger, F. et al. (1977). "DNA sequencing with chain-terminating inhibitors" P.N.A.S. 74(12): 5463–5467.

Stark. R.P. and D.G. Maki. (1984). "Bacteriuria in the catherized patient". N. Engl. J. Med. 311: 560–564.

Tenover, F.C. and E.R. Unger. (1993). "Nucleic Acid Probes for Detection and Identification of . . . " In Persing, et al. Diagnostic Molecular Microbiology Principles and Applications pp. 3–25.

(List continued on next page.)

*Primary Examiner*—Eggerton A. Campbell
*Attorney, Agent, or Firm*—Quarles & Brady LLP

[57] ABSTRACT

The present invention relates to a method for universal detection of bacteria in biological samples and for specific detection of *Escherichia coli, Klebsiella pneumoniae, Enterococcus faecalis, Pseudomonas aeruginosa, Proteus mirabilis, Staphylococcus saprophyticus, Streptococcus pneumoniae, Moraxella catarrhalis* and *Haemophilus influenzae* in urine or any other biological samples, said method comprising denaturation of bacterial DNA to single stranded form and either fixing it on a support or leaving it in solution, contacting said single stranded genetic material with a labeled probe selected from the group consisting of i) fragments of chromosomal DNA of the above-mentioned bacteria and ii) synthetic oligonucleotides whose sequences are derived either from the said fragments of chromosomal DNAs or from sequences available in data banks, all (i and ii) probes being capable to hybridize specifically to their chromosomal DNA or, in case of universal probes, to any bacterial chromosomal DNA.

123 Claims, No Drawings

OTHER PUBLICATIONS

York, M. K. et al. (1992). "Evaluation of the autoSCAN–W/A Rapid System for Identification and Susceptibility Testing of Gram–Negative Fermentation Bacilli". J. Clin. Microbiol. 30: 2903–2910.

Johnson, J.E. and W.E. Stamm (1989). "Urinary tract Infections in Women: Diagnosis and Treatment" Ann. Intern. Med. 111:906–917.

Koenig, C. et al. (1992). "Analyses of the Flash Track DNA Probe and UTIscreen Bioluminescence Tests for Bacteriuria" J. Clin Microbiol. 30(2): 342–345.

Croizé J. (1995). "Les méthodes automatisées d'identification des bactéries à l'aube de 1995". La Lettre de l'Infectiologue. 10(4) : 109–113.

Fani, R. et al. (1993). "Use of random amplified polymorphic DNA (RAPD) for generating specific DNA probes for microorganisms". Molecular Ecology 2:243–250.

SEQUENCE LISTING (1) GENERAL INFORMATION:

(iii) NUMBER OF SEQUENCES: 273

(2) INFORMATION FOR SEQ ID NO:1:

(i) SEQUENCE CHARACTERISTICS:
       (A) LENGTH: 1817 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Enterococcus faecalis (xi) SEQUENCE DESCRIPTION: SEQ ID NO:1:

```
ACAGTAAAAA AGTTGTTAAC GAATGAATTT GTTAACAACT TTTTTGCTAT GGTATTGAGT      60

TATGAGGGGC AATACAGGGA AAAATGTCGG CTGATTAAGG AATTTAGATA GTGCCGGTTA     120

GTAGTTGTCT ATAATGAAAA TAGCAACAAA TATTTACGCA GGGAAAGGGG CGGTCGTTTA     180

ACGGGAAAAA TTAGGGAGGA TAAAGCAATA CTTTTGTTGG AAAAGAAAT AAAAGGAAAC      240

TGGGGAAGGA GTTAATTGTT TGATGAAGGG AAATAAAATT TTATACATTT TAGGTACAGG     300

CATCTTTGTT GGAAGTTCAT GTCTATTTTC TTCACTTTTT GTAGCCGCAG AAGAACAAGT     360

TTATTCAGAA AGTGAAGTTT CAACAGTTTT ATCGAAGTTG GAAAAGGAGG CAATTTCTGA     420

GGCAGCTGCT GAACAATATA CGGTTGTAGA TCGAAAAGAA GACGCGTGGG GGATGAAGCA     480

TCTTAAGTTA GAAAAGCAAA CGGAAGGCGT TACTGTTGAT TCAGATAATG TGATTATTCA     540

TTTAGATAAA AACGGTGCAG TAACAAGTGT TACAGGAAAT CCAGTTGATC AAGTTGTGAA     600

AATTCAATCG GTTGATGCAA TCGGTGAAGA AGGAGTTAAA AAAATTGTTG CTTCTGATAA     660

TCCAGAAACT AAAGATCTTG TCTTTTTAGC TATTGACAAA CGTGTAAATA ATGAAGGGCA     720

ATTATTTTAT AAAGTCAGAG TAACTTCTTC ACCAACTGGT GACCCCGTAT CATTGGTTTA     780

TAAAGTGAAC GCTACAGATG GAACAATTAT GGAAAAACAA GATTTAACGG AACATGTCGG     840

TAGTGAAGTA ACGTTAAAAA ACTCTTTTCA AGTAACGTTT AATGTACCAG TTGAAAAAAG     900

CAATACGGGA ATTGCTTTAC ACGGAACGGA TAACACAGGG GTTTACCATG CAGTAGTTGA     960

TGGCAAAAAT AATTATTCTA TTATTCAAGC GCCATCACTA GCGACATTAA ATCAGAATGC    1020

TATTGACGCC TATACGCATG GAAAATTTGT GAAAACATAT TATGAAGATC ATTTCCAACG    1080

ACACAGTATT GATGATCGAG GGATGCCCAT CTTGTCAGTT GTTGATGAAC AACATCCAGA    1140

TGCTTATGAC AATGCTTTTT GGGATGGAAA AGCAATGCGT TATGGTGAAA CAAGTACACC    1200

AACAGGAAAA ACGTATGCTT CCTCTTTAGA TGTAGTTGGT CATGAAATGA CACATGGTGT    1260

GACGGAACAT ACTGCCGGTT TAGAATATTT AGGACAATCA GGTGCCTTGA ATGAATCTTA    1320

TTCTGATTTG ATGGGTTATA TTATTTCGGG TGCATCTAAT CCAGAAATTG GTGCGGATAC    1380

TCAGAGTGTT GACCGAAAAA CAGGTATTCG AAATTTACAA ACGCCAAGTA AACACGGACA    1440

ACCAGAAACC ATGGCTCAAT ACGACGATCG AGCACGGTAT AAAGGAACGC CTTATTATGA    1500

TCAAGGCGGT GTTCATTATA ACAGTGGAAT TATTAATCGG ATTGGTTACA CCATTATCCA    1560

GAACTTAGGC ATTGAAAAAG CACAGACTAT TTTCTACAGC TCGTTAGTAA ATTACTTAAC    1620

ACCTAAAGCA CAATTCAGTG ATGCTCGTGA TGCGATGCTT GCTGCTGCAA AAGTTCAATA    1680

TGGCGATGAA GCAGCTTCAG TGGTGTCAGC AGCCTTTAAC TCTGCTGGAA TCGGAGCTAA    1740
```

```
AGAAGACATT CAGGTAAACC AACCAAGTGA ATCTGTTCTG GTCAATGAAT GAAAAAATT        1800

CCCCAATTAA ATAAAAA                                                       1817

(2) INFORMATION FOR SEQ ID NO:2:

(i) SEQUENCE CHARACTERISTICS:
        (A) LENGTH: 2275 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:2:

GGTACCAAAG AAAAAAACGA ACGCCACAAC CAACAGCCTC TAAAGCAACA CCTGCTTCTG         60

AAATTGAGGG AGATTTAGCA AATGTCAATG AGATTCTTTT GGTTCACGAT GATCGTGTCG        120

GGTCAGCAAC GATGGGAATG AAAGTCTTAG AAGAAATTTT AGATAAAGAG AAAATTTCAA        180

TGCCGATTCG AAAAATTAAT ATTAATGAAT TAACTCAACA ACACAGGCT TTAATTGTCA         240

CAAAAGCTGA ACTAACGGAA CAAGCACGTA AAAAGCACC GAAAGCGACA CACTTATCAG         300

TAAAAAGTTA TGGTTAATCC CCAAAAATAT GAAACAGTGG GTTTCGCTCT TAAAAGAAAG        360

TGCCTAGAGA GGAAGAAAAC AATGGAAAAT CTTACGAATA TTTCAATTGA ATTAAATCAA        420

CAGTTTAATA CAAAAGAAGA AGCTATTCGC TTTTCCGGCC AGAAACTAGT CGAGGCAGGC        480

TGTGTTGAGC CCGCTTATAT CGAAGCAATG ATTGAAAGAG ACCAATTGCT ATCTGCCCAT        540

ATGGGGAATT TTATTGCCAT TCCTCATGGA ACAGAAGAAG CCAAAAAATT AGTGAAAAAA        600

TCAGGAATCT GTGTAGTGCA AGTCCCAGAG GGCGTTAATT TTGGCACCGA AGAAGATGAA        660

AAAATTGCTA CCGTATTATT TGGGATTGCC GGAGTCGGTG AAGAACATTT GCAATTAGTC        720

CAACAAATTG CACTTTATTG TAGTGATATG GATAACGTGG TGCAACTTGC CGATGCATTA        780

AGTAAAGAAG AAATAACAGA AAATTTAGCC ATTGCTTAAA GGAGAGAATA AGAATGAACG        840

CAGTACATTT TGGAGCAGGA ATATATTGGAC GCGGCTTTAT TGGCGAAATT TTAGCTAAAA        900

CGGGTTTCAT ATTACCGTTT GTGGATGTTA ATGGAAACCA TCATCAAGCG TTAAAAGAAC        960

GTAAAAGTTA TACAATTGAA TTGGCCGATG CCTCACATCA ACAAATTAAC GTTGAAAATG       1020

TGACCGGGTT AAATAACATG ACAGAACCAG AAAAAGTAGT AGAAGCAATT GCGGAAGCCG       1080

ATTTAGTCAC GACGGCAATT GGTCCTAATA TTTTACCAAG AATTGCTGAA TTAATTGCTC       1140

AAGGAATTGA TGCACGTGCC GAAGCAAATT GTCAAAACGG CCCGCTGGAT ATTATCGCTT       1200

GTGAAAATAT GATTGGTGGT TCAACCTTTT TAGCAGAAGA AGTGGCCATA ATATTTGAAA       1260

AACCCAGCTT ATCTGAACAA TGGATTGGTT TTCCTGATGC GGCAGTTGAT CGGATTGTTC       1320

CATTACAAAA ACATAAAGAT CCACTTTTTG TTCAAGTTGA GCCTTTTTGT GAATGGGTCA       1380

TTGATGATAC CAACCGAAAA GCCAAAGAGA TTCAGTTAGA AGGCGTCATT ACTTGTCGAT       1440

TAGAGCCGTA TATTGAACGA AAATTATTTA GTGTAACCAG TGGCCATGCT ACAGTTGCCT       1500

ATACAGGGGC GTTGTTAGGC TATCAAACCA TTGACGAAGC GATGCAGGAC GCCTTAGTGG       1560

TAGCGCAACT CAAATCAGTT TTGCAGGAAA CCGGTAAACT TTTAGTGGCC AAATGGAATT       1620

TTGATGAACA AGAACATGCA GCCTATATTG AAAAAATTAT CAACCGTTTC CAAAATAAAT       1680

ATATTTCAGA TGCTATTACA CGTGTAGCAC GGACACCAAT CAGAAAATTA GGTGCGCAAG       1740

AACGGTTTAT TCGACCAATC CGTGAATTAC AGGAACGCAA TCTAGTGTCG GCCGCATTTA       1800
```

```
TAGCAATGAT TGGTATTGTC TTTAATTATC ATGATCCAGA AGATGAACAA AGCCGTCAAT    1860

TACAGGAAAT GCTTGACCAA GAAAGTGTTG ATACAGTGGA TCGCTGAAGT AACGGGCATT    1920

GAAGATCCAG AAACGGTTAA AAATATTAAA CAAAACGTAG AACTGCTATG CGCGACCACA    1980

AGTAGCATAA TTAACAAAAT CCTTCTACCA AGATACTTCA CATTTCTTAA TTAAAGAAAA    2040

AACAACCGCG CCTCACCTGA GCCGACCCCC AAAAGTTAGA CCTAGAAATC TAACTTTTGG    2100

AGGTTTTTTT GTATGGCAAA ATACAGTTTT GAAATTTAAA CTTAAACTTG TTCATGACTA    2160

CTTATATGGT CAAGGAGGTC TAAGGTTTCT CGCAAAGAAG TATGGGTTTA AAGATAGTCT    2220

CAAATAAGCA AATGGATAAA TGCCTATAAA GAACTTGGTG AAGAAGGGGG GATCC         2275

(2) INFORMATION FOR SEQ ID NO:3:

(i) SEQUENCE CHARACTERISTICS:
        (A) LENGTH: 227 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli (xi) SEQUENCE DESCRIPTION: SEQ ID NO:3:

GATCCGCCAT GGGTTGTTTT CCGATTGAGG ATTTTATAGA TGGTTTCTGG CGACCTGCAC      60

AGGAGTACGG TGATTTTTAA TTATTGCAAT TGCACAAGAG TCAGTTCTCC CCCAAAGACA     120

GCACCGGTAT CAATATAATG CAGGTTGCCA ATATCCACGC GATGGCGCAA AGGTGTATGA     180

CCAAACCAGA AATGATCGGC CACCTGCATC GCCAGTTCGC GAGTCGG                   227

(2) INFORMATION FOR SEQ ID NO:4:

(i) SEQUENCE CHARACTERISTICS:
        (A) LENGTH: 278 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli (xi) SEQUENCE DESCRIPTION: SEQ ID NO:4:

GATCTAAATC AAATTAATTG GTTAAAGATA ACCACAGCGG GGCCGACATA AACTCTGACA      60

AGAAGTTAAC AACCATATAA CCTGCACAGG ACGCGAACAT GTCTTCTCAT CCGTATGTCA     120

CCCAGCAAAA TACCCCGCTG GCGGACGACA CCACTCTGAT GTCCACTACC GATCTCGCTT     180

TCCAGCGTCA TATTGGGGCG CGCTACGTTG GGCGTGGGC GTAATTGGTC AATCAGGCGC      240

GGGGTCAGCG GATAAACATT CACCATTTTG TCGAGATC                             278

(2) INFORMATION FOR SEQ ID NO:5:

(i) SEQUENCE CHARACTERISTICS:
        (A) LENGTH: 1596 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli
```

(xi) SEQUENCE DESCRIPTION: SEQ ID NO:5:

```
ATGGCTGACA TTCTGCTGCT CGATAATATC GACTCTTTTA CGTACAACCT GGCAGATCAG      60

TTGCGCAGCA ATGGGCATAA CGTGGTGATT TACCGCAACC ATATACCGGC GCAAACCTTA     120

ATTGAACGCT TGGCGACCAT GAGTAATCCG GTGCTGATGC TTTCTCCTGG CCCCGGTGTG     180

CCGAGCGAAG CCGGTTGTAT GCCGGAACTC CTCACCCGCT TGCGTGGCAA GCTGCCCATT     240

ATTGGCATTT GCCTCGGACA TCAGGCGATT GTCGAAGCTT ACGGGGGCTA TGTCGGTCAG     300

GCGGGCGAAA TTCTCCACGG TAAAGCCTCC AGCATTGAAC ATGACGGTCA GGCGATGTTT     360

GCCGGATTAA CAAACCCGCT GCCGGTGGCG CGTTATCACT CGCTGGTTGG CAGTAACATT     420

CCGGCCGGTT TAACCATCAA CGCCCATTTT AATGGCATGG TGATGGCAGT ACGTCACGAT     480

GCGGATCGCG TTTGTGGATT CCAGTTCCAT CCGGAATCCA TTCTCACCAC CCAGGGCGCT     540

CGCCTGCTGG AACAAACGCT GGCCTGGGCG CAGCATAAAC TAGAGCCAGC CAACACGCTG     600

CAACCGATTC TGGAAAAACT GTATCAGGCG CAGACGCTTA GCCAACAAGA AAGCCACCAG     660

CTGTTTTCAG CGGTGGTGCG TGGCGAGCTG AAGCCGGAAC AACTGGCGGC GGCGCTGGTG     720

AGCATGAAAA TTCGCGGTGA GCACCCGAAC GAGATCGCCG GGGCAGCAAC CGCGCTACTG     780

GAAAACGCAG CGCCGTTCCC GCGCCCGGAT TATCTGTTTG CTGATATCGT CGGTACTGGC     840

GGTGACGGCA GCAACAGTAT CAATATTTCT ACCGCCAGTG CGTTTGTCGC CGCGGCCTGT     900

GGGCTGAAAG TGGCGAAACA CGGCAACCGT AGCGTCTCCA GTAAATCTGG TTCGTCCGAT     960

CTGCTGGCGG CGTTCGGTAT TAATCTTGAT ATGAACGCCG ATAAATCGCG CCAGGCGCTG    1020

GATGAGTTAG GTGTATGTTT CCTCTTTGCG CCGAAGTATC ACACCGGATT CCGCCACGCG    1080

ATGCCGGTTC GCCAGCAACT GAAAACCCGC ACCCTGTTCA ATGTGCTGGG GCCATTGATT    1140

AACCCGGCGC ATCCGCCGCT GGCGTTAATT GGTGTTTATA GTCCGGAACT GGTGCTGCCG    1200

ATTGCCGAAA CCTTGCGCGT GCTGGGGTAT CAACGCGCGG CGGTGGTGCA CAGCGGCGGG    1260

ATGGATGAAG TTTCATTACA CGCGCCGACA ATCGTTGCCG AACTGCATGA CGGCGAAATT    1320

AAAAGCTATC AGCTCACCGC AGAAGACTTT GGCCTGACAC CCTACCACCA GGAGCAACTG    1380

GCAGGCGGAA CACCGGAAGA AAACCGTGAC ATTTTAACAC GTTTGTTACA AGGTAAAGGC    1440

GACGCCGCCC ATGAAGCAGC CGTCGCTGCG AACGTCGCCA TGTTAATGCG CCTGCATGGC    1500

CATGAAGATC TGCAAGCCAA TGCGCAAACC GTTCTTGAGG TACTGCGCAG TGGTTCCGCT    1560

TACGACAGAG TCACCGCACT GGCGGCACGA GGGTAA                              1596
```

(2) INFORMATION FOR SEQ ID NO:6:

(i) SEQUENCE CHARACTERISTICS:
        (A) LENGTH: 2703 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:6:

```
GACGACTTAG TTTTGACGGA ATCAGCATAG TTAATCACTT CACTGTGGAA AATGAGGAAA      60

TATTATTTTT TTTGCGCTTC GTAATTAATG GTTATAAGGT CGGCCAGAAA CCTTTCTAAT     120

GCAAGCGATG ACGTTTTTTT ATGTGTCTGA ATTTGCACTG TGTCACAATT CCAAATCTTT     180

ATTAACAACT CACCTAAAAC GACGCTGATC CAGCGTGAAT ACTGGTTTCC CTTATGTTCA     240
```

```
TCAGATTCAT TTAAGCAAGG GTTTCTTCTT CATTCCTGAT GAAAGTGCCA TCTAAAAAGA      300

TGATCTTAAT AAATCTATTA AGAATGAGAT GGAGCACACT GGATATTTTA CTTATGAAAC      360

TGTTTCACTC CTTTACTTAA TTTATAGAGT TACCTTCCGC TTTTTGAAAA TACGCAACGG      420

CCATTTTTTG CACTTAGATA CAGATTTTCT GCGCTGTATT GCATTGATTT GATGCTAATC      480

CTGTGGTTTG CACTAGCTTT AAGTGGTTGA GATCACATTT CCTTGCTCAT CCCCGCAACT      540

CCTCCCTGCC TAATCCCCCG CAGGATGAGG AAGGTCAACA TCGAGCCTGG CAAACTAGCG      600

ATAACGTTGT GTTGAAAATC TAAGAAAAGT GGAACTCCTA TGTCACAACC TATTTTTAAC      660

GATAAGCAAT TTCAGGAAGC GCTTTCACGT CAGTGGCAGC GTTATGGCTT AAATTCTGCG      720

GCTGAAATGA CTCCTCGCCA GTGGTGGCTA GCAGTGAGTG AAGCACTGGC CGAAATGCTG      780

CGTGCTCAGC CATTCGCCAA GCCGGTGGCG AATCAGCGAC ATGTTAACTA CATCTCAATG      840

GAGTTTTTGA TTGGTCGCCT GACGGGCAAC AACCTGTTGA ATCTCGGCTG GTATCAGGAT      900

GTACAGGATT CGTTGAAGGC TTATGACATC AATCTGACGG ACCTGCTGGA AGAAGAGATC      960

GACCCGGCGC TGGGTAACGG TGGTCTGGGA CGTCTGGCGG CGTGCTTCCT CGACTCAATG     1020

GCAACTGTCG GTCAGTCTGC GACGGGTTAC GGTCTGAACT ATCAATATGG TTTGTTCCGC     1080

CAGTCTTTTG TCGATGGCAA ACAGGTTGAA GCGCCGGATG ACTGGCATCG CAGTAACTAC     1140

CCGTGGTTCC GCCACAACGA AGCACTGGAT GTGCAGGTAG GGATTGGCGG TAAAGTGACG     1200

AAAGACGGAC GCTGGGAGCC GGAGTTTACC ATTACCGGTC AAGCGTGGGA TCTCCCCGTT     1260

GTCGGCTATC GTAATGGCGT GGCGCAGCCG CTGCGTCTGT GGCAGGCGAC GCACGCGCAT     1320

CCGTTTGATC TGACTAAATT TAACGACGGT GATTTCTTGC GTGCCGAACA GCAGGGCATC     1380

AATGCGGAAA AACTGACCAA AGTTCTCTAT CCAAACGACA ACCATACTGC CGGTAAAAAG     1440

CTGCGCCTGA TGCAGCAATA CTTCCAGTGT GCCTGTTCGG TAGCGGATAT TTTGCGTCGC     1500

CATCATCTGG CGGGGCGTGA ACTGCACGAA CTGGCGGATT ACTAAGTTAT TCAGCTGAAC     1560

GATACCCACC CAACTATCGC GATTCCAGAA CTGCTGCGCG TGCTGATCGA TGAGCACCAG     1620

ATGAGCTGGG ATGACGCTTG GGCCATTACC AGCAAAACTT TCGCTTACAC CAACCATACC     1680

CTGATGCCAG AAGCGCTGGA ACGCTGGGAT GTGAAACTGG TGAAAGGCTT ACTGCCGCGC     1740

CACATGCAGA TTATTAACGA AATTAATACT CGCTTTAAAA CGCTGGTAGA GAAACCTGG      1800

CCGGGCGATG AAAAAGTGTG GGCCAAACTG GCGGTGGTGC ACGACAAACA AGTGCATATG     1860

GCGAACCTGT GTGTGGTTGG CGGTTTCGCG GTGAACGGTG TTGCGGCGCT GCACTCGGAT     1920

CTGGTGGTGA AGATCTGTT CCCGGAATAT CACCAGCTAT GGCCGAACAA ATTCCATAAC      1980

GTCACCAACG GTATTACCCC ACGTCGCTGG ATCAAACAGT GCAACCCGGC ACTGGCGGCT     2040

CTGTTGGATA AATCACTGCA AAAAGAGTGG GCTAACGATC TCGATCAGCT GATCAATCTG     2100

GTTAAATTGG CTGATGATGC GAAATTCCGT CAGCTTTATC GCGTGATCAA GCAGGCGAAT     2160

AAAGTCCGTC TGGCGGAGTT TGTGAAAGTT CGTACCGGTA TTGACATCAA TCCACAGGCG     2220

ATTTTCGATA TTCAGATCAA ACGTTTGCAC GAGTACAAAC GCCAGCACCT GAATCTGCTG     2280

CGTATTCTGG CGTTGTACAA AGAAATTCGT GAAAACCCGC AGGCTGATCG CGTACCGCGC     2340

GTCTTCCTCT TCGGCGCGAA AGCGGCACCG GGCTACTACC TGGCTAAGAA TATTATCTTT     2400

GCGATCAACA AAGTGGCTGA CGTGATCAAC AACGATCCGC TGGTTGGCGA TAAGTTGAAG     2460

GTGGTGTTCC TGCCGGATTA TTGCGTTTCG GCGGCGAAA AACTGATCCC GGCGGCGGAT      2520

ATCTCCGAAC AAATTTCGAC TGCAGGTAAA GAAGCTTCCG GTACCGGCAA TATGAAACTG     2580

GCGCTCAATG GTGCGCTTAC TGTCGGTACG CTGGATGGGG CGAACGTTGA AATCGCCGAG     2640
```

```
AAAGTCGGTG AAGAAAATAT CTTTATTTTT GGTCATACGG TCAAACAAGT GAAGGCAATC    2700

GAC                                                                 2703

(2) INFORMATION FOR SEQ ID NO:7:

(i) SEQUENCE CHARACTERISTICS:
        (A) LENGTH: 1391 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:7:

AGAGAAGCCT GTCGGCACCG TCTGGTTTGC TTTTGCCACT GCCCGCGGTG AAGGCATTAC      60

CCGGCGGGAT GCTTCAGCGG CGACCGTGAT GCGGTGCGTC GTCAGGCTAC TGCGTATGCA     120

TTGCAGACCT TGTGGCAACA ATTTCTACAA AACACTTGAT ACTGTATGAG CATACAGTAT     180

AATTGCTTCA ACAGAACATA TTGACTATCC GGTATTACCC GGCATGACAG GAGTAAAAAT     240

GGCTATCGAC GAAAACAAAC AGAAAGCGTT GGCGGCAGCA CTGGGCCAGA TTGAGAAACA     300

ATTTGGTAAA GGCTCCATCA TGCGCCTGGG TGAAGACCGT TCCATGGATG TGGAAACCAT     360

CTCTACCGGT TCGCTTTCAC TGGATATCGC GCTTGGGGCA GGTGGTCTGC CGATGGGCCG     420

TATCGTCGAA ATCTACGGAC CGGAATCTTC CGGTAAAACC ACGCTGACGC TGCAGGTGAT     480

CGCCGCAGCG CAGCGTGAAG GTAAAACCTG TGCGTTTATC GATGCTGAAC ACGCGCTGGA     540

CCCAATCTAC GCACGTAAAC TGGGCGTCGA TATCGACAAC CTGCTGTGCT CCCAGCCGGA     600

CACCGGCGAG CAGGCACTGG AAATCTGTGA CGCCCTGGCG CGTTCTGGCG CAGTAGACGT     660

TATCGTCGTT GACTCCGTGG CGGCACTGAC GCCGAAAGCG GAAATCGAAG GCGAAATCGG     720

CGACTCTCAC ATGGGCCTTG CGGCACGTAT GATGAGCCAG GCGATGCGTA AGCTGGCGGG     780

TAACCTGAAG CAGTCCAACA CGCTGCTGAT CTTCATCAAC CAGATCCGTA TGAAAATTGG     840

TGTGATGTTC GGTAACCCGG AAACCACTAC CGGTGGTAAC GCGCTGAAAT TCTACGCCTC     900

TGTTCGTCTC GACATCCGTC GTATCGGCGC GGTGAAAGAG GGCGAAAACG TGGTGGGTAG     960

CGAAACCCGC GTGAAAGTGG TGAAGAACAA AATCGCTGCG CCGTTTAAAC AGGCTGAATT    1020

CCAGATCCTC TACGGCGAAG GTATCAACTT CTACGGCGAA CTGGTTGACC TGGGCGTAAA    1080

AGAGAAGCTG ATCGAGAAAG CAGGCGCGTG GTACAGCTAC AAAGGTGAGA AGATCGGTCA    1140

GGGTAAAGCG AATGCGACTG CCTGGCTGAA AGATAACCCG GAAACCGCGA AAGAGATCGA    1200

GAAGAAAGTA CGTGAGTTGC TGCTGAGCAA CCCGAACTCA ACGCCGGATT TCTCTGTAGA    1260

TGATAGCGAA GGCGTAGCAG AAACTAACGA AGATTTTTAA TCGTCTTGTT TGATACACAA    1320

GGGTCGCATC TGCGGCCCTT TTGCTTTTTT AAGTTGTAAG GATATGCCAT GACAGAATCA    1380

ACATCCCGTC G                                                        1391

(2) INFORMATION FOR SEQ ID NO:8:

(i) SEQUENCE CHARACTERISTICS:
        (A) LENGTH: 238 base pairs
        (B) TYPE: nucleic acid
        (C) STRANDEDNESS: double
        (D) TOPOLOGY: linear (ii) MOLECULE TYPE: DNA (genomic)
```

(vi) ORIGINAL SOURCE:
    (A) ORGANISM: Klebsiella pneumoniae (xi) SEQUENCE DESCRIPTION: SEQ ID NO:8:

| | | | | | |
|---|---|---|---|---|---|
| TCGCCAGGAA | GGCGGCATTC | GGCTGGGTCA | GAGTGACCTG | CAGCGTGGTG | TCGTTCAGCG | 60 |
| CTTTCACCCC | CAACGTCTCG | GGTCCCTTTT | GCCCGAGGGC | AATCTCGCGG | GCGTTGGCGA | 120 |
| TATGCATATT | GCCAGGGTAG | CTCGCGTAGG | GGGAGGCTGT | TGCCGGCGAG | ACCAGCCGTT | 180 |
| GCCAGCTCCA | GACGATATCC | TGCGCTGTAA | TGGCCGTGCC | GTCAGACCAG | GTCAGACC | 238 |

(2) INFORMATION FOR SEQ ID NO:9:

(i) SEQUENCE CHARACTERISTICS:
        (A) LENGTH: 385 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:9:

| | | | | | |
|---|---|---|---|---|---|
| CAGCGTAATG | CGCCGCGGCA | TAACGGCGCC | ACTATCGACA | GTCAGTTCGT | CAGCCTGCAG | 60 |
| CCTGGGCTGA | ATCTGGGACC | ATGGCGCCTG | CCGAACTACA | GCACCTATAG | CCACAGCGAT | 120 |
| AACAACAGCC | GCTGGGAGTC | GGTTTACTCC | TATCTTGCCC | GCGATATTCA | CACCCTACGC | 180 |
| AGCCAGCTGG | TGGTCGGTAA | TACGTATACC | TCTTCCGGCA | TTTTCGACAG | TTTGAGTTTT | 240 |
| ACCGGTCTGC | AGCTCAGTTC | GACAAAGAGA | TGCTGCCGGA | TAGCCTGCAT | GCTTTGCGCC | 300 |
| GACGATTCGA | GGGATCGCGC | GCACCACCGC | GGAGGTCTCG | GTTTATCAGA | ATGGTTACAG | 360 |
| CATTTATAAA | ACCACCGTCG | CTACC | | | | 385 |

(2) INFORMATION FOR SEQ ID NO:10:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:10:

| | | | | | |
|---|---|---|---|---|---|
| CTCTATATTC | AGGACGAACA | TATCTGGACC | TCTGGCGGGG | TCAGTTCCGG | CTTTGATCGC | 60 |
| CCTGCACCCG | CAGCGGGTGA | TCGCCCCTCA | TCTGCTACTG | CGGCGCTGCA | ACAGGCGACG | 120 |
| ATCGATGACG | TTATTCCTGG | CCAGCAAACA | GCAGACCAAT | TAAGGTCTGA | TAGTGGCTCT | 180 |
| CTTCCTCCGG | CGCGCGACGG | TCCAGGCGGC | TCAACAGTTT | GGTGCATAGC | GCTTTGCGGT | 240 |
| TGAGATGACG | CCCTTCGTTA | AGAATATCCA | TCACGATCTC | CGTCCATGGA | GAGTAGCGTT | 300 |
| TATTCCAGAA | TAGGGTTTTT | CAGGATCTCA | TGGATCTGCG | CCTGCTTATC | GCTATTTTGT | 360 |
| AACCAGATCG | CATAAAGTGG | ACGGGATAAC | GTAGCGCTGT | CCATGACCGT | ATGTAACCCA | 420 |
| TGCTTCTCTT | TCGCCCAGCG | AGCAGGTAGC | CAACAGCAGC | CG | | 462 |

(2) INFORMATION FOR SEQ ID NO:11:

(i) SEQUENCE CHARACTERISTICS:
        (A) LENGTH: 730 base pairs (B) TYPE: nucleic acid
            (C) STRANDEDNESS: double
            (D) TOPOLOGY: linear (ii) MOLECULE TYPE: DNA (genomic)

(vi) ORIGINAL SOURCE:
          (A) ORGANISM: Klebsiella pneumoniae (xi) SEQUENCE DESCRIPTION: SEQ ID NO:11:

```
GCTGACCGCT AAACTGGGTT ACCCGATCAC TGACGATCTG GACATCTACA CCCGTCTGGG      60

CGGCATGGTT TGGCGCGCTG ACTCCAAAGG CAACTACGCT TCAACCGGCG TTTCCCGTAG     120

CGAACACGAC ACTGGCGTTT CCCCAGTATT TGCTGGCGGC GTAGAGTGGG CTGTTACTCG     180

TGACATCGCT ACCCGTCTGG AATACCAGTG GGTTAACAAC ATCGGCGACG CGGGCACTGT     240

GGGTACCCGT CCTGATAACG GCATGCTGAG CCTGGGCGTT TCCTACCGCT TCGGTCAGGA     300

AGATGCTGCA CCGGTTGTTG CTCCGGCTCC GGCTCCGGCT CCGGAAGTGG CTACCAAGCA     360

CTTCACCCTG AAGTCTGACG TTCTGTTCAA CTTCAACAAA GCTACCCTGA AACCGGAAGG     420

TCAGCAGGCT CTGGATCAGC TGTACACTCA GCTGAGCAAC ATGGATCCGA AAGACGGTTC     480

CGCTGTTGTT CTGGGCTACA CCGACCGCAT CGGTTCCGAA GCTTACAACC AGCAGCTGTC     540

TGAGAAACGT GCTCAGTCCG TTGTTGACTA CCTGGTTGCT AAAGGCATCC CGGCTGGCAA     600

AATCTCCGCT CGCGGCATGG GTGAATCCAA CCCGGTTACT GGCAACACCT GTGACAACGT     660

GAAAGCTCGC GCTGCCCTGA TCGATTGCCT GGCTCCGGAT CGTCGTGTAG AGATCGAAGT     720

TAAAGGTATC                                                             730
```

(2) INFORMATION FOR SEQ ID NO:12:

(i) SEQUENCE CHARACTERISTICS:
         (A) LENGTH: 225 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Proteus mirabilis (xi) SEQUENCE DESCRIPTION: SEQ ID NO:12:

```
CGCTACTGTT TAAATCTCAT TTGAAACATC GCAAAGTCAG TGAACCACAT ATTCGAGGAT      60

GGCATGCACT AGAAAATATT AATAAGATTT TAGCGAAACC TAATCAGCGC AATATCGCTT     120

AATTATTTTA GGTATGTTCT CTTCTATCCT ACAGTCACGA GGCAGTGTCG AACTTGATCC     180

TCATTTTATT AATCACATGA CCAATGGTAT AAGCGTCGTC ACATA                      225
```

(2) INFORMATION FOR SEQ ID NO:13:

(i) SEQUENCE CHARACTERISTICS:
         (A) LENGTH: 402 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Proteus mirabilis (xi) SEQUENCE DESCRIPTION: SEQ ID NO:13:

```
ACATTTTAAA TAGGAAGCCA CCTGATAACA TCCCCGCAGT TGGATCATCA GATTTATAGC      60

GGCATTTGGT ATCCGCTAGA TAAAAGCAGT CCAACGATCC CGCCAATTGT TAGATGAAAT     120
```

```
TGGACTATTC TTTTTATTTG CTCCGCTTTA TCACAGTGGT TTTCGCTTTG CCGCCCCTGT        180

GCGCCAACAG CTAAGAACAC GCACGCTCTT TAATGTGTTA GGCCCATTAA TTAATCCAGC        240

GCGTTCCGCC TTTAGCATTA ATTGGTGTTT ATAGTCCTGA ATTATTAATG CCTATTGCAG        300

ATACCTTAAA TGTCTTGGGC TACAAACGTG CGGCAGTGGT CCATAGTGGT GGAATGGATG        360

AAGTGTCATT ACATGCTCCC ACACAAGTGG CTGAGTTACA CA                          402

(2) INFORMATION FOR SEQ ID NO:14:

(i) SEQUENCE CHARACTERISTICS:
          (A) LENGTH: 157 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Proteus mirabilis (xi) SEQUENCE DESCRIPTION: SEQ ID NO:14:

CTGAAACGCA TTTATGCGGG AGTCAGTGAA ATCATCACTC AATTTTCACC CGATGTATTT         60

TCTGTTGAAC AAGTCTTTAT GGCAAAAAAT GCAGACTCAG CATTAAAATT AGGCCAAGCA        120

AGAGGTGTGG CGATTTTAGC GGCAGTCAAT AATGATC                                157

(2) INFORMATION FOR SEQ ID NO:15:

(i) SEQUENCE CHARACTERISTICS:
          (A) LENGTH: 1348 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Proteus mirabilis (xi) SEQUENCE DESCRIPTION: SEQ ID NO:15:

TTTCTCTTTA AAATCAATTC TTAAAGAAAT TATTAATAAT TAACTTGATA CTGTATGATT         60

ATACAGTATA ATGAGTTTCA ACAAGCAAAA TCATATACGT TTTAATGGTA GTGACCCATC        120

TTTATGCTTC ACTGCCCAGA GGGAGATAAC ATGGCTATTG ATGAAAACAA ACAAAAAGCA        180

TTGGCCGCAG CACTTGGTCA AATTGAAAAG CAATTTGGTA AAGGTTCTAT CATGCGTCTG        240

GGCGAAGACC GTTCCATGAA CGTAGAAACT ATCTCTACAG GATCTTTATC ATTAGACGTT        300

GCTTTAGGTG CAGGTGGATT GCCACGTGGC CGTATTGTTG AAATCTATGG CCCTGAATCT        360

TCTGGTAAAA CAACCTTGAC TCTACAAGTT ATTGCCTCTG CTCAGCGTGA AGGAAAAATT        420

TGTGCATTTA TTGATGCTGA ACATGCATTA GACCCAATTT ATGCTCAAAA GCTAGGTGTC        480

GATATCGATA ATCTACTCTG CTCTCAACCT GACACAGGTG AACAAGCTCT GGAAATTTGT        540

GATGCATTAT CTCGCTCTGG TGCGGTCGAT GTTATTGTCG TGGACTCCGT GGCAGCATTA        600

ACACCAAAAG CTGAAATTGA AGGTGAAATT GGTGATTCAC ACGTTGGTTT AGCCGCACGT        660

ATGATGAGCC AAGCTATGCG TAAACTAGCG GGTAACCTTA AAAACTCTAA TACACTGCTG        720

ATTTTCATTA ACCAAATTCG TATGAAAATC GGTGTTATGT TTGGTAACCC AGAAACCACG        780

ACCGGTGGTA ATGCGCTTAA ATTCTATGCT TCTGTTCGTT TAGACATTCG TCGCATTGGC        840

TCTGTCAAAA ATGGTGATGA AGTCATTGGT AGTGAGACTC GCGTTAAAGT TGTTAAAAAT        900

AAAGTGGCTG CACCGTTTAA ACAAGCTGAA TTCCAAATTA TGTACGGTGA AGGTATTAAT        960
```

```
ACCTATGGCG AACTGATTGA TTTAGGTGTT AAACATAAGT TAGTAGAGAA AGCAGGTGCT    1020

TGGTATAGCT ACAATGGCGA AAAAATTGGT CAAGGTAAAG CTAACGCAAC CAATTACTTA    1080

AAAGAACATC CTGAAATGTA CAATGAGTTA AACACTAAAT TGCGTGAAAT GTTGTTAAAT    1140

CATGCTGGTG AATTCACAAG TGCTGCGGAT TTTGCAGGTG AAGAGTCAGA CAGTGATGCT    1200

GACGACACAA AAGAGTAATT AGCTGGTTGT CATGCTGTTT GTGTGAAAAT AGACCTTAAA    1260

TCATTGGCTA TTATCACGAC AGCATCCCAT AGAATAACTT GTTTGTATAA ATTTTATTCA    1320

GATGGCAAAG GAAGCCTTAA AAAAGCTT                                       1348
```

(2) INFORMATION FOR SEQ ID NO:16:

(i) SEQUENCE CHARACTERISTICS:
        (A) LENGTH: 2167 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:16:

```
GGTACCGCTG GCCGAGCATC TGCTCGATCA CCACCAGCCG GGCGACGGGA ACTGCACGAT      60

CTACCTGGCG AGCCTGGAGC ACGAGCGGGT TCGCTTCGTA CGGCGCTGAG CGACAGTCAC     120

AGGAGAGGAA ACGGATGGGA TCGCACCAGG AGCGGCCGCT GATCGGCCTG CTGTTCTCCG     180

AAACCGGCGT CACCGCCGAT ATCGAGCGCT CGCACGCGTA TGGCGCATTG CTCGCGGTCG     240

AGCAACTGAA CCGCGAGGGC GGCGTCGGCG GTCGCCCGAT CGAAACGCTG TCCCAGGACC     300

CCGGCGGCGA CCCGGACCGC TATCGGCTGT GCGCCGAGGA CTTCATTCGC AACCGGGGGG     360

TACGGTTCCT CGTGGGCTGC TACATGTCGC ACACGCGCAA GGCGGTGATG CCGGTGGTCG     420

AGCGCGCCGA CGCGCTGCTC TGCTACCCGA CCCCCTACGA GGGCTTCGAG TATTCGCCGA     480

ACATCGTCTA CGGCGGTCCG GCGCCGAACC AGAACAGTGC GCCGCTGGCG GCGTACCTGA     540

TTCGCCACTA CGGCGAGCGG GTGGTGTTCA TCGGCTCGGA CTACATCTAT CCGCGGGAAA     600

GCAACCATGT GATGCGCCAC CTGTATCGCC AGCACGGCGG CACGGTGCTC GAGGAAATCT     660

ACATTCCGCT GTATCCCTCC GACGACGACT TGCAGCGCGC CGTCGAGCGC ATCTACCAGG     720

CGCGCGCCGA CGTGGTCTTC TCCACCGTGG TGGGCACCGG CACCGCCGAG CTGTATCGCG     780

CCATCGCCCG TCGCTACGGC GACGGCAGGC GGCCGCCGAT CGCCAGCCTG ACCACCAGCG     840

AGGCGGAGGT GGCGAAGATG GAGAGTGACG TGGCAGAGGG GCAGGTGGTG GTCGCGCCTT     900

ACTTCTCCAG CATCGATACG CCCGCCAGCC GGGCCTTCGT CCAGGCCTGC CATGGTTTCT     960

TCCCGGAGAA CGCGACCATC ACCGCCTGGG CCGAGGCGGC CTACTGGCAG ACCTTGTTGC    1020

TCGGCCGCGC CGCGCAGGCC GCAGGCAACT GGCGGGTGGA AGACGTGCAG CGGCACCTGT    1080

ACGACATCGA CATCGACGCG CCACAGGGGC CGGTCCGGGT GGAGCGCCAG AACAACCACA    1140

GCCGCCTGTC TTCGCGCATC GCGGAAATCG ATGCGCGCGG CGTGTTCCAG GTCCGCTGGC    1200

AGTCGCCCGA ACCGATTCGC CCCGACCCTT ATGTCGTCGT GCATAACCTC GACGACTGGT    1260

CCGCCAGCAT GGGCGGGGGA CCGCTCCCAT GAGCGCCAAC TCGCTGCTCG GCAGCCTGCG    1320

CGAGTTGCAG GTGCTGGTCC TCAACCCGCC GGGGGAGGTC AGCGACGCCC TGGTCTTGCA    1380

GCTGATCCGC ATCGGTTGTT CGGTGCGCCA GTGCTGGCCG CCGCCGGAAG CCTTCGACGT    1440

GCCGGTGGAC GTGGTCTTCA CCAGCATTTT CCAGAATGGC CACCACGACG AGATCGCTGC    1500
```

```
GCTGCTCGCC GCCGGGACTC CGCGCACTAC CCTGGTGGCG CTGGTGGAGT ACGAAAGCCC     1560

CGCGGTGCTC TCGCAGATCA TCGAGCTGGA GTGCCACGGC GTGATCACCC AGCCGCTCGA     1620

TGCCCACCGG GTGCTGCCTG TGCTGGTATC GGCGCGGCGC ATCAGCGAGG AAATGGCGAA     1680

GCTGAAGCAG AAGACCGAGC AGCTCCAGGA CCGCATCGCC GGCCAGGCCC GGATCAACCA     1740

GGCCAAGGTG TTGCTGATGC AGCGCCATGG CTGGGACGAG CGCGAGGCGC ACCAGCACCT     1800

GTCGCGGGAA GCGATGAAGC GGCGCGAGCC GATCCTGAAG ATCGCTCAGG AGTTGCTGGG     1860

AAACGAGCCG TCCGCCTGAG CGATCCGGGC CGACCAGAAC AATAACAAGA GGGGTATCGT     1920

CATCATGCTG GGACTGGTTC TGCTGTACGT TGGCGCGGTG CTGTTTCTCA ATGCCGTCTG     1980

GTTGCTGGGA AAGATCAGCG GTCGGGAGGT GGCGGTGATC AACTTCCTGG TCGGCGTGCT     2040

GAGCGCCTGC GTCGCGTTCT ACCTGATCTT TTCCGCAGCA GCCGGGCAGG GCTCGCTGAA     2100

GGCCGGAGCG CTGACCCTGC TATTCGCTTT TACCTATCTG TGGGTGGCCG CCAACCAGTT     2160

CCTCGAG                                                              2167

(2) INFORMATION FOR SEQ ID NO:17:

(i) SEQUENCE CHARACTERISTICS:
        (A) LENGTH: 1872 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:17:

GAATTCCCGG GAGTTCCCGA CGCAGCCACC CCCAAAACAC TGCTAAGGGA GCGCCTCGCA       60

GGGCTCCTGA GGAGATAGAC CATGCCATTT GGCAAGCCAC TGGTGGGCAC CTTGCTCGCC      120

TCGCTGACGC TGCTGGGCCT GGCCACCGCT CACGCCAAGG ACGACATGAA AGCCGCCGAG      180

CAATACCAGG GTGCCGCTTC CGCCGTCGAT CCCGCTCACG TGGTGCGCAC CAACGGCGCT      240

CCCGACATGA GTGAAAGCGA GTTCAACGAG GCCAAGCAGA TCTACTTCCA ACGCTGCGCC      300

GGTTGCCACG GCGTCCTGCG CAAGGGCGCC ACCGGCAAGC CGCTGACCCC GGACATCACC      360

CAGCAACGCG GCCAGCAATA CCTGGAAGCG CTGATCACCT ACGGCACCCC GCTGGGCATG      420

CCGAACTGGG GCAGCTCCGG CGAGCTGAGC AAGGAACAGA TCACCCTGAT GGCCAAGTAC      480

ATCCAGCACA CCCCGCCGCA ACCGCCGGAG TGGGGCATGC CGGAGATGCG CGAATCGTGG      540

AAGGTGCTGG TGAAGCCGGA GGACCGGCCG AAGAAACAGC TCAACGACCT CGACCTGCCC      600

AACCTGTTCT CGGTGACCCT GCGCGACGCC GGGCAGATCG CCCTGGTCGA CGGCGACAGC      660

AAAAAGATCG TCAAGGTCAT CGATACCGGC TATGCCGTGC ATATCTCGCG GATGTCCGCT      720

TCCGGCCGCT ACCTGCTGGT GATCGGCCGC GACGCGCGGA TCGACATGAT CGACCTGTGG      780

GCCAAGGAGC CGACCAAGGT CGCCGAGATC AAGATCGGCA TCGAGGCGCG CTCGGTGGAA      840

AGCTCCAAGT TCAAGGGCTA CGAGGACCGC TACACCATCG CCGGCGCCTA CTGGCCGCCG      900

CAGTTCGCGA TCATGGACGG CGAGACCCTG AACCGAAGCG AGATCGTCTC CACCCGCGGC      960

ATGACCGTAG ACACCCAGAC CTACCACCCG GAACCGCGCG TGGCGGCGAT CATCGCCTCC     1020

CACGAGCACC CCGAGTTCAT CGTCAACGTG AAGGAGACCG GCAAGGTCCT GCTGGTCAAC     1080

TACAAGGATA TCGACAACCT CACCGTCACC AGCATCGGTG CGGCGCCGTT CCTCCACGAC     1140

GGCGGCTGGG ACAGCAGCCA CCGCTACTTC ATGACCGCCG CCAACAACTC CAACAAGGTT     1200
```

```
GCCGTGATCG ACTCCAAGGA CCGTCGCCTG TCGGCCCTGG TCGACGTCGG CAAGACCCCG      1260

CACCCGGGGC GTGGCGCCAA CTTCGTGCAT CCCAAGTACG GCCCGGTGTG GAGCACCAGC      1320

CACCTGGGCG ACGGCAGCAT CTCGCTGATC GGCACCGATC CGAAGAACCA TCCGCAGTAC      1380

GCCTGGAAGA AAGTCGCCGA ACTACAGGGC CAGGGCGGCG GCTCGCTGTT CATCAAGACC      1440

CATCCGAAGT CCTCGCACCT CTACGTCGAC ACCACCTTCA ACCCCGACGC CAGGATCAGC      1500

CAGAGCGTCG CGGTGTTCGA CCTGAAGAAC CTCGACGCCA AGTACCAGGT GCTGCCGATC      1560

GCCGAATGGG CCGATCTCGG CGAAGGCGCC AAGCGGGTGG TGCAGCCCGA GTACAACAAG      1620

CGCGGCGATG AAGTCTGGTT CTCGGTGTGG AACGGCAAGA ACGACAGCTC CGCGCTGGTG      1680

GTGGTGGACG ACAAGACCCT GAAGCTCAAG GCCGTGGTCA AGGACCCGCG GCTGATCACC      1740

CCGACCGGTA AGTTCAACGT CTACAACACC CAGCACGACG TGTACTGAGA CCCGCGTGCG      1800

GGGCACGCCC CGCACGCTCC CCCCTACGAG GAACCGTGAT GAAACCGTAC GCACTGCTTT      1860

CGCTGCTCGC CA                                                         1872
```

(2) INFORMATION FOR SEQ ID NO:18:

(i) SEQUENCE CHARACTERISTICS:
        (A) LENGTH: 3451 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:18:

```
TCGAGACGGG AAGCCACTCT CTACGAGAAG ACAGAAGCCC CTCACAGAGG CCTCTGTCTA        60

CGCCTACTAA AGCTCGGCTT ATTCATATGT ATTTATATTC TTTCAATAGA TCACTCAGCG       120

CTATTTTAAG TTCACCCTCT GTAAGTTCAC CTGGGCGCTC TTTCTTTCCT TCGGTAAAGC       180

TGTCGGCCAG ACCAAACATT AAACTCAAGC ATCTCCCAAG CGATGCATCA TCTTGGGCCA       240

GCATCCCTGA ATCGCGCGTC GGACCTCCAA GTCTTAAAAA ATTCTTCGCT GAAGGTTTTC       300

CCATCAATCG ATGAGGCTAA TAGCTTCTTT GCAATATCTA TCATTTCCAT GCTCACCTTA       360

AAGCACCTCA TTTTTCATGT AAAAATTGTA TTGATCCGTG CCAGACTCAA TCCTCCACCC       420

AGAAACAAAC ATCCCATCCT CTCCAATGAT AACAACAATA TTAGTCCTGG CATTGTAATG       480

TACTTTTGAG TTTACTTCGG AGTGGTAAGT CCCTTTTTCT ACGGTTGCAG GATCAGCAAG       540

GTGCTCAAGA ATTTTATCCC TAAACTCTGC AAGCGTTCCA TTGTTGGCGC TTTTTTCACC       600

CAGCCCAAAA TCATATTTGT GGCTATCAAA TTTTTTCTGT AGTTGCCTCC GTGTGAAGAT       660

ACCACTATCA AGAGGACTAC TGAGCATTAC ATAAACAGGT TTGACTCCAG AATCCGCCGG       720

GAAAATCACG ATCAGATCGT TTAGGTCCAG TAGCATTCCC GGATAGGACT CCGGGCCGGT       780

CTTCAACGGT GTGAGGGCCG CTCCCTCATA TACCGGCACC GGCTTCGGTA TGACCGGAGT       840

GGTACTCGAA GGGTTCTGGT TTCCTGGAGG ACTCGCCGGC GTCCAAGTCA GGATCAGTGG       900

CGGCGCTTCT GCGACCGTAG AGGGAACCGT AACCTCGTAC AGTCCTGTTG CGGCGTTATA       960

GGCCCCATCC GGACCGGAAC GCTTTCGGAA CGCTCACACC ATCGGTCTGA CCACCGAAAG      1020

GTCGTCGTGT TGCCTCGCGC CTCGTTGGTC AGGCGCATCG GCAGATCGAC GGTACCGCTG      1080

GCTTTTGCAA CCGCGTTCAG GTTTACGCTT GGGGGAAGCC CCAATTTAGC GGCATCCATG      1140

CCCAGGGCGT AACGAACGCT ATCGGGCGTT TGGTCCTGCC ATTGCTCGGC AGTCCGGGAG      1200
```

| | |
|---|---|
| AGTAGGTCAG ACTGGCAAGC CACGGCCATC ACCGAGGTGC TGAAGCCAGG ACCGCCAGGA | 1260 |
| CGGCAATCGC ATCGGAGATC GCTTGAGCAA GGGATGCGGC GCCTGTGCGA CCTGGATCAG | 1320 |
| ACCCCGCTGC GGCGGTGGCG CACCCGCTGC CATTGGCTGG CATGGCATAA GTATTGGCAG | 1380 |
| CCCTGATCGC CGCTTGACGA GCGATTTCCT TGCGCCTTGC CGTTTCGGCG TTCAGCTTGT | 1440 |
| CCAGCCGTGC TTGCAGGCTG GCGATTTCAT CCACTAGGTA GGACATCGGC GTTGTAGGTT | 1500 |
| GCCTTTTGTT TCTCCAGTGC ATTGGGTGCC TTGGCAATCA AGGCATTGTT TGCAGTCTGC | 1560 |
| AATTCTTCTT ATTGCGATCG CCTGCGTAAG GAGTTGAGTA GCGCGTTCAA GCCACTGCTC | 1620 |
| TGGCGTTGGA TTGGTCAGTT GAGGCAAAGC ATTCCCAGCC TGGTCAAGCT CGGACTGCAC | 1680 |
| TTTTTTCTCG ACATTTGCCT TCCTGGCCTT GTAGTCCGCC TCCACCTCAG CAGCGGCTCG | 1740 |
| CTGGGCTTCT GCTTCCAATG ACCGGGCTTT ATTCTCCAGC TCTTGAGACG TTTGTTTCAA | 1800 |
| GATAGCGATT TGCGCCTTAT AGATATCGGC GCTGTACGCT TTGGCCAGCT CACTCATATG | 1860 |
| GCGATCCAGG AACTCTCCAT AGAATTTTCG GCTGGCCAGC AACTGACTCT GGTACATCGA | 1920 |
| CTCTGACTTC TGAGGAAAGT CTGAAGCCGT ATAAAGATTG GCCGGGCGAT CCTCAATGAC | 1980 |
| CTTTAGCGAT TTTGCTTTGG CATCCATGAG TGCATCAACG ATACTCTTTT CATCGCGGAT | 2040 |
| GTCATTGGCA CTGACCGCTT TACCTGGCAA CCCCGCTTCA CTCTTGAGTT CATCAACCTC | 2100 |
| CTTCAGGGTT TCATTTTTCA GGTTTTTCTT GAGTTCTGAA TGGGACTTAT CAAGCGTACT | 2160 |
| TCTTAGCTTC CTGTACTCCT GCATTCCAGT ACCGACATAC GGACTTGGTC CTGGTGGGAC | 2220 |
| AAATGGTGGA GTACCGTAGC TTGATCGAGC AGGAATATAC TGGATTATGT CACGCCCACC | 2280 |
| ACCCTGCACA TGTGTAATAA CCATCGAACC AGGTTCGTAA TCATTGACAG CCATAGATCG | 2340 |
| CCCCTACATT AATTTGAAAG TGTAATGTAT TGAGCGACTC CCACCTAGAG AACCCTCTCC | 2400 |
| CAGTCAATAA GCCCCAATGC ATCGGCAATA CACTGCAATC AACTTCAATA TCCCGTGTTT | 2460 |
| AGATGATCCA GAAGGTGCGC TCTCTCGCCT CTTATAATCG CGCCTGCGTC AAACGGTCAT | 2520 |
| TTCCTTAACG CACACCTCAT CTACCCCGGC CAGTCACGGA AGCCGCATAC CTTCGGTTCA | 2580 |
| TTAACGAACT CCCACTTTCA AAATTCATCC ATGCCGCCCC TTCGCGAGCT TCCGGACAAA | 2640 |
| GCCACGCTGA TTGCGAGCCC AGCGTTTTTG ATTGCAAGCC GCTGCAGCTG GTCAGGCCGT | 2700 |
| TTCCGCAACG CTTGAAGTCC TGGCCGATAT ACCGGCAGGG CCAGCCATCG TTCGACGAAT | 2760 |
| AAAGCCACCT CAGCCATGAT GCCCTTTCCA TCCCCAGCGG AACCCCGACA TGGACGCCAA | 2820 |
| AGCCCTGCTC CTCGGCAGCC TCTGCCTGGC CGCCCCATTC GCCGACGCGG CGACGCTCGA | 2880 |
| CAATGCTCTC TCCGCCTGCC TCGCCGCCCG GCTCGGTGCA CCGCACACGG CGGAGGGCCA | 2940 |
| GTTGCACCTG CCACTCACCC TTGAGGCCCG GCGCTCCACC GGCGAATGCG GCTGTACCTC | 3000 |
| GGCGCTGGTG CGATATCGGC TGCTGGCCAG GGGCGCCAGC GCCGACAGCC TCGTGCTTCA | 3060 |
| AGAGGGCTGC TCGATAGTCG CCAGGACACG CCGCGCACGC TGACCCTGGC GGCGGACGCC | 3120 |
| GGCTTGGCGA GCGGCCGCGA ACTGGTCGTC ACCCTGGGTT GTCAGGCGCC TGACTGACAG | 3180 |
| GCCGGGCTGC CACCACCAGG CCGAGATGGA CGCCCTGCAT GTATCCTCCG ATCGGCAAGC | 3240 |
| CTCCCGTTCG CACATTCACC ACTCTGCAAT CCAGTTCATA AATCCCATAA AAGCCCTCTT | 3300 |
| CCGCTCCCCG CCAGCCTCCC CGCATCCCGC ACCCTAGACG CCCCGCCGCT CTCCGCCGGC | 3360 |
| TCGCCCGACA AGAAAAACCA ACCGCTCGAT CAGCCTCATC CTTCACCCAT CACAGGAGCC | 3420 |
| ATCGCGATGC ACCTGATACC CCATTGGATC C | 3451 |

(2) INFORMATION FOR SEQ ID NO:19:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:19:

```
GGGTTCAGCA AGCGTTCAGG GGCGGTTCAG TACCCTGTCC GTACTCTGCA AGCCGTGAAC      60

GACACGACTC TCGCAGAACG GAGAAACACC ATGAAAGCAC TCAAGACTCT CTTCATCGCC     120

ACCGCCCTGC TGGGTTCCGC CGCCGGCGTC CAGGCCGCCG ACAACTTCGT CGGCCTGACC     180

TGGGGCGAGA CCAGCAACAA CATCCAGAAA TCCAAGTCGC TGAACCGCAA CCTGAACAGC     240

CCGAACCTCG ACAAGGTGAT CGACAACACC GGCACCTGGG GCATCCGCGC CGGCCAGCAG     300

TTCGAGCAGG GCCGCTACTA CGCGACCTAC GAGAACATCT CCGACACCAG CAGCGGCAAC     360

AAGCTGCGCC AGCAGAACCT GCTCGGCAGC TACGACGCCT TCCTGCCGAT CGGCGACAAC     420

AACACCAAGC TGTTCGGCGG TGCCACCCTC GGCCTGGTCA AGCTGGAACA GGACGGCAAG     480

GGCTTCAAGC GCGACAGCGA TGTCGGCTAC GCTGCCGGGC TGCAGGCCGG TATCCTGCAG     540

GAGCTGAGCA AGAATGCCTC GATCGAAGGC GGCTATCGTT ACCTGCGCAC CAACGCCAGC     600

ACCGAGATGA CCCCGCATGG CGGCAACAAG CTGGGCTCCC TGGACCTGCA CAGCAGCTCG     660

CAATTCTACC TGGGCGCCAA CTACAAGTTC TAAATGACCG CGCAGCGCCC GCGAGGGCAT     720

GCTTCGATGG CCGGGCCGGA AGGT                                           744
```

(2) INFORMATION FOR SEQ ID NO:20:

(i) SEQUENCE CHARACTERISTICS:
        (A) LENGTH: 2760 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:20:

```
CTGCAGCTGG TCAGGCCGTT TCCGCAACGC TTGAAGTCCT GGCCGATATA CCGGCAGGGC      60

CAGCCATCGT TCGACGAATA AAGCCACCTC AGCCATGATG CCCTTTCCAT CCCCAGCGGA     120

ACCCCGACAT GGACGCCAAA GCCCTGCTCC TCGGCAGCCT CTGCCTGGCC GCCCCATTCG     180

CCGACGCGGC GACGCTCGAC AATGCTCTCT CCGCCTGCCT CGCCGCCCGG CTCGGTGCAC     240

CGCACACGGC GGAGGGCCAG TTGCACCTGC CACTCACCCT TGAGGCCCGG CGCTCCACCG     300

GCGAATGCGG CTGTACCTCG GCGCTGGTGC GATATCGGCT GCTGGCCAGG GGCGCCAGCG     360

CCGACAGCCT CGTGCTTCAA GAGGGCTGCT CGATAGTCGC CAGGACACGC CGCGCACGCT     420

GACCCTGGCG GCGGACGCCG GCTTGGCGAG CGGCCGCGAA CTGGTCGTCA CCCTGGGTTG     480

TCAGGCGCCT GACTGACAGG CCGGGCTGCC ACCACCAGGC CGAGATGGAC GCCCTGCATG     540

TATCCTCCGA TCGGCAAGCC TCCCGTTCGC ACATTCACCA CTCTGCAATC CAGTTCATAA     600

ATCCCATAAA AGCCCTCTTC CGCTCCCCGC CAGCCTCCCC GCATCCCGCA CCCTAGACGC     660

CCCGCCGCTC TCCGCCGGCT CGCCCGACAA GAAAAACCAA CCGCTCGATC AGCCTCATCC     720

TTCACCCATC ACAGGAGCCA TCGCGATGCA CCTGATACCC CATTGGATCC CCCTGGTCGC     780
```

```
CAGCCTCGGC CTGCTCGCCG GCGGCTCGTC CGCGTCCGCC GCCGAGGAAG CCTTCGACCT    840

CTGGAACGAA TGCGCCAAAG CCTGCGTGCT CGACCTCAAG GACGGCGTGC GTTCCAGCCG    900

CATGAGCGTC GACCCGGCCA TCGCCGACAC CAACGGCCAG GGCGTGCTGC ACTACTCCAT    960

GGTCCTGGAG GGCGGCAACG ACGCGCTCAA GCTGGCCATC GACAACGCCC TCAGCATCAC   1020

CAGCGACGGC CTGACCATCC GCCTCGAAGG CGGCGTCGAG CCGAACAAGC CGGTGCGCTA   1080

CAGCTACACG CGCCAGGCGC GCGGCAGTTG GTCGCTGAAC TGGCTGGTAC CGATCGGCCA   1140

CGAGAAGCCC TCGAACATCA AGGTGTTCAT CCACGAACTG AACGCCGGCA ACCAGCTCAG   1200

CCACATGTCG CCGATCTACA CCATCGAGAT GGGCGACGAG TTGCTGGCGA AGCTGGCGCG   1260

CGATGCCACC TTCTTCGTCA GGGCGCACGA GAGCAACGGA ATGCAGCCGA CGCTCGCCAT   1320

CAGCCATGCC GGGGTCAGCG TGGTCATGGC CCAGACCCAG CCGCGCCGGG AAAAGCGCTG   1380

GAGCGAATGG GCCAGCGGCA AGGTGTTGTG CCTGCTCGAC CCGCTGGACG GGGTCTACAA   1440

CTACCTCGCC CAGCAACGCT GCAACCTCGA CGATACCTGG GAAGGCAAGA TCTACCGGGT   1500

GCTCGCCGGC AACCCGGCGA AGCATGACCT GGACATCAAA CCCACGGTCA TCAGTCATCG   1560

CCTGCACTTT CCCGAGGGCG GCAGCCTGGC CGCGCTGACC GCGCACCAGG CTTGCCACCT   1620

GCCGCTGGAG ACTTTCACCC GTCATCGCCA GCCGCGCGGC TGGGAACAAC TGGAGCAGTG   1680

CGGCTATCCG GTGCAGCGGC TGGTCGCCCT CTACCTGGCG GCGCGGCTGT CGTGGAACCA   1740

GGTCGACCAG GTGATCCGCA ACGCCCTGGC CAGCCCCGGC AGCGGCGGCG ACCTGGGCGA   1800

AGCGATCCGC GAGCAGCCGG AGCAGGCCCG TCTGGCCCTG ACCCTGGCCG CCGCCGAGAG   1860

CGAGCGCTTC GTCCGGCAGG GCACCGGCAA CGACGAGGCC GGCGCGGCCA ACGCCGACGT   1920

GGTGAGCCTG ACCTGCCCGG TCGCCGCCGG TGAATGCGCG GGCCCGGCGG ACAGCGGCGA   1980

CGCCCTGCTG GAGCGCAACT ATCCCACTGG CGCGGAGTTC CTCGGCGACG GCGGCGACGT   2040

CAGCTTCAGC ACCCGCGGCA CGCAGAACTG GACGGTGGAG CGGCTGCTCC AGGCGCACCG   2100

CCAACTGGAG GAGCGCGGCT ATGTGTTCGT CGGCTACCAC GGCACCTTCC TCGAAGCGGC   2160

GCAAAGCATC GTCTTCGGCG GGGTGCGCGC GCGCAGCCAG GACCTCGACG CGATCTGGCG   2220

CGGTTTCTAT ATCGCCGGCG ATCCGGCGCT GGCCTACGGC TACGCCCAGG ACCAGGAACC   2280

CGACGCACGC GGCCGGATCC GCAACGGTGC CCTGCTGCGG GTCTATGTGC CGCGCTCGAG   2340

CCTGCCGGGC TTCTACCGCA CCAGCCTGAC CCTGGCCGCG CCGGAGGCGG CGGGCGAGGT   2400

CGAACGGCTG ATCGGCCATC CGCTGCCGCT GCGCCTGGAC GCCATCACCG GCCCCGAGGA   2460

GGAAGGCGGG CGCCTGGAGA CCATTCTCGG CTGGCCGCTG GCCGAGCGCA CCGTGGTGAT   2520

TCCCTCGGCG ATCCCCACCG ACCCGCGCAA CGTCGGCGGC GACCTCGACC CGTCCAGCAT   2580

CCCCGACAAG GAACAGGCGA TCAGCGCCCT GCCGGACTAC GCCAGCCAGC CCGGCAAACC   2640

GCCGCGCGAG GACCTGAAGT AACTGCCGCG ACCGGCCGGC TCCCTTCGCA GGAGCCGGCC   2700

TTCTCGGGGC CTGGCCATAC ATCAGGTTTT CCTGATGCCA GCCCAATCGA ATATGAATTC   2760
```

(2) INFORMATION FOR SEQ ID NO:21:

(i) SEQUENCE CHARACTERISTICS:
        (A) LENGTH: 172 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:21:

TTGATGAAAT GCATCGATTA ATAAATTTTC ATGTACGATT AAAACGTTTT TACCCTTACC        60

TTTTCGTACT ACCTCTGCCT GAAGTTGACC ACCTTTAAAG TGATTCGTTG AAATCCATTA       120

TGCTCATTAT TAATACGATC TATAAAAACA AATGGAATGT GATGATCGAT GA              172

(2) INFORMATION FOR SEQ ID NO:22:

(i) SEQUENCE CHARACTERISTICS:
        (A) LENGTH: 155 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:22:

GTTCCATTGA CTCTGTATCA CCTGTTGTAA CGAACATCCA TATGTCCTGA AACTCCAACC        60

ACAGGTTTGA CCACTTCCAA TTTCAGACCA CCAAGTTTGA CACGTGAAGA TTCATCTTCT       120

AATATTTCGG AATTAATATC ATATTATTTA AATAG                                  155

(2) INFORMATION FOR SEQ ID NO:23:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:23:

ACATAGAAAA ACTCAAAAGA TTTACTTTTT TCAAATGGAA AATAAGGGTA CACACGATAT        60

TTCCCGTCAT CTTCAGTTAC CGGTACAACA TCCTCTTTAT TAACCTGCAC ATAATCTGAC       120

TCCGCTTCAC TCATCAAACT ACTAA                                             145

(2) INFORMATION FOR SEQ ID NO:24:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:24:

TTTCACTGGA ATTACATTTC GCTCATTACG TACAGTGACA ATCGCGTCAG ATAGTTTCTT        60

CTGGTTAGCT TGACTCTTAA CAATCTTGTC TAAATTTTGT TTAATTCTTT GATTCGTACT       120

AGAAATTTTA CTTCTAATTC CTTGTAATTC ATAACTTGCA TTATCATATA AATCATAAGT       180

ATCACATTTT TGATGAATAC TTTGATATAA ATCTGACAAT ACAGGCAGTT GCTCCATTCT       240

ATCGTTAAGA ATAGGGTAAT TAATAG                                            266

(2) INFORMATION FOR SEQ ID NO:25:

(i) SEQUENCE CHARACTERISTICS:
        (A) LENGTH: 845 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:25:

```
TGTTAAATTT CTTTAACAGG GATTTTGTTA TTTAAATTAA ACCTATTATT TTGTCGCTTC    60

TTTCACTGCA TCTACTGCTT GAGTTGCTTT TTCTGAAACC GCCTCTTTCA TTTCACTTGC   120

TTTTTCTGAT GCTGCTTCTT TCATTTCGCC TACTTTTTCT GACGCTGCTT CTGTTGCTGA   180

TTTAATTACT TCTTTCGCAT CTTCCACTTT CTCTGCTACT TTATTTTTCA CGTCTGTAGA   240

AAGCTGCTGT GCTTTTTCCT TTACTTCAGT CATTGTATTA GCTGCAGCAT CTTTTGTTTC   300

TGATGCGACT GATGCTACAG TTTGCTTCGT ATCCTCAACT TTTTGTTTTG CTTCTTGCTT   360

ATCAAAACAA CCTGTCACGA CTAAAGCTGA ACCTAAAACC AATGCTAATG TTAATTTTTT   420

CATTATTTTC TCCATAGAAT AATTTGATTG TTACAAAGCC CTATTACTTT GATGCAGTTT   480

AGTTTACGGG AATTTTCATA AAAAGAAAAA CAGTAATAGT AAAACTTTAC CTTTCTTTAA   540

AAAGATTACT TTATAAAAAA ACATCTAAGA TATTGATTTT TAATAGATTA TAAAAAACCA   600

ATAAAAATTT TATTTTTTGT AAAAAAAAAG AATAGTTTAT TTTAAATAAA TTACAGGAGA   660

TGCTTGATGC ATCAATATTT CTGATTTATT ACCATCCCAT AATAATTGAG CAATAGTTGC   720

AGGATAAAAT GATATTGGAT TTCGTTTTCC ATACAGTTCA GCAACAATTT CTCCCACTAA   780

GGGCAAATGG GAAACAATTA ATACAGATTT AACGCCCTCG TCTTTTAGCA CTTCTAAATA   840

ATCAA                                                              845
```

(2) INFORMATION FOR SEQ ID NO:26:

(i) SEQUENCE CHARACTERISTICS:
        (A) LENGTH: 1598 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:26:

```
GAATAGAGTT GCACTCAATA GATTCGGGCT TTATAATTGC CCAGATTTTT ATTTATAACA    60

AAGGGTTCCA AATGAAAAAA TTTAATCAAT CTCTATTAGC AACTGCAATG TTGTTGGCTG   120

CAGGTGGTGC AAATGCGGCA GCGTTTCAAT TGGCGGAAGT TTCTACTTCA GGTCTTGGTC   180

GTGCCTATGC GGGTGAAGCG GCGATTGCAG ATAATGCTTC TGTCGTGGCA ACTAACCCAG   240

CTTTGATGAG TTTATTTAAA ACGGCACAGT TTTCCACAGG TGGCGTTTAT ATTGATTCTA   300

GAATTAATAT GAATGGTGAT GTAACTTCTT ATGCTCAGAT AATAACAAAT CAGATTGGAA   360

TGAAAGCAAT AAAGGACGGC TCAGCTTCAC AGCGTAATGT TGTTCCCGGT GCTTTTGTGC   420

CAAATCTTTA TTTCGTTGCG CCAGTGAATG ATAAATTCGC GCTGGGTGCT GGAATGAATG   480

TCAATTTCGG TCTAAAAAGT GAATATGACG ATAGTTATGA TGCTGGTGTA TTTGGTGGAA   540

AAACTGACTT GAGTGCTATC AACTTAAATT TAAGTGGTGC TTATCGAGTA ACAGAAGGTT   600
```

```
TGAGCCTAGG TTTAGGGGTA AATGCGGTTT ATGCTAAAGC CCAAGTTGAA CGGAATGCTG      660

GTCTTATTGC GGATAGTGTT AAGGATAACC AAATAACAAG CGCACTCTCA ACACAGCAAG      720

AACCATTCAG AGATCTTAAG AAGTATTTGC CCTCTAAGGA CAAATCTGTT GTGTCATTAC      780

AAGATAGAGC CGCTTGGGGC TTTGGCTGGA ATGCAGGTGT AATGTATCAA TTTAATGAAG      840

CTAACAGAAT TGGTTTAGCC TATCATTCTA AAGTGGACAT TGATTTTGCT GACCGCACTG      900

CTACTAGTTT AGAAGCAAAT GTCATCAAAG AAGGTAAAAA AGGTAATTTA ACCTTTACAT      960

TGCCAGATTA CTTAGAACTT TCTGGTTTCC ATCAATTAAC TGACAAACTT GCAGTGCATT     1020

ATAGTTATAA ATATACCCAT TGGAGTCGTT TAACAAAATT ACATGCCAGC TTCGAAGATG     1080

GTAAAAAAGC TTTTGATAAA GAATTACAAT ACAGTAATAA CTCTCGTGTT GCATTAGGGG     1140

CAAGTTATAA TCTTTATGAA AAATTGACCT TACGTGCGGG TATTGCTTAC GATCAAGCGG     1200

CATCTCGTCA TCACCGTAGT GCTGCAATTC CAGATACCGA TCGCACTTGG TATAGTTTAG     1260

GTGCAACCTA TAAATTCACG CCGAATTTAT CTGTTGATCT TGGCTATGCT TACTTAAAAG     1320

GCAAAAAAGT TCACTTTAAA GAAGTAAAAA CAATAGGTGA CAAACGTACA TTGACATTGA     1380

ATACAACTGC AAATTATACT TCTCAAGCAC ACGCAAATCT TTACGGTTTG AATTTAAATT     1440

ATAGTTTCTA ATCCGTTAAA AAATTTAGCA TAATAAAGCA CAATTCCACA CTAAGTGTGC     1500

TTTTCTTTTA TAAAACAAGG CGAAAAATGA CCGCACTTTA TTACACTTAT TACCCCTCGC     1560

CAGTCGGACG GCTTTTGATT TTATCTGACG GCGAAACA                             1598

(2) INFORMATION FOR SEQ ID NO:27:

(i) SEQUENCE CHARACTERISTICS:
        (A) LENGTH: 9100 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:27:

GTCAAAAATT GCGTGCATTC TAGCGAAAAA ATGGGCTTTT GGGAACTGTG GGATTTATTT       60

AAAATCTTAG AAAATCTTAC CGCACTTTTA AGCTATAAAG TGCGGTGAAA TTTAGTGGCG      120

TTTATAATGG AGAATTACTC TGGTGTAATC CATTCGACTG TCCAGCTTCC AGTACCTTCT      180

GGAACTAATG TTTTTGTGAG ATAAGGCAAA ATTTCTTTCA TTTGGGTTTC TAATGTCCAA      240

GGTGGATTAA TTACCACCAT ACCGCTCGCA GTCATTCCTC GTTGATCGCT ATCTGGGCGA      300

ACGGCGAGTT CAATTTTTAG AATTTTTCTA ATTCCCGTTG CTTCTAAACC CTTAAAAATA      360

CGTTTAGTTT GTTGGCGTAA TACAACAGGA TACCAAATCG CATAAGTGCC AGTGGCAAAA      420

CGTTTATAGC CCTCTTCAAT GGCTTTAACA ACGAGATCAT AATCATCTTT TAATTCATAA      480

GGCGGATCGA TGAGTACTAA GCCTCGGCGT TCTTTTGGCG GAAGCGTTGC TTTGACTTGT      540

TGAAAGCCAT TGTCACATTT TACGGTGACA TTTTTGTCGT CGCTAAAATT ATTGCGAAGA      600

ATTGGATAAT CGCTAGGATG AAGCTCGGTC AATAGTGCGC GATCTTGTGA GCGCAACAAT      660

TCCGCGGCAA TTAATGGAGA ACCCGCGTAA TAACGTAGTT CTTTGCCACC ATAATTGAGT      720

TTTTTGATCA TTTTTACATA ACGAGCAATA TCTTCGGGTA AATCTGTTTG ATCCCACAGG      780

CGTCCAATAC CTTCTTTATA TTCCCCCGTT TTTTCTGATT CATTTGAGGA TAAACGATAA      840

CGCCCCACAC CAGAGTGCGT ATCCAAATAA AAAAAGCCTT TTTCTTTGAG TTTAAGATTT      900
```

```
TCCAAAATGA GCATTAAAAC AATATGTTTC AAGACATCGG CATGATTGCC AGCGTGAAAT     960

GAGTGATGAT AACTCAGCAT AATATATTCC TTATATATTC CTTATTTGTT TAATAACGAA    1020

GGCGAGCCAA TTGACTCGCC CGATTACACA CTAAAGTGCG GTCATTTTTA GAAGAGTTCT    1080

TGTGGTTGCG TCGCTGGCGT ATTGCCTTCA TTATTTAAGC GTTGCTGTAA CTCAGTAGGA    1140

ACATAATAAC CACGCTCTTG CATTTCCGAA AGATAGGTAC GTGTCGGTTC TGTTCCCGCA    1200

ATAAAATATT CTTTGCGCCC ACCGTTTGGA GAAAGCAAAC CTGTCAAAGT ATCAATGTTT    1260

TTTTCCACAA TTTTTGGCGG TAGCGACAAT TTACGTTCTG GCTTATCACT CAAAGCCGTT    1320

TTCATATAAG TGATCCAAGC AGGCATTGCT GTTTTTGCTC CTGCTTCTCC ACGCCCAAGT    1380

ACTCGTTTGT TATCATCAAA CCCGACATAA GTTGTGGTTA CTAAGTTTGC ACCAAATCCC    1440

GCATACCAAG CCACTTTTGA ACTGTTGGTA GTACCTGTTT TACCGCCTAT ATCGCTACGT    1500

TTAATGCTTT GTGCAATACG CCAGCTGGTG CCTTTCCAGT CTAAACCTTG TTCGCCATAA    1560

ATTGCCGTAT TTAAGGCACT ACGAATGAGA AAAGCAAGTT CGCCACTAAT GACACGTGGC    1620

GCATATTCTA TTTTCGACGA AGCATTTTTT GCAGCAGCCA TTAAATCAAT CGCATCTTCT    1680

TTAAGTGCGG TCATATTTGA TTGTAATTCT GGCAGTTCAG GCACAGTTTC AGGTTGTTGA    1740

TCTAATTCTT CGCCATTGGT GCTGTCATCT GTTGGTTTTA AGGCATTCTC GCCTAAAGGA    1800

ATATTGGCAA AGCCGTTGAT TTTGTCTTTG GTTTCGCCAT AAATTACAGG TATATCATTA    1860

CATTCAATGC AAGCAATTTT AGGGTTTGCA ATAAATAAGT CTTTACCCGT GTTATCTTGA    1920

ATTTTTTCAA TGATATAAGG TTCAATGAGG AAGCCACCAT TATCAAACAC CGCATAAGCT    1980

CGCGCCATTT CTAATGGTGT GAAAGAGGCT GCGCCAAGTG CTAAGGCTTC ACTGGCAAAA    2040

TATTGATCAC GTTTAAAACC AAAACGTTGT AAAAATTCTG CTGTGAAATC AATACCTGCC    2100

GTTTGGATAG CACGAATAGC AATTATATTT TTGGATTGAC CTAATCCTAC GCGTAAACGC    2160

ATCGGGCCAT CATAACGATC AGGCGAGTTT TTCGGTTGCC ACATTTTTTG TCCCGGTTTT    2220

TGAATAGAAA TCGGGCTGTC TTGTAATACG CTTGAAAGTG TTAAGCCTTT TTCTAATGCT    2280

GCCGCGTAAA TAAATGGTTT GATAGAAGAA CCCACTTGAA CTAAAGACTG TGTGGCTCGA    2340

TTGAATTTAC TTTGTTCATA GCTAAAGCCA CCGACCACTG CTTCAATCGC ACCATTATCT    2400

GAATTAAGAG AAACTAATGC TGAATTTGCT GCGGGAATTT GTCCTAATTG CCATTCCCCA    2460

TTAGCACGCT GATGAATCCA AATTTGCTCG CCGACTTTCA CAGGATTGCT TCTGCCTGTC    2520

CAACGCATTG CATTGGTTGA TAAGGTCATT TTTTCCCCAG AAGCGAGCAA TATATCAGCA    2580

CCGCCTTTTA CAATTCCAAT CACTGCCGCA GGAATAAATG GCTCTGAATC AGGTAGTTTG    2640

CGTAGAAAAC CGACAATGCG ATCATTGTCC AAGCGGCTT CATTTTTTTG CCATAATGGC    2700

GCGCCACCGC GATAACCGTG ACGCATATCG TAATCAATCA AGTTATTACG CACAGCTTTT    2760

TGGGCTTCAG CTTGGTCTTT TGAAAGTACA GTGGTAAATA CTTTATAACC ACTGGTGTAA    2820

GCATTTCTT CGCCAAAACG ACGCACCATT TCTTGACGCA CCATTTCAGT GACATAATCG    2880

GCTCGAAATT CAAATTTTGC GCCGTGATAG CTCGCCACAA TCGGCTCTTT CAATGCAGCA    2940

TCATATTCTT CTTTGCTGAT GTATTTTCA TCTAACATAC GGCTTAGCAC CACATTGCGG    3000

CGTTCTTCTG AACGTTTTAA AGAATAAAGC GGGTTCATTG TTGAAGGTGC TTTAGGTAAA    3060

CCAGCAATAA TCGCCATTTC CGATAAGGTC AATTCATTCA ATGATTTACC GAAATAGGTT    3120

TGTGCTGCCG CTGCAACACC ATAAGAACGA TAGCCTAAAA AGATTTTGTT TAAATAAAGC    3180

TCTAATATTT CTTGTTTGTT GAGAGTATTT TCGATTTCTA CCGCAAGCAC GGCTTCACGA    3240

GCTTTACGAA TAATGGTTTT TTCTGAGGTT AAGAAAAAGT TACGCGCTAA TTGTTGAGTA    3300
```

```
ATCGTACTTG CGCCTTGTGA TGCACCGCCA TTACTCACTG CGACAAACAA TGCACGGGCA      3360

ATGCCGATAG GGTCTAATCC GTGATGATCG TAAAAACGAC TGTCTTCCGT CGCTAAAAAT      3420

GCGTCAATTA AGCGTTGTGG CACATCGGCT AATTTCACTG GAATACGGCG TTGCTCACCC      3480

ACTTCGCCAA TTAATTTACC GTCAGCCGTA TAAATCTGCA TTGGTTGCTG TAATTCAACG      3540

GTTTTTAATG TTTCTACTGA GGGCAATTCA GATTTTAAGT GGAAATACAA CATTCCGCCT      3600

GCTACTAAAC CTAAAATACA TAAAGTTAAT AGGGTGTTTA ATATTAATTT TGCGATCCGC      3660

ATCGTAAAAT TCTCGCTTCG TTAATGAATA TTCTTGTCAA GAGACCTATG ATTTGGCTGT      3720

TAAGTATAAA AGATTCAGCC TTTAAAGAAT AGGAAAGAAT ATGCAATTCT CCCTGAAAAA      3780

TTACCGCACT TTACAAATCG GCATTCATCG TAAGCAGAGT TATTTTGATT TTGTGTGGTT      3840

TGATGATCTC GAACAGCCAC AAAGTTATCA AATCTTTGTT AATGATCGTT ATTTTAAAAA      3900

TCGTTTTTTA CAACAGCTAA AAACACAATA TCAAGGGAAA ACCTTCCTT TGCAGTTTGT       3960

AGCAAGCATT CCCGCCCACT TAACTTGGTC GAAAGTATTA ATGTTGCCAC AAGTGTTAAA      4020

TGCGCAAGAA TGTCATCAAC AATGTAAATT TGTGATTGAA AAAGAGCTGC CTATTTTTTT     4080

AGAAGAATTG TGGTTTGATT ATCGTTCTAC CCCGTTAAAG CAAGGTTTTC GATTAGAGGT     4140

TACTGCAATT CGTAAAAGTA GCGCTCAAAC TTATTTGCAA GATTTTCAGC CATTTAATAT     4200

TAATATATTG GATGTTGCGT CAAATGCTGT TTTGCGTGCA TTTCAATATC TGTTGAATGA     4260

ACAAGTGCGG TCAGAAAATA CCTTATTTTT ATTTCAAGAA GATGACTATT GCTTGGCGAT    4320

TTGTGAAAGA TCTCAGCAAT CACAAATTTT ACAATCTCAC GAAAATTTGA CCGCACTTTA     4380

TGAACAATTT ACCGAACGTT TTGAAGGACA ACTTGAACAA GTTTTTGTTT ATCAAATTCC    4440

CTCAAGTCAT ACACCATTAC CCGAAAACTG GCAGCGAGTA GAAACAGAAC TCCCTTTTAT   4500

TGCGCTGGGC AACGCGCTAT GGCAAAAAGA TTTACATCAA CAAAAAGTGG GTGGTTAAAT    4560

GTCGATGAAT TTATTGCCTT GGCGTACTTA TCAACATCAA AAGCGTTTAC GTCGTTTAGC   4620

TTTTTATATC GCTTTATTTA TCTTGCTTGC TATTAATTTA ATGTTGGCTT TTAGCAATTT    4680

GATTGAACAA CAGAAACAAA ATTTGCAGGC ACAGCAAAAG TCGTTTGAAC AACTTAATCA   4740

ACAGCTTCAT AAAACTACCA TGCAAATTGA TCAGTTACGC ATTGCGGTGA AGTTGGTGA     4800

AGTTTTGACA TCTATTCCCA ACGAGCAAGT AAAAAAGAGT TTACAACAGC TAAGTGAATT   4860

ACCTTTTCAA CAAGGAGAAC TGAATAAATT TAAACAAGAT GCCAATAACT TAAGCTTGGA  4920

AGGTAACGCG CAAGATCAAA CAGAATTTGA ACTGATTCAT CAATTTTTAA AGAAACATTT   4980

TCCCAATGTG AAATTAAGTC AGGTTCAACC TGAACAAGAT ACATTGTTTT TCACTTTGA    5040

TGTGGAACAA GGGGCGGAAA AATGAAAGCT TTTTTTAACG ATCCTTTTAC TCCTTTTGGA   5100

AAATGGCTAA GTCAGCCTTT TTATGTGCAC GGTTTAACCT TTTTATTGCT ATTAAGTGCG    5160

GTGATTTTTC GCCCCGTTTT AGATTATATA GAGGGGAGTT CACGTTTCCA TGAAATTGAA   5220

AATGAGTTAG CGGTGAAACG TTCAGAATTG TTGCATCAAC AGAAAATTTT AACCTCTTTA   5280

CAACAGCAGT CGGAAAGTCG AAAACTTTCT CCAGAACTGG CTGCACAAAT TATTCCTTTG   5340

AATAAACAAA TTCAACGTTT AGCTGCGCGT AACGGTTTAT CTCAGCATTT ACGTTGGGAA   5400

ATGGGGCAAA AGCCTATTTT GCATTTACAG CTTACAGGTC ATTTTGAAAA AACGAAGACA   5460

TTTTTATCCG CACTTTTGGC TAATTCGTCA CAGCTTTCTG TAAGTCGGTT GCAATTTATG   5520

AAACCCGAAG ACGCCCATT GCAAACCGAG ATCATTTTTC AGCTAGATAA GGAAACAAAA    5580

TGAAACATTG GTTTTCCTG ATTATATTAT TTTTTATGAA TTGCAGTTGG GGACAAGATC    5640

CTTTCGATAA AACACAGCGT AACCGTTCTC AGTTTGATAA CGCACAAACA GTAATGGAGC   5700
```

```
AAACAGAAAT AATTTCCTCA GATGTGCCTA ATAATCTATG CGGAGCGGAT GAAAATCGCC    5760

AAGCGGCTGA AATTCCTTTG AACGCTTTAA AATTGGTGGG GGTAGTGATT TCTAAAGATA    5820

AAGCCTTTGC CTTGTTGCAA GATCAAGGTT TGCAAGTTTA CAGCGTTTTA GAGGGCGTTG    5880

ATGTGGCTCA AGAGGGCTAT ATTGTAGAAA AAATCAACCA AAACAATGTT CAATTTATGC    5940

GTAAGCTAGG AGAGCAATGT GATAGTAGTG AATGGAAAAA ATTAAGTTTT TAAGGAAGA     6000

TTATGAAGAA ATATTTTTTA AAGTGCGGTT ATTTTTTAGT ATGTTTTTGT TTGCCATTAA    6060

TCGTTTTTGC TAATCCTAAA ACAGATAACG AACGTTTTTT TATTCGTTTA TCGCAAGCAC    6120

CTTTAGCTCA AACACTGGAG CAATTAGCTT TTCAACAAGA TGTGAATTTA GTGATTGGAG    6180

ATATATTGGA AAACAAGATC TCTTTGAAAT TAAACAATAT TGATATGCCA CGTTTGCTAC    6240

AAATAATCGC AAAAAGTAAG CATCTTACTT TGAATAAAGA TGATGGGATT TATTATTTAA    6300

ACGGCAGTCA ATCTGGCAAA GGTCAGGTTG CAGGAAATCT TACGACAAAT GAACCGCACT    6360

TAGTGAGTCA CACGGTAAAA CTCCATTTTG CTAAAGCTTC TGAATTAATG AAATCCTTAA    6420

CAACAGGAAG TGGCTCTTTG CTTTCTCCCG CTGGGAGCAT TACCTTTGAT GATCGCAGTA    6480

ATTTGCTGGT TATTCAGGAT GAACCTCGTT CTGTGCAAAA TATCAAAAAA CTGATTGCTG    6540

AAATGGATAA GCCTATTGAA CAGATCGCTA TTGAAGCGCG AATTGTGACA ATTACGGATG    6600

AGAGTTTGAA AGAACTTGGC GTTCGGTGGG GGATTTTTAA TCCAACTGAA AATGCAAGAC    6660

GAGTTGCGGG CAGCCTTACA GGCAATAGCT TTGAAAATAT TGCGGATAAT CTTAATGTAA    6720

ATTTTGCGAC AACGACGACA CCTGCTGGCT CTATAGCATT ACAAGTCGCC AAAATTAATG    6780

GGCGATTGCT TGATTTAGAA TTGAGTGCGT TGGAGCGTGA AAATAATGTA GAAATTATTG    6840

CAAGCCCTCG CTTACTCACT ACCAATAAGA AAAGTGCGAG CATTAAACAG GGGACAGAAA    6900

TTCCTTACAT CGTGAGTAAT ACTCGTAACG ATACGCAATC TGTGGAATTT CGTGAGGCGG    6960

TGCTTGGTTT GGAAGTGACG CCACATATTT CTAAAGATAA CAATATCTTA CTTGATTTAT    7020

TGGTAAGTCA AAATTCCCCT GGTTCTCGTG TCGCTTATGG ACAAAATGAG GTGGTTTCTA    7080

TTGATAAACA AGAAATTAAT ACTCAGGTTT TTGCCAAAGA TGGGGAAACC ATTGTGCTTG    7140

GCGGCGTATT TCACGATACA ATCACGAAAA GCGAAGATAA AGTGCCATTG CTTGGCGATA    7200

TACCCGTTAT TAAACGATTA TTTAGCAAAG AAAGTGAACG ACATCAAAAA CGTGAGCTAG    7260

TGATTTTCGT CACGCCACAT ATTTTAAAAG CAGGAGAAAA CGTTAGAGGC GTTGAAACAA    7320

AAAAGTGAGG GTAAAAAATA ACTTTTTAAA TGATGAATTT TTTTAATTTT CGCTGTATCC    7380

ACTGTCGTGG CAATCTTCAT ATCGCAAAAA ATGGGTTATG TTCAGGTTGC CAAAAACAAA    7440

TTAAATCTTT TCCTTATTGC GGTCATTGTG GTTCGGAATT GCAATATTAT GCGCAGCATT    7500

GTGGGAATTG TCTTAAACAA GAACCAAGTT GGGATAAGAT GGTCATTATT GGGCATTATA    7560

TTGAACCTCT TTCGATATTG ATTCAGCGTT TTAAATTTCA AAATCAATTT TGGATTGACC    7620

GCACTTTAGC TCGGCTTTTA TATCTTGCGG TACGTGATGC TAAACGAACG CATCAACTTA    7680

AATTGCCAGA GGCAATCATT CCAGTGCCTT TATATCATTT TCGTCAGTGG CGACGGGGTT    7740

ATAATCAGGC AGATTATTA TCTCAGCAAT TAAGTCGTTG GCTGGATATT CCTAATTTGA     7800

ACAATATCGT AAAGCGTGTG AAACACACCT ATACTCAACG TGGTTTGAGT GCAAAAGATC    7860

GTCGTCAGAA TTTAAAAAAT GCCTTTTCTC TTGCTGTTTC GAAAAATGAA TTTCCTTATC    7920

GTCGTGTTGC GTTGGTGGAT GATGTGATTA CTACTGGTTC TACACTCAAT GAAATCTCAA    7980

AATTGTTGCG AAAATTAGGT GTGGAGGAGA TTCAAGTGTG GGGGCTGGCA CGAGCTTAAT    8040

ATAAAGCACT GGAAAAAAAA GCGCGATAAG CGTATTATTC CCGATACTTT CTCTCAAGTA    8100
```

```
TTTAGGACAT AATTATGGAA CAAGCAACCC AGCAAATCGC TATTTCTGAT GCCGCACAAG    8160

CGCATTTTCG AAAACTTTTA GACACCCAAG AAGAAGGAAC GCATATTCGT ATTTTCGCGG    8220

TTAATCCTGG TACGCCTAAT GCGGAATGTG GCGTATCTTA TTGCCCCCCG AATGCCGTGG    8280

AAGAAAGCGA TATTGAAATG AAATATAATA CTTTTTCTGC ATTTATTGAT GAAGTGAGTT    8340

TGCCTTTCTT AGAAGAAGCA GAAATTGATT ATGTTACCGA AGAGCTTGGT GCGCAACTGA    8400

CCTTAAAAGC ACCGAATGCC AAAATGCGTA AGGTGGCTGA TGATGCGCCA TTGATTGAAC    8460

GTGTTGAATA TGTAATTCAA ACTCAAATTA ACCCACAGCT TGCAAATCAC GGTGGACGTA    8520

TAACCTTAAT TGAAATTACT GAAGATGGTT ACGCAGTTTT ACAATTTGGT GGTGGCTGTA    8580

ACGGTTGTTC AATGGTGGAT GTTACGTTAA AAGATGGGGT AGAAAAACAA CTTGTTAGCT    8640

TATTCCCGAA TGAATTAAAA GGTGCAAAAG ATATAACTGA GCATCAACGT GGCGAACATT    8700

CTTATTATTA GTGAGTTATA AAAGAAGATT TATAATGACC GCACTTTTGA AAGTGCGGTT    8760

ATTTTTATGG AGAAAAAATG AAAATACTTC AACAAGATGA TTTTGGTTAT TGGTTGCTTA    8820

CACAAGGTTC TAATCTGTAT TTAGTGAATA ATGAATTGCC TTTTGGTATC GCTAAAGATA    8880

TTGATTTGGA AGGATTGCAG GCAATGCAAA TTGGGGAATG GAAAAATTAT CCGTTGTGGC    8940

TTGTGGCTGA GCAAGAAAGT GATGAACGAG AATATGTGAG TTTGAGTAAC TTGCTTTCAC    9000

TGCCAGAGGA TGAATTCCAT ATATTAAGCC GAGGTGTGGA AATTAATCAT TTTCTGAAAA    9060

CCCATAAATT CTGTGGAAAG TGCGGTCATA AAACACAACA                         9100

(2) INFORMATION FOR SEQ ID NO:28:

(i) SEQUENCE CHARACTERISTICS:
        (A) LENGTH: 525 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:28:

AAAAATCGAC TGCCGTCATT TTCAACCACC ACATAGCTCA TATTCGCAAG CCAATGTATT      60

GACCGTTGGG AATAATAACA GCCCCAAAAC AATGAAACAT ATGGTGATGA GCCAAACATA     120

CTTTCCTGCA GATTTTGGAA TCATATCGCC ATCAGCACCA GTATGGTTTG ACCAGTATTT     180

AACGCCATAG ACATGTGTAA AAAAATTAAA TAACGGTGCA AGCATGAGAC CAACGGCACC     240

TGATGTACCT TGTACGATGA CCTCACCTGC TGTGGCAACC ATACCAAGTC CATTGCCTGT     300

GATATTTTTG CGAAAAGACA AACTTACCAC ACAGACCAAG CCGATGATTG AGATGACAAA     360

ATAAAACCAA TCCAAATGCG TGTGAGCTGT TGTGGTCCAA AATCCAGTAA ATAGTGCAAT     420

AAATCCGCAA ACAAACCAAA GTAGCACCCA GCTTGTTGTC CAATCTTTTT TACCAAAGCC     480

TGTGATGTTA TCTAAAATAT CAATTTTCAT CAGATTTTCC CTAAT                     525

(2) INFORMATION FOR SEQ ID NO:29:

(i) SEQUENCE CHARACTERISTICS:
        (A) LENGTH: 466 base pairs
        (B) TYPE: nucleic acid
        (C) STRANDEDNESS: double
        (D) TOPOLOGY: linear (ii) MOLECULE TYPE: DNA (genomic)
```

(vi) ORIGINAL SOURCE:
    (A) ORGANISM: Moraxella catarrhalis (xi) SEQUENCE DESCRIPTION: SEQ ID NO:29:

```
TAATGATAAC CAGTCAAGCA AGCTCAAATC AGGGTCAGCC TGTTTTGAGC TTTTTATTTT      60
TTGATCATCA TGCTTAAGAT TCACTCTGCC ATTTTTTTAC AACCTGCACC ACAAGTCATC     120
ATCGCATTTG CAAAAATGGT ACAAACAAGC CGTCAGCGAC TTAAACAAAA AAAGGCTCAA     180
TCTGCGTGTG TGCGTTCACT TTTACAAATC ACCATGCACC GCTTTGACAT TGTTGGTGAA     240
TTTCATGACC ATGCACACCC TTATTATATT AACTCAAATA AAATACGCTA CTTTGTCAGC     300
TTTAGCCATT CAGATAATCA AGTCGCTCTC ATCATCAGCT TAACACCTTG TGCCATTGAC     360
ATAGAAGTTA ACGATATTAA ATACAGTGTG GTTGAACGAT ACTTTCATCC CAATGAAATT     420
TATCTACTTA CTCAATTTAG CTCTACTGAT AGGCAACAGC TTATTA                    466
```

(2) INFORMATION FOR SEQ ID NO:30:

(i) SEQUENCE CHARACTERISTICS:
      (A) LENGTH: 631 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
       (A) ORGANISM: Streptococcus pneumoniae (xi) SEQUENCE DESCRIPTION: SEQ ID NO:30:

```
GATCTTTGAT TTTCATTGAG TATTACTCTC TCTTGTCACT TCTTTCTATT TTACCATAAA      60
GTCCAGCCTT TGAAGAACTT TTACTAGAAG ACAAGGGGCT TCTGTCTCTA TTTGCCATCT     120
TAGGCATCAA AAAAGAGGGG TCATCCCTCT TTACGAATTC AATGCTACTA GGGTATCCAA     180
ATACTGGTTG TTGATGACTG CCAAAATATA GGTATCTGCT TCAAGAGGT CATCTGGTCC      240
AAATTCAACA TCCAATGGGG AATTTTCCTG CTCTCGGAAA CCCAAAATAT TCAGATTGTA     300
TTTGCCACGG AGGTCTAATT TACTTCAGAC TTTGACCTGC CCAAGACTGA GGAATTTTCA     360
TCTCCACGAT AGACACATTT TTATCCAACT GAAAGACATC AACACTATTA TGAAAAGAAT     420
GGTCTGTGCT AGAGACTGCC CCATTTCATA CTCTGGCGAG ATAACCGAGT CAGCTCCAAT     480
CTTTTCTAGC ACTTTCTTAG CGGTCTGACT TTTGACCTTA GCAATAACAG TCGGTACCCC     540
CAAACTCTTA CAGTGCATAA CCGCAAGCAC ACTCGACTCC AGATTTTCAC CTGTCGCGAC     600
TACAACGGTA TCGCAGGTAT CAATCCCTGC T                                    631
```

(2) INFORMATION FOR SEQ ID NO:31:

(i) SEQUENCE CHARACTERISTICS:
      (A) LENGTH: 3754 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
       (A) ORGANISM: Streptococcus pneumoniae (xi) SEQUENCE DESCRIPTION: SEQ ID NO:31:

```
CCAATATTTT GGTCAGCATA GTGTTCTTTT TCAGTGGTAA CAGCTTGCAA TACTTGAGCA      60
GAAATGGCAG ATTTATCAAG GAAAAGTTA ACGTAAGGTC CTGTTGCGAC AACTTTTTCA      120
AAGGCTTGGC TGTTCATTTT TTCAGCCAGT TCAGCCGCAA TCATTTGTGG TGCTTTACGT     180
```

```
TCGACTTTTG CAAGAGAAAA AGCAGGGAAA GCAATGTCTC CCATTTCTGA GTTTTTAGGG      240

GTTTCCAGTA ACTTTAAAAT AGCCTCTTGG TCCAGGCTAT CAATGATGCT AGATAATTCG      300

CTAGCAATCA ATTCTTTTGT ATTCATTAAG AGCTCCTTTT TGGACTTTTC TACTATTTTA      360

TCACAATTTT AAAGAAAGAA GAAAAAATTT TTGAAATCTC CTGTTTTTTT GGTATAATAT      420

GGTTATAAAT ATAGTTATAA ATATAGTTAT AAATATGCAC GCAAGAGGAT TTTATGAGAA      480

AAAGAGATCG TCATCAGTTA ATAAAAAAAA TGATTACTGA GGAGAAATTA AGTACACAAA      540

AAGAAATTCA AGATCGGTTG GAGGCGCACA ATGTTTGTGT GACGCAGACA ACCTTGTCTC      600

GTGATTTGCG CGAAATCGGC TTGACCAAGG TCAAGAAAAA TGATATGGTG TATTATGTAC      660

TAGTAAATGA GACAGAAAAG ATTGATTTGG TGGAATTTTT GTCTCATCAT TTAGAAGGTG      720

TTGCAAGAGC AGAGTTTACC TTGGTGCTTC ATACCAAATT GGGAGAAGCC TCTGTTTTGG      780

CAAATATTGT AGATGTAAAC AAGGATGAAT GGATTTTAGG AACAGTTGCT GGTGCCAATA      840

CCTTATTGGT TATTTGTCGA GATCAGCACG TTGCCAAACT CATGGAAGAT CGTTTGCTAG      900

ATTTGATGAA AGATAAGTAA GGTCTTGGGA GTTGCTCTCA AGACTTATTT TTGAAAAGGA      960

GAGACAGAAA ATGGCGATAG AAAAGCTATC ACCCGGCATG CAACAGTATG TGGATATTAA      1020

AAAGCAATAT CCAGATGCTT TTTTGCTCTT TCGGATGGGT GATTTTTATG AATTATTTTA      1080

TGAGGATGCG GTCAATGCTG CGCAGATTCT GGAAATTTCC TTAACGAGTC GCAACAAGAA      1140

TGCCGACAAT CCGATCCCTA TGGCGGGTGT TCCCTATCAT TCTGCCCAAC AGTATATCGA      1200

TGTCTTGATT GAGCAGGGTT ATAAGGTGGC TATCGCAGAG CAGATGGAAG ATCCTAAACA      1260

AGCAGTTGGG GTTGTTAAAC GAGAGGTTGT TCAGGTCATT ACGCCAGGGA CAGTGGTCGA      1320

TAGCAGTAAG CCGGACAGTC AGAATAATTT TTTGGTTTCC ATAGACCGCG AAGGCAATCA      1380

ATTTGGCCTA GCTTATATGG ATTTGGTGAC GGGTGACTTT TATGTGACAG GTCTTTTGGA      1440

TTTCACGCTG GTTTGTGGGG AAATCCGTAA CCTCAAGGCT CGAGAAGTGG TGTTGGGTTA      1500

TGACTTGTCT GAGGAAGAAG AACAAATCCT CAGCCGCCAG ATGAATCTGG TACTCTCTTA      1560

TGAAAAAGAA AGCTTTGAAG ACCTTCATTT ATTGGATTTG CGATTGGCAA CGGTGGAGCA      1620

AACGGCATCT AGTAAGCTGC TCCAGTATGT TCATCGGACT CAGATGAGGG AATTGAACCA      1680

CCTCAAACCT GTTATCCGCT ACGAAATTAA GGATTTCTTG CAGATGGATT ATGCGACCAA      1740

GGCTAGTCTG GATTTGGTTG AGAATGCTCG CTCAGGTAAG AAACAAGGCA GTCTTTTCTG      1800

GCTTTTGGAT GAAACCAAAA CGGCTATGGG GATGCGTCTC TTGCGTTCTT GGATTCATCG      1860

CCCCTTGATT GATAAGGAAC GAATCGTCCA ACGTCAAGAA GTAGTGCAGG TCTTTCTCGA      1920

CCATTTCTTT GAGCGTAGTG ACTTGACAGA CAGTCTCAAG GGTGTTTATG ACATTGAGCG      1980

CTTGGCTAGT CGTGTTTCTT TTGGCAAAAC CAATCCAAAG GATCTCTTGC AGTTGGCGAC      2040

TACCTTGTCT AGTGTGCCAC GGATTCGTGC GATTTTAGAA GGGATGGAGC AACCTACTCT      2100

AGCCTATCTC ATCGCACAAC TGGATGCAAT CCCTGAGTTG GAGAGTTTGA TTAGCGCAGC      2160

GATTGCTCCT GAAGCTCCTC ATGTGATTAC AGATGGGGGA ATTATCCGGA CTGGATTTGA      2220

TGAGACTTTA GACAAGTATC GTTGCGTTCT CAGAGAAGGG ACTAGCTGGA TTGCTGAGAT      2280

TGAGGCTAAG GAGCGAGAAA ACTCTGGTAT CAGCACGCTC AAGATTGACT ACAATAAAAA      2340

GGATGGCTAC TATTTTCATG TGACCAATTC GCAACTGGGA AATGTGCCAG CCCACTTTTT      2400

CCGCAAGGCG ACGCTGAAAA ACTCAGAACG CTTTGGAACC GAAGAATTAG CCCGTATCGA      2460

GGGAGATATG CTTGAGGCGC GTGAGAAGTC AGCCAACCTC GAATACGAAA TATTTATGCG      2520

CATTCGTGAA GAGGTCGGCA AGTACATCCA GCGTTTACAA GCTCTAGCCC AAGGAATTGC      2580
```

```
GACGGTTGAT GTCTTACAGA GTCTGGCGGT TGTGGCTGAA ACCCAGCATT TGATTCGACC      2640

TGAGTTTGGT GACGATTCAC AAATTGATAT CCGGAAAGGG CGCCATGCTG TCGTTGAAAA      2700

GGTTATGGGG GCTCAGACCT ATATTCCAAA TACGATTCAG ATGGCAGAAG ATACCAGTAT      2760

TCAATTGGTT ACAGGGCCAA ACATGAGTGG GAAGTCTACC TATATGCGTC AGTTAGCCAT      2820

GACGGCGGTT ATGGCCCAGC TGGGTTCCTA TGTTCCTGCT GAAAGCGCCC ATTTACCGAT      2880

TTTTGATGCG ATTTTTACCC GTATCGGAGC AGCAGATGAC TTGGTTTCGG GTCAGTCAAC      2940

CTTTATGGTG GAGATGATGG AGGCCAATAA TGCCATTTCG CATGCGACCA AGAACTCTCT      3000

CATTCTCTTT GATGAATTGG GACGTGGAAC TGCAACTTAT GACGGGATGG CTCTTGCTCA      3060

GTCCATCATC GAATATATCC ATGAGCACAT CGGAGCTAAG ACCCTCTTTG CGACCCACTA      3120

CCATGAGTTG ACTAGTCTGG AGTCTAGTTT ACAACACTTG GTCAATGTCC ACGTGGCAAC      3180

TTTGGAGCAG GATGGGCAGG TCACCTTCCT TCACAAGATT GAACCGGGAC CAGCTGATAA      3240

ATCCTACGGT ATCCATGTTG CCAAGATTGC TGGCTTGCCA GCAGACCTTT TAGCAAGGGC      3300

GGATAAGATT TTGACTCAGC TAGAGAATCA AGGAACAGAG AGTCCTCCTC CCATGAGACA      3360

AACTAGTGCT GTCACTGAAC AGATTTCACT CTTTGATAGG GCAGAAGAGC ATCCTATCCT      3420

AGCAGAATTA GCTAAACTGG ATGTGTATAA TATGACACCT ATGCAGGTTA TGAATGTCTT      3480

AGTAGAGTTA AAACAGAAAC TATAAAACCA AGACTCACTA GTTAATCTAG CTGTATCAAG      3540

GAGACTTCTT TGACAATTCT CCACTTTTTT GCTAGAATAA CATCACACAA ACAGAATGAA      3600

AAGGGCTGAC GCATTGTCGC TCCCTTTTGT CTATTTTTTA AGGAGAAAGT ATGCTGATTC      3660

AGAAAATAAA AACCTACAAG TGGCAGGCCC TGCTTCGCTC CTGATGACAG GCTTGATGGT      3720

TGCTAGTTCA CTTCTGCAAC CGCGTTATCT GCAG                                 3754

(2) INFORMATION FOR SEQ ID NO:32:

(i) SEQUENCE CHARACTERISTICS:
        (A) LENGTH: 1337 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:32:

AACAAAATAA AAGAACTTAC CTATTTTCCA TCCAAAATGT TTAGCAATCA TCATCTGCAA        60

GGCAACGTAT TGCATGGCAT TGATGTGATG AGCAACTAAT ATGTCATTAG AACGTTGCGT       120

CAAACTAGCA TCTAAATAAA GATCGAAATG CAGTTATCAA AAATGCAAGC TCCTATCGGC       180

CCTTGTTTTA ATTATTACTC ACATTGCCTT AATGTATTTA CTTGCTTATT ATTAACTTTT       240

TTGCTAAGTT AGTAGCGTCA GTTATTCATT GAAAGGACAT TATTATGAAA ATTCTTGTAA       300

CAGGCTTTGA TCCCTTTGGC GGCGAAGCTA TTAATCCTGC CCTTGAAGCT ATCAAGAAAT       360

TGCCAGCAAC CATTCATGGA GCAGAAATCA AATGTATTGA AGTTCCAACG GTTTTTCAAA       420

AATCTGCCGA TGTGCTCCAG CAGCATATCG AAAGCTTTCA ACCTGATGCA GTCCTTTGTA       480

TTGGGCAAGC TGGTGGCCGG ACTGGACTAA CGCCAGAACG CGTTGCCATT AATCAAGACG       540

ATGCTCGCAT TCCTGATAAC GAAGGGAATC AGCCTATTGA TACACCTATT CGTGCAGATG       600

GTAAAGCAGC TTATTTTTCA ACCTTGCCAA TCAAAGCGAT GGTTGCTGCC ATTCATCAGG       660

CTGGGCTTCC TGCTTCTGTT TCTAATACAG CTGGTACCTT TGTTTGCAAT CATTTGATGT       720
```

```
ATCAAGCCCT TTACTTAGTG GATAAATATT GTCCAAATGC CAAAGCTGGG TTTATGCATA      780

TTCCCTTTAT GATGGAACAG GTTGTTGATA AACCTAATAC AGCTGCCATG AACCTCGATG      840

ATATTACAAG AGGAATTGAG GCTGCTATTT TTGCCATTGT CGATTTCAAA GATCGTTCCG      900

ATTTAAAACG TGTAGGGGGC GCTACTCACT GACTGTGACG CTACTAAACC TATTTTAAAA      960

AAACAGAGAT ATGAACTAAC TCTGTTTTTT TTGTGCTAAA AATGAAAGAC CTAGGGAAAC     1020

TTTTCATCGG TCTTTCTCAA TTGTCATCTT AATCTAATAC TACTTCTAAC ATCAGCGGGT     1080

ATAGTTTGCC AGTAATTAAG AAACGTTGTT GATCTAAATG AGCAATCCCA TTCAAAACAT     1140

TAAGGTCAGG GTAATGGGAC TTATCAAGAT TTAAGGCTTT TAACAAAGGA CTAATATCAT     1200

AGGTGGCTAC CACCTTTCCA GAATCAGGTT GGAGTTTGAC AATAGTATTG GTTTGCCAAA     1260

TATTGGCATA GAGATAACCA TCTACATACT CTAATTCGTT AAGCATTGAG ATAGGGACAC     1320

TTTCTATAGC AACTAGT                                                    1337
```

(2) INFORMATION FOR SEQ ID NO:33:

(i) SEQUENCE CHARACTERISTICS:
        (A) LENGTH: 1837 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:33:

```
TCATGTTTGA CAGCTTATCA TCGATAAGCT TACTTTTCGA ATCAGGTCTA TCCTTGAAAC       60

AGGTGCAACA TAGATTAGGG CATGGAGATT TACCAGACAA CTATGAACGT ATATACTCAC      120

ATCACGCAAT CGGCAATTGA TGACATTGGA ACTAAATTCA ATCAATTTGT TACTAACAAG      180

CAACTAGATT GACAACTAAT TCTCAACAAA CGTTAATTTA ACAACATTCA AGTAACTCCC      240

ACCAGCTCCA TCAATGCTTA CCGTAAGTAA TCATAACTTA CTAAAACCTT GTTACATCAA      300

GGTTTTTTCT TTTTGTCTTG TTCATGAGTT ACCATAACTT TCTATATTAT TGACAACTAA      360

ATTGACAACT CTTCAATTAT TTTTCTGTCT ACTCAAAGTT TTCTTCATTT GATATAGTCT      420

AATTCCACCA TCACTTCTTC CACTCTCTCT ACCGTCACAA CTTCATCATC TCTCACTTTT      480

TCGTGTGGTA ACACATAATC AAATATCTTT CCGTTTTTAC GCACTATCGC TACTGTGTCA      540

CCTAAAATAT ACCCCTTATC AATCGCTTCT TTAAACTCAT CTATATATAA CATATTTCAT      600

CCTCCTACCT ATCTATTCGT AAAAAGATAA AAATAACTAT TGTTTTTTTT GTTATTTTAT      660

AATAAAATTA TTAATATAAG TTAATGTTTT TTAAAAATAT ACAATTTTAT TCTATTTATA      720

GTTAGCTATT TTTTCATTGT TAGTAATATT GGTGAATTGT AATAACCTTT TTAAATCTAG      780

AGGAGAACCC AGATATAAAA TGGAGGAATA TTAATGGAAA ACAATAAAAA AGTATTGAAG      840

AAAATGGTAT TTTTTGTTTT AGTGACATTT CTTGGACTAA CAATCTCGCA AGAGGTATTT      900

GCTCAACAAG ACCCCGATCC AAGCCAACTT CACAGATCTA GTTTAGTTAA AAACCTTCAA      960

AATATATATT TTCTTTATGA GGGTGACCCT GTTACTCACG AGAATGTGAA ATCTGTTGAT     1020

CAACTTTTAT CTCACGATTT AATATATAAT GTTTCAGGGC CAAATTATGA TAAATAAAA     1080

ACTGAACTTA AGAACCAAGA GATGGCAACT TTATTTAAGG ATAAAAACGT TGATATTTAT     1140

GGTGTAGAAT ATTACCATCT CTGTTATTTA TGTGAAAATG CAGAAAGGAG TGCATGTATC     1200

TACGGAGGGG TAACAAATCA TGAAGGGAAT CATTTAGAAA TTCCTAAAAA GATAGTCGTT     1260
```

| | |
|---|---|
| AAAGTATCAA TCGATGGTAT CCAAAGCCTA TCATTTGATA TTGAAACAAA TAAAAAAATG | 1320 |
| GTAACTGCTC AAGAATTAGA CTATAAAGTT AGAAAATATC TTACAGATAA TAAGCAACTA | 1380 |
| TATACTAATG GACCTTCTAA ATATGAAACT GGATATATAA AGTTCATACC TAAGAATAAA | 1440 |
| GAAAGTTTTT GGTTTGATTT TTTCCCTGAA CCAGAATTTA CTCAATCTAA ATATCTTATG | 1500 |
| ATATATAAAG ATAATGAAAC GCTTGACTCA ACACAAGCC AAATTGAAGT CTACCTAACA | 1560 |
| ACCAAGTAAC TTTTTGCTTT TGGCAACCTT ACCTACTGCT GGATTTAGAA ATTTTATTGC | 1620 |
| AATTCTTTTA TTAATGTAAA AACCGCTCAT TTGATGAGCG GTTTTGTCTT ATCTAAAGGA | 1680 |
| GCTTTACCTC CTAATGCTGC AAAATTTTAA ATGTTGGATT TTTGTATTTG TCTATTGTAT | 1740 |
| TTGATGGGTA ATCCCATTTT TCGACAGACA TCGTCGTGCC ACCTCTAACA CCAAAATCAT | 1800 |
| AGACAGGAGC TTGTAGCTTA GCAACTATTT TATCGTC | 1837 |

(2) INFORMATION FOR SEQ ID NO:34:

(i) SEQUENCE CHARACTERISTICS:
        (A) LENGTH: 841 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:34:

| | |
|---|---|
| GATCAATATG TCCAAGAAAC CACATGTTCC TAAGACAAGA GCTAACAGAC TGGCCGTCAA | 60 |
| TAATAGTATT GTTCTTTTTT TCATCATTAC TCCTTAACTA GTGTTTAACT GATTAATTAG | 120 |
| CCAGTAAATA GTTTATCTTT ATTTACACTA TCTGTTAAGA TATAGTAAAA TGAAATAAGA | 180 |
| ACAGGACAGT CAAATCGATT TCTAACAATG TTTTAGAAGT AGAGGTATAC TATTCTAATT | 240 |
| TCAATCTACT ATATTTTGCA CATTTTCATA AAAAAAATGA GAACTAGAAC TCACATTCTG | 300 |
| CTCTCATTTT TCGTTTTCCC GTTCTCCTAT CCTGTTTTTA GGAGTTAGAA AATGCTGCTA | 360 |
| CCTTTACTTA CTCTCCTTTA ATAAAGCCAA TAGTTTTTCA GCTTCTGCCA TAATAGTATT | 420 |
| GTTGTCCTGG GTGCCAAATA GTAAATTATT TTTTAATCCT GTGAGAGTCT CTTTGGCATT | 480 |
| GGACTTGATA ATTGGATTCT GGATTTTTCC AAGTAAATCT TCAGCCTCTC TCAGTTTTCT | 540 |
| TAACCTTTCA GTCTCGACCT GAGGTTCTTC TGATTCCTCT GGTGATTCTT CTGGTGATTC | 600 |
| TTCTTCTGGT TCCTCTGTTG GTTTTGGAGA CTCTGGTTTC TCGCTTTGCG GTTTCTCTTC | 660 |
| TCGAGGGGTT TCTTCCTCAG GTTTTTCTGT CTGAGGTTTC TCCTCGTTTG GTTTTTCCGT | 720 |
| TTGATTGGTA TCAGCTTGAC CATTTTTGTT TCTTTGAACA TGGTCGCTAG CGTTACCAAA | 780 |
| ACCATTATCT GAATGCGACG TTCGTTTGGA TGTTCGACAT AGTACTTGAC AGTCGCCAAA | 840 |
| A | 841 |

(2) INFORMATION FOR SEQ ID NO:35:

(i) SEQUENCE CHARACTERISTICS:
        (A) LENGTH: 4500 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:35:

```
GATCAGGACA GTCAAATCGA TTTCTAACAA TGTTTTAGAA GTAGATGTGT ACTATTCTAG      60

TTTCAATCTA TTATATTTAT AGAATTTTTT GTTGCTAGAT TTGTCAAATT GCTTAAAATA     120

ATTTTTTTCA GAAAGCAAAA GCCGATACCT ATCGAGTAGG GTAGTTCTTG CTATCGTCAG     180

GCTTGTCTGT AGGTGTTAAC ACTTTTCAAA AATCTCTTCA ACAACGTCA GCTTTGCCTT      240

GCCGTATATA TGTTACTGAC TTCGTCAGTT CTATCTGCCA CCTCAAAACG GTGTTTTGAG     300

CTGACTTCGT CAGTTCTATC CACAACCTCA AAACAGTGTT TTGAGCTGAC TTCGTCAGTT     360

CTATCCACAA CCTCAAAACA GTGTTTTGAG CTGACTTTGT CAGTCTTATC TACAACCTCA     420

AAACAGTGTT TTGAGCATCA TGCGGCTAGC TTCTTAGTTT GCTCTTTGAT TTTCATTGAG     480

TATAAAAACA GATGAGTTTC TGTTTTCTTT TTATGGACTA TAAATGTTCA GCTGAAACTA     540

CTTTCAAGGA CATTATTATA TAAAAGAATT TTTTGAAACT AAAATCTACT ATATTACACT     600

ATATTGAAAG CGTTTTAAAA ATGAGGTATA ATAAATTTAC TAACACTTAT AAAAAGTGAT     660

AGAATCTATC TTTATGTATA TTTAAAGATA GATTGCTGTA AAAATAGTAG TAGCTATGCG     720

AAATAACAGA TAGAGAGAAG GGATTGAAGC TTAGAAAAGG GGAATAATAT GATATTTAAG     780

GCATTCAAGA CAAAAAAGCA GAGAAAAAGA CAAGTTGAAC TACTTTTGAC AGTTTTTTTC     840

GACAGTTTTC TGATTGATTT ATTTCTTCAC TTATTTGGGA TTGTCCCCTT TAAGCTGGAT     900

AAGATTCTGA TTGTGAGCTT GATTATATTT CCCATTATTT CTACAAGTAT TTATGCTTAT     960

GAAAAGCTAT TTGAAAAAGT GTTCGATAAG GATTGAGCAG GAAGTATGGT GTAAATAGCA    1020

TAAGCTGATG TCCATCATTT GCTTATAAAG AGATATTTTA GTTTAATTGC AGCGGTGTCC    1080

TGGTAGATAA ACTAGATTGG CAGGAGTCTG ATTGGAGAAA GGAGAGGGGA AATTTGGCAC    1140

CAATTTGAGA TAGTTTGTTT AGTTCATTTT TGTCATTTAA ATGAACTGTA GTAAAAGAAA    1200

GTTAATAAAA GACAAACTAA GTGCATTTTC TGGAATAAAT GTCTTATTTC AGAAATCGGG    1260

ATATAGATAT AGAGAGGAAC AGTATGAATC GGAGTGTTCA AGAACGTAAG TGTCGTTATA    1320

GCATTAGGAA ACTATCGGTA GGAGCGGTTT CTATGATTGT AGGAGCAGTG GTATTTGGAA    1380

CGTCTCCTGT TTTAGCTCAA GAAGGGGCAA GTGAGCAACC TCTGGCAAAT GAAACTCAAC    1440

TTTCGGGGA GAGCTCAACC CTAACTGATA CAGAAAAGAG CCAGCCTTCT TCAGAGACTG     1500

AACTTTCTGG CAATAAGCAA GAACAAGAAA GGAAAGATAA GCAAGAAGAA AAAATTCCAA    1560

GAGATTACTA TGCACGAGAT TTGGAAAATG TCGAAACAGT GATAGAAAAA GAAGATGTTG    1620

AAACCAATGC TTCAAATGGT CAGAGAGTTG ATTTATCAAG TGAACTAGAT AAACTAAAGA    1680

AACTTGAAAA CGCAACAGTT CACATGGAGT TTAAGCCAGA TGCCAAGGCC CCAGCATTCT    1740

ATAATCTCTT TTCTGTGTCA AGTGCTACTA AAAAAGATGA GTACTTCACT ATGGCAGTTT    1800

ACAATAATAC TGCTACTCTA GAGGGCGTG GTTCGGATGG GAAACAGTTT TACAATAATT     1860

ACAACGATGC ACCCTTAAAA GTTAAACCAG GTCAGTGGAA TTCTGTGACT TTCACAGTTG    1920

AAAAACCGAC AGCAGAACTA CCTAAAGGCC GAGTGCGCCT CTACGTAAAC GGGGTATTAT    1980

CTCGAACAAG TCTGAGATCT GGCAATTTCA TTAAAGATAT GCCAGATGTA ACGCATGTGC    2040

AAATCGGAGC AACCAAGCGT GCCAACAATA CGGTTTGGGG GTCAAATCTA CAGATTCGGA    2100

ATCTCACTGT GTATAATCGT GCTTTAACAC CAGAAGAGGT ACAAAAACGT AGTCAACTTT    2160

TTAAACGCTC AGATTTAGAA AAAAAACTAC CTGAAGGAGC GGCTTAACA GAGAAAACGG     2220

ACATATTCGA AAGCGGGCGT AACGGTAAAC CAAATAAAGA TGGAATCAAG AGTTATCGTA    2280

TTCCAGCACT TCTCAAGACA GATAAAGGAA CTTTGATCGC AGGTGCAGAT GAACGCCGTC    2340
```

```
TCCATTCGAG TGACTGGGGT GATATCGGTA TGGTCATCAG ACGTAGTGAA GATAATGGTA    2400

AAACTTGGGG TGACCGAGTA ACCATTACCA ACTTACGTGA CAATCCAAAA GCTTCTGACC    2460

CATCGATCGG TTCACCAGTG AATATCGATA TGGTGTTGGT TCAAGATCCT GAAACCAAAC    2520

GAATCTTTTC TATCTATGAC ATGTTCCCAG AAGGGAAGGG AATCTTTGGA ATGTCTTCAC    2580

AAAAAGAAGA AGCCTACAAA AAAATCGATG GAAAAACCTA TCAAATCCTC TATCGTGAAG    2640

GAGAAAAGGG AGCTTATACC ATTCGAGAAA ATGGTACTGT CTATACACCA GATGGTAAGG    2700

CGACAGACTA TCGCGTTGTT GTAGATCCTG TTAAACCAGC CTATAGCGAC AAGGGGGATC    2760

TATACAAGGG TAACCAATTA CTAGGCAATA TCTACTTCAC AACAAACAAA ACTTCTCCAT    2820

TTAGAATTGC CAAGGATAGC TATCTATGGA TGTCCTACAG TGATGACGAC GGGAAGACAT    2880

GGTCAGCGCC TCAAGATATT ACTCCGATGG TCAAAGCCGA TTGGATGAAA TTCTTGGGTG    2940

TAGGTCCTGG AACAGGAATT GTACTTCGGA ATGGGCCTCA CAAGGGACGG ATTTTGATAC    3000

CGGTTTATAC GACTAATAAT GTATCTCACT TAAATGGCTC GCAATCTTCT CGTATCATCT    3060

ATTCAGATGA TCATGGAAAA ACTTGGCATG CTGGAGAAGC GGTCAACGAT AACCGTCAGG    3120

TAGACGGTCA AAAGATCCAC TCTTCTACGA TGAACAATAG ACGTGCGCAA AATACAGAAT    3180

CAACGGTGGT ACAACTAAAC AATGGAGATG TTAAACTCTT TATGCGTGGT TTGACTGGAG    3240

ATCTTCAGGT TGCTACAAGT AAAGACGGAG GAGTGACTTG GGAGAAGGAT ATCAAACGTT    3300

ATCCACAGGT TAAAGATGTC TATGTTCAAA TGTCTGCTAT CCATACGATG CACGAAGGAA    3360

AAGAATACAT CATCCTCAGT AATGCAGGTG GACCGAAACG TGAAAATGGG ATGGTCCACT    3420

TGGCACGTGT CGAAGAAAAT GGTGAGTTGA CTTGGCTCAA ACACAATCCA ATTCAAAAAG    3480

GAGAGTTTGC CTATAATTCG CTCCAAGAAT TAGGAAATGG GGAGTATGGC ATCTTGTATG    3540

AACATACTGA AAAAGGACAA AATGCCTATA CCCTATCATT TAGAAAATTT AATTGGGACT    3600

TTTTGAGCAA AGATCTGATT TCTCCTACCG AAGCGAAAGT GAAGCGAACT AGAGAGATGG    3660

GCAAAGGAGT TATTGGCTTG GAGTTCGACT CAGAAGTATT GGTCAACAAG CTCCAACCC    3720

TTCAATTGGC AAATGGTAAA ACAGCACGCT TCATGACCCA GTATGATACA AAAACCCTCC    3780

TATTTACAGT GGATTCAGAG GATATGGGTC AAAAAGTTAC AGGTTTGGCA GAAGGTGCAA    3840

TTGAAAGTAT GCATAATTTA CCAGTCTCTG TGGCGGGCAC TAAGCTTTCG AATGGAATGA    3900

ACGGAAGTGA AGCTGCTGTT CATGAAGTGC CAGAATACAC AGGCCCATTA GGGACATCCG    3960

GCGAAGAGCC AGCTCCAACA GTCGAGAAGC CAGAATACAC AGGCCCACTA GGGACATCCG    4020

GCGAAGAGCC AGCCCCGACA GTCGAGAAGC CAGAATACAC AGGCCCACTA GGGACAGCTG    4080

GTGAAGAAGC AGCTCCAACA GTCGAGAAGC CAGAATTTAC AGGGGGAGTT AATGGTACAG    4140

AGCCAGCTGT TCATGAAATC GCAGAGTATA AGGGATCTGA TTCGCTTGTA ACTCTTACTA    4200

CAAAAGAAGA TTATACTTAC AAAGCTCCTC TTGCTCAGCA GGCACTTCCT GAAACAGGAA    4260

ACAAGGAGAG TGACCTCCTA GCTTCACTAG GACTAACAGC TTTCTTCCTT GGTCTGTTTA    4320

CGCTAGGGAA AAAGAGAGAA CAATAAGAGA AGAATTCTAA ACATTTGATT TTGTAAAAAT    4380

AGAAGGAGAT AGCAGGTTTT CAAGCCTGCT ATCTTTTTTT GATGACATTC AGGCTGATAC    4440

GAAATCATAA GAGGTCTGAA ACTACTTTCA GAGTAGTCTG TTCTATAAAA TATAGTAGAT    4500

(2) INFORMATION FOR SEQ ID NO:36:

(i) SEQUENCE CHARACTERISTICS:
        (A) LENGTH: 705 base pairs
        (B) TYPE: nucleic acid
        (C) STRANDEDNESS: double
```

(D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:36:

GATCCAAGCT TATCGATATC ATCAAAAAGT TGGCGAACCT TTTCAAATTT TGGTTCAAAT      60

TCTTGAGATG TATAGAATTC AAAATATTTA CCATTTGCAT AGTCTGATTG CTCAAAGTCT     120

TGATACTTTT CTCCACGCTC TTTTGCAATT TCCATTGAAC GTTCGATGGA ATAATAGTTC     180

ATAATCATAA AGAATATATT AGCAAAGTCT TTTGCTTCTT CAGATTCATA GCCAATTTTA     240

TTTTTAGCTA GATAACCATG TAAGTTCATT ACTCCTAGTC AACAGAATG TAGTTCACTA      300

TTCGCTTTTT TTACACCTGG TGCATTTTGA ATATTTGCTT CATCACTTAC AACTGTAAGA     360

GCATCCATAC CTGTGAACAC AGAATCTCTG AATTTACCTG ATTCCATAAC ATTCACTATA     420

TTCAATGAGC CTAAGTTACA TGAAATATCT CTTTTAATTT CATCTTCAAT TCCATAGTCG     480

TTAATTACTG ATGTCTCTTG TAATTGGAAA ATTTCAGTAC ATAAATTACT CATTTTAATT     540

TGCCCAATAT TTGAATTCGC ATGTACTTTG TTTGCATTAT CTTTAAACAT AAGATATGGA     600

TAACCAGACT GTAATTGTGT TTGTGCAATC ATATTTAACA TTTCACGTGC GTCTTTTTTC     660

TTTTTATCGA TTTCGAACCC GGGGTACCGA ATTCCTCGAG TCTAG                     705

(2) INFORMATION FOR SEQ ID NO:37:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus aureus (xi) SEQUENCE DESCRIPTION: SEQ ID NO:37:

GATCAATCTT TGTCGGTACA CGATATTCTT CACGACTAAA TAAACGCTCA TTCGCGATTT      60

TATAAATGAA TGTTGATAAC AATGTTGTAT TATCTACTGA AATCTCATTA CGTTGCATCG     120

GAAACATTGT GTTCTGTATG TAAAAGCCGT CTTGATAATC TTTAGTAGTA CCGAAGCTGG     180

TCATACGAGA GTTATATTTT CCAGCCAAAA CGATATTTTT ATAATCATTA CGTGAAAAAG     240

GTTTCCCTTC ATTATCACAC AAATATTTTA GCTTTTCAGT TTCTATATCA ACTGTAGCTT     300

CTTTATCCAT ACGTTGAATA ATTGTACGAT TCTGACGCAC CATCTTTTGC ACACCTTTAA     360

TGTTATTTGT TTTAAAAGCA TGAATAAGTT TTTCAACACA ACGATGTGAA TCTTCTAAGA     420

AGTCACCGTA AAATGAAGGA TC                                              442

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:38:

GCAATACAGG GAAAAATGTC                                                         20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:39:

CTTCATCAAA CAATTAACTC                                                         20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:40:

GAACAGAAGA AGCCAAAAAA                                                         20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:41:

GCAATCCCAA ATAATACGGT                                                         20

(2) INFORMATION FOR SEQ ID NO:42:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:42:

GCTTTCCAGC GTCATATTG                                                          19

(2) INFORMATION FOR SEQ ID NO:43:

(i) SEQUENCE CHARACTERISTICS:
        (A) LENGTH: 19 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:43:

GATCTCGACA AAATGGTGA                                                      19

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:44:

CACCCGCTTG CGTGGCAAGC TGCCC                                               25

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:45:

CGTTTGTGGA TTCCAGTTCC ATCCG                                               25

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:46:

TCACCCGCTT GCGTGGC                                                        17

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli
```

(xi) SEQUENCE DESCRIPTION: SEQ ID NO:47:

GGAACTGGAA TCCACAAAC                    19

(2) INFORMATION FOR SEQ ID NO:48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:48:

TGAAGCACTG GCCGAAATGC TGCGT              25

(2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:49:

GATGTACAGG ATTCGTTGAA GGCTT              25

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:50:

TAGCGAAGGC GTAGCAGAAA CTAAC              25

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:51:

GCAACCCGAA CTCAACGCCG GATTT              25

(2) INFORMATION FOR SEQ ID NO:52:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Escherichia coli (xi) SEQUENCE DESCRIPTION: SEQ ID NO:52:

ATACACAAGG GTCGCATCTG CGGCC                                              25

(2) INFORMATION FOR SEQ ID NO:53:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Escherichia coli (xi) SEQUENCE DESCRIPTION: SEQ ID NO:53:

TGCGTATGCA TTGCAGACCT TGTGGC                                             26

(2) INFORMATION FOR SEQ ID NO:54:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Escherichia coli (xi) SEQUENCE DESCRIPTION: SEQ ID NO:54:

GCTTTCACTG GATATCGCGC TTGGG                                              25

(2) INFORMATION FOR SEQ ID NO:55:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Escherichia coli (xi) SEQUENCE DESCRIPTION: SEQ ID NO:55:

GCAACCCGAA CTCAACGCC                                                     19

(2) INFORMATION FOR SEQ ID NO:56:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
              (A) ORGANISM: Escherichia coli (xi) SEQUENCE DESCRIPTION: SEQ ID NO:56:

GCAGATGCGA CCCTTGTGT                                                  19

(2) INFORMATION FOR SEQ ID NO:57:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: Klebsiella pneumoniae (xi) SEQUENCE DESCRIPTION: SEQ ID NO:57:

GTGGTGTCGT TCAGCGCTTT CAC                                             23

(2) INFORMATION FOR SEQ ID NO:58:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: Klebsiella pneumoniae (xi) SEQUENCE DESCRIPTION: SEQ ID NO:58:

GCGATATTCA CACCCTACGC AGCCA                                           25

(2) INFORMATION FOR SEQ ID NO:59:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: Klebsiella pneumoniae (xi) SEQUENCE DESCRIPTION: SEQ ID NO:59:

GTCGAAAATG CCGGAAGAGG TATACG                                          26

(2) INFORMATION FOR SEQ ID NO:60:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: Klebsiella pneumoniae (xi) SEQUENCE DESCRIPTION: SEQ ID NO:60:

ACTGAGCTGC AGACCGGTAA AACTCA                                          26

(2) INFORMATION FOR SEQ ID NO:61:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:61:

GACAGTCAGT TCGTCAGCC                                                     19

(2) INFORMATION FOR SEQ ID NO:62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:62:

CGTAGGGTGT GAATATCGC                                                     19

(2) INFORMATION FOR SEQ ID NO:63:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:63:

CGTGATGGAT ATTCTTAACG AAGGGC                                   26

(2) INFORMATION FOR SEQ ID NO:64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:64:

ACCAAACTGT TGAGCCGCCT GGA                                         23

(2) INFORMATION FOR SEQ ID NO:65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear

```
    (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:65:

GTGATCGCCC CTCATCTGCT ACT                                            23

(2) INFORMATION FOR SEQ ID NO:66:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:66:

CGCCCTTCGT TAAGAATATC CATCAC                                         26

(2) INFORMATION FOR SEQ ID NO:67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:67:

TCGCCCCTCA TCTGCTACT                                                 19

(2) INFORMATION FOR SEQ ID NO:68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:68:

GATCGTGATG GATATTCTT                                                 19

(2) INFORMATION FOR SEQ ID NO:69:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:69:

CAGGAAGATG CTGCACCGGT TGTTG                                          25
```

(2) INFORMATION FOR SEQ ID NO:70:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:70:

TGGTTCACTG ACTTTGCGAT GTTTC                                                25

(2) INFORMATION FOR SEQ ID NO:71:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:71:

TCGAGGATGG CATGCACTAG AAAAT                                                25

(2) INFORMATION FOR SEQ ID NO:72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:72:

CGCTGATTAG GTTTCGCTAA AATCTTATTA                                      30

(2) INFORMATION FOR SEQ ID NO:73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:73:

TTGATCCTCA TTTTATTAAT CACATGACCA                                      30

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
            (A) ORGANISM: Proteus mirabilis (xi) SEQUENCE DESCRIPTION: SEQ ID NO:74:

GAAACATCGC AAAGTCAGT                                                        19

(2) INFORMATION FOR SEQ ID NO:75:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Proteus mirabilis (xi) SEQUENCE DESCRIPTION: SEQ ID NO:75:

ATAAAATGAG GATCAAGTTC                                                       20

(2) INFORMATION FOR SEQ ID NO:76:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Proteus mirabilis (xi) SEQUENCE DESCRIPTION: SEQ ID NO:76:

CCGCCTTTAG CATTAATTGG TGTTTATAGT                                            30

(2) INFORMATION FOR SEQ ID NO:77:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Proteus mirabilis (xi) SEQUENCE DESCRIPTION: SEQ ID NO:77:

CCTATTGCAG ATACCTTAAA TGTCTTGGGC                                            30

(2) INFORMATION FOR SEQ ID NO:78:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Streptococcus pneumoniae (xi) SEQUENCE DESCRIPTION: SEQ ID NO:78:

AGTAAAATGA AATAAGAACA GGACAG                                              26

(2) INFORMATION FOR SEQ ID NO:79:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:79:

AAAACAGGAT AGGAGAACGG GAAAA                                               25

(2) INFORMATION FOR SEQ ID NO:80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:80:

TTGAGTGATG ATTTCACTGA CTCCC                                               25

(2) INFORMATION FOR SEQ ID NO:81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:81:

GTCAGACAGT GATGCTGACG ACACA                                               25

(2) INFORMATION FOR SEQ ID NO:82:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:82:

TGGTTGTCAT GCTGTTTGTG TGAAAAT                                             27

(2) INFORMATION FOR SEQ ID NO:83:

(i) SEQUENCE CHARACTERISTICS:
        (A) LENGTH: 19 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:83:

CGAGCGGGTG GTGTTCATC                                                19

(2) INFORMATION FOR SEQ ID NO:84:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:84:

CAAGTCGTCG TCGGAGGGA                                                19

(2) INFORMATION FOR SEQ ID NO:85:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:85:

TCGCTGTTCA TCAAGACCC                                                19

(2) INFORMATION FOR SEQ ID NO:86:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:86:

CCGAGAACCA GACTTCATC                                                19

(2) INFORMATION FOR SEQ ID NO:87:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:87:

AATGCGGCTG TACCTCGGCG CTGGT                                      25

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:88:

GGCGGAGGGC CAGTTGCACC TGCCA                                      25

(2) INFORMATION FOR SEQ ID NO:89:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:89:

AGCCCTGCTC CTCGGCAGCC TCTGC                                      25

(2) INFORMATION FOR SEQ ID NO:90:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:90:

TGGCTTTTGC AACCGCGTTC AGGTT                                      25

(2) INFORMATION FOR SEQ ID NO:91:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:91:

GCGCCCGCGA GGGCATGCTT CGATG                                      25

(2) INFORMATION FOR SEQ ID NO:92:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:92:

ACCTGGGCGC CAACTACAAG TTCTA                                              25

(2) INFORMATION FOR SEQ ID NO:93:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:93:

GGCTACGCTG CCGGGCTGCA GGCCG                                              25

(2) INFORMATION FOR SEQ ID NO:94:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:94:

CCGATCTACA CCATCGAGAT GGGCG                                              25

(2) INFORMATION FOR SEQ ID NO:95:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:95:

GAGCGCGGCT ATGTGTTCGT CGGCT                                              25

(2) INFORMATION FOR SEQ ID NO:96:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Staphylococcus saprophyticus (xi) SEQUENCE DESCRIPTION: SEQ ID NO:96:

CGTTTTTACC CTTACCTTTT CGTACTACC                              29

(2) INFORMATION FOR SEQ ID NO:97:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Staphylococcus saprophyticus (xi) SEQUENCE DESCRIPTION: SEQ ID NO:97:

TCAGGCAGAG GTAGTACGAA AAGGTAAGGG                              30

(2) INFORMATION FOR SEQ ID NO:98:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Staphylococcus saprophyticus (xi) SEQUENCE DESCRIPTION: SEQ ID NO:98:

CGTTTTTACC CTTACCTTTT CGTACT                                 26

(2) INFORMATION FOR SEQ ID NO:99:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Staphylococcus saprophyticus (xi) SEQUENCE DESCRIPTION: SEQ ID NO:99:

ATCGATCATC ACATTCCATT TGTTTTTA                               28

(2) INFORMATION FOR SEQ ID NO:100:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Staphylococcus saprophyticus (xi) SEQUENCE DESCRIPTION: SEQ ID NO:100:

CACCAAGTTT GACACGTGAA GATTCAT                                27

(2) INFORMATION FOR SEQ ID NO:101:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:101:

ATGAGTGAAG CGGAGTCAGA TTATGTGCAG                                    30

(2) INFORMATION FOR SEQ ID NO:102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:102:

CGCTCATTAC GTACAGTGAC AATCG                                         25

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:103:

CTGGTTAGCT TGACTCTTAA CAATCTTGTC                                    30

(2) INFORMATION FOR SEQ ID NO:104:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:104:

GACGCGATTG TCACTGTACG TAATGAGCGA                                    30

(2) INFORMATION FOR SEQ ID NO:105:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: Haemophilus influenzae (xi) SEQUENCE DESCRIPTION: SEQ ID NO:105:

GCGTCAGAAA AAGTAGGCGA AATGAAAG                                            28

(2) INFORMATION FOR SEQ ID NO:106:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:106:

AGCGGCTCTA TCTTGTAATG ACACA                                               25

(2) INFORMATION FOR SEQ ID NO:107:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:107:

GAAACGTGAA CTCCCCTCTA TATAA                                               25

(2) INFORMATION FOR SEQ ID NO:108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:108:

GCCCCAAAAC AATGAAACAT ATGGT                                               25

(2) INFORMATION FOR SEQ ID NO:109:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:109:

CTGCAGATTT TGGAATCATA TCGCC                                               25

(2) INFORMATION FOR SEQ ID NO:110:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catharralis (xi) SEQUENCE DESCRIPTION: SEQ ID NO:110:

TGGTTTGACC AGTATTTAAC GCCAT                                        25

(2) INFORMATION FOR SEQ ID NO:111:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catharralis (xi) SEQUENCE DESCRIPTION: SEQ ID NO:111:

CAACGGCACC TGATGTACCT TGTAC                                        25

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:112:

GGCACCTGAT GTACCTTG                                                18

(2) INFORMATION FOR SEQ ID NO:113:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:113:

AACAGCTCAC ACGCATT                                                 17

(2) INFORMATION FOR SEQ ID NO:114:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:114:

TTACAACCTG CACCACAAGT CATCA                                             25

(2) INFORMATION FOR SEQ ID NO:115:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:115:

GTACAAACAA GCCGTCAGCG ACTTA                                             25

(2) INFORMATION FOR SEQ ID NO:116:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:116:

CAATCTGCGT GTGTGCGTTC ACT                                               23

(2) INFORMATION FOR SEQ ID NO:117:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:117:

GCTACTTTGT CAGCTTTAGC CATTCA                                            26

(2) INFORMATION FOR SEQ ID NO:118:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:118:

```
TGTTTTGAGC TTTTTATTTT TTGA                                                  24

(2) INFORMATION FOR SEQ ID NO:119:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Moraxella catarrhalis (xi) SEQUENCE DESCRIPTION: SEQ ID NO:119:

CGCTGACGGC TTGTTTGTAC CA                                                    22

(2) INFORMATION FOR SEQ ID NO:120:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Streptococcus pneumoniae (xi) SEQUENCE DESCRIPTION: SEQ ID NO:120:

TCTGTGCTAG AGACTGCCCC ATTTC                                                 25

(2) INFORMATION FOR SEQ ID NO:121:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Streptococcus pneumoniae (xi) SEQUENCE DESCRIPTION: SEQ ID NO:121:

CGATGTCTTG ATTGAGCAGG GTTAT                                                 25

(2) INFORMATION FOR SEQ ID NO:122:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:122:

ATCCCACCTT AGGCGGCTGG CTCCA                                                 25

(2) INFORMATION FOR SEQ ID NO:123:

(i) SEQUENCE CHARACTERISTICS:
         (A) LENGTH: 31 base pairs
         (B) TYPE: nucleic acid
         (C) STRANDEDNESS: single
         (D) TOPOLOGY: linear
```

(ii) MOLECULE TYPE: DNA (genomic)

(xi) SEQUENCE DESCRIPTION: SEQ ID NO:123:

ACGTCAAGTC ATCATGGCCC TTACGAGTAG G                                31

(2) INFORMATION FOR SEQ ID NO:124:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:124:

GTGTGACGGG CGGTGTGTAC AAGGC                                      25

(2) INFORMATION FOR SEQ ID NO:125:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:125:

GAGTTGCAGA CTCCAATCCG GACTACGA                                   28

(2) INFORMATION FOR SEQ ID NO:126:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:126:

GGAGGAAGGT GGGGATGACG                                            20

(2) INFORMATION FOR SEQ ID NO:127:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:127:

ATGGTGTGAC GGGCGGTGTG                                            20

(2) INFORMATION FOR SEQ ID NO:128:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:128:

```
CCCTATACAT CACCTTGCGG TTTAGCAGAG AG                                       32
```

(2) INFORMATION FOR SEQ ID NO:129:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

```
GGGGGGACCA TCCTCCAAGG CTAAATAC                                            28
```

(2) INFORMATION FOR SEQ ID NO:130:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

```
CGTCCACTTT CGTGTTTGCA GAGTGCTGTG TT                                       32
```

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:131:

```
CAGGAGTACG GTGATTTTTA                                                     20
```

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:132:

```
ATTTCTGGTT TGGTCATACA                                                     20
```

(2) INFORMATION FOR SEQ ID NO:133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: Proteus mirabilis (xi) SEQUENCE DESCRIPTION: SEQ ID NO:133:

CGGGAGTCAG TGAAATCATC                                                    20

(2) INFORMATION FOR SEQ ID NO:134:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:134:

CTAAAATCGC CACACCTCTT                                                    20

(2) INFORMATION FOR SEQ ID NO:135:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:135:

GCAGCGTGGT GTCGTTCA                                                      18

(2) INFORMATION FOR SEQ ID NO:136:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:136:

AGCTGGCAAC GGCTGGTC                                                      18

(2) INFORMATION FOR SEQ ID NO:137:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:137:

ATTCACACCC TACGCAGCCA                                                    20

(2) INFORMATION FOR SEQ ID NO:138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:138:

ATCCGGCAGC ATCTCTTTGT                                                    20

(2) INFORMATION FOR SEQ ID NO:139:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:139:

CTGGTTAGCT TGACTCTTAA CAATC                                              25

(2) INFORMATION FOR SEQ ID NO:140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:140:

TCTTAACGAT AGAATGGAGC AACTG                                              25

(2) INFORMATION FOR SEQ ID NO:141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:141:

TGAAAATTCT TGTAACAGGC                                                    20

(2) INFORMATION FOR SEQ ID NO:142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: Streptococcus pyogenes (xi) SEQUENCE DESCRIPTION: SEQ ID NO:142:

GGCCACCAGC TTGCCCAATA                                                   20

(2) INFORMATION FOR SEQ ID NO:143:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:143:

ATATTTTCTT TATGAGGGTG                                                   20

(2) INFORMATION FOR SEQ ID NO:144:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:144:

ATCCTTAAAT AAAGTTGCCA                                                   20

(2) INFORMATION FOR SEQ ID NO:145:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:145:

ATCAAAAAGT TGGCGAACCT TTTCA                                             25

(2) INFORMATION FOR SEQ ID NO:146:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:146:

CAAAAGAGCG TGGAGAAAAG TATCA                                             25

(2) INFORMATION FOR SEQ ID NO:147:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: Staphylococcus epidermidis (xi) SEQUENCE DESCRIPTION: SEQ ID NO:147:

TCTCTTTTAA TTTCATCTTC AATTCCATAG                                    30

(2) INFORMATION FOR SEQ ID NO:148:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: Staphylococcus epidermidis (xi) SEQUENCE DESCRIPTION: SEQ ID NO:148:

AAACACAATT ACAGTCTGGT TATCCATATC                                    30

(2) INFORMATION FOR SEQ ID NO:149:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: Staphylococcus aureus (xi) SEQUENCE DESCRIPTION: SEQ ID NO:149:

CTTCATTTTA CGGTGACTTC TTAGAAGATT                                    30

(2) INFORMATION FOR SEQ ID NO:150:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: Staphylococcus aureus (xi) SEQUENCE DESCRIPTION: SEQ ID NO:150:

TCAACTGTAG CTTCTTTATC CATACGTTGA                                    30

(2) INFORMATION FOR SEQ ID NO:151:

(i) SEQUENCE CHARACTERISTICS:
       (A) LENGTH: 30 base pairs
       (B) TYPE: nucleic acid
       (C) STRANDEDNESS: single
       (D) TOPOLOGY: linear

```
        (ii) MOLECULE TYPE: DNA (genomic)

(vi) ORIGINAL SOURCE:
             (A) ORGANISM: Staphylococcus aureus (xi) SEQUENCE DESCRIPTION: SEQ ID NO:151:

ATATTTTAGC TTTTCAGTTT CTATATCAAC                                      30

(2) INFORMATION FOR SEQ ID NO:152:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Staphylococcus aureus (xi) SEQUENCE DESCRIPTION: SEQ ID NO:152:

AATCTTTGTC GGTACACGAT ATTCTTCACG                                      30

(2) INFORMATION FOR SEQ ID NO:153:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Staphylococcus aureus (xi) SEQUENCE DESCRIPTION: SEQ ID NO:153:

CGTAATGAGA TTTCAGTAGA TAATACAACA                                      30

(2) INFORMATION FOR SEQ ID NO:154:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Haemophilus influenzae (xi) SEQUENCE DESCRIPTION: SEQ ID NO:154:

TTTAACGATC CTTTTACTCC TTTTG                                           25

(2) INFORMATION FOR SEQ ID NO:155:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Haemophilus influenzae (xi) SEQUENCE DESCRIPTION: SEQ ID NO:155:
```

```
ACTGCTGTTG TAAAGAGGTT AAAAT                                           25

(2) INFORMATION FOR SEQ ID NO:156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:156:

ATTTGGTGAC GGGTGACTTT                                                 20

(2) INFORMATION FOR SEQ ID NO:157:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:157:

GCTGAGGATT TGTTCTTCTT                                                 20

(2) INFORMATION FOR SEQ ID NO:158:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:158:

GAGCGGTTTC TATGATTGTA                                                 20

(2) INFORMATION FOR SEQ ID NO:159:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:159:

ATCTTTCCTT TCTTGTTCTT                                                 20

(2) INFORMATION FOR SEQ ID NO:160:

(i) SEQUENCE CHARACTERISTICS:
        (A) LENGTH: 18 base pairs
        (B) TYPE: nucleic acid
```

(C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:160:

GCTCAAATCA GGGTCAGC                                                    18

(2) INFORMATION FOR SEQ ID NO:161:

(i) SEQUENCE CHARACTERISTICS:
        (A) LENGTH: 861 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:161:

ATGAGTATTC AACATTTCCG TGTCGCCCTT ATTCCCTTTT TTGCGGCATT TTGCCTTCCT        60

GTTTTTGCTC ACCCAGAAAC GCTGGTGAAA GTAAAAGATG CTGAAGATCA GTTGGGTGCA       120

CGAGTGGGTT ACATCGAACT GGATCTCAAC AGCGGTAAGA TCCTTGAGAG TTTTCGCCCC       180

GAAGAACGTT TTCCAATGAT GAGCACTTTT AAAGTTCTGC TATGTGGCGC GGTATTATCC       240

CGTGTTGACG CCGGGCAAGA GCAACTCGGT CGCCGCATAC ACTATTCTCA GAATGACTTG       300

GTTGAGTACT CACCAGTCAC AGAAAAGCAT CTTACGGATG GCATGACAGT AAGAGAATTA       360

TGCAGTGCTG CCATAACCAT GAGTGATAAC ACTGCGGCCA ACTTACTTCT GACAACGATC       420

GGAGGACCGA AGGAGCTAAC CGCTTTTTTG CACAACATGG GGATCATGT AACTCGCCTT        480

GATCGTTGGG AACCGGAGCT GAATGAAGCC ATACCAAACG ACGAGCGTGA CACCACGATG       540

CCTGCAGCAA TGGCAACAAC GTTGCGCAAA CTATTAACTG GCGAACTACT TACTCTAGCT       600

TCCCGGCAAC AATTAATAGA CTGGATGGAG GCGGATAAAG TTGCAGGACC ACTTCTGCGC       660

TCGGCCCTTC CGGCTGGCTG GTTTATTGCT GATAAATCTG GAGCCGGTGA GCGTGGGTCT       720

CGCGGTATCA TTGCAGCACT GGGGCCAGAT GGTAAGCCCT CCCGTATCGT AGTTATCTAC       780

ACGACGGGGA GTCAGGCAAC TATGGATGAA CGAAATAGAC AGATCGCTGA GATAGGTGCC       840

TCACTGATTA AGCATTGGTA A                                                861

(2) INFORMATION FOR SEQ ID NO:162:

(i) SEQUENCE CHARACTERISTICS:
        (A) LENGTH: 918 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:162:

ATGTTAAATA AGTTAAAAAT CGGCACATTA TTATTGCTGA CATTAACGGC TTGTTCGCCC        60

AATTCTGTTC ATTCGGTAAC GTCTAATCCG CAGCCTGCTA GTGCGCCTGT GCAACAATCA       120

GCCACACAAG CCACCTTTCA ACAGACTTTG GCGAATTTGG AACAGCAGTA TCAAGCCCGA       180

ATTGGCGTTT ATGTATGGGA TACAGAAACG GGACATTCTT TGTCTTATCG TGCAGATGAA       240

CGCTTTGCTT ATGCGTCCAC TTTCAAGGCG TTGTTGGCTG GGGCGGTGTT GCAATCGCTG       300

CCTGAAAAAG ATTTAAATCG TACCATTTCA TATAGCCAAA AAGATTTGGT TAGTTATTCT       360

```
CCCGAAACCC AAAAATACGT TGGCAAAGGC ATGACGATTG CCCAATTATG TGAAGCAGCC      420

GTGCGGTTTA GCGACAACAG CGCGACCAAT TTGCTGCTCA AGAATTGGG TGGCGTGGAA       480

CAATATCAAC GTATTTTGCG ACAATTAGGC GATAACGTAA CCCATACCAA TCGGCTAGAA      540

CCCGATTTAA ATCAAGCCAA ACCCAACGAT ATTCGTGATA CGAGTACACC CAAACAAATG     600

GCGATGAATT TAAATGCGTA TTTATTGGGC AACACATTAA CCGAATCGCA AAAAACGATT    660

TTGTGGAATT GGTTGGACAA TAACGCAACA GGCAATCCAT TGATTCGCGC TGCTACGCCA     720

ACATCGTGGA AAGTGTACGA TAAAAGCGGG GCGGGTAAAT ATGGTGTACG CAATGATATT    780

GCGGTGGTTC GCATACCAAA TCGCAAACCG ATTGTGATGG CAATCATGAG TACGCAATTT     840

ACCGAAGAAG CCAAATTCAA CAATAAATTA GTAGAAGATG CAGCAAAGCA AGTATTTCAT     900

ACTTTACAGC TCAACTAA                                                   918

(2) INFORMATION FOR SEQ ID NO:163:

(i) SEQUENCE CHARACTERISTICS:
        (A) LENGTH: 864 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:163:

ATGCGTTATA TTCGCCTGTG TATTATCTCC CTGTTAGCCA CCCTGCCGCT GGCGGTACAC      60

GCCAGCCCGC AGCCGCTTGA GCAAATTAAA CTAAGCGAAA GCCAGCTGTC GGGCCGCGTA     120

GGCATGATAG AAATGGATCT GGCCAGCGGC CGCACGCTGA CCGCCTGGCG CGCCGATGAA     180

CGCTTTCCCA TGATGAGCAC CTTTAAAGTA GTGCTCTGCG GCGCAGTGCT GGCGCGGGTG    240

GATGCCGGTG ACGAACAGCT GGAGCGAAAG ATCCACTATC GCCAGCAGGA TCTGGTGGAC    300

TACTCGCCGG TCAGCGAAAA ACACCTTGCC GACGCAATGA CGGTCGGCGA ACTCTGCGCC     360

GCCGCCATTA CCATGAGCGA TAACAGCGCC GCCAATCTGC TACTGGCCAC CGTCGGCGGC     420

CCCGCAGGAT TGACTGCCTT TTTGCGCCAG ATCGGCGACA ACGTCACCCG CCTTGACCGC     480

TGGGAAACGG AACTGAATGA GGCGCTTCCC GGCGACGCCC GCGACACCAC TACCCCGGCC     540

AGCATGGCCG CGACCCTGCG CAACGTTGGC CTGACCAGCC AGCGTCTGAG CGCCCGTTCG     600

CAACGGCAGC TGCTGCAGTG GATGGTGGAC GATCGGGTCG CCGGACCGTT GATCCGCTCC     660

GTGCTGCCGG CGGGCTGGTT TATCGCCGAT AAGACCGGAG CTGGCGAGCG GGTGCGCGC     720

GGGATTGTCG CCCTGCTTGG CCCGAATAAC AAAGCAGAGC GCATTGTGGT GATTTATCTG    780

CGGGATACCC CGGCGAGCAT GGCCGAGCGA ATCAGCAAA TCGCCGGGAT CGGCAAGGCG      840

CTGTACGAGC ACTGGCAACG CTAA                                            864

(2) INFORMATION FOR SEQ ID NO:164:

(i) SEQUENCE CHARACTERISTICS:
        (A) LENGTH: 534 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:164:

ATGGACACAA CGCAGGTCAC ATTGATACAC AAAATTCTAG CTGCGGCAGA TGAGCGAAAT      60

CTGCCGCTCT GGATCGGTGG GGGCTGGGCG ATCGATGCAC GGCTAGGGCG TGTAACACGC    120
```

```
AAGCACGATG ATATTGATCT GACGTTTCCC GGCGAGAGGC GCGGCGAGCT CGAGGCAATA    180

GTTGAAATGC TCGGCGGGCG CGTCATGGAG GAGTTGGACT ATGGATTCTT AGCGGAGATC    240

GGGGATGAGT TACTTGACTG CGAACCTGCT TGGTGGGCAG ACGAAGCGTA TGAAATCGCG    300

GAGGCTCCGC AGGGCTCGTG CCCAGAGGCG GCTGAGGGCG TCATCGCCGG GCGGCCAGTC    360

CGTTGTAACA GCTGGGAGGC GATCATCTGG GATTACTTTT ACTATGCCGA TGAAGTACCA    420

CCAGTGGACT GGCCTACAAA GCACATAGAG TCCTACAGGC TCGCATGCAC CTCACTCGGG    480

GCGGAAAAGG TTGAGGTCTT GCGTGCCGCT TTCAGGTCGC GATATGCGGC CTAA          534

(2) INFORMATION FOR SEQ ID NO:165:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:165:

ATGGGCATCA TTCGCACATG TAGGCTCGGC CCTGACCAAG TCAAATCCAT GCGGGCTGCT     60

CTTGATCTTT TCGGTCGTGA GTTCGGAGAC GTAGCCACCT ACTCCCAACA TCAGCCGGAC    120

TCCGATTACC TCGGGAACTT GCTCCGTAGT AAGACATTCA TCGCGCTTGC TGCCTTCGAC    180

CAAGAAGCGG TTGTTGGCGC TCTCGCGGCT TACGTTCTGC CCAGGTTTGA GCAGCCGCGT    240

AGTGAGATCT ATATCTATGA TCTCGCAGTC TCCGGCGAGC ACCGGAGGCA GGGCATTGCC    300

ACCGCGCTCA TCAATCTCCT CAAGCATGAG GCCAACGCGC TTGGTGCTTA TGTGATCTAC    360

GTGCAAGCAG ATTACGGTGA CGATCCCGCA GTGGCTCTCT ATACAAAGTT GGGCATACGG    420

GAAGAAGTGA TGCACTTTGA TATCGACCCA AGTACCGCCA CCTAA                    465

(2) INFORMATION FOR SEQ ID NO:166:

(i) SEQUENCE CHARACTERISTICS:
        (A) LENGTH: 861 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:166:

ATGCATACGC GGAAGGCAAT AACGGAGGCG CTTCAAAAAC TCGGAGTCCA AACCGGTGAC     60

CTATTGATGG TGCATGCCTC ACTTAAAGCG ATTGGTCCGG TCGAAGGAGG AGCGGAGACG    120

GTCGTTGCCG CGTTACGCTC CGCGGTTGGG CCGACTGGCA CTGTGATGGG ATACGCATCG    180

TGGGACCGAT CACCCTACGA GGAGACTCGT AATGGCGCTC GGTTGGATGA CAAAACCCGC    240

CGTACCTGGC CGCCGTTCGA TCCCGCAACG GCCGGGACTT ACCGTGGGTT CGGCCTGCTG    300

AATCAGTTTC TGGTTCAAGC CCCCGGCGCG CGGCGCAGCG CGCACCCCGA TGCATCGATG    360

GTCGCGGTTG GTCCACTGGC TGAAACGCTG ACGGAGCCTC ACAAGCTCGG TCACGCCTTG    420

GGGGAAGGGT CGCCCGTCGA GCGGTTCGTT CGCCTTGGCG GGAAGGCCCT GCTGTTGGGT    480

GCGCCGCTAA ACTCCGTTAC CGCATTGCAC TACGCCGAGG CGGTTGCCGA TATCCCCAAC    540

AAACGGCGGG TGACGTATGA GATGCCGATG CTTGGAAGCA ACGGCGAAGT CGCCTGGAAA    600

ACGGCATCGG ATTACGATTC AAACGGCATT CTCGATTGCT TTGCTATCGA AGGAAAGCCG    660

GATGCGGTCG AAACTATAGC AAATGCTTAC GTGAAGCTCG GTCGCCATCG AGAAGGTGTC    720
```

```
GTGGGCTTTG CTCAGTGCTA CCTGTTCGAC GCGCAGGACA TCGTGACGTT CGGCGTCACC       780

TATCTTGAGA AGCATTTCGG AACCACTCCG ATCGTGCCAG CACACGAAGT CGCCGAGTGC       840

TCTTGCGAGC CTTCAGGTTA G                                                861
```

(2) INFORMATION FOR SEQ ID NO:167:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:167:

```
ATGACCGATT TGAATATCCC GCATACACAC GCGCACCTTG TAGACGCATT TCAGGCGCTC        60

GGCATCCGCG CGGGGCAGGC GCTCATGCTG CACGCATCCG TTAAAGCAGT GGGCGCGGTG       120

ATGGGCGGCC CCAATGTGAT CTTGCAGGCG CTCATGGATG CGCTCACGCC CGACGGCACG       180

CTGATGATGT ATGCGGGATG GCAAGACATC CCCGACTTTA TCGACTCGCT GCCGGACGCG       240

CTCAAGGCCG TGTATCTTGA GCAGCACCCA CCCTTTGACC CCGCCACCGC CGCGCCGTG        300

CGCGAAAACA GCGTGCTAGC GGAATTTTTG CGCACATGGC CGTGCGTGCA TCGCAGCGCA       360

AACCCCGAAG CCTCTATGGT GGCGGTAGGC AGGCAGGCCG CTTTGCTGAC CGCTAATCAC       420

GCGCTGGATT ATGGCTACGG AGTCGAGTCG CCGCTGGCTA AACTGGTGGC AATAGAAGGA       480

TACGTGCTGA TGCTTGGCGC GCCGCTGGAT ACCATCACAC TGCTGCACCA CGCGGAATAT       540

CTGGCCAAGA TGCGCCACAA GAACGTGGTC CGCTACCCGT GCCCGATTCT GCGGGACGGG       600

CGCAAAGTGT GGGTGACCGT TGAGGACTAT GACACCGGTG ATCCGCACGA CGATTATAGT       660

TTTGAGCAAA TCGCGCGCGA TTATGTGGCG CAGGGCGGCG GCACACGCGG CAAAGTCGGT       720

GATGCGGATG CTTACCTGTT CGCCGCGCAG GACCTCACAC GGTTTGCGGT GCAGTGGCTT       780

GAATCACGGT TCGGTGACTC AGCGTCATAC GGATAG                                816
```

(2) INFORMATION FOR SEQ ID NO:168:

(i) SEQUENCE CHARACTERISTICS:
        (A) LENGTH: 498 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:168:

```
ATGCTCTATG AGTGGCTAAA TCGATCTCAT ATCGTCGAGT GGTGGGCGG AGAAGAAGCA         60

CGCCCGACAC TTGCTGACGT ACAGGAACAG TACTTGCCAA GCGTTTTAGC GCAAGAGTCC       120

GTCACTCCAT ACATTGCAAT GCTGAATGGA GAGCCGATTG GGTATGCCCA GTCGTACGTT       180

GCTCTTGGAA GCGGGACGG ATGGTGGGAA GAAGAAACCG ATCCAGGAGT ACGCGGAATA        240

GACCAGTTAC TGGCGAATGC ATCACAACTG GGCAAAGGCT TGGGAACCAA GCTGGTTCGA       300

GCTCTGGTTG AGTTGCTGTT CAATGATCCC GAGGTCACCA AGATCCAAAC GGACCCGTCG       360

CCGAGCAACT TGCGAGCGAT CCGATGCTAC GAGAAAGCGG GGTTTGAGAG GCAAGGTACC       420

GTAACCACCC CAGATGGTCC AGCCGTGTAC ATGGTTCAAA CACGCCAGGC ATTCGAGCGA       480

ACACGCAGTG ATGCCTAA                                                    498
```

(2) INFORMATION FOR SEQ ID NO:169:

(i) SEQUENCE CHARACTERISTICS:
    (A) LENGTH: 2007 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:169:

```
ATGAAAAAGA TAAAAATTGT TCCACTTATT TTAATAGTTG TAGTTGTCGG GTTTGGTATA      60
TATTTTTATG CTTCAAAAGA TAAAGAAATT AATAATACTA TTGATGCAAT TGAAGATAAA     120
AATTTCAAAC AAGTTTATAA AGATAGCAGT TATATTTCTA AAAGCGATAA TGGTGAAGTA     180
GAAATGACTG AACGTCCGAT AAAAATATAT AATAGTTTAG GCGTTAAAGA TATAAACATT     240
CAGGATCGTA AAATAAAAAA AGTATCTAAA AATAAAAAAC GAGTAGATGC TCAATATAAA     300
ATTAAAACAA ACTACGGTAA CATTGATCGC AACGTTCAAT TTAATTTTGT TAAAGAAGAT     360
GGTATGTGGA AGTTAGATTG GGATCATAGC GTCATTATTC CAGGAATGCA GAAAGACCAA     420
AGCATACATA TTGAAAATTT AAAATCAGAA CGTGGTAAAA TTTTAGACCG AAACAATGTG     480
GAATTGGCCA ATACAGGAAC ACATATGAGA TTAGGCATCG TTCCAAAGAA TGTATCTAAA     540
AAAGATTATA AAGCAATCGC TAAAGAACTA AGTATTTCTG AAGACTATAT CAACAACAAA     600
TGGATCAAAA TTGGGTACAA GATGATACCT TCGTTCCACT TAAAACCGT TAAAAAAATG     660
GATGAATATT TAAGTGATTT CGCAAAAAAA TTTCATCTTA CAACTAATGA AACAGAAAGT     720
CGTAACTATC CTCTAGAAAA AGCGACTTCA CATCTATTAG GTTATGTTGG TCCCATTAAC     780
TCTGAAGAAT TAAAACAAAA AGAATATAAA GGCTATAAAG ATGATGCAGT TATTGGTAAA     840
AAGGGACTCG AAAAACTTTA CGATAAAAAG CTCCAACATG AAGATGGCTA TCGTGTCACA     900
ATCGTTGACG ATAATAGCAA TACAATCGCA CATACATTAA TAGAGAAAAA GAAAAAAGAT     960
GGCAAAGATA TTCAACTAAC TATTGATGCT AAAGTTCAAA GAGTATTTA TAACAACATG    1020
AAAAATGATT ATGGCTCAGG TACTGCTATC CACCCTCAAA CAGGTGAATT ATTAGCACTT    1080
GTAAGCACAC CTTCATATGA CGTCTATCCA TTTATGTATG GCATGAGTAA CGAAGAATAT    1140
AATAAATTAA CCGAAGATAA AAAAGAACCT CTGCTCAACA AGTTCCAGAT TACAACTTCA    1200
CCAGGTTCAA CTCAAAAAAT ATTAACAGCA ATGATTGGGT TAAATAACAA AACATTAGAC    1260
GATAAAACAA GTTATAAAAT CGATGGTAAA GGTTGGCAAA AGATAAATC TTGGGGTGGT    1320
TACAACGTTA CAAGATATGA AGTGGTAAAT GGTAATATCG ACTTAAAACA AGCAATAGAA    1380
TCATCAGATA ACATTTTCTT TGCTAGAGTA GCACTCGAAT TAGGCAGTAA GAAATTTGAA    1440
AAAGGCATGA AAAAACTAGG TGTTGGTGAA GATATACCAA GTGATTATCC ATTTTATAAT    1500
GCTCAAATTT CAAACAAAAA TTTAGATAAT GAAATATTAT TAGCTGATTC AGGTTACGGA    1560
CAAGGTGAAA TACTGATTAA CCCAGTACAG ATCCTTTCAA TCTATAGCGC ATTAGAAAAT    1620
AATGGCAATA TTAACGCACC TCACTTATTA AAAGACACGA AAAACAAAGT TTGGAAGAAA    1680
AATATTATTT CCAAAGAAAA TATCAATCTA TTAAATGATG GTATGCAACA AGTCGTAAAT    1740
AAAACACATA AAGAAGATAT TTATAGATCT TATGCAAACT TAATTGGCAA ATCCGGTACT    1800
GCAGAACTCA AAATGAAACA AGGAGAAAGT GGCAGACAAA TTGGGTGGTT TATATCATAT    1860
GATAAAGATA ATCCAAACAT GATGATGGCT ATTAATGTTA AAGATGTACA AGATAAAGGA    1920
ATGGCTAGCT ACAATGCCAA AATCTCAGGT AAAGTGTATG ATGAGCTATA TGAGAACGGT    1980
AATAAAAAAT ACGATATAGA TGAATAA                                        2007
```

(2) INFORMATION FOR SEQ ID NO:170:

(i) SEQUENCE CHARACTERISTICS:
        (A) LENGTH: 2607 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:170:

| | | | | | |
|---|---|---|---|---|---|
| ATGAATAACA | TCGGCATTAC | TGTTTATGGA | TGTGAGCAGG | ATGAGGCAGA | TGCATTCCAT | 60 |
| GCTCTTTCGC | CTCGCTTTGG | CGTTATGGCA | ACGATAATTA | ACGCCAACGT | GTCGGAATCC | 120 |
| AACGCCAAAT | CCGCGCCTTT | CAATCAATGT | ATCAGTGTGG | GACATAAATC | AGAGATTTCC | 180 |
| GCCTCTATTC | TTCTTGCGCT | GAAGAGAGCC | GGTGTGAAAT | ATATTTCTAC | CCGAAGCATC | 240 |
| GGCTGCAATC | ATATAGATAC | AACTGCTGCT | AAGAGAATGG | GCATCACTGT | CGACAATGTG | 300 |
| GCGTACTCGC | CGGATAGCGT | TGCCGATTAT | ACTATGATGC | TAATTCTTAT | GGCAGTACGC | 360 |
| AACGTAAAAT | CGATTGTGCG | CTCTGTGGAA | AAACATGATT | TCAGGTTGGA | CAGCGACCGT | 420 |
| GGCAAGGTAC | TCAGCGACAT | GACAGTTGGT | GTGGTGGGAA | CGGGCCAGAT | AGGCAAAGCG | 480 |
| GTTATTGAGC | GGCTGCGAGG | ATTTGGATGT | AAAGTGTTGG | CTTATAGTCG | CAGCCGAAGT | 540 |
| ATAGAGGTAA | ACTATGTACC | GTTTGATGAG | TTGCTGCAAA | ATGCGATAT | CGTTACGCTT | 600 |
| CATGTGCCGC | TCAATACGGA | TACGCACTAT | ATTATCAGCC | ACGAACAAAT | ACAGAGAATG | 660 |
| AAGCAAGGAG | CATTTCTTAT | CAATACTGGG | CGCGGTCCAC | TTGTAGATAC | CTATGAGTTG | 720 |
| GTTAAAGCAT | TAGAAAACGG | GAAACTGGGC | GGTGCCGCAT | GGATGTATT | GGAAGGAGAG | 780 |
| GAAGAGTTTT | TCTACTCTGA | TTGCACCCAA | AAACCAATTG | ATAATCAATT | TTTACTTAAA | 840 |
| CTTCAAAGAA | TGCCTAACGT | GATAATCACA | CCGCATACGG | CCTATTATAC | CGAGCAAGCG | 900 |
| TTGCGTGATA | CCGTTGAAAA | AACCATTAAA | AACTGTTTGG | ATTTTGAAAG | GAGACAGGAG | 960 |
| CATGAATAGA | ATAAAAGTTG | CAATACTGTT | TGGGGGTTGC | TCAGAGGAGC | ATGACGTATC | 1020 |
| GGTAAAATCT | GCAATAGAGA | TAGCCGCTAA | CATTAATAAA | GAAAAATACG | AGCCGTTATA | 1080 |
| CATTGGAATT | ACGAAATCTG | GTGTATGGAA | AATGTGCGAA | AAACCTTGCG | CGGAATGGGA | 1140 |
| AAACGACAAT | TGCTATTCAG | CTGTACTCTC | GCCGGATAAA | AAAATGCACG | GATTACTTGT | 1200 |
| TAAAAAGAAC | CATGAATATG | AAATCAACCA | TGTTGATGTA | GCATTTTCAG | CTTTGCATGG | 1260 |
| CAAGTCAGGT | GAAGATGGAT | CCATACAAGG | TCTGTTTGAA | TTGTCCGGTA | TCCCTTTTGT | 1320 |
| AGGCTGCGAT | ATTCAAAGCT | CAGCAATTTG | TATGGACAAA | TCGTTGACAT | ACATCGTTGC | 1380 |
| GAAAAATGCT | GGGATAGCTA | CTCCCGCCTT | TTGGGTTATT | AATAAAGATG | ATAGGCCGGT | 1440 |
| GGCAGCTACG | TTTACCTATC | CTGTTTTTGT | TAAGCCGGCG | CGTTCAGGCT | CATCCTTCGG | 1500 |
| TGTGAAAAAA | GTCAATAGCG | CGGACGAATT | GGACTACGCA | ATTGAATCGG | CAAGACAATA | 1560 |
| TGACAGCAAA | ATCTTAATTG | AGCAGGCTGT | TTCGGGCTGT | GAGGTCGGTT | GTGCGGTATT | 1620 |
| GGGAAACAGT | GCCGCGTTAG | TTGTTGGCGA | GGTGGACCAA | ATCAGGCTGC | AGTACGGAAT | 1680 |
| CTTTCGTATT | CATCAGGAAG | TCGAGCCGGA | AAAAGGCTCT | GAAAACGCAG | TTATAACCGT | 1740 |
| TCCCGCAGAC | CTTTCAGCAG | AGGAGCGAGG | ACGGATACAG | GAAACGGCAA | AAAAAATATA | 1800 |
| TAAAGCGCTC | GGCTGTAGAG | GTCTAGCCCG | TGTGGATATG | TTTTTACAAG | ATAACGGCCG | 1860 |
| CATTGTACTG | AACGAAGTCA | ATACTCTGCC | CGGTTTCACG | TCATACAGTC | GTTATCCCCG | 1920 |
| TATGATGGCC | GCTGCAGGTA | TTGCACTTCC | CGAACTGATT | GACCGCTTGA | TCGTATTAGC | 1980 |
| GTTAAAGGGG | TGATAAGCAT | GGAAATAGGA | TTTACTTTTT | TAGATGAAAT | AGTACACGGT | 2040 |

```
GTTCGTTGGG ACGCTAAATA TGCCACTTGG GATAATTTCA CCGGAAAACC GGTTGACGGT      2100

TATGAAGTAA ATCGCATTGT AGGGACATAC GAGTTGGCTG AATCGCTTTT GAAGGCAAAA      2160

GAACTGGCTG CTACCCAAGG GTACGGATTG CTTCTATGGG ACGGTTACCG TCCTAAGCGT      2220

GCTGTAAACT GTTTTATGCA ATGGGCTGCA CAGCCGGAAA ATAACCTGAC AAAGGAAAGT      2280

TATTATCCCA ATATTGACCG AACTGAGATG ATTTCAAAAG GATACGTGGC TTCAAAATCA      2340

AGCCATAGCC GCGGCAGTGC CATTGATCTT ACGCTTTATC GATTAGACAC GGGTGAGCTT      2400

GTACCAATGG GGAGCCGATT TGATTTTATG GATGAACGCT CTCATCATGC GGCAAATGGA      2460

ATATCATGCA ATGAAGCGCA AAATCGCAGA CGTTTGCGCT CCATCATGGA AAACAGTGGG      2520

TTTGAAGCAT ATAGCCTCGA ATGGTGGCAC TATGTATTAA GAGACGAACC ATACCCCAAT      2580

AGCTATTTTG ATTTCCCCGT TAAATAA                                         2607

(2) INFORMATION FOR SEQ ID NO:171:

(i) SEQUENCE CHARACTERISTICS:
        (A) LENGTH: 1288 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:171:

GGATCCATCA GGCAACGACG GGCTGCTGCC GGCCATCAGC GGACGCAGGG AGGACTTTCC       60

GCAACCGGCC GTTCGATGCG GCACCGATGG CCTTCGCGCA GGGGTAGTGA ATCCGCCAGG      120

ATTGACTTGC GCTGCCCTAC CTCTCACTAG TGAGGGGCGG CAGCGCATCA GCGGTGAGC      180

GCACTCCGGC ACCGCCAACT TTCAGCACAT GCGTGTAAAT CATCGTCGTA GAGACGTCGG      240

AATGGCCGAG CAGATCCTGC ACGGTTCGAA TGTCGTAACC GCTGCGGAGC AAGGCCGTCG      300

CGAACGAGTG GCGGAGGGTG TGCGGTGTGG CGGGCTTCGT GATGCCTGCT TGTTCTACGG      360

CACGTTTGAA GGCGCGCTGA AAGGTCTGGT CATACATGTG ATGGCGACGC ACGACACCGC      420

TCCGTGGATC GGTCGAATGC GTGTGCTGCG CAAAAACCCA GAACCACGGC CAGGAATGCC      480

CGGCGCGCGG ATACTTCCGC TCAAGGGCGT CGGGAAGCGC AACGCCGCTG CGGCCCTCGG      540

CCTGGTCCTT CAGCCACCAT GCCCGTGCAC GCGACAGCTG CTCGCGCAGG CTGGGTGCCA      600

AGCTCTCGGG TAACATCAAG GCCCGATCCT TGGAGCCCTT GCCCTCCCGC ACGATGATCG      660

TGCCGTGATC GAAATCCAGA TCCTTGACCC GCAGTTGCAA ACCCTCACTG ATCCGCATGC      720

CCGTTCCATA CAGAAGCTGG GCGAACAAAC GATGCTCGCC TTCCAGAAAA CCGAGGATGC      780

GAACCACTTC ATCGGGGTC AGCACCACCG GCAAGCGCCG CGACGGCCGA GGTCTTCCGA      840

TCTCCTGAAG CCAGGGCAGA TCCGTGCACA GCACCTTGCC GTAGAAGAAC AGCAAGGCCG      900

CCAATGCCTG ACGATGCGTG GAGACCGAAA CCTTGCGCTC GTTCGCCAGC CAGGACAGAA      960

ATGCCTCGAC TTCGCTGCTG CCCAAGGTTG CCGGGTGACG CACACCGTGG AAACGGATGA     1020

AGGCACGAAC CCAGTGGACA TAAGCCTGTT CGGTTCGTAA GCTGTAATGC AAGTAGCGTA     1080

TGCGCTCACG CAACTGGTCC AGAACCTTGA CCGAACGCAG CGGTGGTAAC GGCGCAGTGG     1140

CGGTTTTCAT GGCTTGTTAT GACTGTTTTT TTGTACAGTC TATGCCTCGG GCATCCAAGC     1200

AGCAAGCGCG TTACGCCGTG GGTCGATGTT TGATGTTATG GAGCAGCAAC GATGTTACGC     1260

AGCAGGGCAG TCGCCCTAAA ACAAAGTT                                        1288

(2) INFORMATION FOR SEQ ID NO:172:
```

(i) SEQUENCE CHARACTERISTICS:
    (A) LENGTH: 1650 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:172:

```
GTTAGATGCA CTAAGCACAT AATTGCTCAC AGCCAAACTA TCAGGTCAAG TCTGCTTTTA      60
TTATTTTTAA GCGTGCATAA TAAGCCCTAC ACAAATTGGG AGATATATCA TGAAAGGCTG     120
GCTTTTTCTT GTTATCGCAA TAGTTGGCGA AGTAATCGCA ACATCCGCAT TAAAATCTAG     180
CGAGGGCTTT ACTAAGCTTG CCCCTTCCGC CGTTGTCATA ATCGGTTATG GCATCGCATT     240
TTATTTTCTT TCTCTGGTTC TGAAATCCAT CCCTGTCGGT GTTGCTTATG CAGTCTGGTC     300
GGGACTCGGC GTCGTCATAA TTACAGCCAT TGCCTGGTTG CTTCATGGGC AAAAGCTTGA     360
TGCGTGGGGC TTTGTAGGTA TGGGGCTCAT AATTGCTGCC TTTTTGCTCG CCCGATCCCC     420
ATCGTGGAAG TCGCTGCGGA GGCCGACGCC ATGGTGACGG TGTTCGGCAT TCTGAATCTC     480
ACCGAGGACT CCTTCTTCGA TGAGAGCCGG CGGCTAGACC CCGCCGGCGC TGTCACCGCG     540
GCGATCGAAA TGCTGCGAGT CGGATCAGAC GTCGTGGATG TCGGACCGGC CGCCAGCCAT     600
CCGGACGCGA GGCCTGTATC GCCGGCCGAT GAGATCAGAC GTATTGCGCC GCTCTTAGAC     660
GCCCTGTCCG ATCAGATGCA CCGTGTTTCA ATCGACAGCT TCCAACCGGA AACCCAGCGC     720
TATGCGCTCA AGCGCGGCGT GGGCTACCTG AACGATATCC AAGGATTTCC TGACCCTGCG     780
CTCTATCCCG ATATTGCTGA GGCGGACTGC AGGCTGGTGG TTATGCACTC AGCGCAGCGG     840
GATGGCATCG CCACCCGCAC CGGTCACCTT CGACCCGAAG ACGCGCTCGA CGAGATTGTG     900
CGGTTCTTCG AGGCGCGGGT TTCCGCCTTG CGACGGAGCG GGGTCGCTGC CGACCGGCTC     960
ATCCTCGATC CGGGGATGGG ATTTTTCTTG AGCCCCGCAC CGGAAACATC GCTGCACGTG    1020
CTGTCGAACC TTCAAAAGCT GAAGTCGGCG TTGGGGCTTC CGCTATTGGT CTCGGTGTCG    1080
CGGAAATCCT TCTTGGGCGC CACCGTTGGC CTTCCTGTAA AGGATCTGGG TCCAGCGAGC    1140
CTTGCGGCGG AACTTCACGC GATCGGCAAT GGCGCTGACT ACGTCCGCAC CCACGCGCCT    1200
GGAGATCTGC GAAGCGCAAT CACCTTCTCG GAAACCCTCG CGAAATTTCG CAGTCGCGAC    1260
GCCAGAGACC GAGGGTTAGA TCATGCCTAG CATTCACCTT CCGGCCGCCC GCTAGCGGAC    1320
CCTGGTCAGG TTCCGCGAAG GTGGGCGCAG ACATGCTGGG CTCGTCAGGA TCAAACTGCA    1380
CTATGAGGCG GCGGTTCATA CCGCGCCAGG GGAGCGAATG GACAGCGAGG AGCCTCCGAA    1440
CGTTCGGGTC GCCTGCTCGG GTGATATCGA CGAGGTTGTG CGGCTGATGC ACGACGCTGC    1500
GGCGTGGATG TCCGCCAAGG GAACGCCCGC CTGGGACGTC GCGCGGATCG ACCGGACATT    1560
CGCGGAGACC TTCGTCCTGA GATCCGAGCT CCTAGTCGCG AGTTGCAGCG ACGGCATCGT    1620
CGGCTGTTGC ACCTTGTCGG CCGAGGATCC                                    1650
```

(2) INFORMATION FOR SEQ ID NO:173:

(i) SEQUENCE CHARACTERISTICS:
        (A) LENGTH: 630 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:173:

```
ATGGGTCCGA ATCCTATGAA AATGTATCCT ATAGAAGGAA ACAAATCAGT ACAATTTATC      60
```

```
AAACCTATTT TAGAAAAATT AGAAAATGTT GAGGTTGGAG AATACTCATA TTATGATTCT      120

AAGAATGGAG AAACTTTTGA TAAGCAAATT TTATATCATT ATCCAATCTT AAACGATAAG      180

TTAAAAATAG GTAAATTTTG CTCAATAGGA CCAGGTGTAA CTATTATTAT GAATGGAGCA      240

AATCATAGAA TGGATGGCTC AACATATCCA TTTAATTTAT TTGGTAATGG ATGGGAGAAA      300

CATATGCCAA AATTAGATCA ACTACCTATT AAGGGGGATA CAATAATAGG TAATGATGTA      360

TGGATAGGAA AAGATGTTGT AATTATGCCA GGAGTAAAAA TCGGGGATGG TGCAATAGTA      420

GCTGCTAATT CTGTTGTTGT AAAAGATATA GCGCCATACA TGTTAGCTGG AGGAAATCCT      480

GCTAACGAAA TAAAACAAAG ATTTGATCAA GATACAATAA ATCAGCTGCT TGATATAAAA      540

TGGTGGAATT GGCCAATAGA CATTATTAAT GAGAATATAG ATAAAATTCT TGATAATAGC      600

ATCATTAGAG AAGTCATATG GAAAAAATGA                                       630

(2) INFORMATION FOR SEQ ID NO:174:

(i) SEQUENCE CHARACTERISTICS:
        (A) LENGTH: 1440 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:174:

ATGAATATAG TTGAAAATGA AATATGTATA AGAACTTTAA TAGATGATGA TTTTCCTTTG       60

ATGTTAAAAT GGTTAACTGA TGAAAGAGTA TTAGAATTTT ATGGTGGTAG AGATAAAAAA      120

TATACATTAG AATCATTAAA AAAACATTAT ACAGAGCCTT GGGAAGATGA AGTTTTTAGA      180

GTAATTATTG AATATAACAA TGTTCCTATT GGATATGGAC AAATATATAA AATGTATGAT      240

GAGTTATATA CTGATTATCA TTATCCAAAA ACTGATGAGA TAGTCTATGG TATGGATCAA      300

TTTATAGGAG AGCCAAATTA TTGGAGTAAA GGAATTGGTA CAAGATATAT TAAATTGATT      360

TTTGAATTTT TGAAAAAAGA AAGAAATGCT AATGCAGTTA TTTTAGACCC TCATAAAAAT      420

AATCCAAGAG CAATAAGGGC ATACCAAAAA TCTGGTTTTA GAATTATTGA AGATTTGCCA      480

GAACATGAAT TACACGAGGG CAAAAAAGAA GATTGTTATT AATGGAATA TAGATATGAT      540

GATAATGCCA CAAATGTTAA GGCAATGAAA TATTTAATTG AGCATTACTT TGATAATTTC      600

AAAGTAGATA GTATTGAAAT AATCGGTAGT GGTTATGATA GTGTGGCATA TTTAGTTAAT      660

AATGAATACA TTTTTAAAAC AAAATTTAGT ACTAATAAGA AAAAAGGTTA TGCAAAAGAA      720

AAAGCAATAT ATAATTTTTT AAATACAAAT TTAGAAACTA ATGTAAAAAT TCCTAATATT      780

GAATATTCGT ATATTAGTGA TGAATTATCT ATACTAGGTT ATAAAGAAAT TAAAGGAACT      840

TTTTTAACAC CAGAAATTTA TTCTACTATG TCAGAAGAAG AACAAAATTT GTTAAAACGA      900

GATATTGCCA GTTTTTTAAG ACAAATGCAC GGTTTAGATT ATACAGATAT TAGTGAATGT      960

ACTATTGATA ATAAACAAAA TGTATTAGAA GAGTATATAT TGTTGCGTGA AACTATTTAT     1020

AATGATTTAA CTGATATAGA AAAAGATTAT ATAGAAAGTT TATGGAAAG ACTAAATGCA     1080

ACAACAGTTT TTGAGGGTAA AAAGTGTTTA TGCCATAATG ATTTTAGTTG TAATCATCTA     1140

TTGTTAGATG GCAATAATAG ATTAACTGGA ATAATTGATT TTGGAGATTC TGGAATTATA     1200

GATGAATATT GTGATTTTAT ATACTTACTT GAAGATAGTG AAGAAGAAAT AGGAACAAAT     1260

TTTGAGAAAG ATATATTAAG AATGTATGGA AATATAGATA TTGAGAAAGC AAAAGAATAT     1320

CAAGATATAG TTGAAGAATA TTATCCTATT GAAACTATTG TTTATGGAAT TAAAAATATT     1380
```

AAACAGGAAT TTATCGAAAA TGGTAGAAAA GAAATTTATA AAAGGACTTA TAAAGATTGA    1440

(2) INFORMATION FOR SEQ ID NO:175:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:175:

TTGAATTTAA ACAATGACCA TGGACCTGAT CCCGAAAATA TTTTACCGAT AAAAGGGAAT      60

CGGAATCTTC AATTTATAAA ACCTACTATA ACGAACGAAA ACATTTTGGT GGGGGAATAT     120

TCTTATTATG ATAGTAAGCG AGGAGAATCC TTTGAAGATC AAGTCTTATA TCATTATGAA     180

GTGATTGGAG ATAAGTTGAT TATAGGAAGA TTTTGTTCAA TTGGTCCCGG AACAACATTT     240

ATTATGAATG GTGCAAACCA TCGGATGGAT GGATCAACAT ATCCTTTTCA TCTATTCAGG     300

ATGGGTTGGG AGAAGTATAT GCCTTCCTTA AAAGATCTTC CCTTGAAAGG GGACATTGAA     360

ATTGGAAATG ATGTATGGAT AGGTAGAGAT GTAACCATTA TGCCTGGGGT GAAAATTGGG     420

GACGGGGCAA TCATTGCTGC AGAAGCTGTT GTCACAAAGA ATGTTGCTCC CTATTCTATT     480

GTCGGTGGAA ATCCCTTAAA ATTTATAAGA AAAAGGTTTT CTGATGGAGT TATCGAAGAA     540

TGGTTAGCTT TACAATGGTG GAATTTAGAT ATGAAAATTA TTAATGAAAA TCTTCCCTTC     600

ATAATAAATG GAGATATCGA AATGCTGAAG AGAAAAAGAA AACTTCTAGA TGACACTTGA     660

(2) INFORMATION FOR SEQ ID NO:176:

(i) SEQUENCE CHARACTERISTICS:
        (A) LENGTH: 1569 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:176:

ATGAAAATAA TGTTAGAGGG ACTTAATATA AAACATTATG TTCAAGATCG TTTATTGTTG      60

AACATAAATC GCCTAAAGAT TTATCAGAAT GATCGTATTG GTTTAATTGG TAAAAATGGA     120

AGTGGAAAAA CAACGTTACT TCACATATTA TATAAAAAAA TTGTGCCTGA AGAAGGTATT     180

GTAAAACAAT TTTCACATTG TGAACTTATT CCTCAATTGA AGCTCATAGA ATCAACTAAA     240

AGTGGTGGTG AAGTAACACG AAACTATATT CGGCAAGCGC TTGATAAAAA TCCAGAACTG     300

CTATTAGCAG ATGAACCAAC AACTAACTTA GATAATAACT ATATAGAAAA ATTAGAACAG     360

GATTTAAAAA ATTGGCATGG AGCATTTATT ATAGTTTCAC ATGATCGCGC TTTTTTAGAT     420

AACTTGTGTA CTACTATATG GGAAATTGAC GAGGGAAGAA TAACTGAATA TAAGGGGAAT     480

TATAGTAACT ATGTTGAACA AAAAGAATTA GAAAGACATC GAGAAGAATT AGAATATGAA     540

AAATATGAAA AAGAAAAGAA ACGATTGGAA AAAGCTATAA ATATAAAAGA ACAGAAAGCT     600

CAACGAGCAA CTAAAAAACC GAAAAACTTA AGTTTATCTG AAGGCAAAAT AAAAGGAGCA     660

AAGCCATACT TTGCAGGTAA GCAAAAGAAG TTACGAAAAA CTGTAAAATC TCTAGAAACC     720

AGACTAGAAA AACTTGAAAG CGTCGAAAAG AGAAACGAAC TTCCTCCACT TAAAATGGAT     780

TTAGTGAACT TAGAAAGTGT AAAAAATAGA ACTATAAATAC GTGGTGAAGA TGTCTCGGGT     840

ACAATTGAAG GACGGGTATT GTGGAAAGCA AAAGTTTTA GTATTCGCGG AGGAGACAAG      900

| | | | | |
|---|---|---|---|---|
| ATGGCAATTA | TCGGATCTAA | TGGTACAGGA | AAGACAACGT | TTATTAAAAA AATTGTGCAT | 960 |
| GGGAATCCTG | GTATTTCATT | ATCGCCATCT | GTCAAATCG | GTTATTTTAG CCAAAAAATA | 1020 |
| GATACATTAG | AATTAGATAA | GAGCATTTTA | GAAAATGTTC | AATCTTCTTC ACAACAAAAT | 1080 |
| GAAACTCTTA | TTCGAACTAT | TCTAGCTAGA | ATGCATTTTT | TTAGAGATGA TGTTTATAAA | 1140 |
| CCAATAAGTG | TCTTAAGTGG | TGGAGAGCGA | GTTAAAGTAG | CACTAACTAA AGTATTCTTA | 1200 |
| AGTGAAGTTA | ATACGTTGGT | ACTAGATGAA | CCAACAAACT | TTCTTGATAT GGAAGCTATA | 1260 |
| GAGGCGTTTG | AATCTTTGTT | AAAGGAATAT | AATGGCAGTA | TAATCTTTGT ATCTCACGAT | 1320 |
| CGTAAATTTA | TCGAAAAAGT | AGCCACTCGA | ATAATGACAA | TTGATAATAA AGAAATAAAA | 1380 |
| ATATTTGATG | GCACATATGA | ACAATTTAAA | CAAGCTGAAA | AGCCAACAAG GAATATTAAA | 1440 |
| GAAGATAAAA | AACTTTTACT | TGAGACAAAA | ATTACAGAAG | TACTCAGTCG ATTGAGTATT | 1500 |
| GAACCTTCGG | AAGAATTAGA | ACAAGAGTTT | CAAAACTTAA | TAAATGAAAA AAGAAATTTG | 1560 |
| GATAAATAA | | | | | 1569 |

(2) INFORMATION FOR SEQ ID NO:177:

(i) SEQUENCE CHARACTERISTICS:
        (A) LENGTH: 1467 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:177:

| | | | | |
|---|---|---|---|---|
| ATGGAACAAT | ATACAATTAA | ATTTAACCAA | ATCAATCATA | AATTGACAGA TTTACGATCA | 60 |
| CTTAACATCG | ATCATCTTTA | TGCTTACCAA | TTTGAAAAAA | TAGCACTTAT TGGGGGTAAT | 120 |
| GGTACTGGTA | AAACCACATT | ACTAAATATG | ATTGCTCAAA | AACAAAACC AGAATCTGGA | 180 |
| ACAGTTGAAA | CGAATGGCGA | AATTCAATAT | TTTGAACAGC | TTAACATGGA TGTGGAAAAT | 240 |
| GATTTTAACA | CGTTAGACGG | TAGTTTAATG | AGTGAACTCC | ATATACCTAT GCATACAACC | 300 |
| GACAGTATGA | GTGGTGGTGA | AAAAGCAAAA | TATAAATTAC | GTAATGTCAT ATCAAATTAT | 360 |
| AGTCCGATAT | TACTTTTAGA | TGAACCTACA | AATCACTTGG | ATAAAATTGG TAAAGATTAT | 420 |
| CTGAATAATA | TTTTAAAATA | TTACTATGGT | ACTTTAATTA | TAGTAAGTCA CGATAGAGCA | 480 |
| CTTATAGACC | AAATTGCTGA | CACAATTTGG | GATATACAAG | AAGATGGCAC AATAAGAGTG | 540 |
| TTTAAAGGTA | ATTACACACA | GTATCAAAAT | CAATATGAAC | AAGAACAGTT AGAACAACAA | 600 |
| CGTAAATATG | AACAGTATAT | AAGTGAAAAA | CAAAGATTGT | CCCAAGCCAG TAAAGCTAAA | 660 |
| CGAAATCAAG | CGCAACAAAT | GGCACAAGCA | TCATCAAAAC | AAAAAAATAA AAGTATAGCA | 720 |
| CCAGATCGTT | TAAGTGCATC | AAAAGAAAAA | GGCACGGTTG | AGAAGGCTGC TCAAAAACAA | 780 |
| GCTAAGCATA | TTGAAAAAAG | AATGGAACAT | TTGGAAGAAG | TTGAAAAACC ACAAAGTTAT | 840 |
| CATGAATTCA | ATTTTCCACA | AAATAAAATT | TATGATATCC | ATAATAATTA TCCAATCATT | 900 |
| GCACAAAATC | TAACATTGGT | TAAAGGAAGT | CAAAAACTGC | TAACACAAGT ACGATTCCAA | 960 |
| ATACCATATG | GCAAAAATAT | AGCGCTCGTA | GGTGCAAATG | GTGTAGGTAA GACAACTTTA | 1020 |
| CTTGAAGCTA | TTTACCACCA | AATAGAGGGA | ATTGATTGTT | CTCCTAAAGT GCAAATGGCA | 1080 |
| TACTATCGTC | AACTTGCTTA | TGAAGACATG | CGTGACGTTT | CATTATTGCA ATATTTAATG | 1140 |
| GATGAAACGG | ATTCATCAGA | ATCATTCAGT | AGAGCTATTT | TAAATAACTT GGGTTTAAAT | 1200 |
| GAAGCACTTG | AGCGTTCTTG | TAATGTTTTG | AGTGGTGGGG | AAAGAACGAA ATTATCGTTA | 1260 |
| GCAGTATTAT | TTTCAACGAA | AGCGAATATG | TTAATTTTGG | ATGAACCAAC TAATTTTTTA | 1320 |

```
GATATTAAAA CATTAGAAGC ATTAGAAATG TTTATGAATA AATATCCTGG AATCATTTTG    1380

TTTACATCAC ATGATACAAG GTTTGTTAAA CATGTATCAG ATAAAAAATG GGAATTAACA    1440

GGACAATCTA TTCATGATAT AACTTAA                                       1467

(2) INFORMATION FOR SEQ ID NO:178:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:178:

ATGAACAAAT TGTTAAATC ATTATTAGTT GCAGGTTCTG TAGCTGCATT AGCGGCTTGT    60

AGTTCCTCTA ACAACGATGC TGCAGGCAAT GGTGCTGCTC AAACTTTTGG CGGATACTCT   120

GTTGCTGATC TTCAACAACG TTACAACACC GTATATTTTG GTTTTGATAA ATACGACATC   180

ACCGGTGAAT ACGTTCAAAT CTTAGATGCG CACGCAGCAT ATTTAAATGC AACGCCAGCT   240

GCTAAAGTAT TAGTAGAAGG TAATACTGAT GAACGTGGTA CACCAGAATA CAACATCGCA   300

TTAGGACAAC GTCGTGCAGA TGCAGTTAAA GGTTATTTAG CAGGTAAAGG TGTTGATGCT   360

GGTAAATTAG GCACAGTATC TTACGGTGAA GAAAAACCTG CAGTATTAGG TCACGATGAA   420

GCTGCATATT CTAAAAACCG TCGTGCAGTG TTAGCGTACT AA                     462

(2) INFORMATION FOR SEQ ID NO:179:

(i) SEQUENCE CHARACTERISTICS:
        (A) LENGTH: 2865 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:179:

ATGACACAAA AATTCGAAAT GGCAGACCGT TTTAATCCGT CTGCGGTAGA ACAAGCCCTT    60

TATCAACGTT GGGAAGAGAG CGGTTATTTT AAACCGTCTG AAAATGAAAA TGCGCCGAGC   120

TATTGCATTG CAATTCCGCC GCCGAACGTA ACAGGTTCTC TACACATGGG GCATGCTTTC   180

CAACAAACCT TAATGGATAC CTTAATCCGT TTTAACCGTA TGGAAGGGCA TAACACCTTA   240

TGGCAAACGG GACAGACCA CGCGGGTATT GCGACCCAAA TGGTGGTGGA ACGTAAAATT    300

GCGGCTGAAG AAGGCAAAAC TCGCCACGAT TATGGTCGCG AAGCGTTCAT CAATAAAATT   360

TGGGATTGGA AAGCCTATTC AGGTGGCACA ATCAGCCAAC AAATGCGCCG TTTAGGGAAC   420

TCAATCGACT GGGAACGTGA GCGTTTCACG ATGGACGATG GTTTATCGAA TGCAGTAAAA   480

GAAGTGTTTG TTCGTTTGCA CGAAGAAGGG TTGATTTACC GTGGCAAACG CTTGGTAAAC   540

TGGGATCCAA AACTTCACAC CGCAATTTCT GATTTAGAAG TTGAAAATAA AGAAAGCAAA   600

GGCTCCCTTT GGCATTTCCG TTATCCGTTA GCAAACGATG CAAAAACGGC AGATGGTAAA   660

GATTATTTAG TGGTGGCAAC CACACGTCCA GAAACTATGT TGGGCGATAC GGCGGTGGCG   720

GTACATCCTG AAGATGAGCG TTACCAATCT TTAATTGGTA AAACTGTTGT TCTACCACTG    780
```

```
GCTAACCGTG AAATTCCGAT TATTGCCGAT GAATATGTGG ATCGTGAATT CGGTACAGGT      840

GTCGTGAAAA TCACCCCAGC ACACGATTTC AACGACTATG AAGTGGGTAA ACGTCATAAT      900

TTACCAATGG TAAATGTATT GACGCTGAAC GCAAATATTG TGATGAAGC GGAAATTATC       960

GGTACTGACG GCAAACCACT TGCTGGCTAT GAAGCGACTA TTCCTGCGGA TTACCGTGGC     1020

TTAGAACGTT TTGCTGCGCG TAAGAAAATT GTCGCAGATT TGAAGCACT GGGTTTATTA     1080

GACGAAATTA AACCACACGA TTTGAAAGTG CCTTATGGCG ACCGTGGCGG TGTGCCAATT     1140

GAGCCGATGC TAACTGACCA ATGGTATGTA AGCGTAAAAC CACTTGCTGA TGTGGCAATT     1200

AAAGCGGTGG AAGATGGCGA AATCCAATTC GTGCCGAAAC AATACGAAAA CCTTTACTTC     1260

TCTTGGATGC GTGATATTCA AGATTGGTGT ATTTCTCGCC AACTTTGGTG GGACACCGC     1320

ATTCCAGCGT GGTATGACGC GGAAGGCAAT GTTTATGTCG CACGTAACGA AGAAGAAGTG    1380

CGGTCAAAAT ATAACTTAGA TTCTGCGGTT GAACTCAAAC AAGATGAAGA CGTGTTAGAT    1440

ACGTGGTTCT CATCAGGCTT ATGGACGTTC TCTACCTTAG GTTGGCCAGA GCAAACTAAA    1500

GAGCTCAAAA TGTTCCACCC AACGGATGTG TTAATCACAG GTTTTGATAT CATCTTCTTC    1560

TGGGTTGCAC GTATGATAAT GTTTACGATG CACTTCGTAA AAGATGAAAA CGGCAAACCA    1620

CAAGTGCCAT TCAAAACCGT GTATGTAACA GGCTTGATCC GTGATGAACA AGGTCAAAAA    1680

ATGTCGAAAT CGAAAGGTAA CGTGCTTGAC CCAATCGATA TGATTGACGG TATTAGCCTT    1740

GAAGATTTAC TTGAAAAACG TACTGGCAAC ATGATGCAGC CGCAATTAGC AGAAAAAATT    1800

GCTAAAGCGA CTCGCAAAGA ATTTGCTGAA GGTATTGCGG CTCACGGTAC AGATGCATTG    1860

CGTTTCACAT TAGCTGCATT GGCTTCAAAC GGTCGTGACA TTAACTGGGA TATGAAACGT    1920

TTAGAGGGCT ACCGTAATTT CTGTAACAAA TTATGGAATG CAAGCCGTTT CGTCTTAACA    1980

AATGAAAAAT TAGATTTAAG CCAAGGCGAG ATCGAATTCT CATTAGCGGA TCGTTGGATT    2040

CAATCGGAAT TCAATCGCAC AGTGGAAACT TTCCGTAGCT CATTAAGCCA ATATCGTTTC    2100

GACCTTTGTG CCAATGCGAT TTATGAGTTT ACCTGGAACC AATTCTGTGA CTGGTATTTA    2160

GAATTAACTA AACCAGTATT TGCAAACGGC AACGCAGCAC AAATCCGTGC GGCAAGCCAA    2220

ACCTTGGTTC ACGTGTTAGA AAAATTATTA CGTTTAGCGC ATCCGCTTAT TCCATTTATT    2280

ACCGAAGAAA TTTGGCAAAA AGTGAAAGGA TTTGTCGGCA TTACTGCTGA CAGCATTATG    2340

TTACAACCTT TCCCACAAGT GGAAGAGAGC GGCTTTGATC CAGAAGCAGA AGCTGAAATT    2400

GAGTGGTTAA AAGAAGTGAT CGTTGCGGTG CGTAATATTC GTGCAGAAAG CAACATCGCA    2460

CCAAGTAAAG GTTTAGATCT GTTATTCCGT AATTTAAGTG CAGAAAATGC AAAAATTCTC    2520

GAAAAACAGA CCGCTCTTTT AAAAGCCATG GCGAAGTTAG ACAACGTTCA AGTGTTAGCC    2580

ACAAACGAAA CAGCACCACT TGCGGTAGCG AAACTCGTGG GCAATGCTGA ATTGCTTGTG    2640

CCAATGGCTG GCTTTATCAA TAAAGAAGCA GAGCTTGCCC GTTTAACCAA AGAGATTGAA    2700

AAATATCAAA ACGAAGTGAA ACGCATCGAA AACAAACTTA GCAATGAAGC TTTCGTGGCT    2760

AAAGCACCTG AAGCGGTTAT TGCGAAAGAA CGCGAAAAAC AAGCGGAATA CCAATCTGGA    2820

TTAGAAAAAA TCCAAGAGCA GTATAAAGCG ATTGAGGCGT TGTAA                    2865
```

(2) INFORMATION FOR SEQ ID NO:180:

(i) SEQUENCE CHARACTERISTICS:
        (A) LENGTH: 612 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Proteus mirabilis (xi) SEQUENCE DESCRIPTION: SEQ ID NO:180:

```
ATGAAATTGT ACTACACGCC GGGTAGTTGC TCGCTTTCTC CTCATATCGT TCTACGTGAA      60
ACGGGTCTCG ACTTTTCTAT TGAGCGCATT GATTTACGCA CCAAAAAAAC AGAGTCAGGG     120
AAAGATTTTC TTGCCATCAA CCCTAAAGGG CAAGTTCCGG TTCTTCAATT AGATAATGGT     180
GATATTTTAA CGGAGGGTGT TGCTATTGTG CAGTATCTTG CCGATCTGAA GCCAGATAGA     240
AATCTTATTG CCCCACCAAA AGCATTAGAA CGTTATCATC AAATTGAGTG GCTAAACTTT     300
CTTGCCAGTG AAGTTCATAA AGGCTACAGC CCTCTATTTT CATCTGATAC GCCTGAAAGT     360
TATCTCCCTG TGGTAAAAAA CAAACTAAAA AGTAAATTTG TTTATATTAA TGATGTACTA     420
AGCAAACAAA AATGTGTTTG TGGTGATCAC TTTACTGTGG CGGATGCGTA TCTGTTTACG     480
TTAAGTCAAT GGGCACCTCA TGTGGCGCTA GATTTAACCG ACTTAAGCCA TTTACAAGAC     540
TATCTAGCAC GTATTGCACA ACGTCCTAAT GTGCATAGTG CACTAGTCAC GGAAGGATTA     600
ATAAAAGAGT AA                                                         612
```

(2) INFORMATION FOR SEQ ID NO:181:

(i) SEQUENCE CHARACTERISTICS:
        (A) LENGTH: 237 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:181:

```
ATGAAAGCAA AAATTGTACT AGGTGCGGTA ATTCTGGCTT CAGGCCTATT AGCAGGTTGT      60
TCTTCTAGCA ACAACGCACA ATTAGACCAA ATCTCTTCTG ATGTAAACCG TTTAAATACG     120
CAAGTTCAAC AACTAAGTAG TGATGTTCAA TCAGCTAACG CTCAAGCAAA AGCCGCTTAT     180
GAAGCAGCTC GTGCTAATCA GCGTCTAGAT AACCAAGTAA CTACTTATAA AAAATAA       237
```

(2) INFORMATION FOR SEQ ID NO:182:

(i) SEQUENCE CHARACTERISTICS:
        (A) LENGTH: 1335 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:182:

```
ATGCCTACTG CGCGCTGCTC GATGAGAGCG TCCTCAACCG CGCCAGTCAG GATGATGGCT      60
ACCGCAGGTG GCGCAAGGAT CGGCGCCATT CTGCGCGTCA CGTCCGGTAA CTTTCTCGAA     120
CAGTTCGACT TTTTCCTGTT CGGGTTTTAT GCCACCTACA TCGCCCATAC CTTTTTTCCG     180
GCGAGCAGTG AATTCGCCTC GCTGATGATG ACCTTCGCAG TCTTTGGCGC CGGCTTTTTG     240
ATGCGCCCCA TCGGCGCTAT CGTACTTGGC GCCTATATCG ACAAGGTGGG GCGGCGCAAG     300
GGGCTGATCG TCACCCTGTC GATCATGGCC ACCGGCACCT TCCTGATCGT GCTGATCCCC     360
```

```
TCTTATCAGA CCATTGGCCT GTGGGCGCCG CTGCTGGTGC TGATCGGCCG TCTGCTGCAG    420

GGCTTTTCCG CAGGCGCCGA GCTGGGCGGG GTGTCGGTCT ATCTGGCCGA GATCGCCACC    480

CCGGGCCGCA AAGGCTTTTA CACCAGCTGG CAGTCGGGCA GTCAGCAGGT TGCCATCATG    540

GTGGCAGCCG CGATGGGCTT TGCCCTCAAC GCGGTACTGG AGCCGAGCGC TATCAGCGAC    600

TGGGGCTGGC GTATTCCGTT CCTTTTCGGC GTCCTGATTG TTCCGTTCAT TTTTATCCTG    660

CGCCGTAAGC TGGAGGAGAC CCAGGAGTTT ACTGCCCGCC GCCATCATCT GGCGATGCGC    720

CAGGTATTCG CCACCCTGCT GGCGAACTGG CAGGTGGTTA TCGCCGGGAT GATGATGGTG    780

GCGATGACCA CCACCGCGTT CTACCTGATC ACCGTCTATG CCCCGACCTT TGGTAAAAAG    840

GTGCTGATGC TCAGCGCCTC TGACAGCCTG CTGGTCACGC TGCTGGTGGC GATTTCCAAC    900

TTCTTCTGGC TGCCGGTGGG CGGGGCGCTG TCCGACCGCT TTGGCCGCCG GTCGGTGCTG    960

ATCGCCATGA CCCTGCTGGC GCTGGCTACC GCCTGGCCTG CGCTGACCAT GCTGGCGAAC   1020

GCCCCGAGCT TTTTGATGAT GCTGAGCGTG CTGCTGTGGC TGTCGTTTAT CTACGGCATG   1080

TACAACGGGG CGATGATCCC GGCGCTGACC GAAATTATGC CCGCCGAAGT GCGCGTGGCA   1140

GGTTTCTCGC TGGCCTACAG CCTGGCGACC GCGGTGTTTG GCGGCTTCAC GCCGGTGATT   1200

TCCACGGCGC TGATTGAGTA TACCGGTGAT AAAGCGTCTC CCGGCTACTG GATGAGCTTT   1260

GCCGCCATCT GCGGTCTGCT GGCCACTTGC TACCTCTATC GCCGTAGCGC CGTTGCGCTG   1320

CAGACGGCAC GTTAA                                                    1335

(2) INFORMATION FOR SEQ ID NO:183:

(i) SEQUENCE CHARACTERISTICS:
        (A) LENGTH: 1563 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:183:

ATGAAACCTG AAAACTTCCG TGCAGATACC AAGCGCCCGT TAACCGGTGA AGAGTACCTG     60

AAGAGCCTGC AGGACGGCCG CGAAATCTAT ATTTACGGTG AACGCGTTAA AGACGTGACC    120

ACCCATCCCG CGTTCCGCAA CGCCGCCGCC TCCGTCGCCC AATTGTACGA CGCGCTGCAT    180

AACCCCGAGC TGCAGAATAC CCTGTGCTGG GGCACCGACA CCGGCAGCGG CGGCTACACC    240

CACAAGTTCT TCCGCGTGGC GAAAAGCGCC GATGACCTGC GCCAGCAGCG CGACGCCATC    300

GCCGAATGGT CGCGCCTGAG CTACGGCTGG ATGGGCCGCA CCCCGGACTA CAAGGCCGCG    360

TTCGGTGGCG GACTCGGCGC GAACCCGGGA TTTTACGGCC AGTTCGAGCA GAACGCCCGC    420

GACTGGTACA CCCGCATCCA GGAAACCGGC CTGTACTTTA CCACGCCAT CGTCAACCCG     480

CCGATCGATC GCCATAAGCC CGCCGATGAA GTGAAAGATG TTTATATCAA GCTGGAGAAA    540

GAGACCGACG CTGGGATCAT CGTCAGCGGC GCGAAGGTGG TGGCCACCAA CTCGGCGCTG    600

ACCCACTACA ACATGATCGG CTTCGGCTCG GCGCAGGTGA TGGGCGAAAA CCCGACTTC     660

GCGCTGATGT TCGTCGCGCC GATGGATGCC GAAGGCGACA AGCTTATCTC CCGCGCCTCC    720

TATGAGCTGG TCGCCGGCGC CACCGGATCG CCGTACGACT ATCCGCTCTC CAGCCGCTTC    780

GACGAAAATG ATGCGATCCT GGTGATGGAT AACGTGCTGA TCCCATGGGA AAACGTCCTG    840

ATCTATCGCG ACTTCGACCG CTGCCGCCGC TGGACGATGG AAGGCGGCTT CGCCCGCATG    900
```

```
TATCCGCTGC AGGCCTGCGT GCGCCTGGCG GTGAAGCTCG ATTTCATCAC CGCCCTGCTG      960

AAACGCTCGC TGGAGTGTAC CGGCACCCTT GAGTTCCGCG GCGTGCAGGC CGAGCTCGGC     1020

GAAGTGGTGG CCTGGCGCAA TATGTTCTGG GCGCTGAGCG ATTCAATGTG CGCCGAAGCG     1080

ACGCCGTGGG TCAACGGCGC GTATCTGCCG GATCACGCCG CGCTGCAAAC CTACCGCGTG     1140

ATGGCGCCGA TGCCCTACGC CAAAATCAAA AACATTATCG AGCGCAGCGT CACCAGCGGC     1200

CTGATCTACC TGCCGTCCAG CGCCCGCGAT CTCAACAACC CGCAGATCAA CGATACCCTG     1260

GCGAAATACG TGCGCGGATC GAACGGTATG GATCACGTCG AGCGTATCAA GATCCTCAAA     1320

CTGATGTGGG ACGCGATCGG CAGCGAATTC GGCGGTTGCC ATGAGCTGTA TGAAATCAAC     1380

TATTCCGGTA GCCAGGATGA GATTCGCCTG CAGTGCCTGC GTCAGGCGCA AAGCTCCGGC     1440

AACATGGACA AAATGATGGC GATGGTGGAT CGCTGCCTGT CCGAGTACGA CCAGAACGGC     1500

TGGACGGTGC CGCATCTGCA CAACAATACC GATATCAACA TGCTGGATAA GCTGCTGAAG     1560

TAA                                                                  1563

(2) INFORMATION FOR SEQ ID NO:184:

(i) SEQUENCE CHARACTERISTICS:
        (A) LENGTH: 438 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Enterococcus faecium (xi) SEQUENCE DESCRIPTION: SEQ ID NO:184:

TACATTGATG AAGAAACGAT GCACCTGCAT CATGACAAGC ATCACAATAC TTACGTAACG       60

AATTTAAATG CAGCAATCGA AAAATATCCA GAATTAGGCG AAAAAACAGT AGAAGAATTA      120

TTATCTGATA TGGATGCTGT TCCAACAGAT ATCAAAACAG CTGTACGCAA CAATGGTGGT      180

GGACATGCTA ACCATTCATT TTTCTGGGAA ATCATGGCAC CGAATGCGGG CGGCGAGCCT      240

ACTGGGGCAA TAAAAGAAGC AATTAATGAA GCTTTTGGCG ATTTTTCTTC TTTTAAAGAA      300

GAATTCAAAA AAGCAGCAGC TGGACGTTTT GGTTCTGGTT GGGCTTGGCT TGTAATGGAG      360

AATGGGAAAT TAGCTATTAC CTCTACTGCA AATCAAGATT CTCCATTGAT GGAAGGTAAG      420

ACACCAATTC TAGGTTTA                                                   438

(2) INFORMATION FOR SEQ ID NO:185:

(i) SEQUENCE CHARACTERISTICS:
        (A) LENGTH: 1185 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:185:

ATGTCTAAAG AAAAATTTGA ACGTACAAAA CCGCACGTAA ACGTGGGTAC AATCGGCCAC       60

GTTGACCACG GTAAAACAAC TTTAACAGCA GCAATCACAA CCGTATTGGC AAAACATTAC      120

GGTGGTGCAG CGCGTGCATT CGACCAAATT GATAACGCGC CAGAAGAAAA AGCGCGTGGT      180

ATTACCATCA ACACTTCACA CGTTGAATAC GATACACCGA CTCGCCACTA TGCACACGTA      240
```

```
GACTGTCCGG GACACGCCGA CTATGTTAAA AATATGATTA CTGGTGCGGC ACAAATGGAT    300

GGTGCTATTT TAGTAGTAGC AGCAACAGAT GGTCCTATGC CGCAAACTCG TGAACACATC    360

TTATTAGGTC GCCAAGTAGG TGTTCCATAC ATCATCGTAT TCTTAAACAA ATGCGACATG    420

GTAGATGACG AAGAGTTATT AGAATTAGTC GAAATGAAG TTCGTGAACT TCTATCTCAA    480

TATGACTTCC CAGGTGACGA TACACCAATC GTACGTGGTT CAGCATTACA AGCGTTAAAC    540

GGCGTAGCAG AATGGGAAGA AAAAATCCTT GAGTTAGCAA ACCACTTAGA TACTTACATC    600

CCAGAACCAG AACGTGCGAT TGACCAACCG TTCCTTCTTC CAATCGAAGA TGTGTTCTCA    660

ATCTCAGGTC GTGGTACTGT AGTAACAGGT CGTGTAGAAC GAGGTATTAT CCGTACAGGT    720

GATGAAGTAG AAATCGTCGG TATCAAAGAT ACAGCGAAAA CTACTGTAAC GGGTGTTGAA    780

ATGTTCCGTA AATTACTTGA CGAAGGTCGT GCAGGTGAAA ACATCGGTGC ATTATTACGT    840

GGTACCAAAC GTGAAGAAAT CGAACGTGGT CAAGTATTAG CGAAACCAGG TTCAATCACA    900

CCACACACTG ACTTCGAATC AGAAGTGTAC GTATTATCAA AGATGAAGG TGGTCGTCAT    960

ACTCCATTCT TCAAAGGTTA CCGTCCACAA TTCTATTTCC GTACAACAGA CGTGACTGGT    1020

ACAATCGAAT TACCAGAAGG CGTGGAAATG GTAATGCCAG GCGATAACAT CAAGATGACA    1080

GTAAGCTTAA TCCACCCAAT TGCGATGGAC CAAGGTTTAC GTTTCGCAAT CCGTGAAGGT    1140

GGCCGTACAG TAGGTGCGGG CGTTGTTGCA AAAATCATCA AATAA                   1185

(2) INFORMATION FOR SEQ ID NO:186:

(i) SEQUENCE CHARACTERISTICS:
        (A) LENGTH: 2814 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:186:

ATGGAAAATA TCGATATTCG CGGGGCTAGA ACCCATAACC TGAAAAATAT TAATTTAACC    60

ATTCCACGCA ATAAACTTGT GGTAATCACA GGGCTTTCAG GTTCGGGGAA ATCTTCTTTA   120

GCCTTTGATA CGCTTTATGC GGAAGGGCAA CGCCGTTATG TTGAATCACT TTCCGCTTAT   180

GCCCGTCAGT TTTTATCTTT AATGGAAAAG CCTGATGTGG ATTCTATTGA GGGGCTTTCC   240

CCTGCAATTT CCATTGAACA AAAATCCACC TCACACAATC CACGTTCTAC AGTGGGAACC   300

ATTACGGAAA TTTACGATTA TTTGCGTTTA TTGTTTGCAC GAGTAGGGGA GCCGCGTTGT   360

CCCGATCATA ATGTTCCATT AACGGCACAA ACAATTAGTC AAATGGTGGA TAAAGTATTA   420

AGTTTGCCAG AAGACAGTAA GATGATGTTA CTTGCGCCAG TTGTCAAAAA TCGAAAAGGC   480

GAACATCTCA AGATTTTAGA AAATATTGCT GCGCAAGGTT ATATTCGTGC GCGTATTGAT   540

GGCGAAATTT GCGATTTATC TGATCCGCCA AAATTAGCCT TACAGAAAAA ACATACTATT   600

GAAGTAGTGG TTGATCGTTT TAAAGTGCGG TCAGATTTAG CAACACGTTT AGCCGAATCT   660

TTTGAAACCG CATTAGAGCT TTCTGGTGGC ACTGCGATTG TGGCAGATAT GGATAATCCG   720

AAAGCAGAAG AATTAGTTTT TTCGGCAAAT TTTGCTTGTC CTCATTGTGG TTATTCTGTG   780

CCAGAATTAG AGCCTCGTTT ATTTTCCTTT AACAATCCTG CAGGTGCTTG CCCAACTTGT   840

GATGGCTTGG GTGTGCAGCA ATATTTTGAT GAAGATCGTG TGGTGCAAAA TCCAACTATT   900

TCTCTTGCTG GTGGTGCGGT AAAAGGTTGG GATCGTCGTA ATTTCTATTA TTATCAAATG   960
```

```
CTTACCTCAT TGGCGAAACA TTATCATTTT GATGTTGAAG CGCCCTATGA ATCTTTGCCA      1020

AAGAAGATTC AACATATCAT TATGCATGGC TCAGGCAAAG AGGAAATTGA ATTCCAATAT      1080

ATGAATGATC GTGGCGATGT GGTTATTCGC AAGCATCCTT TTGAAGGTAT TTTGAATAAT      1140

ATGGCTCGCC GATATAAAGA AACGGAATCA ATGTCGGTGC GTGAAGAATT AGCGAAAAAT      1200

ATTAGTAATC GACCTTGTAT AGACTGTGGC GGTTCTCGTT TGCGACCCGA AGCGCGTAAT      1260

GTGTATATTG AAAAACCAA TTTGCCGATA ATTGCGGAAA AAGCATTGG CGAAACCCTC        1320

GAATTTTTTA CCGCACTTTC TTTAACAGGT CAAAAAGCAC AAATTGCGGA AAAAATTCTT      1380

AAAGAAATGC GCGAGCGTTT GCAGTTTTTA GTCAATGTAG GTTTGAATTA TCTTTCTCTT      1440

TCTCGTTCAG CTGAAACTCT TTCAGGTGGG AAGCGCAAC GTATTCGCCT TGCGAGTCAA       1500

ATTGGTGCGG GACTTGTTGG CGTAATGTAT GTATTAGATC AACCCTCTAT TGGCTTGCAC     1560

CAACGTGATA ATGAACGCTT ACTTAATACG TTAATTCATT TGCGTAATCT TGGTAATACG     1620

GTAATTGTCG TGGAACACGA TGAAGACGCG ATTCGTGCAG CTGACCATAT TATTGATATT     1680

GGGCCTGGTG CTGGCGTGCA TGGCGGACAA GTTATTGCGC AAGGAAATGC CGATGAAATT     1740

ATGCTCAATC CAAATTCCAT CACGGGAAAA TTTTTATCGG GCGCAGATAA AATCGAAATC     1800

CCGAAAAAAC GCACCGCACT TGATAAGAAA AAATGGCTCA AACTTAAAGG CGCATCAGGT     1860

AATAACTTAA AAAATGTGAA TTTAGATATT CCCGTTGGTT TATTTACTTG CGTGACTGGT     1920

GTATCTGGTT CGGAAAAATC CACACTTATT AATGACACCT TATTTCCACT TGCGCAAAAT     1980

ACGTTAAATA GAGCAGAAAA GACGGATTAC GCACCTTATC AATCTATCGA GGGATTAGAG     2040

CATTTCGATA AAGTTATCGA CATTAATCAA AGCCCGATTG GACGCACGCC ACGTTCAAAT     2100

CCAGCCACTT ATACAGGCTT ATTTACCCCA ATTCGTGAAC TTTTTGCTGG CGTACCAGAA     2160

GCGCGTGCGC GCGGTTATAA TCCAGGACGT TTTAGCTTTA ACGTACGAGG TGGACGCTGT     2220

GAAGCCTGTC AAGGCGACGG TGTACTCAAA GTTGAAATGC ACTTTTTGCC CGATGTTTAT     2280

GTTCCTTGCG ACCAATGTAA AGGTAAACGC TATAATCGCG AAACCTTAGA AATTCGTTAC     2340

AAAGGTAAAA CCATCCATCA AGTTTTAGAT ATGACAGTGG AAGAAGCACG CGAGTTTTTT     2400

GATGCGATTC CAATGATTGC AAGAAAATTA CAAACCTTGA TGGATGTGGG ATTATCCTAT     2460

ATTCGATTAG GTCAATCTTC CACCACACTT TCGGGTGGCG AAGCACAACG TGTTAAGTTA     2520

GCTACTGAGC TTTCTAAACG TGATACAGGC AAAACCTTGT ATATTTTAGA TGAACCGACG     2580

ACTGGTTTGC ATTTCGCTGA CATTAAGCAA TTACTTGAAG TGCTGCATCG ATTACGCGAC     2640

CAAGGAAATA CTATTGTCGT CATTGAACAC AATCTTGATG TGATTAAAAC CGCAGACTGG     2700

ATTGTTGATC TTGGCCCTGA AGGCGGAAGT GGTGGCGGAC AAATTATTGC GACGGGTACA     2760

CCAGAACAAG TTGCCAAAGT AGAAAGTTCC CATACCGCCC GCCCGCTTCC TTAA           2814
```

(2) INFORMATION FOR SEQ ID NO:187:

(i) SEQUENCE CHARACTERISTICS:
        (A) LENGTH: 1374 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:187:

```
ATGTCAGCAG GAAAAATTGT ACAAATCATC GGTGCGGTGA TTGACGTTGA ATTTCCACAA        60
```

```
GATGCAGTGC CAAAAGTTTA CGATGCATTA AAAGTTGAAT CAGGTTTAAC ACTTGAGGTG      120

CAACAACAAT TAGGTGGCGG AGTAGTTCGT TGTATTGCAT TGGGTACATC TGATGGTTTA      180

AAACGTGGCT TAAAAGTAGA AAACACAAAT AACCCAATTC AAGTACCAGT AGGCACAAAA      240

ACACTTGGTC GTATTATGAA TGTGTTGGGC GAACCAATTG ACGAACAAGG AGCAATTGGT      300

GAAGAAGAGC GTTGGGCTAT CCACCGTTCG GCACCGAGCT ATGAAGAACA ATCAAACAGT      360

ACGGAATTAT TAGAAACTGG TATCAAAGTG ATCGACTTAA TTTGTCCATT CGCAAAAGGT      420

GGTAAAGTTG GTTTATTCGG CGGTGCAGGT GTAGGTAAAA CCGTAAATAT GATGGAGTTG      480

ATTCGTAATA TTGCGATTGA GCATTCAGGT TACTCTGTAT TTGCGGGTGT AGGCGAACGT      540

ACTCGTGAAG GTAATGACTT CTATCATGAA ATGAAAGATT CTAACGTATT AGATAAAGTA      600

TCTTTGGTTT ATGGTCAAAT GAACGAGCCA CCAGGTAACC GTTTACGTGT TGCATTGACT      660

GGTTTAACTA TGGCTGAAAA ATTCCGTGAT GAAGGTCGAG ATGTATTATT CTTTGTGGAT      720

AATATCTATC GTTATACCCT TGCTGGTACG GAAGTATCTG CGTTATTAGG TCGTATGCCA      780

TCCGCGGTAG GTTACCAACC GACATTGGCA GAAGAAATGG GTGTGTTACA AGAACGTATC      840

ACTTCAACCA AAACAGGTTC TATCACTTCT GTGCAAGCGG TGTACGTACC AGCGGATGAC      900

TTAACTGACC CATCTCCAGC AACAACTTTC GCACATTTAG ACTCAACTGT TGTATTAAGT      960

CGTCAAATCG CATCTTTAGG TATTTACCCT GCAGTTGATC CATTAGATTC AACTTCACGT     1020

CAGCTAGACC CGCTTGTTGT TGGTCAAGAA CATTATGATG TTGCTCGTGG TGTACAAGGT     1080

ATTTTACAAC GTTATAAAGA ATTGAAAGAT ATTATCGCAA TTCTTGGTAT GGATGAATTA     1140

TCTGAAGAAG ATAAACTAGT GGTAGCACGT GCACGTAAAA TTGAACGTTT CTTATCACAA     1200

CCATTCTTTG TTGCAGAAGT CTTCACAGGT TCACCAGGTA AATACGTGAC ATTAAAAGAC     1260

ACCATCCGTG GCTTCAAAGG TATCTTAGAT GGCGAATATG ACCATATTCC TGAACAAGCG     1320

TTCTATATGG TTGGTTCAAT CGATGAAGTG TTAGAAAAAG CCAAAAATAT GTAA          1374
```

(2) INFORMATION FOR SEQ ID NO:188:

(i) SEQUENCE CHARACTERISTICS:
        (A) LENGTH: 831 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:188:

```
ATGAAAAACA CAATACATAT CAACTTCGCT ATTTTTTTAA TAATTGCAAA TATTATCTAC       60

AGCAGCGCCA GTGCATCAAC AGATATCTCT ACTGTTGCAT CTCCATTATT TGAAGGAACT      120

GAAGGTTGTT TTTTACTTTA CGATGCATCC ACAAACGCTG AAATTGCTCA ATTCAATAAA      180

GCAAAGTGTG CAACGCAAAT GGCACCAGAT TCAACTTTCA AGATCGCATT ATCACTTATG      240

GCATTTGATG CGGAAATAAT AGATCAGAAA ACCATATTCA AATGGGATAA AACCCCCAAA      300

GGAATGGAGA TCTGGAACAG CAATCATACA CCAAAGACGT GGATGCAATT TTCTGTTGTT      360

TGGGTTTCGC AAGAAATAAC CCAAAAAATT AGATTAAATA AAATCAAGAA TTATCTCAAA      420

GATTTTGATT ATGGAAATCA AGACTTCTCT GGAGATAAAG AAAGAAACAA CGGATTAACA      480

GAAGCATGGC TCGAAAGTAG CTTAAAAATT TCACCAGAAG AACAAATTCA ATTCCTGCGT      540

AAAATTATTA ATCACAATCT CCCAGTTAAA AACTCAGCCA TAGAAAACAC CATAGAGAAC      600

ATGTATCTAC AAGATCTGGA TAATAGTACA AAACTGTATG GGAAAACTGG TGCAGGATTC      660
```

```
ACAGCAAATA GAACCTTACA AAACGGATGG TTTGAAGGGT TTATTATAAG CAAATCAGGA      720

CATAAATATG TTTTTGTGTC CGCACTTACA GGAAACTTGG GGTCGAATTT AACATCAAGC      780

ATAAAAGCCA AGAAAAATGC GATCACCATT CTAAACACAC TAAATTTATA A              831

(2) INFORMATION FOR SEQ ID NO:189:

(i) SEQUENCE CHARACTERISTICS:
        (A) LENGTH: 846 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:189:

TTGAAAAAGT TAATATTTTT AATTGTAATT GCTTTAGTTT TAAGTGCATG TAATTCAAAC       60

AGTTCACATG CCAAAGAGTT AAATGATTTA GAAAAAAAAT ATAATGCTCA TATTGGTGTT      120

TATGCTTTAG ATACTAAAAG TGGTAAGGAA GTAAAATTTA ATTCAGATAA GAGATTTGCC      180

TATGCTTCAA CTTCAAAAGC GATAAATAGT GCTATTTTGT TAGAACAAGT ACCTTATAAT      240

AAGTTAAATA AAAAGTACA TATTAACAAA GATGATATAG TTGCTTATTC TCCTATTTTA       300

GAAAAATATG TAGGAAAAGA TATCACTTTA AAAGCACTTA TTGAGGCTTC AATGACATAT      360

AGTGATAATA CAGCAAACAA TAAAATTATA AAAGAAATCG GTGGAATCAA AAAAGTTAAA     420

CAACGTCTAA AAGAACTAGG AGATAAAGTA ACAAATCCAG TTAGATATGA GATAGAATTA     480

AATTACTATT CACCAAAGAG CAAAAAAGAT ACTTCAACAC CTGCTGCTTT CGGTAAGACT     540

TTAAATAAAC TTATCGCAAA TGGAAAATTA AGCAAAGAAA ACAAAAAATT CTTACTTGAT     600

TTAATGTTAA ATAATAAAAG CGGAGATACT TTAATTAAAG ACGGTGTTCC AAAAGACTAT     660

AAGGTTGCTG ATAAAAGTGG TCAAGCAATA ACATATGCTT CTAGAAATGA TGTTGCTTTT    720

GTTTATCCTA AGGGCCAATC TGAACCTATT GTTTTAGTCA TTTTTACGAA TAAAGACAAT    780

AAAAGTGATA AGCCAAATGA TAAGTTGATA AGTGAAACCG CCAAGAGTGT AATGAAGGAA    840

TTTTAA                                                              846

(2) INFORMATION FOR SEQ ID NO:190:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:190:

ATGTCCGCGA GCACCCCCCC CATAACTCTT CGCCTCATGA CCGAGCGCGA CCTGCCGATG       60

CTCCATGACT GGCTCAACCG GCCGCACATC GTTGAGTGGT GGGGTGGCGA CGAAGAGCGA     120

CCGACTCTTG ATGAAGTGCT GGAACACTAC CTGCCCAGAG CGATGGCGGA AGAGTCCGTA     180

ACACCGTACA TCGCAATGCT GGGCGAGGAA CCGATCGGCT ATGCTCAGTC GTACGTCGCG     240

CTCGGAAGCG GTGATGGCTG GTGGGAAGAT GAAACTGATC CAGGAGTGCG AGGAATAGAC     300

CAGTCTCTGG CTGACCCGAC ACAGTTGAAC AAAGGCCTAG AACAAGGCT TGTCCGCGCT      360

CTCGTTGAAC TACTGTTCTC GGACCCCACC GTGACGAAGA TTCAGACCGA CCCGACTCCG    420

AACAACCATC GAGCCATACG CTGCTATGAG AAGGCAGGAT TCGTGCGGGA GAAGATCATC    480

ACCACGCCTG ACGGGCCGGC GGTTTACATG GTTCAAACAC GACAAGCCTT CGAGAGAAAG    540
```

|     |     |
| --- | --- |
| CGCGGTGTTG CCTAA | 555 |

(2) INFORMATION FOR SEQ ID NO:191:

(i) SEQUENCE CHARACTERISTICS:
        (A) LENGTH: 1029 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:191:

|     |     |
| --- | --- |
| ATGAATAAAA TAAAAGTCGC AATTATCTTC GGCGGTTGCT CGGAGGAACA TGATGTGTCG | 60 |
| GTAAAATCCG CAATAGAAAT TGCTGCGAAC ATTAATACTG AAAAATTCGA TCCGCACTAC | 120 |
| ATCGGAATTA CAAAAAACGG CGTATGGAAG CTATGCAAGA AGCCATGTAC GGAATGGGAA | 180 |
| GCCGATAGTC TCCCCGCCAT ATTCTCCCCG GATAGGAAAA CGCATGGTCT GCTTGTCATG | 240 |
| AAAGAAAGAG AATACGAAAC TCGGCGTATT GACGTGGCTT TCCCGGTTTT GCATGGCAAA | 300 |
| TGCGGGGAGG ATGGTGCGAT ACAGGGTCTG TTTGAATTGT CTGGTATCCC CTATGTAGGC | 360 |
| TGCGATATTC AAAGCTCCGC AGCTTGCATG GACAAATCAC TGGCCTACAT TCTTACAAAA | 420 |
| AATGCGGGCA TCGCCGTCCC CGAATTTCAA ATGATTGAAA AAGGTGACAA ACCGGAGGCG | 480 |
| AGGACGCTTA CCTACCCTGT CTTTGTGAAG CCGGCACGGT CAGGTTCGTC CTTTGGCGTA | 540 |
| ACCAAAGTAA ACAGTACGGA AGAACTAAAC GCTGCGATAG AAGCAGCAGG ACAATATGAT | 600 |
| GGAAAAATCT TAATTGAGCA AGCGATTTCG GGCTGTGAGG TCGGCTGCGC GGTCATGGGA | 660 |
| AACGAGGATG ATTTGATTGT CGGCGAAGTG GATCAAATCC GGTTGAGCCA CGGTATCTTC | 720 |
| CGCATCCATC AGGAAAACGA GCCGGAAAAA GGCTCAGAGA ATGCGATGAT TATCGTTCCA | 780 |
| GCAGACATTC CGGTCGAGGA ACGAAATCGG GTGCAAGAAA CGGCAAAGAA AGTATATCGG | 840 |
| GTGCTTGGAT GCAGAGGGCT TGCTCGTGTT GATCTTTTTT TGCAGGAGGA TGGCGGCATC | 900 |
| GTTCTAAACG AGGTCAATAC CCTGCCCGGT TTTACATCGT ACAGCCGCTA TCCACGCATG | 960 |
| GCGGCTGCCG CAGGAATCAC GCTTCCCGCA CTAATTGACA GCCTGATTAC ATTGGCGATA | 1020 |
| GAGAGGTGA | 1029 |

(2) INFORMATION FOR SEQ ID NO:192:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:192:

|     |     |
| --- | --- |
| ATGAACCAGA AAACCCTAA AGACACGCAA AATTTTATTA CTTCTAAAAA GCATGTAAAA | 60 |
| GAAATATTGA ATCACACGAA TATCAGTAAA CAAGACAACG TAATAGAAAT CGGATCAGGA | 120 |
| AAAGGACATT TTACCAAAGA GCTAGTCAAA ATGAGTCGAT CAGTTACTGC TATAGAAATT | 180 |
| GATGGAGGCT TATGTCAAGT GACTAAAGAA GCGGTAAACC CCTCTGAGAA TATAAAAGTG | 240 |
| ATTCAAACGG ATATTCTAAA ATTTTCCTTC CCAAAACATA TAAACTATAA GATATATGGT | 300 |
| AATATTCCTT ATAACATCAG TACGGATATT GTCAAAAGAA TTACCTTTGA AAGTCAGGCT | 360 |
| AAATATAGCT ATCTTATCGT TGAGAAGGGA TTTGCGAAAA GATTGCAAAA TCTGCAACGA | 420 |
| GCTTTGGGTT TACTATTAAT GGTGGAGATG GATATAAAAA TGCTCAAAAA AGTACCACCA | 480 |

| | |
|---|---:|
| CTATATTTTC ATCCTAAGCC AAGTGTAGAC TCTGTATTGA TTGTTCTTGA ACGACATCAA | 540 |
| CCATTGATTT CAAAGAAGGA CTACAAAAAG TATCGATCTT TTGTTTATAA GTGGGTAAAC | 600 |
| CGTGAATATC GTGTTCTTTT CACTAAAAAC CAATTCCGAC AGGCTTTGAA GCATGCAAAT | 660 |
| GTCACTAATA TTAATAAACT ATCGAAGGAA CAATTTCTTT CTATTTTCAA TAGTTACAAA | 720 |
| TTGTTTCACT AA | 732 |

(2) INFORMATION FOR SEQ ID NO:193:

(i) SEQUENCE CHARACTERISTICS:
        (A) LENGTH: 738 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:193:

| | |
|---|---:|
| ATGAACAAAA ATATAAAATA TTCTCAAAAC TTTTTAACGA GTGAAAAAGT ACTCAACCAA | 60 |
| ATAATAAAAC AATTGAATTT AAAAGAAACC GATACCGTTT ACGAAATTGG AACAGGTAAA | 120 |
| GGGCATTTAA CGACGAAACT GGCTAAAATA AGTAAACAGG TAACGTCTAT TGAATTAGAC | 180 |
| AGTCATCTAT TCAACTTATC GTCAGAAAAA TTAAAATCGA ATACTCGTGT CACTTTAATT | 240 |
| CACCAAGATA TTCTACAGTT TCAATTCCCT AACAAACAGA GGTATAAAAT TGTTGGGAAT | 300 |
| ATTCCTTACC ATTAAGCAC ACAAATTATT AAAAAAGTGG TTTTTGAAAG CCATGCGTCT | 360 |
| GACATCTATC TGATTGTTGA AGAAGGATTC TACAAGCGTA CCTTGGATAT TCACCGAACA | 420 |
| CTAGGGTTGC TCTTGCACAC TCAAGTCTCG ATTCAGCAAT TGCTTAAGCT GCCAGCGGAA | 480 |
| TGCTTTCATC CTAAACCAAG AGTAAACAGT GTCTTAATAA AACTTACCCG CCATACCACA | 540 |
| GATGTTCCAG ATAAATATTG GAAGCTATAT ACGTACTTTG TTTCAAAATG GGTCAATCGA | 600 |
| GAATATCGTC AACTGTTTAC TAAAAATCAG TTTCATCAAG CAATGAAACA CGCCAAAGTA | 660 |
| AACAATTTAA GTACCGTTAC TTATGAGCAA GTATTGTCTA TTTTTAATAG TTATCTATTA | 720 |
| TTTAACGGGA GGAAATAA | 738 |

(2) INFORMATION FOR SEQ ID NO:194:

(i) SEQUENCE CHARACTERISTICS:
        (A) LENGTH: 735 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:194:

| | |
|---|---:|
| ATGAACGAGA AAAATATAAA ACACAGTCAA AACTTTATTA CTTCAAAACA TAATATAGAT | 60 |
| AAAATAATGA CAAATATAAG ATTAAATGAA CATGATAATA TCTTTGAAAT CGGCTCAGGA | 120 |
| AAAGGGCATT TTACCCTTGA ATTAGTACAG AGGTGTAATT TCGTAACTGC CATTGAAATA | 180 |
| GACCATAAAT TATGCAAAAC TACAGAAAAT AAACTTGTTG ATCACGATAA TTTCCAAGTT | 240 |
| TTAAACAAGG ATATATTGCA GTTTAAATTT CCTAAAAACC AATCCTATAA AATATTTGGT | 300 |
| AATATACCTT ATAACATAAG TACGGATATA ATACGCAAAA TTGTTTTTGA TAGTATAGCT | 360 |
| GATGAGATTT ATTTAATCGT GGAATACGGG TTTGCTAAAA GATTATTAAA TACAAAACGC | 420 |
| TCATTGGCAT TATTTTTAAT GGCAGAAGTT GATATTTCTA TATTAAGTAT GGTTCCAAGA | 480 |
| GAATATTTTC ATCCTAAACC TAGAGTGAAT AGCTCACTTA TCAGATTAAA TAGAAAAAAA | 540 |

```
TCAAGAATAT CACACAAAGA TAAACAGAAG TATAATTATT TCGTTATGAA ATGGGTTAAC        600

AAAGAATACA AGAAAATATT TACAAAAAAT CAATTTAACA ATTCCTTAAA ACATGCAGGA        660

ATTGACGATT TAAACAATAT TAGCTTTGAA CAATTCTTAT CTCTTTTCAA TAGCTATAAA        720

TTATTTAATA AGTAA                                                        735
```

(2) INFORMATION FOR SEQ ID NO:195:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:195:

```
CTATGTGGCG CGGTATTATC                                                    20
```

(2) INFORMATION FOR SEQ ID NO:196:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:196:

```
CGCAGTGTTA TCACTCATGG                                                    20
```

(2) INFORMATION FOR SEQ ID NO:197:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:197:

```
CTGAATGAAG CCATACCAAA                                                    20
```

(2) INFORMATION FOR SEQ ID NO:198:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:198:

```
ATCAGCAATA AACCAGCCAG                                                    20
```

(2) INFORMATION FOR SEQ ID NO:199:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:199:

```
TACGCCAACA TCGTGGAAAG                                               20

(2) INFORMATION FOR SEQ ID NO:200:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:200:

TTGAATTTGG CTTCTTCGGT                                               20

(2) INFORMATION FOR SEQ ID NO:201:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:201:

GGGATACAGA AACGGGACAT                                               20

(2) INFORMATION FOR SEQ ID NO:202:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:202:

TAAATCTTTT TCAGGCAGCG                                               20

(2) INFORMATION FOR SEQ ID NO:203:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:203:

TTACCATGAG CGATAACAGC                                               20

(2) INFORMATION FOR SEQ ID NO:204:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:204:

CTCATTCAGT TCCGTTTCCC                                               20

(2) INFORMATION FOR SEQ ID NO:205:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:205:

CAGCTGCTGC AGTGGATGGT                                         20

(2) INFORMATION FOR SEQ ID NO:206:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:206:

CGCTCTGCTT TGTTATTCGG                                         20

(2) INFORMATION FOR SEQ ID NO:207:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:207:

GATGGTTTGA AGGGTTTATT ATAAG                                   25

(2) INFORMATION FOR SEQ ID NO:208:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:208:

AATTTAGTGT GTTTAGAATG GTGAT                                   25

(2) INFORMATION FOR SEQ ID NO:209:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:209:

ACTTCAACAC CTGCTGCTTT C                                       21

(2) INFORMATION FOR SEQ ID NO:210:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:210:

TGACCACTTT TATCAGCAAC C                                            21

(2) INFORMATION FOR SEQ ID NO:211:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:211:

GGCAATAGTT GAAATGCTCG                                              20

(2) INFORMATION FOR SEQ ID NO:212:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:212:

CAGCTGTTAC AACGGACTGG                                              20

(2) INFORMATION FOR SEQ ID NO:213:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:213:

TCTATGATCT CGCAGTCTCC                                              20

(2) INFORMATION FOR SEQ ID NO:214:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:214:

ATCGTCACCG TAATCTGCTT                                              20

(2) INFORMATION FOR SEQ ID NO:215:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:215:

CATTCTCGAT TGCTTTGCTA                                                    20

(2) INFORMATION FOR SEQ ID NO:216:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:216:

CCGAAATGCT TCTCAAGATA                                                    20

(2) INFORMATION FOR SEQ ID NO:217:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:217:

CTGGATTATG GCTACGGAGT                                                    20

(2) INFORMATION FOR SEQ ID NO:218:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:218:

AGCAGTGTGA TGGTATCCAG                                                    20

(2) INFORMATION FOR SEQ ID NO:219:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:219:

GACTCTTGAT GAAGTGCTGG                                                    20

(2) INFORMATION FOR SEQ ID NO:220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:220:

CTGGTCTATT CCTCGCACTC                                                    20

(2) INFORMATION FOR SEQ ID NO:221:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:221:

TATGAGAAGG CAGGATTCGT                                                       20

(2) INFORMATION FOR SEQ ID NO:222:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:222:

GCTTTCTCTC GAAGGCTTGT                                                       20

(2) INFORMATION FOR SEQ ID NO:223:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:223:

GAGTTGCTGT TCAATGATCC                                                       20

(2) INFORMATION FOR SEQ ID NO:224:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:224:

GTGTTTGAAC CATGTACACG                                                       20

(2) INFORMATION FOR SEQ ID NO:225:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:225:

TGTAGAGGTC TAGCCCGTGT                                                       20

(2) INFORMATION FOR SEQ ID NO:226:

(i) SEQUENCE CHARACTERISTICS:
            (A) LENGTH: 20 base pairs
            (B) TYPE: nucleic acid
            (C) STRANDEDNESS: single -continued (D) TOPOLOGY: linear (ii) MOLECULE TYPE: DNA (genomic)

(xi) SEQUENCE DESCRIPTION: SEQ ID NO:226:

ACGGGGATAA CGACTGTATG                                           20

(2) INFORMATION FOR SEQ ID NO:227:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:227:

ATAAAGATGA TAGGCCGGTG                                           20

(2) INFORMATION FOR SEQ ID NO:228:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:228:

TGCTGTCATA TTGTCTTGCC                                           20

(2) INFORMATION FOR SEQ ID NO:229:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:229:

ATTATCTTCG GCGGTTGCTC                                           20

(2) INFORMATION FOR SEQ ID NO:230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:230:

GACTATCGGC TTCCCATTCC                                           20

(2) INFORMATION FOR SEQ ID NO:231:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:231:

CGATAGAAGC AGCAGGACAA                                              20

(2) INFORMATION FOR SEQ ID NO:232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:232:

CTGATGGATG CGGAAGATAC                                              20

(2) INFORMATION FOR SEQ ID NO:233:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:233:

TCCAATCATT GCACAAAATC                                              20

(2) INFORMATION FOR SEQ ID NO:234:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:234:

AATTCCCTCT ATTTGGTGGT                                              20

(2) INFORMATION FOR SEQ ID NO:235:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:235:

TCCCAAGCCA GTAAAGCTAA                                              20

(2) INFORMATION FOR SEQ ID NO:236:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:236:

TGGTTTTTCA ACTTCTTCCA                                              20

(2) INFORMATION FOR SEQ ID NO:237:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:237:

TCATAGAATG GATGGCTCAA                                            20

(2) INFORMATION FOR SEQ ID NO:238:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:238:

AGCTACTATT GCACCATCCC                                            20

(2) INFORMATION FOR SEQ ID NO:239:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:239:

CAATAAGGGC ATACCAAAAA TC                                         22

(2) INFORMATION FOR SEQ ID NO:240:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:240:

CCTTAACATT TGTGGCATTA TC                                         22

(2) INFORMATION FOR SEQ ID NO:241:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:241:

TTGGGAAGAT GAAGTTTTTA GA                                         22

(2) INFORMATION FOR SEQ ID NO:242:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:242:

CCTTTACTCC AATAATTTGG CT                                           22

(2) INFORMATION FOR SEQ ID NO:243:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:243:

TTTCATCTAT TCAGGATGGG                                              20

(2) INFORMATION FOR SEQ ID NO:244:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:244:

GGAGCAACAT TCTTTGTGAC                                              20

(2) INFORMATION FOR SEQ ID NO:245:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:245:

TGTGCCTGAA GAAGGTATTG                                              20

(2) INFORMATION FOR SEQ ID NO:246:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:246:

CGTGTTACTT CACCACCACT                                              20

(2) INFORMATION FOR SEQ ID NO:247:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:247:

TATCTTATCG TTGAGAAGGG ATT         23

(2) INFORMATION FOR SEQ ID NO:248:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:248:

CTACACTTGG CTTAGGATGA AA         22

(2) INFORMATION FOR SEQ ID NO:249:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:249:

CTATCTGATT GTTGAAGAAG GATT         24

(2) INFORMATION FOR SEQ ID NO:250:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:250:

GTTTACTCTT GGTTTAGGAT GAAA         24

(2) INFORMATION FOR SEQ ID NO:251:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:251:

CTTGTTGATC ACGATAATTT CC         22

(2) INFORMATION FOR SEQ ID NO:252:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:252:

ATCTTTTAGC AAACCCGTAT TC         22

(2) INFORMATION FOR SEQ ID NO:253:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:253:

GTGATCGAAA TCCAGATCC                                                   19

(2) INFORMATION FOR SEQ ID NO:254:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:254:

ATCCTCGGTT TTCTGGAAG                                                   19

(2) INFORMATION FOR SEQ ID NO:255:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:255:

CTGGTCATAC ATGTGATGG                                                   19

(2) INFORMATION FOR SEQ ID NO:256:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:256:

GATGTTACCC GAGAGCTTG                                                   19

(2) INFORMATION FOR SEQ ID NO:257:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:257:

TTAAGCGTGC ATAATAAGCC                                                  20

(2) INFORMATION FOR SEQ ID NO:258:

(i) SEQUENCE CHARACTERISTICS:
           (A) LENGTH: 20 base pairs
           (B) TYPE: nucleic acid
           (C) STRANDEDNESS: single (D) TOPOLOGY: linear (ii) MOLECULE TYPE: DNA (genomic)

(xi) SEQUENCE DESCRIPTION: SEQ ID NO:258:

TTGCGATTAC TTCGCCAACT                                           20

(2) INFORMATION FOR SEQ ID NO:259:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:259:

TTTACTAAGC TTGCCCCTTC                                           20

(2) INFORMATION FOR SEQ ID NO:260:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:260:

AAAAGGCAGC AATTATGAGC                                           20

(2) INFORMATION FOR SEQ ID NO:261:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:261:

AACAGGTGAA TTATTAGCAC TTGTAAG                                   27

(2) INFORMATION FOR SEQ ID NO:262:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:262:

ATTGCTGTTA ATATTTTTG AGTTGAA                                    27

(2) INFORMATION FOR SEQ ID NO:263:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:

(A) ORGANISM: Enterococcus faecium (xi) SEQUENCE DESCRIPTION: SEQ ID NO:263:

ACGCAACAAT GGTGGTGGAC A                                            21

(2) INFORMATION FOR SEQ ID NO:264:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Enterococcus faecium (xi) SEQUENCE DESCRIPTION: SEQ ID NO:264:

TCTTGATTTG CAGTAGAGGT AATAG                                        25

(2) INFORMATION FOR SEQ ID NO:265:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 12
        (D) OTHER INFORMATION: /mod_base= i (xi) SEQUENCE DESCRIPTION: SEQ ID NO:265:

GAAATTGCAG GNAAATTGAT TGA                                          23

(2) INFORMATION FOR SEQ ID NO:266:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 12
        (D) OTHER INFORMATION: /mod_base= i (xi) SEQUENCE DESCRIPTION: SEQ ID NO:266:

TTACGCATGG CNTGACTCAT CAT                                          23

(2) INFORMATION FOR SEQ ID NO:267:

(i) SEQUENCE CHARACTERISTICS:
        (A) LENGTH: 438 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:267:

```
TCGCTTCTCC AGAAGAAATT TTAGAAACAT ATCTAGAAAA TCCCAAATTA GATAAACCGT      60

TTATATTATG TGAATACGCA CATGCAATGG GAAATTCACC AGGAGATCTT AATGCATATC     120

AAACATTAAT TGAAAAATAT GATAGTTTTA TTGGCGGTTT TGTTTGGGAA TGGTGTGATC     180

ATAGCATTCA GGTTGGGATA AAGGAAGGTA AACCAATTTT TAGATATGGT GGAGATTTTG     240

GTGAGGCCTT ACATGACGGT AATTTTTGTG TTGATGGTAT TGTTTCGCCA GATCGAATTC     300

CACATGAAGG TTATTATGAG TTTAAACATG AACATAGACC TTTGAGATTG GTTAACGAAG     360

AGGATTATCG GTTTACATTG AAGAATCAAT TTGATTTTAC AAATGCGGAG GATAGTTTGA     420

TTGTTGAGGG AGAAGCGA                                                   438
```

(2) INFORMATION FOR SEQ ID NO:268:

(i) SEQUENCE CHARACTERISTICS:
        (A) LENGTH: 692 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus mutans (xi) SEQUENCE DESCRIPTION: SEQ ID NO:268:

```
GGGCCGGAAT CTTCTGGTAA GACAACTGTC GCTCTTCATG CTGCTGCTCA GGCGCAAAAA      60

GATGGCGGTA TTGCCGCTTT CATTGATGCA GAACATGCCC TTGATCCAGC CTATGCTGCT     120

GCTCTTGGCG TTAATATTGA TGAGCTTTTG CTTTCACAAC CAGATTCAGG AGAACAGGGT     180

CTTGAAATTG CAGGGAAATT GATTGATTCT GGCGCTGTTG ATTTAGTTGT TGTTGACTCA     240

GTGGCAGCTT TAGTACCACG TGCGGAGATT GACGGAGATA TTGGTAATAG TCATGTTGGC     300

TTACAAGCAC GCATGATGAG TCAAGCGATG CGTAAATTAT CAGCTTCAAT CAATAAAACA     360

AAAACCATTG CTATTTTTAT TAATCAATTG CGGGAAAAAG TTGGTATTAT GTTTGGTAAT     420

CCAGAAACAA CCCCTGGCGG GCGTGCCTTG AAGTTTTATT CTTCTGTGCG TCTTGATGTC     480

CGCGGCAATA CTCAAATTAA AGGAACCGGG GAACAAAAAG ACAGCAATAT TGGTAAAGAG     540

ACCAAAATTA AAGTTGTTAA AAATAAAGTT GCTCCACCAT TTAAGGAAGC TTTTGTAGAA     600

ATTATATATG GTGAAGGCAT TTCTCGTACA GGTGAATTAG TTAAGATTGC CAGTGATTTG     660

GGAATTATCC AAAAAGCTGG AGCTTGGTAC TC                                   692
```

(2) INFORMATION FOR SEQ ID NO:269:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:269:

```
GCAAGGTTAA AACTCAAATG AATTGACGGG GG                                    32
```

(2) INFORMATION FOR SEQ ID NO:270:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:270:

GTGTGACGGG CGGTGTGTAC AAGGC                25

(2) INFORMATION FOR SEQ ID NO:271:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:271:

AGCGGTGGAG CATGTGGTTT AATTC                25

(2) INFORMATION FOR SEQ ID NO:272:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:272:

GACTTAACCC AACATTTCAC AACAC                25

(2) INFORMATION FOR SEQ ID NO:273:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:273:

TCGCTTCTCC                                 10

SPECIES-SPECIFIC AND UNIVERSAL DNA PROBES AND AMPLIFICATION PRIMERS TO RAPIDLY DETECT AND IDENTIFY COMMON BACTERIAL PATHOGENS AND ASSOCIATED ANTIBIOTIC RESISTANCE GENES FROM CLINICAL SPECIMENS FOR ROUTINE DIAGNOSIS IN MICROBIOLOGY LABORATORIES

This is a continuation-in-part of U.S. application which Ser. No. is 08/536,840 filed Sept. 11, 1995.

BACKGROUND OF THE INVENTION

Classical Identification of Bacteria

Bacteria are classically identified by their ability to utilize different substrates as a source of carbon and nitrogen through the use of biochemical tests such as the API20E™ system (bioMérieux). Susceptibility testing of gram-negative bacilli has progressed to microdilution tests. Although the API and the microdilution systems are cost-effective, at least two days are required to obtain preliminary results due to the necessity of two successive overnight incubations to isolate and identify the bacteria from the clinical specimen. Some faster detection methods with sophisticated and expensive apparatus have been developed. For example, the fastest identification system, the autoSCAN-Walk-Away™ system (Dade Diagnostics) identifies both gram-negative and gram-positive bacterial species from isolated colonies in as little as 2 hours and gives susceptibility patterns to antibiotics in only 7 hours. However, this system has an unacceptable margin of error, especially with bacterial species other than *Enterobacteriaceae* (Croizé J., 1995, La Lettre de l'Infectiologue 10:109–113; York et al., 1992. J. Clin. Microbiol. 30:2903–2910). Nevertheless, even this fastest method requires primary isolation of the bacteria as a pure culture, a process which takes at least 18 hours for a pure culture or 2 days for a mixed culture.

Urine Specimens

A large proportion (40–50%) of specimens received in routine diagnostic microbiology laboratories for bacterial identification are urine specimens (Pezzlo, 1988, Clin. Microbiol. Rev. 1:268–280). Urinary tract infections (UTI) are extremely common (affect up to 20% of women) and account for extensive morbidity and increased mortality among hospitalized patients (Johnson and Stamm, 1989, Ann. Intern. Med. 111:906–917). UTI are usually of bacterial etiology and require antimicrobial therapy. The gram-negative bacillus *Escherichia coli* is by far the most prevalent urinary pathogen and accounts for 50 to 60% of UTI (Pezzlo, 1988, Clin. Microbiol. Rev. 1:268–280). The prevalence for bacterial pathogens isolated from urine specimens observed recently at the "Centre Hospitalier de l'Universite Laval (CHUL)" is given in Tables 1 and 2.

Conventional Pathogen Identification from Urine Specimens

The search for pathogens in urine specimens is so preponderant in the routine microbiology laboratory that a myriad of tests have been developed. The gold standard is still the classical semi-quantitative plate culture method in which a calibrated loop of urine is streaked on plates and incubated for 18–24 hours. Colonies are then counted to determine the total number of colony forming units (CFU) per liter of urine. A bacterial UTI is normally associated with a bacterial count of $10^7$ CFU/L or more in urine. However, infections with less than $10^7$ CFU/L in urine are possible, particularly in patients with a high incidence of diseases or those catheterized (Stark and Maki, 1984, N. Engl. J. Med. 311:560–564). Importantly, close to 80% of urine specimens tested are considered negative (less than $10^7$ CFU/L; Table 3).

Accurate and rapid urine screening methods for bacterial pathogens would allow a faster identification of negative specimens and a more efficient clinical investigation of the patient. Several rapid identification methods (Uriscreen™, UTIscreen™, Flash Track™ DNA probes and others) were recently compared to slower standard biochemical methods which are based on culture of the bacterial pathogens. Although much faster, these rapid tests showed low sensitivities and poor specificities as well as a high number of false negative and false positive results (Koenig et al., 1992. J. Clin. Microbiol. 30:342–345; Pezzlo et al., 1992. J. Clin. Microbiol. 30:680–684).

Urine specimens found positive by culture are further characterized using standard biochemical tests to identify the bacterial pathogen and are also tested for susceptibility to antibiotics. The biochemical and susceptibility testing normally require 18–24 hours of incubation.

Any Clinical Specimens

As with urine specimens which were used here as an example to show the need for rapid and accurate diagnostic tests for bacterial detection and identification directly from clinical specimens, our probes and amplification primers are also applicable for bacterial detection and identification directly from any other clinical specimens such as blood cultures, blood, sputum, cerebrospinal fluid and others (Table 4). The DNA-based tests proposed in this invention are superior in terms of both rapidity and accuracy to standard biochemical methods currently used for routine diagnosis from any clinical specimens in Microbiology Laboratories. Clinical specimens from organisms other than humans (e.g. other primates, mammals, farm animals or livestock) may also be used.

A High Percentage of Culture Negative Specimens

Among all the clinical specimens received for routine diagnosis, approximately 80% of urine specimens and even more (around 95%) for other types of clinical specimens are negative for the presence of bacterial pathogen (Table 4). It would therefore be desirable, not only to identify bacterial species, but also to screen out the high proportion of negative clinical specimens by detecting the presence of any bacteria (i.e. universal bacterial detection).

Towards the Development of Rapid DNA-Based Diagnostic Tests

A rapid diagnostic test should have a significant impact on the management of infections. For the identification of pathogens and antibiotic resistance genes in clinical samples, DNA probe and DNA amplification technologies offer several advantages over conventional methods. There is no need for culture of the bacterial pathogens, hence the organisms can be detected directly from clinical samples thereby reducing the time associated with the isolation and identification of pathogens. DNA-based technologies have proven to be extremely useful for specific applications in the clinical microbiology laboratory. For example, kits for the detection of fastidious organisms based on the use of hybridization probes or DNA amplification for the direct detection of pathogens from clinical specimens are commercially available (Tenover F. C., and E. R. Unger. 1993. "Nucleic Acid Probes for Detection and Identification of Infectious Agents", pp. 3–25. In Persing, D. H., T. F. Smith, F. C. Tenover, and T. J. White (ed.) Diagnostic Molecular Microbiology: Principles and Applications. American Society for Microbiology, Washington, D.C.).

Others have developed DNA-based tests for the detection and identification of some of the bacterial pathogens for which we have identified species-specific sequences (PCT patent application Ser. No. WO 93/03186). However, their strategy was based on the amplification of the highly conserved 16S rRNA gene followed by hybridization with internal species-specific oligonucleotides. The strategy from the present invention is different, simpler and more rapid because it allows the direct amplification of species-specific, genus-specific or universal bacterial targets using oligonucleotides derived from genomic DNA fragments other than the 16S rRNA genes or from antibiotic resistance DNA sequences which are derived either from the genome or from extrachromosomal elements.

Although there are diagnostic kits or methods already used in clinical microbiology laboratories, there is still a need for an advantageous alternative to the conventional culture identification methods to improve the accuracy and the speed of the diagnosis of bacterial infections. Besides being much faster, DNA-based diagnostic tests are more accurate than standard biochemical tests presently used for diagnosis because the bacterial genotype (e.g. DNA level) is more stable than the bacterial phenotype (e.g. biochemical properties).

Knowledge on the genomic sequences of bacterial species continuously increases as verified from the number of sequences available from data banks. From the sequences readily available from data banks, there is no indication therefrom as to their potential for diagnostic purposes. For determining good candidates for diagnostic purposes, one could select sequences for either (i) the species-specific or genus-specific detection and identification of commonly encountered bacterial pathogens, (ii) the universal detection of bacterial pathogens from clinical specimens and/or (iii) the specific detection and identification of antibiotic resistance genes.

In our co-pending U.S. patent application (Ser. No. 08/526,840), we described DNA sequences suitable for (i) the species-specific detection and identification of 12 clinically important bacterial pathogens, (ii) the universal detection of bacteria, and (iii) the detection of 17 antibiotic resistance genes. This application described proprietary DNA sequences and DNA sequences selected from data banks (in both cases, fragments of at least 100 base pairs), as well as oligonucleotide probes and amplification primers derived from these sequences. All the nucleic acid sequences described in this patent application enter the composition of diagnostic kits and methods capable of a) detecting the presence of bacteria, b) detecting specifically the presence of 12 bacterial species and 17 antibiotic resistance genes. However, these methods and kits need to be improved since the ideal kit and method should be capable of diagnosing close to 100% of bacterial pathogens and antibiotic resistance genes. For example, infections caused by *Enterococcus faecium* have become a clinical problem because of its resistance to many antibiotics. Both detection of these bacteria and evaluation of their resistance profiles are desirable. Besides that, novel DNA sequences (probes and primers) capable of recognizing the same and other bacterial pathogens or the same and additional antibiotic resistance genes are also desirable to aim at detecting more target genes and complement our earlier patent application.

STATEMENT OF THE INVENTION

It is an object of the present invention to provide a method using probes and/or amplification primers which are specific, ubiquitous and sensitive for determining the presence and/or amount of nucleic acids:

from specific bacterial species selected from the group consisting of *Escherichia coli, Haemophilus influenzae, Klebsiella pneumoniae, Proteus mirabilis, Pseudomonas aeruginosa*, Streptococcus species, *Streptococcus pneumoniae, Streptococcus pyogenes, Staphylococcus aureus, Staphylococcus epidermidis, Staphylococcus saprophyticus, Enterococcus faecalis, Enterococcus faecium* and *Moraxella catarrhalis*, from a bacterial antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int, and optionally from any bacterial species, in any sample suspected of containing said nucleic acids, wherein each of said nucleic acids or a variant or part thereof comprises a selected target region hybridizable with said probe or primers;

said method comprising the steps of contacting said sample with said probes or primers and detecting the presence and/or amount of hybridized probes or amplified products as an indication of the presence and/or amount of said any bacterial species, specific bacterial species and bacterial antibiotic resistance gene.

In a specific embodiment, a similar method directed to each specific bacterial species, antibiotic resistance genes, and universal bacterial detection, separately, is provided.

In a more specific embodiment, the method makes use of DNA fragments (proprietary fragments and fragments obtained from data banks), selected for their capacity to sensitively, specifically and ubiquitously detect the targeted bacterial nucleic acids.

In a particularly preferred embodiment, oligonucleotides of at least 12 nucleotides in length have been derived from the longer DNA fragments, and are used in the present method as probes or amplification primers.

The proprietary oligonucleotides (probes and primers) are also another object of the invention.

Diagnostic kits comprising probes or amplification primers for the detection of a bacterial species selected from the group consisting of *Escherichia coli, Haemophilus influenzae, Klebsiella pneumoniae, Proteus mirabilis, Pseudomonas aeruginosa*, Streptococcus species, *Streptococcus pneumoniae, Streptococcus pyogenes, Staphylococcus aureus, Staphylococcus epidermidis, Staphylococcus saprophyticus, Enterococcus faecalis, Enterococcus faecium* and *Moraxella catarrhalis* are also objects of the present invention.

Diagnostic kits further comprising probes or amplification primers for the detection of an antibiotic resistance gene selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int are also objects of this invention.

Diagnostic kits further comprising probes or amplification primers for the detection of any bacterial species, comprising or not comprising those for the detection of the specific bacterial species listed above, and further comprising or not comprising probes and primers for the antibiotic resistance genes listed above, are also objects of this invention.

In a preferred embodiment, such a kit allows for the separate or the simultaneous detection of the above-listed bacterial species or genus, antibiotic resistance genes and for the detection of any bacterial species.

In the above methods and kits, amplification reactions may include a) polymerase chain reaction (PCR), b) ligase chain reaction, c) nucleic acid sequence-based amplification, d) self-sustained sequence replication, e) strand displacement amplification, f) branched DNA signal amplification, g) transcription-mediated amplification, h) nested PCR, or i) multiplex PCR.

In a preferred embodiment, a PCR protocol is used as an amplification reaction.

In a particularly preferred embodiment, a PCR protocol is provided, comprising, for each amplification cycle, an annealing step of only one second at 55° C. and a denaturation step of only one second at 95° C., without any time allowed specifically for the elongation step. This PCR protocol has been standardized to be suitable for PCR reactions with all selected primer pairs, which greatly facilitates the testing because each clinical sample can be tested with universal, species-specific, genus-specific and antibiotic resistance gene PCR primers under uniform cycling conditions.

We aim at developing a rapid test or kit to be performed simultaneously with the detection and identification of the bacterial species or genus to determine rapidly the bacterial resistance to antibiotics and to discard rapidly all the samples which are negative for bacterial pathogens. Although the sequences from the selected antibiotic resistance genes are available from data banks and have been used to develop DNA-based tests for their detection, our approach is unique because it represents a major improvement over current gold standard diagnostic methods based on bacterial cultures. Using an amplification method for the simultaneous bacterial detection and identification and antibiotic resistance gene detection, there is no need for culturing the clinical sample prior to testing. Moreover, a modified PCR protocol has been developed to detect all target DNA sequences in approximately one hour under uniform amplification conditions. This procedure will save lives by optimizing treatment, diminish antibiotic resistance because less antibiotics will be prescribed, will reduce the use of broad spectrum antibiotics which are expensive, decrease overall health care costs by preventing or shortening hospitalizations, and decrease the time and costs associated with clinical laboratory testing.

In the methods and kits described hereinbelow, the oligonucleotide probes and amplification primers have been derived from larger sequences (i.e. DNA fragments of at least 100 base pairs). All DNA fragments have been obtained from data banks except for the one used for the species-specific detection of Staphylococcus saprophyticus which was obtained by the method of arbitrarily primed PCR (AP-PCR) and the proprietary fragments described in our co-pending application. DNA fragments selected from data banks are newly used in a method of detection according to the present invention, since they have been selected for their diagnostic potential.

It is clear to the individual skilled in the art that other oligonucleotide sequences appropriate for the universal bacterial detection, the species-specific detection of the above bacterial species, the genus-specific detection of Streptococcus, or for the detection of antibiotic resistance genes other than those listed in Annexes I and II may also be derived from the selected data base sequences. For example, the oligonucleotide primers or probes may be shorter or longer than the ones we have chosen; they may also be selected anywhere else in the proprietary DNA fragments or in the sequences selected from data banks; they may be also variants of the same oligonucleotide. If the target DNA or a variant thereof hybridize to a given oligonucleotide or if the target DNA or a variant thereof can be amplified by a given oligonucleotide PCR primer pair the converse is also true; a given target DNA may hybridize to a variant oligonucleotide probe or be amplified by a variant oligonucleotide PCR primer. Alternatively, the oligonucleotides may be designed from any DNA fragment sequences for use in amplification methods other than PCR. Consequently, the core of this invention is the identification of universal, species-specific, genus-specific and resistance gene-specific genomic or non-genomic DNA fragments which are used as a source of specific and ubiquitous oligonucleotide probes or amplification primers. Although the selection of oligonucleotides suitable for diagnostic purposes requires much effort, it is quite possible for the individual skilled in the art to derive, from the selected DNA fragments, oligonucleotides other than the ones listed in Annexes I and II which are suitable for diagnostic purposes. When a DNA fragment is selected for its specificity and ubiquity, it increases the probability that subsets thereof will also be specific and ubiquitous.

Since a high percentage of clinical specimens are negative for bacteria, DNA fragments having a high potential for the selection of universal oligonucleotide probes or primers were selected from data base sequences. The selected oligonucleotide sequences for the universal detection of bacteria are from the bacterial 16S rRNA gene and correspond to highly conserved stretches of that gene. Alternetively, the selected sequences are from the highly conserved bacterial genes tuf, uvrA and atpD and are used to detect the presence of any bacterial pathogens in clinical specimens in order to determine rapidly (approximately one hour) whether it is positive or negative for bacteria. This strategy allows the rapid screening of the numerous negative clinical specimens (around 80% of the specimens received, see Table 4) submitted for bacteriological testing. Tables 8 and 9 provide some relevant information about the data bank sequences selected for diagnostic puposes.

DETAILED DESCRIPTION OF THE INVENTION

Development of Species-Specific, Genus-Specific, Universal and Antibiotic Resistance Gene-Specific DNA Probes and Amplification Primers for Bacteria Novel DNA Fragments DNA fragment probes were developed by us for the following bacterial species: *Escherichia coli, Klebsiella pneumoniae, Proteus mirabilis, Pseudomonas aeruginosa, Streptococcus pneumoniae, Staphylococcus aureus, Staphylococcus epidermidis, Staphylococcus saprophyticus, Haemophilus influenzae* and *Moraxella catarrhalis*. These species-specific fragments were selected from bacterial genomic libraries by hybridization to DNA from a variety of gram-positive and gram-negative bacterial species (Table 5).

The chromosomal DNA from each bacterial species for which probes were sought was isolated using standard methods. DNA was digested with a frequently cutting restriction enzyme such as Sau3AI and then ligated into the bacterial plasmid vector pGEM3Zf (Promega) linearized by appropriate restriction endonuclease digestion. Recombinant plasmids were then used to transform competent *E. coli* strain DH5α thereby yielding a genomic library. The plasmid content of the transformed bacterial cells was analyzed using standard methods. DNA fragments of target bacteria ranging in size from 0.25 to 5.0 kilobase pairs (kbp) were cut out from the vector by digestion of the recombinant plasmid with various restriction endonucleases. The insert was separated from the vector by agarose gel electrophoresis and purified using standard methods. Each of the gel-purified fragments of bacterial genomic DNA was then used as a probe for specificity tests. For each given species, the gel-purified restriction fragments of unknown coding potential were labeled with the radioactive nucleotide α-$^{32}$P (dATP) which was incorporated into the DNA fragment by the random priming labeling reaction. Non-radioactive modified nucleotides could also be incorporated into the DNA by this method to serve as a label.

Each DNA fragment probe (i.e. a segment of bacterial genomic DNA of at least 100 bp in length cut out from clones randomly selected from the genomic library) was then tested for its specificity by hybridization to DNAs from a variety of bacterial species (Tables 5 and 6). The double-stranded labeled DNA probe was heat-denatured to yield labeled single-stranded DNA which could then hybridize to any single-stranded target DNA fixed onto a solid support or in solution. The target DNAs consisted of total cellular DNA from an array of bacterial species found in clinical samples (Table 5). Each target DNA was released from the bacterial cells and denatured by conventional methods and then irreversibly fixed onto a solid support (e.g. nylon or nitrocellulose membranes) or free in solution. The fixed single-stranded target DNAs were then hybridized with the single-stranded probe. Pre-hybridization, hybridization and post-hybridization conditions were as follows: (i) Pre-hybridization; in 1 M NaCl+10% dextran sulfate+1% SDS (sodium dodecyl sulfate)+100 μg/ml salmon sperm DNA at 65° C. for 15 min. (ii) Hybridization; in fresh pre-hybridization solution containing the labeled probe at 65° C. overnight. (iii) Post-hybridization; washes twice in 3× SSC containing 1% SDS (1× SSC is 0.15M NaCl, 0.015M NaCitrate) and twice in 0.1× SSC containing 0.1% SDS; all washes were at 65° C. for 15 min. Autoradiography of washed filters allowed the detection of selectively hybridized probes. Hybridization of the probe to a specific target DNA indicated a high degree of similarity between the nucleotide sequence of these two DNAs.

Species-specific DNA fragments selected from various bacterial genomic libraries ranging in size from 0.25 to 5.0 kbp were isolated for 10 common bacterial pathogens (Table 6) based on hybridization to chromosomal DNAs from a variety of bacteria performed as described above. All of the bacterial species tested (66 species listed in Table 5) were likely to be pathogens associated with common infections or potential contaminants which can be isolated from clinical specimens. A DNA fragment probe was considered specific only when it hybridized solely to the pathogen from which it was isolated. DNA fragment probes found to be specific were subsequently tested for their ubiquity (i.e. ubiquitous probes recognized most isolates of the target species) by hybridization to bacterial DNAs from approximately 10 to 80 clinical isolates of the species of interest (Table 6). The DNAs were denatured, fixed onto nylon membranes and hybridized as described above.

DNA Fragment Isolation From *Staphylococcus saprophyticus* by Arbitrarily Primed PCR DNA sequences of unknown coding potential for the species-specific detection and identification of *Staphylococcus saprophyticus* were obtained by the method arbitrarily primed PCR (AP-PCR; Table 8a).

AP-PCR is a method which can be used to generate specific DNA probes for microorganisms (Fani et al., 1993, Molecular Ecology 2:243–250). A description of the AP-PCR protocol used to isolate a species-specific genomic DNA fragment from *Staphylococcus saprophyticus* follows. Twenty different oligonucleotide primers of 10 nucleotides in length (all included in the AP-PCR kit OPAD (Operon Technologies, Inc., Alameda, Calif.)) were tested systematically with DNAs from 3 bacterial strains of *Staphylococcus saprophyticus* (all obtained from the American Type Culture Collection (ATCC): numbers 15305, 35552 and 43867) as well as with bacterial strains of four other staphylococcal species (*Staphylococcus aureus* ATCC 25923, *Staphylococcus epidermidis* ATCC 14990, *Staphylococcus haemolyticus* ATCC 29970 and *Staphylococcus hominis* ATCC 35982). For all bacterial species, amplification was performed from a bacterial suspension adjusted to a standard 0.5 McFarland which corresponds to approximately 1.5×10$^8$ bacteria/mL. One μL of the standardized bacterial suspension was transferred directly to 19 μL of a PCR reaction mixture containing 50 mM KCl, 10 mM Tris-HCl (pH 9.0), 0.1% Triton X-100, 2.5 mM MgCl$_2$, 1.2 μM of only one of the 20 different AP-PCR primers OPAD, 200 μM of each of the four dNTPs, 0.5 Unit of Taq DNA polymerase (Promega Corp., Madison, Wis.). PCR reactions were subjected to cycling using a MJ Research PTC-200 thermal cycler (Fisher Scientific Canada Ltd., Mississauga, Ontario, Canada) as follows: 3 min at 96° C. followed by 35 cycles of 1 min at 95° C. for the denaturation step, 1 min at 32° C. for the annealing step and 1 min at 72° C. for the extension step. A final extension step of 7 min at 72° C. was made after the 35 cycles to ensure complete extension of PCR products. Subsequently, twenty microliters of the PCR amplified mixture was resolved by electrophoresis in a 2% agarose gel containing 0.25 μg/mL of ethidium bromide. The size of the amplification products was estimated by comparison with a 50-bp molecular weight ladder.

Amplification patterns specific for *Staphylococcus saprophyticus* were observed with the AP-PCR primer OPAD-9 (sequence: 5'-TCGCTTCTCC-3'). The sequence of this primer corresponds to SEQ ID NO: 273. Amplification with this primer consistently showed a band corresponding to a DNA fragment of approximately 450 bp for all *Staphylococcus saprophyticus* strains tested but not for any of the four other staphylococcal species tested. This species-specific pattern was confirmed by testing 10 more clinical isolates of *S. saprophyticus* selected from the culture collection of the microbiology laboratory of the CHUL as well as strains from the 22 gram-positive bacterial species listed in Table 5.

The band corresponding to the approximately 450 bp amplicon specific and ubiquitous based on AP-PCR for *S. saprophyticus* was excised from the agarose gel and purified using the QIAquick™ gel extraction kit (QIAGEN Inc.). The gel-purified DNA fragment was cloned into the T/A cloning site of the pCR 2.1™ plasmid vector (Invitrogen Inc.) using T4 DNA ligase (New England BioLabs). Recombinant plasmids were transformed into *E. coli* DH5α competent cells using standard procedures. All reactions were performed according to the manufacturer's instructions. Plasmid DNA isolation was done by the method of Birnboim and Doly (Nucleic Acid Res. 7:1513–1523) for small-scale preparations. All plasmid DNA preparations were digested with the EcoRI restriction endonuclease to ensure the presence of the approximately 450 bp AP-PCR insert into the plasmid. Subsequently, a large-scale and highly purified plasmid DNA preparation was performed from two selected clones shown to carry the AP-PCR insert by using the QIAGEN plasmid purification kit (midi format). These large-scale plasmid preparations were used for automated DNA sequencing.

Both strands of the AP-PCR insert from the two selected clones were sequenced by the dideoxynucleotide chain termination sequencing method with SP6 and T7 sequencing primers by using the Applied Biosystems automated DNA sequencer (model 373A) with their PRISM™ Sequenase®

Terminator Double-stranded DNA Sequencing Kit (Perkin-Elmer Corp., Applied Biosystems Division, Foster City, Calif.). The analysis of the obtained sequences revealed that the DNA sequences for both strands from each clone were 100% complementary. Furthermore, it showed that the entire sequence determined for each clone were both identical. These sequencing data confirm the 100% accuracy for the determined 438 bp sequence (SEQ ID NO: 267). Optimal amplification primers have been selected from the sequenced AP-PCR *Staphylococcus saprophyticus* DNA fragment with the help of the primer analysis software Oligo™ 4.0 (National BioSciences Inc.). The selected primer sequences will be tested in PCR assays to verify their specificity and ubiquity. Preliminary data with DNA preparations from reference ATCC strains of 13 gram-positive bacterial species including 10 different staphylococcal species indicate that the selected primer pairs are specific for *Staphylococcus saprophyticus* since no amplification signal has been observed with DNAs from the other staphylococcal species tested.

Sequencing of the Species-Specific Fragment Probes

The nucleotide sequence of the totality or of a portion of the species-specific DNA fragments isolated from bacterial genomic libraries was determined using the dideoxynucleotide termination sequencing method which was performed using sequencing kits with Sequenase (USB Biochemicals) or T7 DNA polymerase (Pharmnacia). Alternatively the nucleotide sequence was determined by using the Applied Biosystems automated DNA sequencer (model 373A) with their PRISM™ Sequenase® Terminator Double-stranded DNA Sequencing Kit (Perkin-Elmer Corp., Applied Biosystems Division, Foster City, Calif.). These nucleotide sequences are shown in the sequence listing.

DNA Fragments Derived from Data Banks

DNA sequences derived from data banks were selected for (i) the species-specific detection and identification of *Escherichia coli, Enterococcus faecalis, Enterococcus faecium, Haemophilus influenzae, Klebsiella pneumoniae, Proteus mirabilis, Streptococcus pyogenes, Streptococcus pneumoniae* and *Pseudomonas aeruginosa*, (ii) the genus-specific detection and identification of Streptococcus species, (iii) the universal detection of bacteria and (iv) the detection of the 24 above-mentioned antibiotic resistance genes.

Data Bank Selection for Sequences Suitable for Diagnostic Purposes

In order to select sequences which are suitable for species-specific or genus-specific detection and identification of bacteria, the data bank sequences (GenBank, EMBL and Swiss-Prot) were chosen based on their potential for diagnostic purposes according to sequence information and computer analysis performed with these sequences. Initially, all sequence data available for the targeted bacterial species or genus were carefully analyzed. The gene sequences which appear the most promising for diagnostic purposes based on sequence information and on sequence comparisons with the corresponding gene in other bacterial species or genus performed with the Genetics Computer Group (GCG, Wisconsin) programs were selected for testing by PCR. Optimal PCR amplification primers were chosen from the selected data bank sequences with the help of the Oligo™ 4.0 software. The chosen primers were tested in PCR assays for their specificity and ubiquity for the target bacterial species or genus. In general, the identification of data bank sequences from which amplification primers suitable for species-specific or genus-specific detection and identification were selected involved the computer analysis and PCR testing of several candidate gene sequences before obtaining a primer pair which is specific and ubiquitous for the target bacterial species or genus. Annex II provide a list of selected specific and ubiquitous PCR primer pairs. Annex V and example 4 illustrate the strategy used to select PCR primers from the recA gene which are specific and ubiquitous for the bacterial genera Streptococcus. The sequence of the recA gene is available for many bacterial species including five species of streptococci. A similar approach was used to select PCR primers from the sod gene for the specific and ubiquitous detection and identification of *Enterococcus faecium*.

Oligonucleotide Primers and Probes Design and Synthesis

The DNA fragments obtained by us or selected from data banks (GenBank and EMBL) were used as sources of oligonucleotides for diagnostic purposes (Table 8). For this strategy, an array of suitable oligonucleotide primers or probes derived from a variety of genomic DNA fragments (size of more than 100 bp) selected from data bank (Table 8) was tested for their specificity and ubiquity in PCR and hybridization assays as described later. It is important to note that the data bank sequences were selected based on their potential of being species-specific, genus-specific or universal for the detection of bacteria according to available sequence information and extensive analysis and that, in general, several candidate data bank sequences had to be tested in order to obtain the desired specificity and ubiquity.

Oligonucleotide probes and amplification primers derived from species-specific fragments selected from data bank sequences were synthesized using an automated DNA synthesizer (Perkin-Elmer Corp., Applied Biosystems Division). Prior to synthesis, all oligonucleotides (probes for hybridization and primers for DNA amplification) were evaluated for their suitability for hybridization or DNA amplification by polymerase chain reaction (PCR) by computer analysis using standard programs (i.e. the Genetics Computer Group (GCG) programs and the oligonucleotide analysis software Oligo™ 4.0). The potential suitability of the PCR primer pairs was also evaluated prior to the synthesis by verifying the absence of unwanted features such as long stretches of one nucleotide and a high proportion of G or C residues at the 3' end (Persing, D. H. 1993, pp. 88–104 In Persing, D. H., T. F. Smith, F. C. Tenover, and T. J. White (ed.) Diagnostic Molecular Microbiology: Principles and Applications. American Society for Microbiology, Washington, D.C.).

The oligonucleotide primers or probes may be derived from either strand of the duplex DNA. The primers or probes may consist of the bases A, G, C, or T or analogs. The primers or probes may be of any suitable length and may be selected anywhere within the DNA sequences from proprietary fragments or from selected data bank sequences which are suitable for (i) the universal detection of bacteria, (ii) the species-specific detection and identification of the 13 above-mentionned bacterial species, (iii) the genus-specific detection of Streptococcus or (iv) the detection of the 24 above-mentionned clinically important antibiotic resistance genes.

Variants for a given target bacterial gene are naturally occurring and are attributable to sequence variation within that gene during evolution. For example, different strains of the same bacterial species may have a single or more nucleotide variation(s) at the oligonucleotide hybridization site. The person skilled in the art is well aware of the existence of variant bacterial DNA sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variants at the primer hybridization site one has to amplify a larger DNA target with external amplification primers to yield a product which contains the hybridization site of the internal primer between the two amplification primer. A similar strategy may be applied to show variants at the hybridization site of a probe. Insofar as the divergence of the target sequences or a part thereof does not affect the specificity and ubiquity of the amplification primers or probes, variant bacterial DNA is under the scope of this invention. Variants of the selected primers or probes may also be used to amplify or hybridize to a variant DNA.

Hybridization Assays with Oligonucleotide Probes

In hybridization experiments, single-stranded oligonucleotides (size less than 100 nucleotides) have some advantages over DNA fragment probes for the detection of bacteria such as ease of synthesis in large quantities, consistency in results from batch to batch and chemical stability. Briefly, for the hybridizations, oligonucleotides were 5' end-labeled with the radionucleotide $\gamma^{32}P(ATP)$ using T4 polynucleotide kinase (Pharmacia). The unincorporated radionucleotide was removed by passing the labeled oligonucleotide through a Sephadex G-50™ column. Alternatively, oligonucleotides were labeled with biotin, either enzymatically at their 3' ends or incorporated directly during synthesis at their 5' ends, or with digoxigenin. It will be appreciated by the person skilled in the art that labeling means other than the three above labels may be used.

Each oligonucleotide probe was then tested for its specificity by hybridization to DNAs from a variety of bacterial species (Tables 5 and 6). All of the bacterial species tested (66 species) were likely to be pathogens associated with common infections or potential contaminants which can be isolated from clinical specimens. Each target DNA was released from bacterial cells using standard chemical treatments to lyse the cells. Subsequently, the DNA was denatured by conventional methods and then irreversibly fixed onto a solid support (e.g. nylon or nitrocellulose membranes) or free in solution. The fixed single-stranded target DNAs were then hybridized with the oligonucleotide probe. Pre-hybridization conditions were in 1 M NaCl+10% dextran sulfate+1% SDS (sodium dodecyl sulfate)+100 µg/ml salmon sperm DNA at 65° C. for 15 min. Hybridization was performed in fresh pre-hybridization solution containing the labeled probe at 65° C. overnight. Post-hybridization washing conditions were as follows: twice in 3× SSC containing 1% SDS, twice in 2× SSC containing 1% SDS and twice in 1× SSC containing 1% SDS (all of these washes were at 65° C. for 15 min ), and a final wash in 0.1× SSC containing 1% SDS at 25° C. for 15 min. Autoradiography of washed filters allowed the detection of selectively hybridized probes. Hybridization of the probe to a specific target DNA indicated a high degree of similarity between the nucleotide sequence of these two DNAs because of the high stringency of the washes. For non-radioactive labels detection may be colorimetric or by chemiluminescence, for example.

An oligonucleotide probe was considered specific only when it hybridized solely to the pathogen from which it was isolated. Oligonucleotide probes found to be specific were subsequently tested for their ubiquity (i.e. ubiquitous probes recognized most or all isolates of the target species) by hybridization to bacterial DNAs from approximately 80 clinical isolates of the species of interest. The DNAs from strains of the target species were denatured, fixed onto nylon membranes and hybridized as described above. Probes were considered ubiquitous when they hybridized specifically with the DNA from at least 80% of the isolates.

DNA Amplification

For DNA amplification by the widely used PCR (polymerase chain reaction) method, primer pairs were derived from proprietary DNA fragments or from data bank sequences. Prior to synthesis, the potential primer pairs were analyzed by using the Oligo™ 4.0 software to verify that they are good candidates for PCR amplification.

During DNA amplification by PCR, two oligonucleotide primers binding respectively to each strand of the heat-denatured target DNA from the bacterial genome are used to amplify exponentially in vitro the target DNA by successive thermal cycles allowing denaturation of the DNA, annealing of the primers and synthesis of new targets at each cycle (Persing, D. H. 1993, In Vitro Nucleic Acid Amplification Techniques", pp. 51–87 In Persing, D. H., T. F. Smith, F. C. Tenover, and T. J. White (ed.) Diagnostic Molecular Microbiology: Principles and Applications. American Society for Microbiology, Washington, D.C.).

Briefly, the PCR protocols were as follows: Treated clinical specimens or bacterial colonies were amplified in a 50 µL PCR reaction mixture containing 50 mM KCl, 10 mM Tris-HCl (pH 9.0), 2.5 mM $MgCl_2$, 0.4 µM of each primer, 200 µM of each of the four dNTPs and 1.25 Unit of Taq DNA polymerase (Promega). The treatment of the clinical specimens varies with the type of specimen tested since the composition and the sensitivity level required are different for each specimen type. It consists in a rapid protocol to lyse the bacterial cells and eliminate the PCR inhibitory effects (see example 10 for urine specimen preparation). For amplification from bacterial colonies or standardized bacterial suspensions, the samples were added directly to the PCR amplification mixture without any pre-treatment step (see example 9). Primer sequences derived from highly conserved regions of the bacterial 16S ribosomal RNA gene were used to provide an internal control for all PCR reactions. Alternative strategies to provide an internal control which are based on the amplification of non bacterial DNA sequences are currently being tested. The internal control was integrated into all amplification reactions to verify the efficiency of the PCR assays and to ensure that significant PCR inhibition was absent.

PCR reactions were then subjected to thermal cycling (3 min at 95° C. followed by 30 cycles of 1 second at 95° C. for the denaturation step and 1 second at 55° C. for the annealing step without any time allowed for the extension step) using a Perkin Elmer 480™ thermal cycler and subsequently analyzed by standard ethidium bromide-stained agarose gel electrophoresis. The number of cycles performed for the PCR assays varies according to the sensitivity level required. For example, the sensitivity level required for bacterial detection directly from clinical specimens is much higher for blood specimens than for urine specimens. Consequently, more sensitive PCR assays with more thermal cycles are required for direct detection from blood specimens.

It is clear that other methods for the detection of specific amplification products, which may be faster and more practical for routine diagnosis, may be used. Such methods may be based on the detection of fluorescence after amplification (e.g. TaqMan™ system from Perkin Elmer or Amplisensor™ from Biotronics) or liquid hybridization with an oligonucleotide probe binding to internal sequences of the specific amplification product. These novel probes can be generated from the species-specific DNA fragments. Methods based on the detection of fluorescence are particularly promising for utilization in routine diagnosis as they are very rapid and quantitative and can be automated.

To assure PCR efficiency, glycerol or dimethyl sulfoxide (DMSO) or other related solvents, can be used to increase the sensitivity of the PCR and to overcome problems associated with the amplification of target with a high GC content or with strong secondary structures. The concentration ranges for glycerol and DMSO are 5–15% (v/v) and 3–10% (v/v), respectively. For the PCR reaction mixture, the concentration ranges for the amplification primers and the $MgCl_2$ are 0.1–1.5 µM and 1.5–3.5 µmM, respectively. Modifications of the standard PCR protocol using external and nested primers (i.e. nested PCR) or sing more than one primer pair (i.e. multiplex PCR) may also be used (Persing, D. H. 1993, "Target Selection and Optimization of Amplification Reactions", pp. 88–104 In Persing, D. H., T. F. Smith, F. C. Tenover, and T. J. White (ed.) Diagnostic Molecular Microbiology: Principles and Applications. American Society for Microbiology, Washington, D.C.). For more details about the PCR protocols and amplicon detection methods see examples 8 to 13.

The person skilled in the art of DNA amplification knows the existence of other rapid amplification procedures such as ligase chain reaction (LCR), transcription-mediated amplification (TMA), self-sustained sequence replication (3SR), nucleic acid sequence-based amplification (NASBA), strand displacement Amplification (SDA) and branched DNA (bDNA) (Persing, D. H. 1993, "In Vitro Nucleic Acid Amplification Techniques", pp. 51–87 In Persing, D. H., T. F. Smith, F. C. Tenover, and T. J. White (ed.) Diagnostic Molecular Microbiology: Principles and Applications. American Society for Microbiology, Washington, D.C.). The scope of this invention is not limited to the use of amplification by PCR, but rather includes the use of any rapid nucleic acid amplification methods or any other procedures which may be used to increase rapidity and sensitivity of the tests. Any oligonucleotides suitable for the amplification of nucleic acid by approaches other than PCR and derived from the species-specific, genus-specific and universal DNA fragments as well as from selected antibiotic resistance gene sequences included in this document are also under the scope of this invention.

Specificity and Ubiquity Tests for Oligonucleotide Probes and Primers

The specificity of oligonucleotide probes and primers, derived either from our sequenced species-specific fragments or from data bank sequences, was tested by hybridization or amplification of DNA from the array of bacterial species listed in Table 5 as previously described. Oligonucleotides found to be specific were subsequently tested for their ubiquity by hybridization (for probes) or amplification (for primers) with bacterial DNAs from approximately 80 isolates of the target species as described for fragment probes. Results for specificity and ubiquity tests with the oligonucleotide probes and primers are summarized in Tables 6 and 7, respectively. The specificity and ubiquity of the PCR assays using the selected amplification primer pairs were tested directly from cultures (see examples 8 and 9) of the same bacterial strains. All specific and ubiquitous oligonucleotide probes and amplification primers for each of the bacterial species investigated are listed in Annexes I and II, respectively. Divergence in the sequenced DNA fragments can occur and, insofar as the divergence of these sequences or a part thereof does not affect the specificity of the probes or amplification primers. Variant bacterial DNA is under the scope of this invention.

The PCR amplification primers listed in Annex II for the species-specific detection and identification of *Enterococcus faecium* or for the genus-specific detection and identification of Streptococcus were all tested for their specificity and ubiquity using reference strains from the American Type Culture Collection (ATCC) as well as clinical isolates from various geographical locations. Both assays were highly specific as no amplification was observed with the species other than *Enterococcus faecium* or Streptococcus species listed in Table 5. The *Enterococcus faecium* assay was also ubiquitous because DNAs from 42 of 43 strains of *Enterococcus faecium* from various geographical locations tested so far were specifically amplified. The Streptococcus assay was also ubiquitous as all of 40 strains distributed among 10 different streptococcal species were specifically amplified. The 10 Streptococcus species tested included *Streptococcus pneumoniae, Streptococcus pyogenes, Streptococcus salivarius, Streptococcus agalactiae, Streptococcus viridans, Streptococcus bovis, Streptococcus anginosus, Streptococcus mitis, Streptococcus mutans* and *Streptococcus sanguis*.

Antibiotic Resistance Genes

Antimicrobial resistance complicates treatment and often leads to therapeutic failures. Furthermore, overuse of antibiotics inevitably leads to the emergence of bacterial resistance. Our goal is to provide the clinicians, in approximately one hour, the needed information to prescribe optimal treatments. Besides the rapid identification of negative clinical specimens with DNA-based tests for universal bacterial detection and the identification of the presence of a specific pathogen in the positive specimens with DNA-based tests for specific bacterial detection, the clinicians also need timely information about the ability of the bacterial pathogen to resist antibiotic treatments. We feel that the most efficient strategy to evaluate rapidly bacterial resistance to antimicrobials is to detect directly from the clinical specimens the most common and clinically important antibiotic resistance genes (i.e. DNA-based tests for the detection of antibiotic resistance genes). Since the sequence from the most important and common bacterial antibiotic resistance genes are available from data banks, our strategy was to use the sequence from a portion or from the entire gene to design specific oligonucleotide primers or probes which will be used as a basis for the development of rapid DNA-based tests. The sequence from each of the bacterial antibiotic resistance genes selected on the basis of their clinical relevance (i.e. high incidence and importance) is given in the sequence listing. Table 9 summarizes some characteristics of the selected antibiotic resistance genes. Our approach is unique because the antibiotic resistance genes detection and the bacterial detection and identification are performed simultaneously in multiplex assays under uniform PCR amplification conditions (see example 12).

Annex II provides a list of all amplification primers selected from 24 clinically important antibiotic resistance genes which were tested in PCR assays. The various PCR assays for antibiotic resistance genes detection and identification were validated by testing at least several resistant bacterial isolates from various countries known to carry the targeted gene. The testing of a large number of strains which do not carry the targeted resistance gene was also performed to ensure that all assays were specific. So far, all PCR assays for antibiotic resistance genes are highly specific and have detected all control resistant bacterial strains known to carry the targeted gene. Clinical studies to validate the array of PCR assays for the detection and identification of antibiotic resistance genes and correlate these DNA-based assays with standard antimicrobials susceptibility testing methods are currently in progress.

Universal Bacterial Detection

In the routine microbiology laboratory a high percentage of clinical specimens sent for bacterial identification is negative (Table 4). For example, over a 2 year period, around 80% of urine specimens received by the laboratory at the "Centre Hospitalier de l'Université Laval (CHUL)" were negative (i.e.<$10^7$ CFU/L) (Table 3). Testing clinical samples with universal probes or universal amplification primers to detect the presence of bacteria prior to specific identification and screen out the numerous negative specimens is thus useful as it saves costs and may rapidly orient the clinical management of the patients. Several oligonucleotides probes and amplification primers were therefore synthesized from highly conserved portions of bacterial 16S or 23S ribosomal RNA gene sequences as well as from the gene sequences of uvrA, tuf and atpD (Table 8), all available in data banks.

For the identification of data bank sequences suitable for the universal detection of bacteria, we took advantage of the fact that the complete genome sequences for two distant microorganisms (i.e. *Mycoplasma genitalium* and *Haemophilus influenzae*) are now available. A comparison of the amino acid sequence for all proteins encoded by the genome of these two distant microorganisms led to the identification of highly homologous proteins. An analysis of these homologous proteins allowed to select some promising candidates for the development of universal DNA-based assays for the detection of bacteria. The selected proteins are implicated in essential cellular processes: DNA repair (uvrA gene product), protein synthesis (tuf gene product) and generation of energy-producing molecules such as ATP (atpD gene product). Subsequently, an extensive nucleotide sequence analysis was performed with the three above selected genes. All computer analysis of amino acid sequences and nucleotide sequences were performed by using the GCG programs. Amplification primers derived from highly conserved regions of the genes uvrA, tuf or atpD which are suitable for the universal detection of bacteria (i.e. can amplify specifically any bacterial species) are currently being tested in PCR assays. In hybridization tests, a pool of seven oligonucleotides (Annex III; Table 6) hybridized strongly to DNA from all bacterial species listed in Table 5. This pool of universal probes labeled with radionucleotides or with any other modified nucleotides is useful for detection of bacteria in urine samples with a sensitivity range of $\geq 10^7$ CFU/L. These probes can also be applied for bacterial detection from other clinical samples.

Amplification primers also derived from the sequence of highly conserved 16S ribosomal RNA genes were used as an alternative strategy for universal bacterial detection directly from clinical specimens (Annex IV; Table 7). The DNA amplification strategy was developed to increase the sensitivity and the rapidity of the test. This amplification test was ubiquitous for the detection of bacteria since it specifically amplified DNA from all bacterial species listed in Table 5.

EXAMPLES

The following examples are intended to be illustrative of the various methods and compounds of the invention, rather than limiting the scope thereof.

Example 1

Isolation and cloning of fragments. Genomic DNAs from *Escherichia coli* strain ATCC 25922, *Klebsiella pneumoniae* strain CK2, *Pseudomonas aeruginosa* strain ATCC 27853, *Proteus mirabilis* strain ATCC 35657, *Streptococcus pneumoniae* strain ATCC 27336, *Staphylococcus aureus* strain ATCC 25923, *Staphylococcus epidermidis* strain ATCC 12228, *Staphylococcus saprophyticus* strain ATCC 15305, *Haemophilus influenzae* reference strain Rd and *Moraxella catarrhalis* strain ATCC 53879 were prepared using standard procedures. It is understood that the bacterial genomic DNA may have been isolated from strains other than the ones mentioned above. For *Enterococcus faecalis, Enterococcus faecium, Streptococcus pyogenes* and Streptococcus species, oligonucleotide sequences were derived exclusively from data banks. Each DNA was digested with a restriction enzyme which frequently cuts DNA such as Sau3AI. The resulting DNA fragments were ligated into a plasmid vector (pGEM3Zf) to create recombinant plasmids and transformed into competent *E. coli* cells (DH5α). It is understood that the vectors and corresponding competent cells should not be limited to the ones herein above specifically exemplified. The objective of obtaining recombinant plasmids and transformed cells is to provide an easily reproducible source of DNA fragments useful as probes. Therefore, insofar as the inserted fragments are specific and selective for the target bacterial DNA, any recombinant plasmids and corresponding transformed host cells are under the scope of this invention. The plasmid content of the transformed bacterial cells was analyzed using standard methods. DNA fragments from target bacteria ranging in size from 0.25 to 5.0 kbp (Table 6) were cut out from the vector by digestion of the recombinant plasmid with various restriction endonucleases. The insert was separated from the vector by agarose gel electrophoresis and purified using standard methods. Each gel-purified fragments was then used for specificity tests.

Labeling of DNA fragment probes. The label used was $\alpha^{32}$P(dATP), a radioactive nucleotide which can be incorporated enzymatically into a double-stranded DNA molecule. The fragment of interest is first denatured by heating at 95° C. for 5 min, then a mixture of random primers is allowed to anneal to the strands of the fragments. These primers, once annealed, provide a starting point for synthesis of DNA. DNA polymerase, usually the Klenow fragment, is provided along with the four nucleotides, one of which is radioactive. When the reaction is terminated, the mixture of new DNA molecules is once again denatured to provide radioactive single-stranded DNA molecules (i.e. the probe). As mentioned earlier, other modified nucleotides may be used to label the probes.

Specificity and ubiquity tests for the DNA fragment probes. Species-specific DNA fragments ranging in size from 0.25 to 5.0 kbp were isolated for 10 common bacterial pathogens (Table 6) based on hybridization to chromosomal DNAs from a variety of bacteria. Samples of whole cell DNA for each bacterial strain listed in Table 5 were transferred onto a nylon membrane using a dot blot apparatus, washed and denatured before being irreversibly fixed. Hybridization conditions were as described earlier. A DNA fragment probe was considered specific only when it hybridized solely to the pathogen from which it was isolated. Labeled DNA fragments hybridizing specifically only to target bacterial species (i.e. specific) were then tested for their ubiquity by hybridization to DNAs from approximately 10 to 80 isolates of the species of interest as described earlier. The conditions for pre-hybridization, hybridization and post-hybridization washes were as described earlier. After autoradiography (or other detection means appropriate for the non-radioactive label used), the specificity of each individual probe can be determined. Each probe found to be specific (i.e. hybridizing only to the DNA from the bacterial species from which it was isolated) and ubiquitous (i.e. hybridizing to most isolates of the target species) was kept for further experimentations.

Example 2

Same as example 1 except that testing of the strains is by colony hybridization. The bacterial strains were inoculated onto a nylon membrane placed on nutrient agar. The membranes were incubated at 37° C. for two hours and then bacterial lysis and DNA denaturation were carried out according to standard procedures. DNA hybridization was performed as described earlier.

Example 3

Same as example 1 except that bacteria were detected directly from clinical samples. Any biological samples were loaded directly onto a dot blot apparatus and cells were lysed in situ for bacterial detection. Blood samples should be heparizined in order to avoid coagulation interfering with their convenient loading on a dot blot apparatus.

Example 4

Strategy used to select genus-specific PCR primers for Streptococcus. As shown in Annex V the comparison of the various bacterial recA gene sequences available from data banks (GenBank and EMBL) was used as a basis for the selection of PCR primers which are specific and ubiquitous for the bacterial genera Streptococcus. Since the sequence of the recA gene is available for many bacterial species including five species of streptococci, it was possible to choose sequences well conserved within the genus Streptococcus but distinct from the recA sequences for other bacterial genera. When there was mismatches between the recA gene sequences from the five Streptococcus species, an inosine residue was incorporated into the primer (Annex V). Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches may be used. The selected primers, each containing one inosine and no degenerescence (Annex V), were tested in PCR assays for their specificity and ubiquity.

The specifity test for the Streptococcus-specific PCR assay was performed by testing the 66 bacterial species listed in Table 5. The amplification results showed that genomic DNA from all species of the bacterial genera Streptococcus were efficiently amplified with the selected primer pair and that species of bacterial genera other than Streptococcus were not amplified with this primer combination. These results confirmed the specificity of the assay for the genus Streptococcus. The ubiquity of this assay was confirmed by testing 40 strains distributed among 10 different streptococcal species. The results showed that DNAs from all Streptococcus species tested were specifically amplified thereby showing an excellent ubiquity for this DNA-based assay. The 10 Streptococcus species tested included *Streptococcus pneumoniae, Streptococcus pyogenes, Streptococcus salivarius, Streptococcus agalactiae, Streptococcus viridans, Streptococcus bovis, Streptococcus anginosus, Streptococcus mitis, Streptococcus mutans* and *Streptococcus sanguis.*

Example 5

Nucleotide sequencing of DNA fragments. The nucleotide sequence of the totality or a portion of each fragment found to be specific and ubiquitous (Examples 1 and 4) was determined using the dideoxynucleotide termination sequencing method (Sanger et al., 1977, Proc. Natl. Acad. Sci. U.S.A. 74: 5463–5467). These DNA sequences are shown in the sequence listing.

Oligonucleotide primers and probes selection. Oligonucleotide probes and amplification primers were selected from the given proprietary DNA fragments or data banks sequences and were synthesized with an automated ABI DNA synthesizer (Model 391, Perkin-Elmer Corp., Applied Biosystems Division) using phosphoramidite chemistry.

Labeling of oligonucleotides for hybridization assays. Each oligonucleotide was 5' end-labeled with $\gamma^{32}$P-ATP by the T4 polynucleotide kinase (Pharmacia) as described earlier. The label could also be non-radioactive.

Specificity test for oligonucleotide probes. All labeled oligonucleotide probes were tested for their specificity by hybridization to DNAs from a variety of gram-positive and gram-negative bacterial species as described earlier (Table 5). Species-specific probes were those hybridizing only to DNA from the bacterial species from which it was isolated. Oligonucleotide probes found to be specific were submitted to ubiquity tests as follows.

Ubiquity test for oligonucleotide probes. Specific oligonucleotide probes were then used in ubiquity tests with approximately 80 strains of the target species. Chromosomal DNAs from the isolates were transferred onto nylon membranes and hybridized with labeled oligonucleotide probes as described for specificity tests. The batteries of approximately 80 isolates constructed for each target species contain reference ATCC strains as well as a variety of clinical isolates obtained from various sources. Ubiquitous probes were those hybridizing to at least 80% of DNAs from the battery of clinical isolates of the target species. Examples of specific and ubiquitous oligonucleotide probes are listed in Annex I.

Example 6

Same as example 5 except that a pool of specific oligonucleotide probes is used for bacterial identification (i) to increase sensitivity and assure 100% ubiquity or (ii) to identify simultaneously more than one bacterial species. Bacterial identification could be done from isolated colonies or directly from clinical specimens.

Example 7

Same as example 5 except that bacteria were detected directly from clinical samples. Any biological samples were loaded directly onto a dot blot apparatus and cells were lysed in situ for bacterial detection. Blood samples should be heparizined in order to avoid coagulation interfering with their convenient loading on a dot blot apparatus.

Example 8

PCR amplification. The technique of PCR was used to increase the sensitivity and the rapidity of the assays. The sets of primers were tested in PCR assays performed directly from bacterial colonies or from a standardized bacterial suspension (see Example 9) to determine their specificity and ubiquity (Table 7). Examples of specific and ubiquitous PCR primer pairs are listed in Annex II.

Specificity and ubiquity tests for amplification primers. The specificity of all selected PCR primer pairs was tested against the battery of gram-negative and gram-positive bacteria used to test the oligonucleotide probes (Table 5).

Primer pairs found specific for each species were then tested for their ubiquity to ensure that each set of primers could amplify at least 80% of DNAs from a battery of approximately 80 isolates of the target species. The batteries of isolates constructed for each species contain reference ATCC strains and various clinical isolates representative of the clinical diversity for each species.

Standard precautions to avoid false positive PCR results should be taken. Methods to inactivate PCR amplification products such as the inactivation by uracil-N-glycosylase may be used to control PCR carryover.

Example 9

Amplification directly from a bacterial colony or suspension. PCR assays were performed either directly from a bacterial colony or from a bacterial suspension, the latter being adjusted to a standard McFarland 0.5 (corresponds to approximately $1.5 \times 10^8$ bacteria/mL). In the case of direct amplification from a colony, a portion of the colony was transferred directly to a 50 µL PCR reaction mixture (containing 50 mM KCl, 10 mM Tris (pH 9.0), 2.5 mM $MgCl_2$, 0.4 µM of each primer, 200 µM of each of the four dNTPs and 1.25 Unit of Taq DNA polymerase (Promega)) using a plastic rod. For the bacterial suspension, 2 µL of the cell suspension was added to 48 µL of the same PCR reaction mixture. For both strategies, the reaction mixture was overlaid with 50 µL of mineral oil and PCR amplifications were carried out using an initial denaturation step of 3 min at 95° C. followed by 30 cycles consisting of a 1 second denaturation step at 95° C. and of a 1 second annealing step at 55° C. in a Perkin Elmer 480™ thermal cycler. No time was specifically allowed to an extension step.

Primer sequences derived from highly conserved regions of the bacterial 16S ribosomal RNA gene were used to provide an internal control for all PCR reactions because they can amplify genomic DNA from any bacterial species (universal bacterial amplification). The internal control was integrated into all amplification reactions to verify the efficiency of the PCR assays and to ensure that significant PCR inhibition was absent. The internal control and the species-specific amplifications were performed simultaneously in multiplex PCR assays using 0.4 µM of each species-specific primer and 0.04 µM of each 16S ribosomal RNA universal primer. The universal primers were used in a limiting concentration to avoid detrimental competition with the species-specific amplification.

Alternative strategies to provide an internal control which are based on the amplification of non bacterial DNA sequences are currently being tested.

PCR amplification products were then analyzed by standard agarose gel (2%) electrophoresis. Amplification products were visualized in agarose gels containing 0.25 µg/mL of ethidium bromide under UV at 254 nm. The entire PCR assay can be completed in approximately one hour.

Alternatively, amplification from bacterial cultures was performed as described above but using a "hot start" protocol. In that case, an initial reaction mixture containing the target DNA, primers and dNTPs was heated at 85° C. prior to the addition of the other components of the PCR reaction mixture. The final concentration of all reagents was as described above. Subsequently, the PCR reactions were submitted to thermal cycling and analysed as described above.

Example 10

Amplification directly from urine specimens. For amplification performed directly from urine specimens, 2 µL of urine was mixed with 8 µL of a lysis solution containing 500 mM KCl, 100 mM tris-HCl (pH 9.0), 1% triton X-100. After incubation for at least 15 minutes at room temperature, 2 µL of the treated urine specimen was added directly to 48 µL of the PCR reaction mixture. The final concentration of the PCR reagents was 50 mM KCl, 10 mM Tris (pH 9.0), 2.5 mM $MgCl_2$, 0.4 µM of each primer, 200 µM of each of the four dNTPs. In addition, each 50 µL reaction contained and 1.25 Unit of Taq DNA polymerase (Promega).

Strategies for the internal control, PCR amplification and agarose gel detection of the amplicons are as previously described in example 9.

Example 11

Detection of antibiotic resistance genes. The presence of specific antibiotic resistance genes which are frequently encountered and clinically relevant is identified using the PCR amplification or hybridization protocols described in previous sections. Specific oligonucleotides used as a basis for the DNA-based tests are selected from the antibiotic resistance gene sequences. These tests, which allow to evaluate rapidly bacterial resistance to antimicrobial agents, can be performed either directly from clinical specimens or from a bacterial colony and should complement diagnostic tests for the universal detection of bacteria as well as for the species-specific and genus-specific bacterial identification.

Example 12

Same as examples 9 and 10 except that assays were performed by multiplex PCR (i.e. using several pairs of primers in a single PCR reaction) to reach an ubiquity of 100% for the specific targeted pathogen. For more heterogeneous bacterial species, a combination of PCR primer pairs may be required to detect and identify all representatives of the target species.

Multiplex PCR assays could also be used to (i) detect simultaneously several bacterial species or, alternatively, (ii) to simultaneously detect and identify the bacterial pathogen and detect specific antibiotic resistance genes either directly from a clinical specimen or from a bacterial colony.

For these applications, amplicon detection methods should be adapted to differentiate the various amplicons produced. Standard agarose gel electrophoresis could be used because it discriminates the amplicons based on their sizes. Another useful strategy for this purpose would be detection using a variety of fluorochromes emitting at different wavelengths. The fluorochromes can be each coupled with a specific oligonucleotide linked to a fluorescence quencher which is degraded during amplification to release the fluorochrome (e.g. TaqMan™, Perkin Elmer).

Example 13

Detection of amplification products. The person skilled in the art will appreciate that alternatives other than standard agarose gel electrophoresis (Example 9) may be used for the revelation of amplification products. Such methods may be based on fluorescence polarization or on the detection of fluorescence after amplification (e.g. Amplisensor™, Biotronics; TaqMan™, Perkin-Elmer Corp.) or other labels such as biotin (SHARP Signal™ system, Digene Diagnostics). These methods are quantitative and may be automated. One of the amplification primers or an internal oligonucleotide probe specific to the amplicon(s) derived from the species-specific DNA fragment is coupled with the fluorochrome or with any other label. Methods based on the detection of fluorescence are particularly suitable for diagnostic tests since they are rapid and flexible as fluorochromes emitting at different wavelengths are available.

Example 14

Species-specific, genus-specific, universal and antibiotic resistance gene amplification primers can be used in other rapid amplification procedures such as the ligase chain reaction (LCR), transcription-mediated amplification (TMA), self-sustained sequence replication (3SR), nucleic acid sequence-based amplification (NASBA), strand displacement amplification (SDA) and branched DNA (bDNA) or any other methods to increase the sensitivity of the test. Amplifications can be performed from an isolated bacterial colony or directly from clinical specimens. The scope of this invention is therefore not limited to the use of the DNA sequences from the enclosed Sequence Listing for PCR only but rather includes the use of any procedures to specifically identify bacterial DNA and which may be used to increase rapidity and sensitivity of the tests.

Example 15

A test kit would contain sets of probes specific for each bacterial species or genus as well as a set of universal probes. The kit is provided in the form of test components, consisting of the set of universal probes labeled with non-radioactive labels as well as labeled species- or genus-specific probes for the detection of each pathogen of interest in specific clinical samples. The kit will also include test reagents necessary to perform the pre-hybridization, hybridization, washing steps and hybrid detection. Finally, test components for the detection of known antibiotic resistance genes (or derivatives therefrom) will be included. Of course, the kit will include standard samples to be used as negative and positive controls for each hybridization test.

Components to be included in the kits will be adapted to each specimen type and to detect pathogens commonly encountered in that type of specimen. Reagents for the universal detection of bacteria will also be included. Based on the sites of infection, the following kits for the specific detection of pathogens may be developed:

A kit for the universal detection of bacterial pathogens from all clinical specimens which contains sets of probes specific for highly conserved regions of the bacterial genomes.

A kit for the detection of bacterial pathogens retrieved from urine samples, which contains 9 specific test components (sets of probes for the detection of *Escherichia coli, Enterococcus faecalis, Enterococcus faecium, Klebsiella pneumoniae, Proteus mirabilis, Pseudomonas aeruginosa, Staphylococcus saprophyticus, Staphylococcus aureus* and *Staphylococcus epidermidis*).

A kit for the detection of respiratory pathogens which contains 8 specific test components (sets of probes for the detection of *Moraxella catarrhalis, Haemophilus influenzae, Klebsiella pneumoniae, Pseudomonas aeruginosa, Streptococcus pneumoniae, Streptococcus pyogenes*, Streptococcus species and *Staphylococcus aureus*).

A kit for the detection of pathogens retrieved from blood samples, which contains 13 specific test components (sets of probes for the detection of *Streptococcus pneumoniae, Moraxella catarrhalis, Haemophilus influenzae, Proteus mirabilis, Klebsiella pneumoniae, Pseudomonas aeruginosa, Escherichia coli, Enterococcus faecalis, Enterococcus faecium, Staphylococcus aureus, Streptococcus pyogenes*, Streptococcus species and *Staphylococcus epidermidis*).

A kit for the detection of pathogens causing meningitis, which contains 5 specific test components (sets of probes for the detection of *Haemophilus influenzae, Streptococcus pneumoniae*, Streptococcus species, *Escherichia coli* and *Pseudomonas aeruginosa*).

A kit for the detection of clinically important antibiotic resistance genes which contains sets of probes for the specific detection of at least one of the 24 following genes associated with bacterial resistance: $bla_{tem}$, $bla_{rob}$, $bla_{shv}$, blaZ, $bla_{oxa}$, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int.

Other kits adapted for the detection of pathogens from skin, abdominal wound or any other clinically relevant kits may also be developed.

Example 16

Same as example 15 except that the test kits contain all reagents and controls to perform DNA amplification assays. Diagnostic kits will be adapted for amplification by PCR (or other amplification methods) performed directly either from clinical specimens or from bacterial colonies. Components required for (i) universal bacterial detection, (ii) species-specific and genus-specific bacterial detection and identification and (iii) detection of antibiotic resistance genes will be included.

Amplification assays could be performed either in tubes or in microtitration plates having multiple wells. For assays in plates, the wells will contain the specific amplification primers and control DNAs and the detection of amplification products will be automated. Reagents and amplification primers for universal bacterial detection will be included in kits for tests performed directly from clinical specimens. Components required for species-specific and genus-specific bacterial detection and identification as well as for the simultaneous antibiotic resistance genes detection will be included in kits for testing directly from bacterial colonies or from 0.5 MacFarland bacterial suspension as well as in kits for testing directly from clinical specimens.

The kits will be adapted for use with each type of specimen as described in example 15 for hybridization-based diagnostic kits.

Example 17

It is understood that the use of the probes and amplification primers described in this invention for bacterial detection and identification is not limited to clinical microbiology applications. In fact, we feel that other sectors could also benefit from these new technologies. For example, these tests could be used by industries for quality control of food, water, pharmaceutical products or other products requiring microbiological control. These tests could also be applied to detect and identify bacteria in biological samples from organisms other than humans (e.g. other primates, mammals, farm animals and live stocks). These diagnostic tools could also be very useful for research purposes including clinical trials and epidemiological studies.

TABLE 1

Distribution of urinary isolates from positive urine samples ($\geq 10^7$ CFU/L) at the Centre Hospitalier de l'Universite Laval (CHUL) for the 1992–1994 period.

| | % of isolates | | | |
|---|---|---|---|---|
| Organisms | Nov 92 n = 267[a] | April 93 n = 265 | July 93 n = 238 | Jan 94 n = 281 |
| Escherichia coli | 53.2 | 51.7 | 53.8 | 54.1 |
| Enterococcus faecalis | 13.8 | 12.4 | 11.7 | 11.4 |
| Klebsiella pneumoniae | 6.4 | 6.4 | 5.5 | 5.3 |
| Staphylococcus epidermidis | 7.1 | 7.9 | 3.0 | 6.4 |
| Proteus mirabilis | 2.6 | 3.4 | 3.8 | 2.5 |
| Pseudomonas aeruginosa | 3.7 | 3.0 | 5.0 | 2.9 |
| Staphylococcus saprophyticus | 3.0 | 1.9 | 5.4 | 1.4 |
| Others[b] | 10.2 | 13.3 | 11.8 | 16.0 |

[a] n = total number of isolates for the indicated month.
[b] See table 2.

TABLE 2

Distribution of uncommon[a] urinary isolates from positive urine samples ($\geq 10^7$ CFU/L) at the Centre Hospitalier de l'Universite Laval (CHUL) for the 1992–1994 period.

| | % of isolates | | | |
|---|---|---|---|---|
| Organisms[a] | Nov 92 | April 93 | July 93 | Jan 94 |
| Staphylococcus aureus | 0.4 | 1.1 | 1.3 | 1.4 |
| Staphylococcus spp. | 2.2 | 4.9 | 1.7 | 6.0 |
| Micrococcus spp. | 0.0 | 0.0 | 0.4 | 0.7 |
| Enterococcus faecium | 0.4 | 0.4 | 1.3 | 1.4 |
| Citrobacter spp. | 1.4 | 0.8 | 0.4 | 0.7 |
| Enterobacter spp. | 1.5 | 1.1 | 1.3 | 1.4 |
| Klebsiella oxytoca | 1.1 | 1.5 | 2.5 | 1.8 |
| Serratia spp. | 0.8 | 0.0 | 0.5 | 0.0 |
| Proteus spp. | 0.4 | 0.4 | 0.0 | 1.1 |
| Morganella and Providencia | 0.4 | 0.8 | 0.4 | 0.0 |
| Hafnia alvei | 0.8 | 0.0 | 0.0 | 0.0 |
| NFB[b] (Stenotrophomonas, Acinetobacter) | 0.0 | 0.4 | 1.3 | 1.1 |
| Candida spp. | 0.8 | 1.9 | 0.7 | 0.4 |

[a] Uncommon urinary isolates are those identified as "Others" in Table 1.
[b] NFB: non fermentative bacilli.

TABLE 3

Distribution of positive[a] (bacterial count $\geq 10^7$ CFU/L[b]) and negative (bacterial count $<10^7$ CFU/L) urine specimens tested at the Centre Hospitalier de l'Universite Laval (CHUL) for the 1992–1994 period.

| | Number of isolates (%) | | | |
|---|---|---|---|---|
| Specimens | Nov 92 | April 93 | July 93 | Jan 94 |
| received: | 1383(100) | 1338(100) | 1139(100) | 1345(100) |
| positive: | 267(19.3) | 265(19.8) | 238(20.9) | 281(20.9) |
| negative: | 1116(80.7) | 1073(80.2) | 901(79.1) | 1064(79.1) |

[a] Based on standard diagnostic methods, the minimal number of bacterial pathogens in urine samples to indicate an urinary tract infection is normally $10^7$ CFU/L.
[b] CFU/L stands for "colony forming unit per liter".

TABLE 4

Distribution of positive and negative clinical specimens tested in the Microbiology Laboratory of the CHUL.

| Clinical specimens[a] | No. of samples tested | % of positive specimens | % of negative specimens |
|---|---|---|---|
| Urine | 17,981 | 19.4 | 80.6 |
| Blood culture/marrow | 10,010 | 6.9 | 93.1 |
| Sputum | 1,266 | 68.4 | 31.6 |
| Superficial pus | 1,136 | 72.3 | 27.7 |
| Cerebrospinal fluid | 553 | 1.0 | 99.0 |
| Synovial fluid-articular | 523 | 2.7 | 97.3 |
| Respiratory tract | 502 | 56.6 | 43.4 |
| Deep pus | 473 | 56.8 | 43.2 |
| Ears | 289 | 47.1 | 52.9 |
| Pleural and pericardial fluid | 132 | 1.0 | 99.0 |
| Peritonial fluid | 101 | 28.6 | 71.4 |
| Total: | 32,966 | 20.0 | 80.0 |

[a] Specimens tested from February 1994 to January 1995.

TABLE 5

Bacterial species (66) used for testing the specificity of DNA fragment probes, oligonucleotide probes and PCR primers.

| Bacterial species | Number of strains tested | Bacterial species | Number of strains tested |
|---|---|---|---|
| Gram negative: | | Gram positive: | |
| Acinetobacter calcoaceticus | 1 | Corynebacterium diphteriae | 1 |
| Acinetobacter lwoffi | 1 | Corynebacterium spp.[a] | 1 |
| Bordetella pertussis | 2 | Enterococcus durans | 1 |
| Burkholderia cepacia | 2 | Enterococcus faecalis | 2 |
| Citrobacter diversus | 1 | Enterococcus faecium | 1 |
| Citrobacter freundii | 1 | Lactobacillus acidophilus | 1 |
| Comamonas acidovorans | 2 | Micrococcus luteus | 2 |

TABLE 5-continued

Bacterial species (66) used for testing the specificity of DNA fragment probes, oligonucleotide probes and PCR primers.

| Bacterial species | Number of strains tested | Bacterial species | Number of strains tested |
|---|---|---|---|
| *Enterobacter aerogenes* | 2 | *Staphylococcus aureus* | 2 |
| *Enterobacter agglomerans* | 2 | *Staphylococcus capitis* | 2 |
| *Enterobacter cloacae* | 2 | *Staphylococcus epidermidis* | 2 |
| *Escherichia coli* | 5 | *Staphylococcus haemolyticus* | 2 |
| *Haemophilus aegyptius* | 1 | *Staphylococcus hominis* | 2 |
| *Haemophilus haemolyticus* | 2 | *Staphylococcus ludgunensis* | 1 |
| *Haemophilus influenzae* | 5 | *Staphylococcus saprophyticus* | 5 |
| *Haemophilus parahaemolyticus* | 2 | *Staphylococcus simulans* | 2 |
| *Haemophilus parainfluenzae* | 2 | *Staphylococcus warneri* | 1 |
| *Hafnia alvei* | 2 | *Streptococcus agalactiae* | 2 |
| *Kingella indologenes* | 1 | *Streptococcus bovis* | 1 |
| *Klebsiella oxytoca* | 2 | *Streptococcus pneumoniae* | 7 |
| *Klebsiella pneumoniae* | 5 | *Streptococcus pyogenes* | 2 |
| *Moraxella atlantae* | 1 | *Streptococcus salivarius* | 2 |
| *Moraxella catarrhalis* | 5 | *Streptococcus viridans* | 2 |
| *Moraxella urethralis* | 1 | | |
| *Morganella morganii* | 2 | | |
| *Neisseria caviae* | 1 | | |
| *Neisseria mucosa* | 1 | | |
| *Neisseria subflava* | 1 | | |
| *Proteus mirabilis* | 5 | | |
| *Proteus vulgaris* | 2 | | |
| *Providencia alcalifaciens* | 1 | | |
| *Providencia rettgeri* | 2 | | |
| *Providencia rustigianii* | 1 | | |
| *Providencia* spp.[a] | 1 | | |
| *Providencia stuartii* | 1 | | |
| *Pseudomonas aeruginosa* | 5 | | |
| *Pseudomonas fluorescens* | 1 | | |
| *Pseudomonas putida* | 2 | | |
| *Salmonella* spp.[a] | 1 | | |
| *Salmonella typhimurium* | 1 | | |
| *Serratia marcescens* | 2 | | |
| *Shigella flexneri* | 1 | | |
| *Shigella sonnei* | 1 | | |
| *Stenotrophomonas maltophilia* | 2 | | |
| *Yersinia enterocolitica* | 1 | | |

[a]Bacterial identification using classical methods was conclusive at the genus level only. "spp." stands for "species".

TABLE 6

Species-specific DNA fragment and oligonucleotide probes for hybridization.

| | Number of fragment probes[b] | | | Number of oligonucleotide probes | | |
|---|---|---|---|---|---|---|
| Organisms[a] | Tested | Specific | Ubiquitous[c] | Synthesized | Specific | Ubiquitous[c] |
| *E. coli*[d] | — | — | — | 20 | 12 | 9[f] |
| *E. coli* | 14 | 2 | 2[e] | — | — | — |
| *K. pneumoniae*[d] | — | — | — | 15 | 1 | 1 |
| *K. pneumoniae* | 33 | 3 | 3 | 18 | 12 | 8 |
| *P. mirabilis*[d] | — | — | — | 3 | 3 | 2 |
| *P. mirabilis* | 14 | 3 | 3[e] | 15 | 8 | 7 |
| *P. aeruginosa*[d] | — | — | — | 26 | 13 | 9 |
| *P. aeruginosa* | 6 | 2 | 2[e] | 6 | 0 | 0 |
| *S. saprophyticus* | 7 | 4 | 4 | 20 | 9 | 7 |
| *H. influenzae*[d] | — | — | — | 16 | 2 | 2 |
| *H. influenzae* | 1 | 1 | 1 | 20 | 1 | 1 |
| *S. pneumoniae*[d] | — | — | — | 6 | 1 | 1 |
| *S. pneumoniae* | 19 | 2 | 2 | 4 | 1 | 1 |
| *M. catarrhalis* | 2 | 2 | 2 | 9 | 8 | 8 |
| *S. epidermidis* | 62 | 1 | 1 | — | — | — |
| *S. aureus* | 30 | 1 | 1 | — | — | — |
| Universal probes[d] | — | — | — | 7 | — | 7[g] |

[a]No DNA fragment or oligonucleotide probes were tested for *E. faecalis*, *S. pyogenes*, *E. faecium* and Streptococcus species.
[b]Sizes of DNA fragments range from 0.25 to 5.0 kbp.

TABLE 6-continued

Species-specific DNA fragment and oligonucleotide probes for hybridization.

| | Number of fragment probes[b] | | | Number of oligonucleotide probes | | |
|---|---|---|---|---|---|---|
| Organisms[a] | Tested | Specific | Ubiquitous[c] | Synthesized | Specific | Ubiquitous[c] |

[c]A specific probe was considered ubiquitous when at least 80% of isolates of the target species (approximately 80 isolates) were recognized by each specific probe. When 2 or more probes are combined, 100% of the isolates are recognized.
[d]These sequences were selected from data banks.
[e]Ubiquity tested with approximately 10 isolates of the target species.
[f]A majority of probes (8/9) do not discriminate *E. coli* and Shigella species.
[g]Ubiquity tests with a pool of the 7 probes detected all 66 bacterial species listed in Table 5.

TABLE 7

PCR amplification for bacterial pathogens commonly encountered in urine, sputum, blood, cerebrospinal fluid and other specimens.

| Organism | Primer pair[a] # (SEQ ID NO) | Amplicon size (bp) | Ubiquity[b] | DNA amplification from colonies[c] | DNA amplification from specimens[d] |
|---|---|---|---|---|---|
| *E. coli* | 1[e] (55–56) | 107 | 75/80 | + | + |
| | 2[e] (46–47) | 297 | 77/80 | + | + |
| | 3 (42–43) | 102 | 78/80 | + | + |
| | 4 (131–132) | 134 | 73/80 | + | + |
| | 1 + 3 + 4 | — | 80/80 | + | + |
| *E. faecalis* | 1[e] (38–39) | 200 | 71/80 | + | + |
| | 2[c] (40–41) | 121 | 79/80 | + | + |
| | 1 + 2 | — | 80/80 | + | + |
| *K. pneumoniae* | 1 (67–68) | 198 | 76/80 | + | + |
| | 2 (61–62) | 143 | 67/80 | + | + |
| | 3 (135–136) | 148 | 78/80 | + | N.T.[j] |
| | 4 (137–138) | 116 | 69/80 | + | N.T. |
| | 1 + 2 + 3 | — | 80/80 | + | N.T. |
| *P. mirabilis* | 1 (74–75) | 167 | 73/80 | + | N.T. |
| | 2 (133–134) | 123 | 80/80 | + | N.T. |
| *P. aeruginosa* | 1[e] (83–84) | 139 | 79/80 | + | N.T. |
| | 2[e] (85–86) | 223 | 80/80 | + | N.T. |
| *S. saprophyticus* | 1 (98–99) | 126 | 79/80 | + | + |
| | 2 (139–140) | 190 | 80/80 | + | N.T. |
| *M. catarrhalis* | 1 (112–113) | 157 | 79/80 | + | N.T. |
| | 2 (118–119) | 118 | 80/80 | + | N.T. |
| | 3 (160–119) | 137 | 80/80 | + | N.T. |
| *H. influenzae* | 1[e] (154–155) | 217 | 80/80 | + | N.T. |
| *S. pneumoniae* | 1[e] (156–157) | 134 | 80/80 | + | N.T. |
| | 2[e] (158–159) | 197 | 74/80 | + | N.T. |
| | 3 (78–79) | 175 | 67/80 | + | N.T. |
| *S. epidermidis* | 1 (147–148) | 175 | 80/80 | + | N.T. |
| | 2 (145–146) | 125 | 80/80 | + | N.T. |
| *S. aureus* | 1 (152–153) | 108 | 80/80 | + | N.T. |
| | 2 (149–150) | 151 | 80/80 | + | N.T. |
| | 3 (149–151) | 176 | 80/80 | + | N.T. |
| *S. pyogenes*[f] | 1[e] (141–142) | 213 | 80/80 | + | N.T. |
| | 2[e] (143–144) | 157 | 24/24 | + | N.T. |
| *E. faecium* | 1[e] (263–264) | 234 | 42/43 | + | N.T.[j] |
| *Streptococcus spp.* | 1[e] (265–266) | 152 | 40/40 | + | N.T. |
| Universal detection[g] | 1[e] (126–127) | 241 | 323/323[h] | + | + |
| | 2[e] (269–270) | 514 | 129/129[i] | + | N.T. |
| | 3[e] (271–272) | 159 | 129/129[i] | + | N.T. |

[a]All primer pairs are specific in PCR assays since no amplification was observed with DNA from 66 different species of both gram-positive and gram-negative bacteria other than the species of interest (Table 5).
[b]The ubiquity was normally tested on 80 strains of the species of interest. All retained primer pairs amplified at least 90% of the isolates. When combinations of primers were used, an ubiquity of 100% was reached.
[c]For all primer pairs and multiplex combinations, PCR amplifications directly performed from a bacterial colony were 100% species-specific.
[d]PCR assays performed directly from urine specimens.
[e]Primer pairs derived from data bank sequences. Primer pairs with no "e" are derived from our species-specific fragments.
[f]For *S. pyogenes*, primer pair #1 is specific for Group A Streptococci (GAS). Primer pair #2 is specific for the GAS-producing erythrogenic toxin gene (SpeA).
[g]The 3 primer pairs selected for universal bacterial detection do not amplify human DNA.
[h]Ubiquity tested on 323 isolates representative of the 66 bacterial species listed in Table 5.

TABLE 7-continued

PCR amplification for bacterial pathogens commonly encountered in urine, sputum, blood, cerebrospinal fluid and other specimens.

| Organism | Primer pair[a] # (SEQ ID NO) | Amplicon size (bp) | Ubiquity[b] | DNA amplification from colonies[c] | from specimens[d] |
|---|---|---|---|---|---|

[i]Ubiquity tested on 129 isolates representative of the 66 bacterial species listed in Table 5. These 2 primer pairs also amplify all yeast DNA tested (*Torulopsis glabrata* and 5 species of the genus Candida).
[j]N.T.: not tested.

TABLE 8

DNA fragments selected from data banks for universal, genus-specific or species-specific bacterial detection and identification.

| Bacterial species | Genes | Protein encoded | SEQ ID NO |
|---|---|---|---|
| *Haemophilus influenzae* | ompP1 | outer membrane protein P1 | 26 |
| | ompP6 | outer membrane protein P6 | 178 |
| | valS | valyl-tRNA synthetase | 179 |
| | TGC[a] | transformation proteins | 27 |
| *Proteus mirabilis* | gstB | glutathione transferase | 180 |
| | lpp | lipoprotein | 181 |
| | recA | recA protein | 15 |
| *Klebsiella pneumoniae* | cit | citrate carrier protein | 182 |
| | hpaA | 4-hydroxyphenylacetate 3-hydroxylase | 183 |
| | ompA | outer membrane protein II | 11 |
| *Enterococcus faecium* | sod | superoxide dismutase | 184 |
| *Enterococcus faecalis* | gelE | gelatinase | 1 |
| | mtlF, mtlD | mtlF enzyme III, mannitol-mtlD-phosphate-dehydrogenase | 2 |
| *Streptococcus pneumoniae* | hexA | repair protein | 31 |
| | nanA | neuraminidase | 35 |
| *Escherichia coli* | trpD | anthranylate synthetase | 5 |
| | malP | glycogen phosphorylase | 6 |
| | recA | recA protein | 7 |
| *Pseudomonas aeruginosa* | amiC | aliphatic amidase | 16 |
| | amiR | nitrite reductase | 17 |
| | toxA | exotoxin A | 18 |
| | oprH | outer membrane protein H1 | 19 |
| | ETA | exotoxin A | 20 |
| *Streptococcus pyogenes* | PCP | pyrrolidone carboxylyl peptidase | 32 |
| | speA | erythrogenic toxin | 33 |
| Streptococcus spp. | recA | recA protein | 268 |
| Universal detection | tuf | translation elongation factor EF-Tu | 185 |
| | uvrA | excinuclease ABC subunit A | 186 |
| | atpD | H[+]-transporting ATPase β-subunit | 187 |
| | 16S rRNA | 16S ribosomal RNA | —[b] |

[a]TQC means "transformation gene cluster"
[b]The sequence of the 16S rRNA gene is not included in the Sequence Listing.

TABLE 8a

DNA fragment produced by AP-PCR for specific detection and identification of *Staphylococcus saprophyticus*.

| Bacterial species | Genes | Protein encoded | SEQ ID NO |
|---|---|---|---|
| *Staphylococcus saprophyticus* | Unknown | Unknown | 267 |

TABLE 9

Selected antibiotic resistance genes for diagnostic purposes.

| Genes | Antibiotics | Bacteria[a] | SEQ ID NO |
|---|---|---|---|
| bla$_{tem}$ | β-lactams | Enterobacteriaceae, Pseudomonadaceae, Haemophilus spp., Neisseria spp. | 161 |
| bla$_{rob}$ | β-lactams | Haemophilus, spp. Pasteurella spp. | 162 |
| bla$_{shv}$ | β-lactams | Klebsiella spp. and other Enterobacteriaceae | 163 |
| bla$_{oxa}$ | β-lactams | Enterobacteriaceae, Pseudomonadoceae | 188 |
| blaZ | β-lactams | Enterococcus spp. | 189 |
| aadB, aacC1, aacC2, aacC3, aacA4 | Aminoglycosides | Enterobacteriaceae, Pseudomonadoceae | 164, 165, 166, 167, 168 |
| aac6′-IIa | Aminoglycosides | Pseudomonadaceae | 190 |
| ermA, ermB, ermC | Macrolides | Staphylococcus spp. | 192, 193, 194 |
| mecA | β-lactams | Staphylococcus spp. | 169 |
| vanH-vanA-vanX | Vancomycin | Enterococcus spp. | 170 |
| vanB | Vancomycin | Enterococcus spp. | 191 |
| satA | Macrolides | Enterococcus spp. | 173 |
| aacA-aphD | Aminoglycosides | Enterococcus spp., Staphylococcus spp. | 174 |
| vat | Macrolides | Staphylococcus spp. | 175 |
| vga | Macrolides | Staphylococcus spp. | 176 |
| msrA | Erythromycin | Staphylococcus spp. | 177 |
| Int and Sul conserved sequences | β-lactams, trimethoprim, aminoglycosides, antiseptic, chloramphenicol | Enterobacteriaceae, Pseudomonadaceae | 171, 172 |

[a]Bacteria having high incidence for the specified antibiotic resistance genes. The presence of these antibiotic resistance genes in other bacteria is not excluded. "spp." stands for "species".

ANNEX I

Specific and ubiquitous oligonucleotides probes for hybridization

| SEQ ID NO | Nucleotide sequence | Originating DNA fragment SEQ ID NO | Nucleotide position |
|---|---|---|---|
| Bacterial species: | Escherichia coli | | |
| 44 | 5′-CAC CCG CTT GCG TGG CAA GCT GCC C | 5[a] | 213–237 |
| 45 | 5′-CGT TTG TGG ATT CCA GTT CCA TCC G | 5[a] | 489–513 |
| 48 | 5′-TGA AGC ACT GGC CGA AAT GCT GCG T | 6[a] | 759–783 |
| 49 | 5′-GAT GTA CAG GAT TCG TTG AAG GCT T | 6[a] | 898–922 |
| 50 | 5′-TAG CGA AGG CGT AGC AGA AAC TAA C | 7[a] | 1264–1288 |
| 51 | 5′-GCA ACC CGA ACT CAA CGC CGG ATT T | 7[a] | 1227–1251 |
| 52 | 5′-ATA CAC AAG GGT CGC ATC TGC GGC C | 7[a] | 1313–1337 |
| 53 | 5′-TGC GTA TGC ATT GCA GAC CTT GTG GC | 7[a] | 111–136 |
| 54 | 5′-GCT TTC ACT GGA TAT CGC GCT TGG G | 7[a] | 373–397 |
| Bacterial species: | Proteus mirabilis | | |
| 70[b] | 5′-TGG TTC ACT GAC TTT GCG ATG TTT C | 12 | 23–47 |
| 71 | 5′-TCG AGG ATG GCA TGC ACT AGA AAA T | 12 | 53–77 |
| 72[b] | 5′-CGC TGA TTA GGT TTC GCT AAA ATC TTA TTA | 12 | 80–109 |
| 73 | 5′-TTG ATC CTC ATT TTA TTA ATC ACA TGA CCA | 12 | 174–203 |
| 76 | 5′-CCG CCT TTA GCA TTA ATT GGT GTT TAT AGT | 13 | 246–275 |
| 77 | 5′-CCT ATT GCA GAT ACC TTA AAT GTC TTG GGC | 13 | 291–320 |

ANNEX I-continued

Specific and ubiquitous oligonucleotides probes for hybridization

| SEQ ID NO | Nucleotide sequence | Originating DNA fragment SEQ ID NO | Nucleotide position |
|---|---|---|---|
| 80[b] | 5'-TTG AGT GAT GAT TTC ACT GAC TCC C | 14 | 18–42 |
| 81 | 5'-GTC AGA CAG TGA TGC TGA CGA CAC A | 15[a] | 1185–1209 |
| 82 | 5'-TGG TTG TCA TGC TGT TTG TGT GAA AAT | 15[a] | 1224–1250 |
| Bacterial species: | *Klebsiella pneumoniae* | | |
| 57 | 5'-GTG GTG TCG TTC AGC GCT TTC AC | 8 | 45–67 |
| 58 | 5'-GCG ATA TTC ACA CCC TAC GCA GCC A | 9 | 161–185 |
| 59[b] | 5'-GTC GAA AAT GCC GGA AGA GGT ATA CG | 9 | 203–228 |
| 60[b] | 5'-ACT GAG CTG CAG ACC GGT AAA ACT CA | 9 | 233–258 |
| 63[b] | 5'-CGT GAT GGA TAT TCT TAA CGA AGG GC | 10 | 250–275 |
| 64[b] | 5'-ACC AAA CTG TTG AGC CGC CTG GA | 10 | 201–223 |
| 65 | 5'-GTG ATC GCC CCT CAT CTG CTA CT | 10 | 77–99 |
| 66 | 5'-CGC CCT TCG TTA AGA ATA TCC ATC AC | 10 | 249–274 |
| 69 | 5'-CAG GAA GAT GCT GCA CCG GTT GTT G | 11[a] | 296–320 |
| Bacterial species: | *Pseudomonas aeruginosa* | | |
| 87 | 5'-AAT GCG GCT GTA CCT CGG CGC TGG T | 18[a] | 2985–3009 |
| 88 | 5'-GGC GGA GGG CCA GTT GCA CCT GCC A | 18[a] | 2929–2953 |
| 89 | 5'-AGC CCT GCT CCT CGG CAG CCT CTG C | 18[a] | 2821–2845 |
| 90 | 5'-TGG CTT TTG CAA CCG CGT TCA GGT T | 18[a] | 1079–1103 |
| 91 | 5'-GCG CCC GCG AGG GCA TGC TTC GAT G | 19[a] | 705–729 |
| 92 | 5'-ACC TGG GCG CCA ACT ACA AGT TCT A | 19[a] | 668–692 |
| 93 | 5'-GGC TAC GCT GCC GGG CTG CAG GCC G | 19[a] | 505–529 |
| 94 | 5'-CCG ATC TAC ACC ATC GAG ATG GGC G | 20[a] | 1211–1235 |
| 95 | 5'-GAG CGC GGC TAT GTG TTC GTC GGC T | 20[a] | 2111–2135 |
| Bacterial species: | *Streptococcus pneumoniae* | | |
| 120 | 5'-TCT GTG CTA GAG ACT GCC CCA TTT C | 30 | 423–447 |
| 121 | 5'-CGA TGT CTT GAT TGA GCA GGG TTA T | 31[a] | 1198–1222 |
| Bacterial species: | *Staphylococcus saprophyticus* | | |
| 96 | 5'-CGT TTT TAC CCT TAC CTT TTC GTA CTA CC | 21 | 45–73 |
| 97[b] | 5'-TCA GGC AGA GGT AGT ACG AAA AGG TAA GGG | 21 | 53–82 |
| 100 | 5'-CAC CAA GTT TGA CAC GTG AAG ATT CAT | 22 | 89–115 |
| 101[b] | 5'-ATG AGT GAA GCG GAG TCA GAT TAT GTG CAG | 23 | 105–134 |
| 102 | 5'-CGC TCA TTA CGT ACA GTG ACA ATC G | 24 | 20–44 |
| 103 | 5'-CTG GTT AGC TTG ACT CTT AAC AAT CTT GTC | 24 | 61–90 |
| 104[b] | 5'-GAC GCG ATT GTC ACT GTA CGT AAT GAG CGA | 24 | 19–48 |

ANNEX I-continued

Specific and ubiquitous oligonucleotides probes for hybridization

| SEQ ID NO | Nucleotide sequence | Originating DNA fragment SEQ ID NO | Nucleotide position |
|---|---|---|---|
| Bacterial species: | *Moraxella catarrhalis* | | |
| 108 | 5'-GCC CCA AAA CAA TGA AAC ATA TGG T-3' | 28 | 81–105 |
| 109 | 5'-CTG CAG ATT TTG GAA TCA TAT CGC C-3' | 28 | 126–150 |
| 110 | 5'-TGG TTT GAC CAG TAT TTA ACG CCA T-3' | 28 | 165–189 |
| 111 | 5'-CAA CGG CAC CTG ATG TAC CTT GTA C-3' | 28 | 232–256 |
| 114 | 5'-TTA CAA CCT GCA CCA CAA GTC ATC A-3' | 29 | 97–121 |
| 115 | 5'-GTA CAA ACA AGC CGT CAG CGA CTT A-3' | 29 | 139–163 |
| 116 | 5'-CAA TCT GCG TGT GTG CGT TCA CT-3' | 29 | 178–200 |
| 117 | 5'-GCT ACT TTG TCA GCT TTA GCC ATT CA-3' | 29 | 287–312 |
| Bacterial species: | *Haemophilus influenzae* | | |
| 105[b] | 5'-GCG TCA GAA AAA GTA GGC GAA ATG AAA G | 25 | 138–165 |
| 106b | 5'-AGC GGC TCT ATC TTG TAA TGA CAC A | 26[a] | 770–794 |
| 107b | 5'-GAA ACG TGA ACT CCC CTC TAT ATA A | 27[a] | 5184–5208 |
| | Universal probes[c] | | |
| 122[a] | 5'-ATC CCA CCT TAG GCG GCT GGC TCC A | — | — |
| 123[a] | 5'-ACG TCA AGT CAT CAT GGC CCT TAC GAG TAG G | — | — |
| 124[a] | 5'-GTG TGA CGG GCG GTG TGT ACA AGG C | — | — |
| 125[a] | 5'-GAG TTG CAG ACT CCA ATC CGG ACT ACG A | — | — |
| 128[a] | 5'-CCC TAT ACA TCA CCT TGC GGT TTA GCA GAG AG | — | — |
| 129[a] | 5'-GGG GGG ACC ATC CTC CAA GGC TAA ATA C | — | — |
| 130[a] | 5'-CGT CCA CTT TCG TGT TTG CAG AGT GCT GTG TT | — | — |

[a]Sequences from data banks
[b]These sequences are from the opposite DNA strand of the sequence of the originating fragment given in the Sequence Listing
[c]Universal probes were derived from 16S or 23S ribosomal RNA gene sequences not included in the Sequence Listing

ANNEX II

Specific and ubiquitous primers for DNA amplification

| SEQ ID NO | Nucleotide sequence | Originating DNA fragment SEQ ID NO | Nucleotide position |
|---|---|---|---|
| Bacterial species: | *Escherichia coli* | | |
| 42 | 5'-GCT TTC CAG CGT CAT ATT G | 4 | 177–195 |
| 43[b] | 5'-GAT CTC GAC AAA ATG GTG A | 4 | 260–278 |
| 46 | 5'-TCA CCC GCT TGC GTG GC | 5[a] | 212–228 |
| 47[b] | 5'-GGA ACT GGA ATC ACA AAA C | 5[a] | 490–508 |
| 55 | 5'-GCA ACC CGA ACT CAA CGC C | 7[a] | 1227–1245 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 56[b] | 5'-GCA GAT GCG ACC CTT GTG T | 7[a] | 1315–1333 |
| 131 | 5'-CAG GAG TAC GGT GAT TTT TA | 3 | 60–79 |
| 132[b] | 5'-ATT TCT GGT TTG GTC ATA CA | 3 | 174–193 |
| Bacterial species: | *Enterococcus faecalis* | | |
| 38 | 5'-GCA ATA CAG GGA AAA ATG TC | 1[a] | 69–88 |
| 39[b] | 5'-CTT CAT CAA ACA ATT AAC TC | 1[a] | 249–268 |
| 40 | 5'-GAA CAG AAG AAG CCA AAA AA | 2[a] | 569–588 |
| 41[b] | 5'-GCA ATC CCA AAT AAT ACG GT | 2[a] | 670–689 |
| Bacterial species: | *Klebsiella pneumoniae* | | |
| 61 | 5'-GAC AGT CAG TTC GTC AGC C | 9 | 37–55 |
| 62[b] | 5'-CGT AGG GTG TGA ATA TCG C | 9 | 161–179 |
| 67 | 5'-TCG CCC CTC ATC TGC TAC T | 10 | 81–99 |
| 68[b] | 5'-GAT CGT GAT GGA TAT TCT T | 10 | 260–278 |
| 135 | 5'-GCA GCG TGG TGT CGT TCA | 8 | 40–57 |
| 136[b] | 5'-AGC TGG CAA CGG CTG GTC | 8 | 170–187 |
| 137 | 5'-ATT CAC ACC CTA CGC AGC CA | 9 | 166–185 |
| 138[b] | 5'-ATC CGG CAG CAT CTC TTT GT | 9 | 262–281 |
| Bacterial species: | *Proteus mirabilis* | | |
| 74 | 5'-GAA ACA TCG CAA AGT CAG T | 12 | 23–41 |
| 75[b] | 5'-ATA AAA TGA GGA TCA AGT TC | 12 | 170–189 |
| 133 | 5'-CGG GAG TCA GTG AAA TCA TC | 14 | 17–36 |
| 134b | 5'-CTA AAA TCG CCA CAC CTC TT | 14 | 120–139 |
| Bacterial species: | *Staphylococcus saprophyticus* | | |
| 98 | 5'-CGT TTT TAC CCT TAC CTT TTC GTA CT | 21 | 45–70 |
| 99[b] | 5'-ATC GAT CAT CAC ATT CCA TTT GTT TTT A | 21 | 143–170 |
| 139 | 5'-CTG GTT AGC TTG ACT CTT AAC AAT C | 24 | 61–85 |
| 140[b] | 5'-TCT AAA CGA TAG AAT GGA GCA ACT G | 24 | 226–250 |
| Bacterial species: | *Pseudomonas aeruginosa* | | |
| 83 | 5'-CGA GCG GGT GGT GTT CAT C | 16[a] | 554–572 |
| 84[b] | 5'-CAA GTC GTC GTC GGA GGG A | 16a | 674–692 |
| 85 | 5'-TCG CTG TTC ATC AAG ACC C | 17[a] | 1423–1441 |
| 86[b] | 5'-CCG AGA ACC AGA CTT CAT C | 17[a] | 1627–1645 |
| Bacterial species: | *Moraxella catarrhalis* | | |
| 112 | 5'-GGC ACC TGA TGT ACC TTG | 28 | 235–252 |
| 113[b] | 5'-AAC AGC TCA CAC GCA TT | 28 | 375–391 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 118 | 5'-TGT TTT GAG CTT TTT ATT TTT TGA | 29 | 41–64 |
| 119[b] | 5'-CGC TGA CGG CTT GTT TGT ACC A | 29 | 137–158 |
| 160 | 5'-GCT CAA ATC AGG GTC AGC | 29 | 22–39 |
| 119[b] | 5'-CGC TGA CGG CTT GTT TGT ACC A | 29 | 137–158 |
| Bacterial species: | *Staphylococcus epidermidis* | | |
| 145 | 5'-ATC AAA AAG TTG GCG AAC CTT TTC A | 36 | 21–45 |
| 146[b] | 5'-CAA AAG AGC GTG GAG AAA AGT ATC A | 36 | 121–145 |
| 147 | 5'-TCT CTT TTA ATT TCA TCT TCA ATT CCA TAG | 36 | 448–477 |
| 148[b] | 5'-AAA CAC AAT TAC AGT CTG GTT ATC CAT ATC | 36 | 593–622 |
| Bacterial species: | *Staphylococcus aureus* | | |
| 149[b] | 5'-CTT CAT TTT ACG GTG ACT TCT TAG AAG ATT | 37 | 409–438 |
| 150 | 5'-TCA ACT GTA GCT TCT TTA TCC ATA CGT TGA | 37 | 288–317 |
| 149[b] | 5'-CTT CAT TTT ACG GTG ACT TCT TAG AAG ATT | 37 | 409–438 |
| 151 | 5'-ATA TTT TAG CTT TTC AGT TTC TAT ATC AAC | 37 | 263–292 |
| 152 | 5'-AAT CTT TGT CGG TAC ACG ATA TTC TTC ACG | 37 | 5–34 |
| 153[b] | 5'-CGT AAT GAG ATT TCA GTA GAT AAT ACA ACA | 37 | 83–112 |
| Bacterial species: | *Haemophilus influenzae* | | |
| 154 | 5'-TTT AAC GAT CCT TTT ACT CCT TTT G | 27[a] | 5074–5098 |
| 155[b] | 5'-ACT GCT GTT GTA AAG AGG TTA AAA T | 27[a] | 5266–5290 |
| Bacterial species: | *Streptococcus pneumoniae* | | |
| 78 | 5'-AGT AAA ATG AAA TAA GAA CAG GAC AG | 34 | 164–189 |
| 79[b] | 5'-AAA ACA GGA TAG GAG AAC GGG AAA A | 34 | 314–338 |
| 156 | 5'-ATT TGG TGA CGG GTG ACT TT | 31[a] | 1401–1420 |
| 157[b] | 5'-GCT GAG GAT TTG TTC TTC TT | 31[a] | 1515–1534 |
| 158 | 5'-GAG CGG TTT CTA TGA TTG TA | 35[a] | 1342–1361 |
| 159[b] | 5'-ATC TTT CCT TTC TTG TTC TT | 35[a] | 1519–1538 |
| Bacterial species: | *Streptococcus pyogenes* | | |
| 141 | 5'-TGA AAA TTC TTG TAA CAG GC | 32[a] | 286–305 |
| 142[b] | 5'-GGC CAC CAG CTT GCC CAA TA | 32[a] | 479–498 |
| 143 | 5'-ATA TTT TCT TTA TGA GGG TG | 33[a] | 966–985 |
| 144[b] | 5'-ATC CTT AAA TAA AGT TGC CA | 33[a] | 1103–1122 |
| Bacterial species: | *Enterococcus faecium* | | |
| 263 | 5'-ACG CAA CAA TGG TGG TGG ACA | 184[a] | 165–185 |
| 264[b] | 5'-TCT TGA TTT GCA GTA GAG GTA ATA G | 184[a] | 374–398 |
| Bacterial genus: | *Streptococcus* | | |
| 265 | 5'-GAA ATT GCA GGI AAA TTG ATT GA | 268[a] | 184–206 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 266[b] | 5'-TTA CGC ATG GCI TGA CTC ATC AT | 268[a] | 313–335 |
| Antibiotic resistance gene: | $bla_{tem}$ | | |
| 195 | 5'-CTA TGT GGC GCG GTA TTA TC | 161[a] | 220–239 |
| 196[b] | 5'-CGC AGT GTT ATC ACT CAT GG | 161[a] | 377–396 |
| 197 | 5'-CTG AAT GAA GCC ATA CCA AA | 161[a] | 499–518 |
| 198[b] | 5'-ATC AGC AAT AAA CCA GCC AG | 161[a] | 674–693 |
| Antibiotic resistance gene: | $bla_{rob}$ | | |
| 199 | 5'-TAC GCC AAC ATC GTG GAA AG | 162[a] | 714–733 |
| 200[b] | 5'-TTG AAT TTG GCT TCT TCG GT | 162[a] | 841–860 |
| 201 | 5'-GGG ATA CAG AAA CGG GAC AT | 162[a] | 197–216 |
| 202[b] | 5'-TAA ATC TTT TTC AGG CAG CG | 162[a] | 296–315 |
| Antibiotic resistance gene: | $bla_{shv}$ | | |
| 203 | 5'-TTA CCA TGA GCG ATA ACA GC | 163[a] | 368–387 |
| 204[b] | 5'-CTC ATT CAG TTC CGT TTC CC | 163[a] | 482–501 |
| 205 | 5'-CAG CTG CTG CAG TGG ATG GT | 163[a] | 607–626 |
| 206b | 5'-CGC TCT GCT TTG TTA TTC GG | 163[a] | 742–761 |
| Antibiotic resistance gene: | $bla_{oxa}$ | | |
| 207 | 5'-GAT GGT TTG AAG GGT TTA TTA TAA G | 188[a] | 686–710 |
| 208[b] | 5'-AAT TTA GTG TGT TTA GAA TGG TGA T | 188[a] | 802–826 |
| Antibiotic resistance gene: | blaZ | | |
| 209 | 5'-ACT TCA ACA CCT GCT GCT TTC | 189[a] | 511–531 |
| 210[b] | 5'-TGA CCA CTT TTA TCA GCA ACC | 189[a] | 663–683 |
| Antibiotic resistance gene: | aadB | | |
| 211 | 5'-GGC AAT AGT TGA AAT GCT CG | 164[a] | 174–193 |
| 212[b] | 5'-CAG CTG TTA CAA CGG ACT GG | 164[a] | 355–374 |
| Antibiotic resistance gene: | aacC1 | | |
| 213 | 5'-TCT ATG ATC TCG CAG TCT CC | 165[a] | 254–273 |
| 214[b] | 5'-ATC GTC ACC GTA ATC TGC TT | 165[a] | 365–384 |
| Antibiotic resistance gene: | aacC2 | | |
| 215 | 5'-CAT TCT CGA TTG CTT TGC TA | 166[a] | 627–646 |
| 216[b] | 5'-CCG AAA TGC TTC TCA AGA TA | 166[a] | 781–800 |
| Antibiotic resistance gene: | aacC3 | | |
| 217 | 5'-CTG GAT TAT GGC TAC GGA GT | 167[a] | 424–443 |
| 218[b] | 5'-AGC ,AGT GTG ATG GTA TCC AG | 167[a] | 505–524 |
| Antibiotic resistance gene: | aac6'-IIa | | |
| 219 | 5'-GAC TCT TGA TGA AGT GCT GG | 190[a] | 123–142 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 220[b] | 5'-CTG GTC TAT TCC TCG CAC TC | 190[a] | 284–303 |
| 221 | 5'-TAT GAG AAG GCA GGA TTC GT | 190[a] | 445–464 |
| 222[b] | 5'-GCT TTC TCT CGA AGG CTT GT | 190[a] | 522–541 |
| Antibiotic resistance gene: | aacA4 | | |
| 223 | 5'-GAG TTG CTG TTC AAT GAT CC | 168[a] | 310–329 |
| 224[b] | 5'-GTG TTT GAA CCA TGT ACA CG | 168[a] | 444–463 |
| Antibiotic resistance gene: | vanH-vanA-vanX | | |
| 225 | 5'-TGT AGA GGT CTA GCC CGT GT | 170[a] | 1814–1833 |
| 226[b] | 5'-ACG GGG ATA ACG ACT GTA TG | 170[a] | 1902–1921 |
| 227 | 5'-ATA AAG ATG ATA GGC CGG TG | 170[a] | 1422–1441 |
| 228[b] | 5'-TGC TGT CAT ATT GTC TTG CC | 170[a] | 1549–1568 |
| Antibiotic resistance gene: | vanB | | |
| 229 | 5'-ATT ATC TTC GGC GGT TGC TC | 191[a] | 22–41 |
| 230[b] | 5'-GAC TAT CGG CTT CCC ATT CC | 191[a] | 171–190 |
| 231 | 5'-CGA TAG AAG CAG CAG GAC AA | 191[a] | 575–594 |
| 232b | 5'-CTG ATG GAT GCG GAA GAT AC | 191[a] | 713–732 |
| Antibiotic resistance gene: | msrA | | |
| 233 | 5'-TCC AAT CAT TGC ACA AAA TC | 177[a] | 891–910 |
| 234[b] | 5'-AAT TCC CTC TAT TTG GTG GT | 177[a] | 1034–1053 |
| 235 | 5'-TCC CAA GCC AGT AAA GCT AA | 177[a] | 640–659 |
| 236[b] | 5'-TGG TTT TTC AAC TTC TTC CA | 177[a] | 812–831 |
| Antibiotic resistance gene: | satA | | |
| 237 | 5'-TCA TAG AAT GGA TGG CTC AA | 173[a] | 243–262 |
| 238b | 5'-AGC TAC TAT TGC ACC ATC CC | 173[a] | 404–423 |
| Antibiotic resistance gene: | aacA-aphD | | |
| 239 | 5'-CAA TAA GGG CAT ACC AAA AAT C | 174[a] | 431–452 |
| 240[b] | 5'-CCT TAA CAT TTG TGG CAT TAT C | 174[a] | 541–562 |
| 241 | 5'-TTG GGA AGA TGA AGT TTT TAG A | 174[a] | 159–180 |
| 242[b] | 5'-CCT TTA CTC CAA TAA TTT GGC T | 174[a] | 311–332 |
| Antibiotic resistance gene: | vat | | |
| 243 | 5'-TTT CAT CTA TTC AGG ATG GG | 175[a] | 286–305 |
| 244[b] | 5'-GGA GCA ACA TTC TTT GTG AC | 175[a] | 451–470 |
| Antibiotic resistance gene: | vga | | |
| 245 | 5'-TGT GCC TGA AGA AGG TAT TG | 176[a] | 162–181 |
| 246b | 5'-CGT GTT ACT TCA CCA CCA CT | 176[a] | 241–260 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| Antibiotic resistance gene: | ermA | | |
| 247 | 5'-TAT CTT ATC GTT GAG AAG GGA TT | 192[a] | 370–392 |
| 248[b] | 5'-CTA CAC TTG GCT TAG GAT GAA A | 192[a] | 487–508 |
| Antibiotic resistance gene: | ermB | | |
| 249 | 5'-CTA TCT GAT TGT TGA AGA AGG ATT | 193[a] | 366–389 |
| 250[b] | 5'-GTT TAC TCT TGG TTT AGG ATG AAA | 193[a] | 484–507 |
| Antibiotic resistance gene: | ermC | | |
| 251 | 5'-CTT GTT GAT CAC GAT AAT TTC C | 194[a] | 214–235 |
| 252[b] | 5'-ATC TTT TAG CAA ACC CGT ATT C | 194[a] | 382–403 |
| Antibiotic resistance gene: | int | | |
| 253 | 5'-GTG ATC GAA ATC CAG ATC C | 171[a] | 665–683 |
| 254[b] | 5'-ATC CTC GGT TTT CTG GAA G | 171[a] | 760–778 |
| 255 | 5'-CTG GTC ATA CAT GTG ATG G | 171[a] | 386–404 |
| 256[b] | 5'-GAT GTT ACC CGA GAG CTT G | 171[a] | 599–617 |
| Antibiotic resistance gene: | sul | | |
| 257 | 5'-TTA AGC GTG CAT AAT AAG CC | 172[a] | 67–86 |
| 258[b] | 5'-TTG CGA TTA CTT CGC CAA CT | 172[a] | 142–161 |
| 259 | 5'-TTT ACT AAG CTT GCC CCT TC | 172[a] | 188–207 |
| 260[b] | 5'-AAA AGG CAG CAA TTATGA GC | 172[a] | 385–404 |
| Antibiotic resistance gene: | mecA | | |
| 261 | 5'-AAC AGG TGA ATT ATT AGC ACT TGT AAG | 169[a] | 1059–1085 |
| 262[b] | 5'-ATT GCT GTT AAT ATT TTT TGA GTT GAA | 169[a] | 1206–1232 |
| | Universal primers[c] | | |
| 126[a] | 5'-GGA GGA AGG TGC GGA TCA CG | — | — |
| 127[a] | 5'-ATG GTG TGA CGG GCG GTG TG | — | — |
| 269[a] | 5'-GCA ACC TTA AAA CTC AAA TGA ATT GAC GGG GC | — | — |
| 270[a] | 5'-GTG TGA CGG GCG GTG TGT ACA AGG C | — | — |
| 271[a] | 5'-AGC GGT GGA GCA TGT GGT TTA ATT C | — | — |
| 272[a] | 5'-GAC TTA ACC CAA CAT TTC ACA ACA C | — | — |

[a]Sequences from data banks
[b]These sequences are from the opposite DNA strand of the sequence of the originating fragment given in the Sequence Listing
[c]Universal primers were derived from the 16S ribosomal RNA gene sequence not included in the Sequence Listing

ANNEX III

Selection of universal probes by alignment of the
sequences of bacterial 16S and 23S ribosomal RNA genes.

| | |
|---|---|
| Reverse strand of SEQ ID NO: 122 | TGGAGCC AGCCGCCTAA GGTGGGAT |
| | 1461                                    1510 |
| *Streptococcus salivarius* | TGAGGTAACC TTTTGGAGCC AGCCGCCTAA GGTGGGATAG ATGANNGGGG |
| *Proteus vulgaris* | TAGCTTAACC TTCGGGAGGG CGCTTACCAC TTTGTGATTC ATGACTGGGG |
| *Pseudomonas aeruginosa* | TAGTCTAACC GCAAGGGGA CGGTTACCAC GGAGTGATTC ATGACTGGGG |
| *Neisseria gonorrhoeae* | TAGGGTAACC GCAAGGAGTC CGCTTACCAC GGTATGCTTC ATGACTGGGG |
| *Streptococcus lactis* | TTGCCTAACC GCAAGGAGGG CGCTTCCTAA GGTAAGACCG ATGACNNGGG |
| SEQ ID NO: 123 | ACGTCAAGTC   ATCATGGC CCTTACGAGT AGG |
| | 1251                                    1300 |
| *Haemophilus influenzae* | GGTNGGGATG ACGTCAAGTC ..ATCATGGC CCTTACGAGT AGGGCTACAC |
| *Neisseria gonorrhoeae* | GGTGGGGATG ACGTCAAGTC ..CTCATGGC CCTTATGACC AGGGCTTCAC |
| *Pseudomonas cepacia* | GGTNGGGATG ACGTCAAGTC ..CTCATGGC CCTTATGGGT AGGGCTTCAC |
| *Serratia marcescens* | GGTGGGGATG ACGTCAAGTC ..ATCATGGC CCTTACGAGT AGGGCTACAC |
| *Escherichia coli* | GGTGGGGATG ACGTCAAGTC ..ATCATGGC CCTTACGACC AGGGCTACAC |
| *Proteus vulgaris* | GGTGGGGATG ACGTTAAGTC GTATCATGGC CCTTACGAGT AGGGCTACAC |
| *Pseudomonas aeruginosa* | GGTGGGGATG ACGTCAAGTC ..ATCATGGC CCTTACGGCN AGGGCTACAC |
| *Clostridium perfringens* | GGTGGGGATG ACGTNNAATC ..ATCATGCC CNTTATGTGT AGGGCTACAC |
| *Mycoplasma hominis* | GGTGGGGATG ACGTCAAATC ..ATCATGCC TCTTACGAGT GGGGCCACAC |
| *Helicobacter pylori* | GGTGGGGACG ACGTCAAGTC ..ATCATGGC CCTTACGCCT AGGGCTACAC |
| *Mycoplasma pneumoniae* | GGAAGGGATG ACGTCAAATC ..ATCATGCC CCTTATGTCT AGGGCTGCAA |
| Reverse of the probe SEQ ID NO: 124 | GCCTTGTACA CACCGCCCGT CACAC |
| | 1451                                    1490 |
| *Escherichia coli* | ACGTTCCCGG GCCTTGTACA CACCGCCCGT CACACCATGG |
| *Neisseria gonorrhoeae* | ACGTTCCCNG NNCTTGTACA CACCGCCCGT CACACCATGG |
| *Pseudomonas cepacia* | ACGTTCCCGG GTCTTGTACA CACNGCCCGT CACACCATGG |
| *Serratia marcescens* | ACGTTCCCGG GCCTTGTACA CACCGCCCGT CACACCATGG |
| *Proteus vulgaris* | ACGTTCCCGG GCCTTGTACA CACCGCCCGT CACACCATGG |
| *Haemophilus influenzae* | ACGTTCCCGG GCNTTGTACA CACCGCCCGT CACACCATGG |
| *Pseudomonas aeruginosa* | ACGTTCCCGG GCCTTGTACA CACCGCCCGT CACACCATGG |
| *Clostridium perfringens* | ACGTTCCCNG GTCTTGTACA CACCGCNCGT CACACCATGA |
| *Mycoplasma hominis* | ACGTTCTCGG GTCTTGTACA CACCGCCCGT CACACCATGG |
| *Helicobacter pylori* | ACGTTCCCGG GTCTTGTACT CACCGCCCGT CACACCATGG |
| *Mycoplasma pneumoniae* | ACGTTCTCGG GTCTTGTACA CACCGCCCGT CAAACTATGA |
| Reverse strand of SEQ ID NO 125: | TCG TAGTCCGGAT TGGAGTCTGC AACTC |
| | 1361                                    1400 |
| *Escherichia coli* | AAGTGCGTCG TAGTCCGGAT TGGAGTCTGC AACTCGACTC |
| *Neisseria gonorrhoeae* | AAACCGATCG TAGTCCGGAT TGCACTCTGC AACTCGAGTG |
| *Pseudomonas cepacia* | AAACCGATCG TAGTCCGGAT TGCACTCTGC AACTCGAGTG |

ANNEX III-continued

Selection of universal probes by alignment of the sequences of bacterial 16S and 23S ribosomal RNA genes.

| | |
|---|---|
| *Serratia marcescens* | AAGTATGTCG TAGTCCGGAT TGGAGTCTGC AACTCGACTC |
| *Proteus vulgaris* | AAGTCTGTCG TAGTCCGGAT TGGAGTCTGC AACTCGACTC |
| *Haemophilus influenzae* | AAGTACGTCT AAGTCCGGAT TGGAGTCTGC AACTCGACTC |
| *Pseudomonas aeruginosa* | AAACCGATCG TAGTCCGGAT CGCAGTCTGC AACTCGACTG |
| *Clostridium perfringens* | AAACCAGTCT CAGTTCGGAT TGTAGGCTGA AACTCGCCTA |
| *Mycoplasma hominis* | AAGCCGATCT CAGTTCGGAT TGGAGTCTGC AATTCGACTC |
| *Helicobacter pylori* | ACACC..TCT CAGTTCGGAT TGTAGGCTGC AACTCGCCTG |
| *Mycoplasma pneumoniae* | AAGTTGGTCT CAGTTCGGAT TGAGGGCTGC AATTCGTCCT |
| Reverse strand of SEQ ID NO: 128 | CT CTCTGCTAAA CCGCAAGGTG ATGTATAGGG |
| | 1991                                          2040 |
| *Lactobacillus lactis* | AAACACAGCT CTCTGCTAAA CCGCAAGGTG ATGTATAGGG GGTGACGCCT |
| *Escherichia coli* | AAACACAGCA CTGTGCAAAC ACGAAAGTGG ACGTATACGG TGTGACGCCT |
| *Pseudomonas aeruginosa* | AAACACAGCA CTCTGCAAAC ACGAAAGTGG ACGTATAGGG TGTGACGCCT |
| *Pseudomonas cepacia* | AAACACAGCA CTCTGCAAAC ACGAAAGTGG ACGTATAGGG TGTGACGCCT |
| *Bacillus stearothermophilus* | AAACACAGGT CTCTGCGAAG TCGTAAGGCG ACGTATAGGG GCTGACACCT |
| *Micrococcus luteus* | AAACACAGGT CCATGCGAAG TCGTAAGACG ATGTATATGG ACTGACTCCT |
| SEQ ID NO: 129 | GGGGGGACC ATCCTCCAAG GCTAAATAC |
| | 481                                          530 |
| *Escherichia coli* | TGTCTGAATA TGGGGGGACC ATCCTCCAAG GCTAAATACT CCTGACTGAC |
| *Pseudomonas aeruginosa* | TGTCTGAACA TGGGGGGACC ATCCTCCAAG GCTAAATACT ACTGACTGAC |
| *Pseudomonas cepacia* | TGTCTGAAGA TGGGGGGACC ATCCTCCAAG GCTAAATACT CGTGATCGAC |
| *Lactobacillus lactis* | AGTTTGAATC CGGAGGACC ATCTCCCAAC CCTAAATACT CCTTAGTGAC |
| *Micrococcus luteus* | CGTGTGAATC TGCCAGGACC ACCTGGTAAG CCTGAATACT ACCTGTTGAC |
| Reverse strand of SEQ ID NO: 130 | AACACAGCA CTCTGCAAAC ACGAAAGTGG ACG |
| | 1981                                          2030 |
| *Pseudomonas aeruginosa* | TGTTTATTAA AAACACAGCA CTCTGCAAAC ACGAAAGTGG ACGTATAGGG |
| *Escherichia coli* | TGTTTATTAA AAACACAGCA CTGTGCAAAC ACGAAAGTGG ACGTATACGG |
| *Pseudomonas cepacia* | TGTTTAATAA AAACACAGCA CTCTGCAAAC ACGAAAGTGG ACGTATAGGG |
| *Bacillus stearothermophilus* | TGTTTATCAA AAACACAGGT CTCTGCGAAG TCGTAAGGCG ACGTATAGGG |
| *Lactobacillus lactis* | TGTTTATCAA AAACACAGCT CTCTGCTAAA CCGCAAGGTG ATGTATAGGG |
| *Micrococcus luteus* | TGTTTATCAA AAACACAGGT CCATGCGAAG TCGTAAGACG ATGTATATGG |

ANNEX IV

Selection of the universal PCR primers by alignment of the bacterial 16S ribosomal RNA genes.

| | |
|---|---|
| SEQ ID NO: 126 | GGAGGAA GGTGGGGATG ACG |
| Reverse strand of SEQ ID NO: 127 | CA CACCGCCCGT CACACCAT |
| | 1241                    1270......1461                    1490 |
| *Escherichia coli* | ACTGGAGGAA GGTGGGGATG ACGTCAAGTC......GCCTTGTACA CACCGCCCGT CACACCATGG |

ANNEX IV-continued

Selection of the universal PCR primers by alignment of the bacterial 16S ribosomal RNA genes.

| | |
|---|---|
| Neisseria gonorrhoeae | GCCGGAGGAA GGTGGGGATG ACGTCAAGTC......NNCTTGTACA CACCGCCCGT CACACCATGG |
| Pseudomonas cepacia | ACCGGAGGAA GGTNGGGATG ACGTCAAGTC......GTCTTGTACA CACNGCCCGT CACACCATGG |
| Serratia marcescens | ACTGGAGGAA GGTGGGGATG ACGTCAAGTC......GCCTTGTACA CACCGCCCGT CACACCATGG |
| Proteus vulgaris | ACCGGAGGAA GGTGGGGATG ACGTTAAGTC......GCCTTGTACA CACCGCCCGT CACACCATGG |
| Haemophilus influenzae | ACTGGAGGAA GGTNGGGATG ACGTCAAGTC......GCNTTGTACA CACCGCCCGT CACACCATGG |
| Legionella pneumophila | ACCGGAGGAA GGCGGGGATG ACGTCAAGTC......GCCTTGTACA CACCGCCCGT CACACCATGG |
| Pseudomonas aeruginosa | ACCGGAGGAA GGTGGGGATG ACGTCAAGTC......GCCTTGTACA CACCGCCCGT CACACCATGG |
| Clostridium perfringens | CCAGGAGGAA GGTGGGGATG ACGTNNAATC......GTCTTGTACA CACCGCNCGT CACACCATGA |
| Mycoplasma hominis | CTGGGAGGAA GGTGGGGATG ACGTCAAATC......GTCTTGTACA CACCGCCCGT CACACCATGG |
| Helicobacter pylori | GGAGGAGGAA GGTGGGGACG ACGTCAAGTC......GTCTTGTACT CACCGCCCGT CACACCATGG |
| Mycoplasma pneumoniae | ATTGGAGGAA GGAAGGGATG ACGTCAAATC......GTCTTGTACA CACCGCCCGT CAAACTATGA |

ANNEX V

Strategy for the selection of the amplification primers specific for the genus Streptococcus from the recA gene.

```
                            181                                                220.....301                                           340
Bordetella pertussis        CTCGAGATCA CCGACGCGCT GGTTCGCTCG GGCTCGGTCG.....CTGCAGGCCC GCCTGATGAG CCAGGCGCTG CGCAAGCTGA
Campylobacter jejuni        TTAGAAATTG TAGAAACTAT AGCAAGAAGT GGGCAGTAG.....CTTCAAGCAA GACTTATGTC TCAAGCTCTA AGAAAACTTA
Chlamydia trachomatis       TTGAGTATTG CAGAGCTCTT AGCCGTTCT GGAGCTGTCG.....TTGCAAGCTC GCATGATGTC GCAGGCTCTA CGCAAATTAA
Enterobacter agglomerans    CTGGAAATCT GTGATGCGCT GACCCGTTCA GGCGCCGTTG.....CTCGCAGCTC GTATGATGAG CCAGGCGATG CGTAAGCTTG
Escherichia coli            CTGGAAATCT GTGACGCCCT GGGCCGTTCT GGCGCAGTAG.....CTTGCGGCAC GTATGATGAG CCAGGCGATG CGTAAGCTGG
Haemophilus influenzae      GCGAACAGAA GAATAGAATT TTAATGCATT ACCGCCTGTG.....AATTTGACCT GTGAGTTTAC GCAAAGCTTG AGACATTAAA
Lactococcus lactis          CTTCAAATTG CTGAAAAATT GATTACTTCT GGAGCGGTTG.....CTACAAGCAC GTATGATGTC ACAAGCCATG CGTAAACTTG
Neisseria gonorrhoeae       TTGGAAATCT GCGACACGCT CGTCCGTTCG GGCGGCATAG.....CTGCAGGCGC GCCTGATGAG TCAGGCTTTG CGCAAACTGA
Proteus mirabilis           CTGGAAATTT GTGATGCATT ATCTCGCTCT GGTGCGGTCG.....TTAGCCGCAC GTATGATGAG CCAAGCTATG CGTAAACTAG
Proteus vulgaris            CTGGAGATCT GTGATGCACT CACGCGCTCT GGCGCTGTTG.....CTTGCGGCAC GTATGATGAG CCAGGCTATG CGTAAACTGG
Pseudomonas aeruginosa      CTGGAAATCA CCGACATGCT GGTGCGCTCG AACGCGGTTG.....CTGCAGGCAC GCCTGATGTC CCAGGCGCTG CGCAAGATCA
Pseudomonas cepacia         CTCGAAATCA CCGATGCGCT GGTGCGCTCG GGCTCGATCG.....CTGCAGGCCG GTTGCAGTTG.....TTGCCAGGCTC GTATGATGAG CCAGGCCATG CGTAAGCTGA
Pseudomonas putida          CTGGAAATCA CCGACATGCT GGTGCGTTCC AACGCGGTTG.....CTGCAGGCAC GCCTGATGTC GCAGGCGCTG CGCAAAATCA
Serratia marcescens         CTGGAAATCT GTGATGCGCT GACCCGCTCG GGCGCGGTTG.....CTGGCGGCGC GCATGATGAG CCAGGCGATG CGTAAGCTGG
Staphylococcus aureus       CTTGAAAATCG CCGAAGCATT TGTTAGAAGT GGTGCAGTTG.....TTACAAGCTC GTTTAATGTC ACAAGCGTTA CGTAAACTTT
Streptococcus gordonii      TTAGAAATTG CAGGAAAATT GATTGACTCT GGGGCAGTTG.....
Streptococcus mutans        CTTGAAATTG CAGGGAAATT GATTGATTCT GGGGCTGTTG.....TTACAAGCAC GCATGATGAG TCAAGCGATG CGTAAATTAT
Streptococcus pneumoniae    CTTGAGATTG CGGGAAAATT GATTGACTCA GGTGCAGTTG.....TTGCAGGCTC GTATGATGAG CCAGGCCATG CGTAAACTTG
Streptococcus pyogenes      CTTGAAATTG CAGGTAAATT GATTGATTCT GGTGCGGTTG.....TTGCCAAGCAC GTATGATGAG TCAAGCCATG CGTAAATTAT
Streptococcus salivarius    CTCGAAATTG CAGGTAAGCT GATTGACTCT GGTGCAGTGG.....CTTCAAGCGC GTATGATGAG TCAAGCCATG CGTAAACTTT
Vibrio cholerae             CTGGAAATTT GTGATGCACT GGCTCGCTCT GGTGCTGTGG.....CTGCAAGCGC GTATGTTGTC GCAAGCAATG CCAGGCTATG CGTAAGCTGA
Yersinia pestis             CTGGAAATTT GTGATGCGCT GACTCGCTCT GGTGCGGTTG.....CTTGCCGCGC GTATGATGAG CCAGGCTATG CGTAAGCTGG G       G   T    GC                                                                           C         G    G
recA sequences for the      GAAATTG CAGGGAAATT GATTGA                                                   ATGATGAG TCAAGCCATG CGTAA
five Streptococcus species:
```

ANNEX V-continued

Strategy for the selection of the amplification primers specific
for the genus *Streptococcus* from the recA gene.

A selected genus-specific    SEQ ID NO: 105                              SEQ ID NO: 106[b]
primer sequences:          GAAATTG CAGGIAAATT GATTGA[a]                 TTACGCAT GGCITGACTC ATCAT[a]

[a]"I" stands for inosine which is a nucleotide analog that can bind to any of the four nucleotides A, C, G or T.
[b]This sequence is the reverse complement of the above recA sequence.

What is claimed is:

1. A method using probes or amplification primers or both which are specific, ubiquitous and sensitive for determining the presence or amount of nucleic acids:
from a bacterial antibiotic resistance gene selected from the group consisting of $bla_{tem}$, $bla_{rod}$, $bla_{shv}$, $bla_{oxa}$, $bal_z$, aadB, aacC1, aacC2, aacC3, aacA4, aac6'-IIa, ermA, ermB, ermC, mecA, vanH, vanX, vanB, satA, aacA-aphD, vat, vga, msrA, sul and int, and
from specific bacterial species selected from the group consisting of Haemophilus influenzae, Klebsiella pneumoniae, Proteus mirabilis, Staphylococcus saprophyticus, Enterococcus faecium, and Streptococcus species, in any sample suspected of containing said bacterial nucleic acids, wherein each of said nucleic acids comprises a selected target region hybridizable with said probes or primers; said method comprising the following steps: contacting said sample with said probes or primers and detecting the presence or amount of said specific bacterial species simultaneously with said bacterial antibiotic resistance gene,
said probes or primers comprising at least one single stranded nucleic acid which nucleotidic sequence has at least twelve nucleotides in length capable of hybridizing with said target region and with any one of:
SEQ ID NO. 178, SEQ ID NO 179 and a complementary sequence thereof, for determining the presence of Haemnophilus influenzae;
SEQ ID NO. 180, SEQ ID NO 181 and a complementary sequence thereof, for determining the presence of Proteus mirabilis;
SEQ ID NO. 182, SEQ ID NO 183 and a complementary sequence thereof, for determining the presence of Klebsiella pneumoniae;
SEQ ID NO. 184 and a complementary sequence thereof, for determining the presence of Enterococcus faecium;
SEQ ID NO. 267 and a complementary sequence thereof, for determining the presence of Staphylococcus saprophyticus;
SEQ ID NO. 268 and a complementary sequence thereof, for determining the presence of Streptococcus species.

2. A method according to claim 1, which further makes use of probes or primers which are specific, ubiquitous and sensitive for simultaneously determining the presence or amount of nucleic acids from any bacterial species.

3. The method of claim 1, which is performed directly on a sample obtained from human patients, animals, environment or food.

4. The method of claim 1, which is performed directly on a sample consisting of one or more bacterial colonies or from a bacterial suspension.

5. The method of claim 1 wherein said nucleic acids are all detected under uniform hybridization or amplification conditions.

6. The method of claim 1, wherein said nucleic acids are amplified by a method selected from the group consisting of:
   a) polymerase chain reaction (PCR),
   b) ligase chain reaction (LCR),
   c) nucleic acid sequence-based amplification (NASBA),
   d) self-sustained sequence replication (3SR),
   e) strand displacement amplification (SDA),
   f) branched DNA signal amplification (bDNA),
   g) transcription-mediated amplification (TMA),
   h) nested PCR, and
   i) multiplex PCR.

7. The method of claim 6 wherein said nucleic acids are amplified by PCR.

8. The method of claim 7 wherein the PCR protocol achieves within one hour under uniform amplification conditions the determination of the presence of said nucleic acids by performing for each amplification cycle an annealing step of only one second at 55° C. and a denaturation step of only one second at 95° C. without any time specifically allowed to an elongation step.

9. A method for the detection, identification or quantification of *Haemophilus influenzae* directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Haemophilus influenzae* and capable of hybridizing with any one of SEQ ID NO. 178, SEQ ID NO. 179 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as in an indication of the presence or amount of *Haemophilus influenzae* in said test sample.

10. A method for detecting the presence or amount of *Haemophilus influenzae* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Haemophilus influenzae* DNA and of any one of SEQ ID NO. 178, SEQ ID NO. 179, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Haemophilus influenzae* in said test sample.

11. A method for the detection, identification or quantification of *Proteus mirabilis* directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Proteus mirabilis* and capable of hybridizing with any one of SEQ ID NO. 180, SEQ ID NO. 181 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as in an indication of the presence or amount of *Proteus mirabilis* in said test sample.

12. A method for detecting the presence or amount of *Proteus mirabilis* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Proteus mirabilis* DNA and of any one of SEQ ID NO. 180, SEQ ID NO. 181, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Proteus mirabilis* in said test sample.

13. A method for the detection, identification or quantification of *Klebsiella pneumoniae* directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Klebsiella pneumoniae* and capable of hybridizing with any one of SEQ ID NO. 182, SEQ ID NO. 183 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as in an indication of the presence or amount of *Klebsiella pneumoniae* in said test sample.

14. A method for detecting the presence or amount of *Klebsiella pneumoniae* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Klebsiella pneumoniae* DNA and of any one of SEQ ID NO. 182, SEQ ID NO. 183, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Klebsiella pneumoniae* in said test sample.

15. A method for the detection, identification or quantification of *Enterococcus faecium* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Enterococcus faecium* and capable of hybridizing with any one of SEQ ID NO. 184 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as in an indication of the presence or amount of *Enterococcus faecium* in said test sample.

16. A method for detecting the presence or amount of *Enterococcus faecium* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Enterococcus faecium* DNA and of SEQ ID NO. 184, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Enterococcus faecium* in said test sample.

17. The method of claim 16, wherein said pair of primers is defined in SEQ ID NO: 263 and SEQ ID NO: 264.

18. A method for the detection, identification or quantification of *Staphylococcus saprophyticus* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Staphylococcus saprophyticus* and capable of hybridizing with any one of SEQ ID NO. 267 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as in an indication of the presence or amount of *Staphylococcus saprophyticus* in said test sample.

19. A method for detecting the presence or amount of *Staphylococcus saprophyticus* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Staphylococcus saprophyticus* DNA and of SEQ ID NO. 267, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of Staphylococcus saprophyticus in said test sample.

20. A method for the detection, identification or quantification of Streptococcus species directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of Streptococcus species and capable of hybridizing with any one of SEQ ID NO. 268 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as in an indication of the presence or amount of Streptococcus species in said test sample.

21. A method for detecting the presence or amount of Streptococcus species in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of Streptococcus species DNA and of SEQ ID NO. 268, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of Streptococcus species in said test sample.

22. The method of claim 21, wherein said pair of primers is defined in SEQ ID NO: 265 and SEQ ID NO: 266.

23. A method for the detection, identification or quantification of any bacterial species directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of any bacterial species and capable of hybridizing with any one of SEQ ID NO. 185, SEQ ID NO. 186, SEQ ID NO. 187 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as in an indication of the presence or amount of any bacterial species in said test sample.

24. A method for detecting the presence or amount of any bacterial species in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of any bacterial species DNA and of any one of SEQ ID NO. 185, SEQ ID NO. 186, SEQ ID NO. 187, that contain a target sequence and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of any bacterial species in said test sample.

25. A method for detecting the presence and/or amount of any bacterial species in a test sample which comprises the following steps:
   a) treating said sample with an aqueous solution containing a pair of universal primers selected from the group consisting of:
      1) SEQ ID NO: 126, SEQ ID NO: 127,
      2) SEQ ID NO: 269, SEQ ID NO: 270,
      3) SEQ ID NO: 271, SEQ ID NO: 272, and
      4) mixtures thereof,
   one of said primers being capable of hybridizing selectively with one of the two complementary strands of said bacterial species DNA that contains a target sequence, and the other of said primers being capable of hybridizing with the other of said strands so as to form an extension product which contains the target sequence as a template;
   b) synthesizing an extension product of each of said primers which extension products contain the target sequence, and amplifying said target sequence, if any, to a detectable level; and
   c) detecting the presence and/or amount of said amplified target sequence as an indication of the presence and/or amount of said any bacterial species in said test sample.

26. A method as defined in claim 1 which comprises the evaluation of the presence of a bacterial resistance to β-lactam antibiotics mediated by the bacterial antibiotic resistance gene $bla_{tem}$ directly from a test sample or from bacterial colonies, which comprises the following steps:
   a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 161 and a sequence complementary thereof under conditions such that the nucleic acid of the probe selectively hybridizes with said bacterial DNA; and c) detecting the presence of a hybridization complex as an indication of the bacterial resistance to β-lactam antibiotics mediated by the bacterial antibiotic resistance gene bla$_{tem}$.

27. A method as defined in claim 1, which comprises the evaluation of the presence of a bacterial resistance to β-lactam antibiotics mediated by the bacterial antibiotic resistance gene bla$_{tem}$ directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 161, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactam antibiotics mediated by the bacterial resistance gene bla$_{tem}$.

28. A method for evaluating the presence of a bacterial resistance to β-lactam antibiotics mediated by the bacterial antibiotic resistance gene bla$_{tem}$ directly from a test sample or from bacterial colonies, which comprises the following steps:

a) treating said sample with an aqueous solution containing at least one pair of primers having a sequence selected in the group consisting of SEQ ID NOs: 195 to 198, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam antibiotics mediated by the bacterial antibiotic resistance gene bla$_{tem}$.

29. A method as defined in claim 1 which comprises the evaluation of the presence of a bacterial resistance to β-lactam antibiotics mediated by the bacterial antibiotic resistance gene bla$_{rob}$ directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 162 and a sequence complementary thereof under conditions such that the nucleic acid of the probe selectively hybridizes with said bacterial DNA; and c) detecting the presence of a hybridization complex as an indication of the bacterial resistance to β-lactam antibiotics mediated by the bacterial antibiotic resistance gene bla$_{rob}$.

30. A method as defined in claim 1, which comprises the evaluation of the presence of a bacterial resistance to β-lactam antibiotics mediated by the bacterial antibiotic resistance gene bla$_{rob}$ directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 162, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactam antibiotics mediated by the bacterial resistance gene bla$_{rob}$.

31. A method for evaluating the presence of a bacterial resistance to β-lactam antibiotics mediated by the bacterial antibiotic resistance gene bla$_{rob}$ directly from a test sample or from bacterial colonies, which comprises the following steps:

a) treating said sample with an aqueous solution containing at least one pair of primer having a sequence selected in the group consisting of SEQ ID NOs: 199 to 202, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam antibiotics mediated by the bacterial antibiotic resistance gene bla$_{rob}$.

32. A method as defined in claim 1 which comprises the evaluation of the presence of a bacterial resistance to β-lactam antibiotics mediated by the bacterial antibiotic resistance gene bla$_{shv}$ directly from a test sample or from bacterial colonies, which comprises the following steps:
   a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which has at least twelve nucleotides in length and is capable of hybridizing with anyone of the nucleotide sequence defined in of SEQ ID NO. 163 and a sequence complementary thereof under conditions such that the nucleic acid of the probe selectively hybridizes with said bacterial DNA; and
   c) detecting the presence of a hybridization complex as an indication of the bacterial resistance to β-lactam antibiotics mediated by the bacterial antibiotic resistance gene bla$_{shv}$.

33. A method as defined in claim 1, which comprises the evaluation of the presence of a bacterial resistance to β-lactam antibiotics mediated by the bacterial antibiotic resistance gene bla$_{shv}$ directly from a test sample or from bacterial colonies, which comprises the following steps:
   a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 163, that contain the target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, in any, to a detectable level; and
   c) detecting the presence or amount of said amplified target sequence as an indication of a bacterial resistance to β-lactam antibiotics mediated by the bacterial resistance gene bla$_{shv}$.

34. A method for evaluating the presence of a bacterial resistance to β-lactam antibiotics mediated by the bacterial antibiotic resistance gene bla$_{shv}$ directly from a test sample or from bacterial colonies, which comprises the following steps:
   a) treating said sample with an aqueous solution containing at least one pair of primer having a sequence selected in the group consisting of SEQ ID NOs: 203 to 206, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of a bacterial resistance to β-lactam antibiotics mediated by the bacterial antibiotic resistance gene bla$_{shv}$.

35. A method as defined in claim 1 which comprises the evaluation of the presence of a bacterial resistance to aminoglycoside antibiotics mediated by the bacterial antibiotic resistance gene aadb directly from a test sample or from bacterial colonies, which comprises the following steps:
   a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which has at least twelve nucleotides in length and is capable of hybridizing with anyone of the nucleotide sequence defined in of SEQ ID NO. 164 and a sequence complementary thereof under conditions such that the nucleic acid of the probe selectively hybridizes with said bacterial DNA; and
   c) detecting the presence of a hybridization complex as an indication of the bacterial resistance to aminoglycosides antibiotics mediated by the bacterial antibiotic resistance gene aadb.

36. A method as defined in claim 1, which comprises the evaluation of the presence of a bacterial resistance to aminoglycoside antibiotics mediated by the bacterial antibiotic resistance gene aadB directly from a test sample or from bacterial colonies, which comprises the following steps:
   a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 164, that contain the target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, in any, to a detectable level; and
   c) detecting the presence or amount of said amplified target sequence as an indication of a bacterial resistance to aminoglycoside antibiotics mediated by the bacterial resistance gene aadB.

37. A method for evaluating the presence of a bacterial resistance to aminoglycoside antibiotics mediated by the bacterial antibiotic resistance gene aadB directly from a test sample or from bacterial colonies, which comprises the following steps:
   a) treating said sample with an aqueous solution containing at least one pair of primer having a sequence selected in the group consisting of SEQ ID NOs: 211 and 212, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aadB.

38. A method as defined in claim 1 which comprises the evaluation of the presence of a bacterial resistance to aminoglycoside antibiotics mediated by the bacterial antibiotic resistance gene aacC1 directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 165 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aacC1.

39. A method as defined in claim 1, which comprises the evaluation of the presence of a bacterial resistance to aminoglycoside antibiotics mediated by the bacterial antibiotic resistance gene aacC1 directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 165, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to aminoglycoside antibiotics mediated by the bacterial resistance gene aacC1.

40. A method for evaluating the presence of a bacterial resistance to aminoglycoside antibiotics mediated by the bacterial antibiotic resistance gene aacC1 directly from a test sample or from bacterial colonies, which comprises the following steps:

a) treating said sample with an aqueous solution containing at least one pair of primer having a sequence selected in the group consisting of SEQ ID NOs: 213, SEQ ID NOs: 214, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aacC1.

41. A method as defined in claim 1 which comprises the evaluation of the presence of a bacterial resistance to aminoglycoside antibiotics mediated by the bacterial antibiotic resistance gene aacC2 directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 166 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aacC2.

42. A method as defined in claim 1, which comprises the evaluation of the presence of a bacterial resistance to aminoglycoside antibiotics mediated by the bacterial antibiotic resistance gene aacC2 directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 166, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to aminoglycoside antibiotics mediated by the bacterial resistance gene aacC2.

43. A method for evaluating the presence of a bacterial resistance to aminoglycoside antibiotics mediated by the bacterial antibiotic resistance gene aacC2 directly from a test sample or from bacterial colonies, which comprises the following steps:

a) treating said sample with an aqueous solution containing at least one pair of primer having a sequence selected in the group consisting of SEQ ID NOs: 215, SEQ ID NOs: 216, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aacC2.

44. A method as defined in claim 1 which comprises the evaluation of the presence of a bacterial resistance to aminoglycoside antibiotics mediated by the bacterial antibiotic resistance gene aacC3 directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 167 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aacC3.

45. A method as defined in claim 1, which comprises the evaluation of the presence of a bacterial resistance to aminoglycoside antibiotics mediated by the bacterial antibiotic resistance gene aacC3 directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 167, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to aminoglycoside antibiotics mediated by the bacterial resistance gene aacC3.

46. A method for evaluating the presence of a bacterial resistance to aminoglycoside antibiotics mediated by the bacterial antibiotic resistance gene aacC3 directly from a test sample or from bacterial colonies, which comprises the following steps:

a) treating said sample with an aqueous solution containing at least one pair of primer having a sequence selected in the group consisting of SEQ ID NOs: 217, SEQ ID NOs: 218, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aacC3.

47. A method as defined in claim 1 which comprises the evaluation of the presence of a bacterial resistance to aminoglycoside antibiotics mediated by the bacterial antibiotic resistance gene aacA4 directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 168 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aacA4.

48. A method as defined in claim 1, which comprises the evaluation of the presence of a bacterial resistance to aminoglycoside antibiotics mediated by the bacterial antibiotic resistance gene aacA4 directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 168, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to aminoglycoside antibiotics mediated by the bacterial resistance gene aacA4.

49. A method for evaluating the presence of a bacterial resistance to aminoglycoside antibiotics mediated by the bacterial antibiotic resistance gene aacA4 directly from a test sample or from bacterial colonies, which comprises the following steps:

a) treating said sample with an aqueous solution containing at least one pair of primer having a sequence selected in the group consisting of SEQ ID NOs: 223, SEQ ID NOs: 224, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aacA4.

50. A method as defined in claim 1 which comprises the evaluation of the presence of a bacterial resistance to β-lactam antibiotics mediated by the bacterial antibiotic resistance gene mecA directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 169 and a sequence complementary thereof under conditions such that the nucleic acid of the probe selectively hybridizes with said bacterial DNA; and c) detecting the presence of a hybridization complex as an indication of the bacterial resistance to β-lactam antibiotics mediated by the bacterial antibiotic resistance gene mecA.

51. A method as defined in claim 1, which comprises the evaluation of the presence of a bacterial resistance to β-lactam antibiotics mediated by the bacterial antibiotic resistance gene mecA directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 169, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactam antibiotics mediated by the bacterial resistance gene mecA.

52. A method for evaluating the presence of a bacterial resistance to β-lactam antibiotics mediated by the bacterial antibiotic resistance gene mecA directly from a test sample or from bacterial colonies, which comprises the following steps:

a) treating said sample with an aqueous solution containing at least one pair of primer having a sequence selected in the group consisting of SEQ ID NOs: 261, SEQ ID NOs: 262, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam antibiotics mediated by the bacterial antibiotic resistance gene mecA.

53. A method as defined in claim 1 which comprises the evaluation of the presence of a bacterial resistance to vancomycin mediated by the bacterial antibiotic resistance gene vanH-vanA-vanX directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 170 and a sequence complementary thereof under conditions such that the nucleic acid of the probe selectively hybridizes with said bacterial DNA; and c) detecting the presence of a hybridization complex as an indication of the bacterial resistance to vancomycin mediated by the bacterial antibiotic resistance gene vanH-vanA-vanX.

54. A method as defined in claim 1, which comprises the evaluation of the presence of a bacterial resistance to vancomycin mediated by the bacterial antibiotic resistance gene vanH-vanA-vanX directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 170, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to vancomycin mediated by the bacterial resistance gene vanH-vanA-vanX.

55. A method for evaluating the presence of a bacterial resistance to vancomycin mediated by the bacterial antibiotic resistance gene vanH-vanA-vanX directly from a test sample or from bacterial colonies, which comprises the following steps:

a) treating said sample with an aqueous solution containing at least one pair of primer having a sequence selected in the group consisting of SEQ ID NOs: 225 to 228, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to vancomycin mediated by the bacterial antibiotic resistance gene vanH-vanA-vanX.

56. A method as defined in claim 1 which comprises the evaluation of the presence of a bacterial resistance to streptogramin A mediated by the bacterial antibiotic resistance gene satA directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 173 and a sequence complementary thereof under conditions such that the nucleic acid of the probe selectively hybridizes with said bacterial DNA; and c) detecting the presence of a hybridization complex as an indication of the bacterial resistance to streptogramin A mediated by the bacterial antibiotic resistance gene satA.

57. A method as defined in claim 1, which comprises the evaluation of the presence of a bacterial resistance to streptogramin A mediated by the bacterial antibiotic resistance gene satA directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 173, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to streptogramin A mediated by the bacterial resistance gene satA.

58. A method for evaluating the presence of a bacterial resistance to streptogramin A mediated by the bacterial antibiotic resistance gene satA directly from a test sample or from bacterial colonies, which comprises the following steps:

a) treating said sample with an aqueous solution containing at least one pair of primer having a sequence selected in the group consisting of SEQ ID NO: 237, SEQ ID NO 238, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to streptogramin A mediated by the bacterial antibiotic resistance gene satA.

59. A method as defined in claim 1 which comprises the evaluation of the presence of a bacterial resistance to aminoglycoside antibiotics mediated by the bacterial antibiotic resistance gene aacA-aphD directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 174 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aacA-aphD.

60. A method as defined in claim 1, which comprises the evaluation of the presence of a bacterial resistance to aminoglycoside antibiotics mediated by the bacterial antibiotic resistance gene aacA-aphD directly from a test sample or from bacterial colonies, which comprises the following steps:
   a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 174, that contain the target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, in any, to a detectable level; and
   c) detecting the presence or amount of said amplified target sequence as an indication of a bacterial resistance to aminoglycoside antibiotics mediated by the bacterial resistance gene aacA-aphD.

61. A method for evaluating the presence of a bacterial resistance to aminoglycoside antibiotics mediated by the bacterial antibiotic resistance gene aacA-aphD directly from a test sample or from bacterial colonies, which comprises the following steps:
   a) treating said sample with an aqueous solution containing at least one pair of primer having a sequence selected in the group consisting of SEQ ID NO: 239 to SEQ ID NO 242, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of a bacterial resistance to aminoglycoside antibiotics mediated by the bacterial antibiotic resistance gene aacA-aphD.

62. A method as defined in claim 1 which comprises the evaluation of the presence of a bacterial resistance to virginiamycin mediated by the bacterial antibiotic resistance gene vat directly from a test sample or from bacterial colonies, which comprises the following steps:
   a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which has at least twelve nucleotides in length and is capable of hybridizing with anyone of the nucleotide sequence defined in of SEQ ID NO. 175 and a sequence complementary thereof under conditions such that the nucleic acid of the probe selectively hybridizes with said bacterial DNA; and
   c) detecting the presence of a hybridization complex as an indication of the bacterial resistance to virginiamycin mediated by the bacterial antibiotic resistance gene vat.

63. A method as defined in claim 1, which comprises the evaluation of the presence of a bacterial resistance to virginiamycin mediated by the bacterial antibiotic resistance gene vat directly from a test sample or from bacterial colonies, which comprises the following steps:
   a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 175, that contain the target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, in any, to a detectable level; and
   c) detecting the presence or amount of said amplified target sequence as an indication of a bacterial resistance to virginiamycin mediated by the bacterial resistance gene vat.

64. A method for evaluating the presence of a bacterial resistance to virginiamycin mediated by the bacterial antibiotic resistance gene vat directly from a test sample or from bacterial colonies, which comprises the following steps:
   a) treating said sample with an aqueous solution containing at least one pair of primer having a sequence selected in the group consisting of SEQ ID NO: 243, SEQ ID NO 244, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of a bacterial resistance to virginiamycin mediated by the bacterial antibiotic resistance gene vat.

65. A method as defined in claim 1 which comprises the evaluation of the presence of a bacterial resistance to virginiamycin mediated by the bacterial antibiotic resistance gene vga directly from a test sample or from bacterial colonies, which comprises the following steps:
   a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 176 and a sequence complementary thereof under conditions such that the nucleic acid of the probe selectively hybridizes with said bacterial DNA; and c) detecting the presence of a hybridization complex as an indication of the bacterial resistance to virginiamycin mediated by the bacterial antibiotic resistance gene vga.

66. A method as defined in claim 1, which comprises the evaluation of the presence of a bacterial resistance to virginiamycin mediated by the bacterial antibiotic resistance gene vga directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 176, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to virginiamycin mediated by the bacterial resistance gene vga.

67. A method for evaluating the presence of a bacterial resistance to virginiamycin mediated by the bacterial antibiotic resistance gene vga directly from a test sample or from bacterial colonies, which comprises the following steps:

a) treating said sample with an aqueous solution containing at least one pair of primer having a sequence selected in the group consisting of SEQ ID NO: 245, SEQ ID NO 246, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to virginiamycin mediated by the bacterial antibiotic resistance gene vga.

68. A method as defined in claim 1 which comprises the evaluation of the presence of a bacterial resistance to erythromycin mediated by the bacterial antibiotic resistance gene msrA directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 177 and a sequence complementary thereof under conditions such that the nucleic acid of the probe selectively hybridizes with said bacterial DNA; and c) detecting the presence of a hybridization complex as an indication of the bacterial resistance to erythromycin mediated by the bacterial antibiotic resistance gene msrA.

69. A method as defined in claim 1, which comprises the evaluation of the presence of a bacterial resistance to erythromycin mediated by the bacterial antibiotic resistance gene msrA directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 177, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to erythromycin mediated by the bacterial resistance gene msrA.

70. A method for evaluating the presence of a bacterial resistance to erythromycin mediated by the bacterial antibiotic resistance gene msrA directly from a test sample or from bacterial colonies, which comprises the following steps:

a) treating said sample with an aqueous solution containing at least one pair of primer having a sequence selected in the group consisting of SEQ ID NO: 233 to SEQ ID NO 236, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to erythromycin mediated by the bacterial antibiotic resistance gene msrA.

71. A method as defined in claim 1 which comprises the evaluation of the presence of a bacterial resistance to β-lactams, aminoglycosides, chloramphenicol, or trimethoprim mediated by the bacterial antibiotic resistance gene int directly from a test sample or from bacterial colonies, which comprises the following steps:

a) depositing and fixing on an inert support or leaving in solution the bacterial DNA of the sample or of the bacterial colonies isolated from this sample, orinoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 171 and a sequence complementary thereof under conditions such that the nucleic acid of the probe selectively hybridizes with said bacterial DNA; and c) detecting the presence of a hybridization complex as an indication of the bacterial resistance to β-lactams, aminoglycosides, chloramphenicol, or trimethoprim mediated by the bacterial antibiotic resistance gene int.

72. A method as defined in claim 1, which comprises the evaluation of the presence of a bacterial resistance to β-lactams, aminoglycosides, chloramphenicol, or trimethoprim mediated by the bacterial antibiotic resistance gene int directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 171, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactams, aminoglycosides, chloramphenicol, or trimethoprim mediated by the bacterial resistance gene int.

73. A method for evaluating the presence of a bacterial resistance to β-lactams, aminoglycosides, chloramphenicol, or trimethoprim mediated by the bacterial antibiotic resistance gene int directly from a test sample or from bacterial colonies, which comprises the following steps:

a) treating said sample with an aqueous solution containing at least one pair of primer having a sequence selected in the group consisting of SEQ ID NO: 253 to SEQ ID NO 256, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam, aminoglycosides, chloramphenicol, or trimethoprim mediated by the bacterial antibiotic resistance gene int.

74. A method as defined in claim 1 which comprises the evaluation of the presence of a bacterial resistance to β-lactams, aminoglycosides, chloramphenicol, or trimethoprim mediated by the bacterial antibiotic resistance gene sul directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 172 and a sequence complementary thereof under conditions such that the nucleic acid of the probe selectively hybridizes with said bacterial DNA; and c) detecting the presence of a hybridization complex as an indication of the bacterial resistance to β-lactams, aminoglycosides, chloramphenicol, or trimethoprim mediated by the bacterial antibiotic resistance gene sul.

75. A method as defined in claim 1, which comprises the evaluation of the presence of a bacterial resistance to β-lactams, aminoglycosides, chloramphenicol, or trimethoprim mediated by the bacterial antibiotic resistance gene sul directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 172, that contain the target sequence, and the other of said primers being capable of hybridizing with the other of said strands so as to form an extension product which contains the target sequence as template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactams, aminoglycosides, chloramphenicol, or trimethoprim mediated by the bacterial resistance gene sul.

76. A method for evaluating the presence of a bacterial resistance to β-lactams, aminoglycosides, chloramphenicol, or trimethoprim mediated by the bacterial antibiotic resistance gene sul directly from a test sample or from bacterial colonies, which comprises the following steps:

a) treating said sample with an aqueous solution containing at least one pair of primer having a sequence selected in the group consisting of SEQ ID NO: 257 to SEQ ID NO 260, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactams, aminoglycosides, chloramphenicol, or trimethoprim mediated by the bacterial antibiotic resistance gene sul.

77. A method as defined in claim 1 which comprises the evaluation of the presence of a bacterial resistance to β-lactam antibiotics mediated by the bacterial antibiotic resistance gene bla$_{oxa}$ directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 188 and a sequence complementary thereof under conditions such that the nucleic acid of the probe selectively hybridizes with said bacterial DNA; and c) detecting the presence of a hybridization complex as an indication of the bacterial resistance to β-lactam antibiotics mediated by the bacterial antibiotic resistance gene bla$_{oxa}$.

78. A method as defined in claim 1, which comprises the evaluation of the presence of a bacterial resistance to β-lactam antibiotics mediated by the bacterial antibiotic resistance gene bla$_{oxa}$ directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 188, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactam antibiotics mediated by the bacterial resistance gene bla$_{oxa}$.

79. A method for evaluating the presence of a bacterial resistance to β-lactam antibiotics mediated by the bacterial antibiotic resistance gene bla$_{oxa}$ directly from a test sample or from bacterial colonies, which comprises the following steps:

a) treating said sample with an aqueous solution containing at least one pair of primer having a sequence selected in the group consisting of SEQ ID NO: 207, SEQ ID NO 208, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam antibiotics mediated by the bacterial antibiotic resistance gene bla$_{oxa}$.

80. A method as defined in claim 1 which comprises the evaluation of the presence of a bacterial resistance to β-lactam antibiotics mediated by the bacterial antibiotic resistance gene blaZ directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 189 and a sequence complementary thereof under conditions such that the nucleic acid of the probe selectively hybridizes with said bacterial DNA; and c) detecting the presence of a hybridization complex as an indication of the bacterial resistance to β-lactam antibiotics mediated by the bacterial antibiotic resistance gene blaZ.

81. A method as defined in claim 1, which comprises the evaluation of the presence of a bacterial resistance to β-lactam antibiotics mediated by the bacterial antibiotic resistance gene blaZ directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 189, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to β-lactam antibiotics mediated by the bacterial resistance gene blaZ.

82. A method for evaluating the presence of a bacterial resistance to β-lactam antibiotics mediated by the bacterial antibiotic resistance gene blaZ directly from a test sample or from bacterial colonies, which comprises the following steps:

a) treating said sample with an aqueous solution containing at least one pair of primer having a sequence selected in the group consisting of SEQ ID NO: 209, SEQ ID NO 210, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to β-lactam antibiotics mediated by the bacterial antibiotic resistance gene blaZ.

83. A method as defined in claim 1 which comprises the evaluation of the presence of a bacterial resistance to aminoglycoside antibiotics mediated by the bacterial antibiotic resistance gene aac6'-IIA directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to releae the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 190 and a sequence complementary thereof under conditions such that the nucleic acid of the probe selectively hybridizes with said bacterial DNA; and c) detecting the presence of a hybridization complex as an indication of the bacterial resistance to aminoglycoside antibiotics mediated by the bacterial antibiotic resistance gene aac6'-IIA.

84. A method as defined in claim 1, which comprises the evaluation of the presence of a bacterial resistance to aminoglycoside antibiotics mediated by the bacterial antibiotic resistance gene aac6'-IIa directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 190, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to aminoglycoside antibiotics mediated by the bacterial resistance gene aac6'-IIa.

85. A method for evaluating the presence of a bacterial resistance to aminoglycoside antibiotics mediated by the bacterial antibiotic resistance gene aac6'-IIa directly from a test sample or from bacterial colonies, which comprises the following steps:

a) treating said sample with an aqueous solution containing at least one pair of primer having a sequence selected in the group consisting of SEQ ID NO: 219 to 222, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to aminoglycoside antibiotics mediated by the bacterial antibiotic resistance gene aac6'-IIa.

86. A method as defined in claim 1 which comprises the evaluation of the presence of a bacterial resistance to erythromycin mediated by the bacterial antibiotic resistance gene ermA directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 192 and a sequence complementary thereof under conditions such that the nucleic acid of the probe selectively hybridizes with said bacterial DNA; and c) detecting the presence of a hybridization complex as an indication of the bacterial resistance to erythromycin mediated by the bacterial antibiotic resistance gene ermA.

87. A method as defined in claim 1, which comprises the evaluation of the presence of a bacterial resistance to erythromycin mediated by the bacterial antibiotic resistance gene ermA directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 192, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to erythromycin mediated by the bacterial resistance gene ermA.

88. A method for evaluating the presence of a bacterial resistance to erythromycin mediated by the bacterial antibiotic resistance gene ermA directly from a test sample or from bacterial colonies, which comprises the following steps:

a) treating said sample with an aqueous solution containing at least one pair of primer having a sequence selected in the group consisting of SEQ ID NO: 247, SEQ ID NO 248, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to erythromycin mediated by the bacterial antibiotic resistance gene ermA.

89. A method as defined in claim 1 which comprises the evaluation of the presence of a bacterial resistance to erythromycin mediated by the bacterial antibiotic resistance gene ermB directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 193 and a sequence complementary thereof under conditions such that the nucleic acid of the probe selectively hybridizes with said bacterial DNA; and c) detecting the presence of a hybridization complex as an indication of the bacterial resistance to erythromycin mediated by the bacterial antibiotic resistance gene ermB.

90. A method as defined in claim 1, which comprises the evaluation of the presence of a bacterial resistance to erythromycin mediated by the bacterial antibiotic resistance gene ermB directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 193, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to erythromycin mediated by the bacterial resistance gene ermB.

91. A method for evaluating the presence of a bacterial resistance to erythromycin mediated by the bacterial antibiotic resistance gene ermB directly from a test sample or from bacterial colonies, which comprises the following steps:

a) treating said sample with an aqueous solution containing at least one pair of primer having a sequence selected in the group consisting of SEQ ID NO: 249, SEQ ID NO 250, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to erythromycin mediated by the bacterial antibiotic resistance gene ermB.

92. A method as defined in claim 1 which comprises the evaluation of the presence of a bacterial resistance to erythromycin mediated by the bacterial antibiotic resistance gene ermC directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 194 and a sequence complementary thereof under conditions such that the nucleic acid of the probe selectively hybridizes with said bacterial DNA; and c) detecting the presence of a hybridization complex as an indication of the bacterial resistance to erythromycin mediated by the bacterial antibiotic resistance gene ermC.

93. A method as defined in claim 1, which comprises the evaluation of the presence of a bacterial resistance to erythromycin mediated by the bacterial antibiotic resistance gene ermC directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 194, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to erythromycin mediated by the bacterial resistance gene ermC.

94. A method for evaluating the presence of a bacterial resistance to erythromycin mediated by the bacterial antibiotic resistance gene ermC directly from a test sample or from bacterial colonies, which comprises the following steps:

a) treating said sample with an aqueous solution containing at least one pair of primer having a sequence selected in the group consisting of SEQ ID NO: 251, SEQ ID NO 252, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to erythromycin mediated by the bacterial antibiotic resistance gene ermC.

95. A method as defined in claim 1 which comprises the evaluation of the presence of a bacterial resistance to vancomycin mediated by the bacterial antibiotic resistance gene vanB directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which has at least twelve nucleotides in length and is capable of hybridizing with anyone of the nucleotide sequence defined in of SEQ ID NO. 191 and a sequence complementary thereof under conditions such that the nucleic acid of the probe selectively hybridizes with said bacterial DNA; and c) detecting the presence of a hybridization complex as an indication of the bacterial resistance to vancomycin mediated by the bacterial antibiotic resistance gene vanB.

96. A method as defined in claim 1, which comprises the evaluation of the presence of a bacterial resistance to vancomycin mediated by the bacterial antibiotic resistance gene vanB directly from a test sample or from bacterial colonies, which comprises the following steps:

a) treating said sample with an aqueous solution comprising at least one pair of primers having at least twelve nucleotides in length, one of said primers being capable of hybridizing selectively with one of the two complementary strands of said antibiotic resistance gene and of SEQ ID NO. 191, that contain the target sequence, and the other of said primers being capable of hybridizing with the other of said strands so as to form an extension product which contains the target sequence as a template;

b) synthesizing an extension product of each of said primers which extension product contains the target sequence, and amplifying said target sequence, in any, to a detectable level; and c) detecting the presence or amount of said amplified target sequence as an indication of a bacterial resistance to vancomycin mediated by the bacterial resistance gene vanB.

97. A method for evaluating the presence of a bacterial resistance to vancomycin mediated by the bacterial antibiotic resistance gene vanB directly from a test sample or from bacterial colonies, which comprises the following steps:

a) treating said sample with an aqueous solution containing at least one pair of primer having a sequence selected in the group consisting of SEQ ID NO: 229 to SEQ ID NO 232, one of said primers being capable of hybridizing selectively with one of the two complementary strands of said bacterial antibiotic resistance gene that contain a target sequence, and another of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of a bacterial resistance to vancomycin mediated by the bacterial antibiotic resistance gene vanB.

98. A nucleic acid having the nucleotide sequence of any one of SEQ ID NOs: 178 to 184, SEQ ID NO: 267, SEQ ID NO: 268, a part thereof and variants thereof which, when in single stranded form, ubiquitously and specifically hybridizes with a target bacterial DNA as a probe or as a primer.

99. An oligonucleotide having the nucleotide sequence of any one of SEQ ID NOs: 195 to 266, SEQ ID NO: 271, SEQ ID NO: 272, a complementary strand, which ubiquitously and specifically hybridizes with a target bacterial DNA as a probe or as a primer.

100. A recombinant plasmid comprising a nucleic acid as defined in claim 98.

101. A recombinant host which has been transformed by a recombinant plasmid according to claim 100.

102. A recombinant host according to claim 101 wherein said host is *Escherichia coli*.

103. A diagnostic kit for the detection or quantification of the nucleic acids of any combination of the bacterial species selected from the group consisting of *Haemophilus influenzae, Klebsiella pneumoniae, Proteus mirabilis, Staphylococcus saprophyticus, Enterococcus faecium* and *Streptococcus* species, comprising any combination of probes of at least 12 nucleotides in length selected from the group consisting of SEQ ID NOs: 178 to 184, SEQ ID NO: 267, SEQ ID NO: 268.

104. A diagnostic kit for the detection or quantification of the nucleic acids of any combination of the bacterial species selected from the group consisting of, *Haemophilus influenzae, Klebsiella pneumoniae, Proteus mirabilis, Staphylococcus saprophyticus, Enterococcus faecium*, and Streptococcus species, comprising any suitable combination of primers of at least 12 nucleotides in length selected from the group consisting of SEQ ID NOs: 178 to 184, SEQ ID NO: 267, SEQ ID NO: 268.

105. A diagnostic kit for the detection or quantification of the nucleic acids of any combination of the bacterial species selected from the group consisting of, *Enterococcus faecium* and Streptococcus species, comprising any suitable combination of primers of at least 12 nucleotides in length selected from the group consisting of SEQ ID NOs: 263 to 266.

106. A diagnostic kit for the detection or quantification of the nucleic acids of any combination of the bacterial resistance genes selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int, comprising any combination of probes of at least 12 nucleotides in length selected from the group consisting of SEQ ID NOs: 161 à 177, SEQ ID NOs: 188 to 194.

107. A diagnostic kit for the detection or quantification of the nucleic acids of any combination of the bacterial resistance genes selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int, comprising any suitable combination of primers of at least 12 nucleotides in length selected from the group consisting of SEQ ID NOs: 161 à 177, SEQ ID NOs: 188 to 194.

108. A diagnostic kit for the detection or quantification of the nucleic acids of any combination of the bacterial resistance genes selected from the group consisting of $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int, comprising any suitable combination of primers of at least 12 nucleotides in length selected from the group consisting of SEQ ID NOs: 195 to 262.

109. A diagnostic kit for the detection or quantification of the nucleic acids of any bacterial species, comprising any combination of probes of at least 12 nucleotides in length selected from the group consisting of SEQ ID NOs: 185 to 187.

110. A diagnostic kit for the detection or quantification of the nucleic acids of any bacterial species, comprising any suitable combination of primers of at least 12 nucleotides in length selected from the group consisting of SEQ ID NOs: 185 to 187.

111. A diagnostic kit for the detection or quantification of the nucleic acids of any bacterial species, comprising any suitable combination of primers of at least 12 nucleotides in length selected from the group consisting of SEQ ID NO: 126, SEQ ID NO: 127, SEQ ID NO: 271, SEQ ID NO: 272.

112. A diagnostic kit, as defined in claim 103, further comprising any combination of probes of at least 12 nucleotides in length selected from the group consisting of SEQ ID NOs: 185 to 187 for the simultaneous detection or quantification of nucleic acids of any bacterial species.

113. A diagnostic kit, as defined in claim 104, further comprising any suitable combination of primers of at least 12 nucleotides in length selected from the group consisting of SEQ ID NOs: 185 to 187 for the simultaneous detection or quantification of nucleic acids of any bacterial species.

114. A diagnostic kit, as defined in claim 105, further comprising any suitable combination of primers of at least 12 nucleotides in length selected from the group consisting of SEQ ID NO: 126, SEQ ID NO: 127, SEQ ID NO: 271, SEQ ID NO: 272 for the simultaneous detection or quantification of nucleic acids of any bacterial species.

115. A diagnostic kit, as defined in claim 103, further comprising any combination of probes of at least 12 nucleotides in length selected from the group consisting of SEQ ID NOs: 161 to 177, SEQ ID NOs: 188 to 194 for the simultaneous detection or quantification of nucleic acids of any bacterial antibiotic resistance genes selected from the group consisting of: $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int.

116. A diagnostic kit, as defined in claim 104, further comprising any suitable combination of primers of at least 12 nucleotides in length selected from the group consisting of SEQ ID NOs: 161 to 177, SEQ ID NOs: 188 to 194 for the simultaneous detection or quantification of nucleic acids of any bacterial antibiotic resistance genes selected from the group consisting of: $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int.

117. A diagnostic kit, as defined in claim 105, further comprising any suitable combination of primers of at least 12 nucleotides in length selected from the group consisting of SEQ ID NOs: 195 to 262 for the simultaneous detection or quantification of nucleic acids of any bacterial antibiotic resistance genes selected from the group consisting of: $bla_{tem}$, $bla_{rob}$, $bla_{shv}$, $bla_{oxa}$, blaZ, aadB, aacC1, aacC2, aacC3, aacA4, aac6'-IIa, ermA, ermB, ermC, mecA, vanH-vanA-vanX, vanB, satA, aacA-aphD, vat, vga, msrA, sul and int.

118. A diagnostic kit, as defined in claim 106, further comprising any combination of probes of at least 12 nucleotides in length selected from the group consisting of SEQ ID NOs: 185 to 187 for the simultaneous detection or quantification of nucleic acids of any bacterial species.

119. A diagnostic kit, as defined in claim 107, further comprising any suitable combination of primers of at least 12 nucleotides in length selected from the group consisting of SEQ ID NOs: 185 to 187 for the simultaneous detection or quantification of nucleic acids of any bacterial species.

120. A diagnostic kit, as defined in claim 108, further comprising any suitable combination of primers of at least 12 nucleotides in length selected from the group consisting of SEQ ID NO: 126, SEQ ID NO: 127, SEQ ID NO: 271, SEQ ID NO: 272 for the simultaneous detection or quantification of nucleic acids of any bacterial species.

121. A diagnostic kit, as defined in claim 115, further comprising any combination of probes of at least 12 nucleotides in length selected from the group consisting of SEQ ID NOs: 185 to 187 for the simultaneous detection or quantification of nucleic acids of any bacterial species.

122. A diagnostic kit, as defined in claim 116, further comprising any suitable combination of primers of at least 12 nucleotides in length selected from the group consisting of SEQ ID NOs: 185 to 187 for the simultaneous detection quantification of nucleic acids of any bacterial species.

123. A diagnostic kit, as defined in claim 117, further comprising any suitable combination of primers of at least 12 nucleotides in length selected from the group consisting of SEQ ID NO: 126, SEQ ID NO: 127, SEQ ID NO: 271, SEQ ID NO: 272 for the simultaneous detection or quantification of nucleic acids of any bacterial species.

* * * * *

UNITED STATES PATENT AND TRADEMARK OFFICE
CERTIFICATE OF CORRECTION

PATENT NO. : 5,994,066          Page 1 of 3
DATED : November 30, 1999
INVENTOR(S) : Michel G. Bergeron, et al.

It is certified that error appears in the above-identified patent and that said Letters Patent is hereby corrected as shown below:

On the title page: Item [56]
References Cited

U.S. PATENT DOCUMENTS

Please add --5,492,811 2/1996 Gilson et al. ................435/6-

FOREIGN PATENT DOCUMENTS

Delete second instance of 2584419 1/1987 France.

Delete second instance of 2599743 12/1987 France.

Delete second instance of 2685334 6/1993 France.

Delete second instance of 2699539 6/1994 France.

Delete second instance of 91/08305 6/1991 WIPO.

Delete second instance of 93/03186 2/1993 WIPO.

Column 9, Line 27:

"Pharmnacia" should be --Pharmacia--.

Column 13, Line 11:

"µmM" should be --µM--.

Column 13, Line 13:

"sing" should be --using--.

Column 29, Table 8, Line 48:

"$^a$TQC" should be --$^a$TGC--.

UNITED STATES PATENT AND TRADEMARK OFFICE
CERTIFICATE OF CORRECTION

PATENT NO. : 5,994,066
DATED : November 30, 1999
INVENTOR(S) : Michel G. Bergeron et al

It is certified that error appears in the above-identified patent and that said Letters Patent is hereby corrected as shown below:

Column 35, ANNEX I:

"frorm" should be --from--.

Columns 41 and 42, ANNEX II, under *aacC3*:

Remove comma after 5'-AGC.

Columns 45 and 46, ANNEX II, under *sul*:

Add a space between TTA and TGA.

UNITED STATES PATENT AND TRADEMARK OFFICE
CERTIFICATE OF CORRECTION

PATENT NO. : 5,994,066
DATED : November 30, 1999
INVENTOR(S) : Michel G. Bergeron et al It is certified that error appears in the above-identified patent and that said Letters Patent is hereby corrected as shown below:

Columns 45 and 46, ANNEX II, under Universal primers$^c$:

"ACC" should be --AGG--.

Columns 45 and 46, ANNEX II:

"165" should be --16S--.

IN THE CLAIMS

Column 280, Line 58:

Add --or-- after detection and before quantification.

Signed and Sealed this

Twenty-sixth Day of December, 2000

Attest:

Q. TODD DICKINSON

*Attesting Officer*   *Director of Patents and Trademarks*